United States Patent [19]
Tan et al.

[11] Patent Number: 5,985,287
[45] Date of Patent: Nov. 16, 1999

[54] COMPOUNDS AND METHODS FOR TREATMENT AND DIAGNOSIS OF MYCOBACTERIAL INFECTIONS

[75] Inventors: Paul Tan; Margot Skinner; Ross Prestidge, all of Auckland, New Zealand

[73] Assignee: Genesis Research and Development Corporation Limited, Parnell, New Zealand

[21] Appl. No.: 08/997,362

[22] Filed: Dec. 23, 1997

Related U.S. Application Data

[63] Continuation-in-part of application No. 08/873,970, Jun. 12, 1997, which is a continuation-in-part of application No. 08/705,347, Aug. 29, 1996.

[51] Int. Cl.[6] .......................... A61K 39/04; A61K 45/00; A61K 35/74
[52] U.S. Cl. .................... 424/248.1; 424/282.1; 435/253.1
[58] Field of Search .............. 424/248.1, 282.1; 435/253.1

[56] References Cited

U.S. PATENT DOCUMENTS

| | | |
|---|---|---|
| 3,956,481 | 5/1976 | Jolles et al. . |
| 4,036,953 | 7/1977 | Adam et al. . |
| 4,716,038 | 12/1987 | Stanford et al. . |
| 4,724,144 | 2/1988 | Rook et al. . |
| 5,599,545 | 2/1997 | Stanford et al. ............... 424/282.1 |
| 5,833,996 | 11/1998 | Stanford et al. ............... 424/248.1 |

FOREIGN PATENT DOCUMENTS

| | | | |
|---|---|---|---|
| 0763361 | 3/1997 | European Pat. Off. ....... | A61K 39/04 |
| 2020758 | 4/1970 | France ........................... | A61K 27/00 |
| 9007935 | 7/1990 | WIPO ............................ | A61K 39/02 |
| 9101751 | 2/1991 | WIPO ............................ | A61K 39/04 |
| 9102542 | 3/1991 | WIPO ............................ | A61K 39/04 |
| 9208488 | 5/1992 | WIPO ............................ | A61K 39/39 |
| 9316727 | 9/1993 | WIPO ............................ | A61K 39/04 |
| 9406466 | 3/1994 | WIPO ............................ | A61K 39/04 |
| 9525744 | 9/1995 | WIPO . | |
| 9526742 | 10/1995 | WIPO ............................ | A61K 35/74 |

OTHER PUBLICATIONS

I.J. Hiu, "The Adjuvant Active Fraction of Delipidated Mycobacteria", Nature, vol. 267, pp. 708–709, 1977.

I.J. Hiu, "Adjuvanticity and Strains of Mycobacteria" Japan J. Exp. Med,. vol. 50, pp. 183–187, 1980.

S.J. Thompson et al., "Modulation of Pristane–Induced Arthritis by Mycobacterial Antigens", Autoimmunity, vol. 11, pp. 35–43, 1991.

C. Abou–Zeid et al. "Induction of a Type 1 Immune Response to a Recombinant Antigen from *Mycobacterium tuberculosis* Expressed in *Mycobacterium vaccae*", Infect. Immun. vol. 65, pp. 1856–1862, 1997.

Meyer et al. "Biologically Active Components from Mycobacterial Cell Walls. III. Production of Experimental Allergic Encephalomyelitis in Guinea–Pigs", Immunology, vol. 28, pp. 219–229, 1975.

Kobatake et al., Agric. Biol. Chem., vol. 51, pp. 691–697, 1987.

Navalkar et al. "Antigen Evaluation of *Mycobacterium vaccae* in Relation to *Mycobacterium leprae*" Int. J. Leprosy, vol. 48, pp. 388–396, 1980.

Hunter et al. "Isolation and Characterization of the Highly Immunogenic Cell Wall–Associated Protein of *Mycobacterium leprae*" Jnl. Immun. vol. 142, pp. 2864–2872, 1989.

Melancon–Kaplan et al "Immunological Significance of *Mycobacterium leprae* Cell Walls" Proc. Natl. Acad. USA, vol. 85, pp. 1917–1921, 1988.

R.G. White et al., "Correlation of Adjuvant Activity and Chemical Structure of Wax D Fractions of Mycobacteria," Immunology 7, pp. 158–171, 1964.

R.G. White, "Characterization of Microbacterial Components of Adjuvant Mixtures," Symposium Series Immunobiol. Standard 6, pp. 49–58, 1967.

R.G. White et al., The Influence of Components of M. Tuberculosis and other Mycobacteria upon Antibody Production to Ovalbumin, Immunology I, pp. 54–66, 1958.

Skinner, Immunization with Heat–Killed *Mycobacterium vaccae* Stimulates CD8[+] Cytotoxic T Cells Specific for Macrophages Infected with *Mycobacterium tuberculosis,* Infection and Immunity 65:11, 4525–4530, 1997.

*Primary Examiner*—Mary E. Mosher
*Attorney, Agent, or Firm*—Janet Sleath; Ann W. Speckman

[57] ABSTRACT

The present invention provides polypeptides comprising an immunogenic portion of a *M. vaccae* protein and DNA molecules encoding such polypeptides, together with methods for their use in the diagnosis and treatment of mycobacterial infection. Methods for enhancing the immune response to an antigen including administration of *M. vaccae* culture filtrate or delipidated *M. vaccae* cells are also provided.

5 Claims, 16 Drawing Sheets

```
M. vaccae:   MRLLDRIRGPW...ARRFGVV.AVATAMMPALVGLAGGSATAGAFSRPGLPVEYLMVPSP
m. bovis:    MQLVDRVRGAVTGMSRRL.VVGAVGAALVSGLVGAVGGTATAGAFSRPGLPVEYLQVPSP
M. tb:       MQLVDRVRGAVTGMSRRL.VVGAVAR.LVSGLVGAVGGTATAGAFSRPGLPVEYLQVPSP
m. leprae.   MKFVDRFRGAVAGMLRRL.VVEAMGVALLSALIGVVG.SAPAEAFSRPGLPVEYLQVPSP
CONSENSUS:   M   DR RG      RR  VV A          L G  G  A A AFSRPGLPVEYL VPSP M. vaccae:   SMGRDIKIQFQSGGENSPALYLLDGLRAQEDFNGWDINTQAFEWFLDSGISVVMPVGGQS
m. bovis:    SMGRDIKVQFQSGGANSPALYLLDGLRAQDDFSGWDINTPAFEWYDQSGLSVVMPVGGQS
M. tb:       SMGRDIKVQFQSGGANSPALYLLDGLRAQDDFSGWDINTPAFEWYDQSGLSVVMPVGGQS
M. leprae:   SMGRDIKVQFQNGGANSPALYLLDGLRAQDDFSGWDINTTAFEWYYQSGISVVMPVGGQS
CONSENSUS:   SMGRDIK QFQ GG NSPALYLLDGLRA   F GWDINT AFEW   SG SVVMPVGGQS M. vaccae:   SFYTDWYAPARNKGPTVTYKWETFLTQELPGWLQANRAVKPTGSGPVGLSMAGSAALNLA
M. bovis:    SFYSDWYQPACGKAGCQTYKWETFLTSELPGWLQANRHVKPTGSAVVGLSMAASSALTLA
M. tb:       SFYSDWYQPACRKAGCQTYKWETFLTSELPGWLQANRHVKPTGSAVVGLSMAASSALTLA
M. leprae:   SFYSDWYSPACGKAGCQTYKWETFLTSELPEYLQSNKQIKPTGSAAVGLSMAGLSALTLA
CONSENSUS:   SFY DWY PA K      TYKWETFLT ELP  LQ N    KPTGS  VGLSMA   AL LA M. vaccae:   TWHPEQFIYAGSMSGFLNPSEGWWPFLINISMGDAGGFKADDMWGKTEGIPTAVGQRNDP
M. bovis:    IYHPQQFVYAGAMSGLLDPSQAMGPTLIGLAMGDAGGYKASDMWGPKEDPAW...QRNDP
M. tb:       IYHPQQFVYAGAMSGLLDPSQAMGPTLIGLAMGDAGGYKASDMWGPKEDPAW...QRNDP
M. leprae:   IYHPDQFIYVGSMSGLLDPSNAMGPSLIGLAMGDAGGYKAADMWGPSTDPAW...KRNDP
CONSENSUS:      HP QF Y G MSG L PS    P LI  MGDAGG KA DMWG          RNDP M. vaccae:   MLNIPTLVANNTRIWVYCGNGQPTELGGGDLPATFLEGLTIRT.NETFRDNYIAAGGHNG
m. bovis:    LLNVGKLIANNTRVWVYCGNGKPSDLGGNNLPAKFLEGF.VRTSNIKFQDAYNAGGGHNG
M. tb:       LLNVGKLIANNTRVWVYCGNGKPSDLGGNNLPAKFLEGF.VRTSNIKFQDAYNAGGRHNG
M. leprae:   TVNVGTLIANNTRIWMYCGNGKPTELGGNNLPAKLLEGL.VRTSNIKFQDGYNAGGGHNA
CONSENSUS:     N   L ANNTR W YCGNG P  LGG  LPA  LEG    RT N  F D Y AG HN M. vaccae:   VFNFPANGTHNWAYWGRELQAMKPDLQAHLL*
M. bovis:    VFDFPDSGTHSWEYWGAQLNAMKPDLQRALGATPNTGPAPQGA*
M. tb:       VFDFPDSGTHSWEYWGAQLNAMKPDLQRHWVPRPTPGP.PQGA*
M. leprae:   VFNFPDSGTHSWEYWGEQLNDMKPDLQQYLGAT..PGA*
CONSENSUS:   VF FP  GTH W YWG  L  MKPDLQ
```

*Fig. 3*

SEQUENCE LISTING

```
(1) GENERAL INFORMATION:

(iii) NUMBER OF SEQUENCES: 194

(2) INFORMATION FOR SEQ ID NO:1:

(i) SEQUENCE CHARACTERISTICS:
          (A) LENGTH: 25 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:1:

Ala Pro Val Gly Pro Gly Xaa Ala Ala Tyr Val Gln Gln Val Pro Asp
  1               5                  10                  15

Gly Pro Gly Ser Val Gln Gly Met Ala
             20                  25

(2) INFORMATION FOR SEQ ID NO:2:

(i) SEQUENCE CHARACTERISTICS:
          (A) LENGTH: 10 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:2:

Met Xaa Asp Gln Leu Lys Val Asn Asp Asp
  1               5                  10

(2) INFORMATION FOR SEQ ID NO:3:

(i) SEQUENCE CHARACTERISTICS:
          (A) LENGTH: 11 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:3:

Met Xaa Pro Val Pro Val Ala Thr Ala Ala Tyr
  1               5                  10

(2) INFORMATION FOR SEQ ID NO:4:

(i) SEQUENCE CHARACTERISTICS:
          (A) LENGTH: 21 amino acids
          (B) TYPE: amino acid
```

(C) STRANDEDNESS: single
            (D) TOPOLOGY: linear (ii) MOLECULE TYPE: protein (xi) SEQUENCE DESCRIPTION: SEQ ID NO:4:

Thr Pro Ala Pro Ala Pro Pro Tyr Val Asp His Val Glu Gln Ala
1               5                   10                  15

Lys Phe Gly Asp Leu
            20

(2) INFORMATION FOR SEQ ID NO:5:

(i) SEQUENCE CHARACTERISTICS:
            (A) LENGTH: 29 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:5:

Met Gln Ala Phe Asn Ala Asp Ala Tyr Ala Phe Ala Lys Arg Glu Lys
1               5                   10                  15

Val Ser Leu Ala Pro Gly Val Pro Xaa Val Phe Glu Thr
            20                  25

(2) INFORMATION FOR SEQ ID NO:6:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:6:

Met Ala Asp Pro Asn Xaa Ala Ile Leu Gln Val Ser Lys Thr Thr Arg
1               5                   10                  15

Gly Gly Gln Ala Ala
            20

(2) INFORMATION FOR SEQ ID NO:7:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:7:

Met Pro Ile Leu Gln Val Ser Gln Thr Gly Arg
1               5                   10

(2) INFORMATION FOR SEQ ID NO:8:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:8:

```
Met Xaa Asp Pro Ile Xaa Leu Gln Leu Gln Val Ser Ser Thr
1               5                   10
```

(2) INFORMATION FOR SEQ ID NO:9:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Lys Ala Thr Tyr Val Gln Gly Gly Leu Gly Arg Ile Glu Ala Arg Val
1               5                   10                  15
```

(2) INFORMATION FOR SEQ ID NO:10:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Lys Xaa Gly Leu Ala Asp Leu Ala Pro
1               5
```

(2) INFORMATION FOR SEQ ID NO:11:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 12...12
        (D) OTHER INFORMATION: Residue can be either Glu or Ile (xi) SEQUENCE DESCRIPTION: SEQ ID NO:11:

```
Lys Xaa Tyr Ala Leu Ala Leu Met Ser Ala Val Xaa Ala Ala
1               5                   10
```

(2) INFORMATION FOR SEQ ID NO:12:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

```
Lys Asn Pro Gln Val Ser Asp Glu Leu Xaa Thr
1               5                   10
```

(2) INFORMATION FOR SEQ ID NO:13:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

Ala Pro Ala Pro Ala Ala Pro Ala Xaa Gly Asp Pro Ala Ala Val Val
 1               5                  10                  15

Ala Ala Met Ser Thr
            20

(2) INFORMATION FOR SEQ ID NO:14:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

Glu Ala Glu Val Xaa Tyr Leu Gly Gln Pro Gly Glu Leu Val Asn
 1               5                  10                  15

(2) INFORMATION FOR SEQ ID NO:15:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 2...2
        (D) OTHER INFORMATION: Residue can be either Gly or Ala
        (A) NAME/KEY: Other
        (B) LOCATION: 15...15
        (D) OTHER INFORMATION: Residue can be either Pro or Ala (xi) SEQUENCE DESCRIPTION: SEQ ID NO:15:

Ala Xaa Val Val Pro Pro Xaa Gly Pro Pro Ala Pro Gly Ala Xaa
 1               5                  10                  15

(2) INFORMATION FOR SEQ ID NO:16:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

Ala Pro Ala Pro Asp Leu Gln Gly Pro Leu Val Ser Thr Leu Ser
 1               5                  10                  15

(2) INFORMATION FOR SEQ ID NO:17:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

```
Ala Thr Pro Asp Trp Ser Gly Arg Tyr Thr Val Val Thr Phe Ala Ser
1               5                   10                  15

Asp Lys Leu Gly Thr Ser Val Ala Ala
            20                  25
```

(2) INFORMATION FOR SEQ ID NO:18:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 15...15
        (D) OTHER INFORMATION: Residue can be either Ala or Arg
        (A) NAME/KEY: Other
        (B) LOCATION: 23...23
        (D) OTHER INFORMATION: Residue can be either Val or Leu (xi) SEQUENCE DESCRIPTION: SEQ ID NO:18:

```
Ala Pro Pro Tyr Asp Asp Arg Gly Tyr Val Asp Ser Thr Ala Xaa Xaa
1               5                   10                  15

Ala Ser Pro Pro Thr Leu Xaa Val Val
            20                  25
```

(2) INFORMATION FOR SEQ ID NO:19:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:19:

```
Glu Pro Glu Gly Val Ala Pro Pro
1               5
```

(2) INFORMATION FOR SEQ ID NO:20:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:20:

```
Glu Pro Ala Gly Ile Pro Ala Gly Phe Pro Asp Val Ser Ala Tyr Ala
1               5                   10                  15

Ala Val Asp Pro Xaa Xaa Tyr Val Val
            20                  25
```

(2) INFORMATION FOR SEQ ID NO:21:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

```
Ala Pro Val Gly Pro Gly Xaa Ala Ala Tyr Val Gln Gln Val Pro
  1               5                  10                  15
```

(2) INFORMATION FOR SEQ ID NO:22:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:22:

```
Phe Ser Arg Pro Gly Leu Pro Val Glu Tyr Leu Met Val Pro Ser
  1               5                  10                  15
```

(2) INFORMATION FOR SEQ ID NO:23:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:23:

```
Phe Ser Arg Pro Gly Leu Pro Val Glu Tyr Leu Met Val Pro Ser Pro
  1               5                  10                  15

Ser Met Gly
```

(2) INFORMATION FOR SEQ ID NO:24:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:24:

```
Phe Ser Arg Pro Gly Leu Pro Val Glu Tyr Leu Asp Val Phe Ser
  1               5                  10                  15
```

(2) INFORMATION FOR SEQ ID NO:25:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:25:

```
Xaa Xaa Thr Gly Leu His Arg Leu Arg Met Met Val Pro Asn
  1               5                  10
```

(2) INFORMATION FOR SEQ ID NO:26:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 16...16
        (D) OTHER INFORMATION: Residue can be either Ser or Val
        (A) NAME/KEY: Other
        (B) LOCATION: 17...17
        (D) OTHER INFORMATION: Residue can be either Gln or Val (xi) SEQUENCE DESCRIPTION: SEQ ID NO:26:

Val Pro Ala Asp Pro Val Gly Ala Ala Ala Gln Ala Glu Pro Ala Xaa
1               5                   10                  15

Xaa Arg Ile Asp
        20

(2) INFORMATION FOR SEQ ID NO:27:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 4...4
        (D) OTHER INFORMATION: Residue can be either Tyr or Pro
        (A) NAME/KEY: Other
        (B) LOCATION: 8...8
        (D) OTHER INFORMATION: Residue can be either Val or Gly
        (A) NAME/KEY: Other
        (B) LOCATION: 9...9
        (D) OTHER INFORMATION: Residue can be either Ile or Tyr (xi) SEQUENCE DESCRIPTION: SEQ ID NO:27:

Asp Pro Xaa Xaa Asp Ile Glu Xaa Xaa Phe Ala Arg Gly Thr
1               5                   10

(2) INFORMATION FOR SEQ ID NO:28:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:28:

Ala Pro Ser Leu Ser Val Ser Asp Tyr Ala Arg Asp Ala Gly Phe
1               5                   10                  15

(2) INFORMATION FOR SEQ ID NO:29:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 2...2
        (D) OTHER INFORMATION: Residue can be either Leu or Pro (xi) SEQUENCE DESCRIPTION: SEQ ID NO:29:

Xaa Xaa Leu Ala Xaa Ala Xaa Leu Gly Xaa Thr Val Asp Ala Asp Gln
1               5                   10                  15

(2) INFORMATION FOR SEQ ID NO:30:

(i) SEQUENCE CHARACTERISTICS:
        (A) LENGTH: 330 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:30:

```
Met Lys Phe Val Asp Arg Phe Arg Gly Ala Val Ala Gly Met Leu Arg
 1               5                  10                  15

Arg Leu Val Val Glu Ala Met Gly Val Ala Leu Leu Ser Ala Leu Ile
            20                  25                  30

Gly Val Val Gly Ser Ala Pro Ala Glu Ala Phe Ser Arg Pro Gly Leu
        35                  40                  45

Pro Val Glu Tyr Leu Gln Val Pro Ser Pro Ser Met Gly Arg Asp Ile
    50                  55                  60

Lys Val Gln Phe Gln Asn Gly Gly Ala Asn Ser Pro Ala Leu Tyr Leu
65                  70                  75                  80

Leu Asp Gly Leu Arg Ala Gln Asp Asp Phe Ser Gly Trp Asp Ile Asn
                85                  90                  95

Thr Thr Ala Phe Glu Trp Tyr Tyr Gln Ser Gly Ile Ser Val Val Met
            100                 105                 110

Pro Val Gly Gly Gln Ser Ser Phe Tyr Ser Asp Trp Tyr Ser Pro Ala
        115                 120                 125

Cys Gly Lys Ala Gly Cys Gln Thr Tyr Lys Trp Glu Thr Phe Leu Thr
    130                 135                 140

Ser Glu Leu Pro Glu Tyr Leu Gln Ser Asn Lys Gln Ile Lys Pro Thr
145                 150                 155                 160

Gly Ser Ala Ala Val Gly Leu Ser Met Ala Gly Leu Ser Ala Leu Thr
                165                 170                 175

Leu Ala Ile Tyr His Pro Asp Gln Phe Ile Tyr Val Gly Ser Met Ser
            180                 185                 190

Gly Leu Leu Asp Pro Ser Asn Ala Met Gly Pro Ser Leu Ile Gly Leu
        195                 200                 205

Ala Met Gly Asp Ala Gly Gly Tyr Lys Ala Ala Asp Met Trp Gly Pro
    210                 215                 220

Ser Thr Asp Pro Ala Trp Lys Arg Asn Asp Pro Thr Val Asn Val Gly
225                 230                 235                 240

Thr Leu Ile Ala Asn Asn Thr Arg Ile Trp Met Tyr Cys Gly Asn Gly
                245                 250                 255

Lys Pro Thr Glu Leu Gly Gly Asn Asn Leu Pro Ala Lys Leu Leu Glu
            260                 265                 270

Gly Leu Val Arg Thr Ser Asn Ile Lys Phe Gln Asp Gly Tyr Asn Ala
        275                 280                 285

Gly Gly Gly His Asn Ala Val Phe Asn Phe Pro Asp Ser Gly Thr His
    290                 295                 300

Ser Trp Glu Tyr Trp Gly Glu Gln Leu Asn Asp Met Lys Pro Asp Leu
305                 310                 315                 320

Gln Gln Tyr Leu Gly Ala Thr Pro Gly Ala
                325                 330
```

(2) INFORMATION FOR SEQ ID NO:31:

(i) SEQUENCE CHARACTERISTICS:
    (A) LENGTH: 327 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:31:

```
Met Ile Asp Val Ser Gly Lys Ile Arg Ala Trp Gly Arg Trp Leu Leu
  1               5                  10                  15

Val Gly Ala Ala Ala Thr Leu Pro Ser Leu Ile Ser Leu Ala Gly Gly
             20                  25                  30

Ala Ala Thr Ala Ser Ala Phe Ser Arg Pro Gly Leu Pro Val Glu Tyr
         35                  40                  45

Leu Gln Val Pro Ser Glu Ala Met Gly Arg Thr Ile Lys Val Gln Phe
     50                  55                  60

Gln Asn Gly Gly Asn Gly Ser Pro Ala Val Tyr Leu Leu Asp Gly Leu
 65                  70                  75                  80

Arg Ala Gln Asp Asp Tyr Asn Gly Trp Asp Ile Asn Thr Ser Ala Phe
                 85                  90                  95

Glu Trp Tyr Tyr Gln Ser Gly Leu Ser Val Val Met Pro Val Gly Gly
            100                 105                 110

Gln Ser Ser Phe Tyr Ser Asp Trp Tyr Ser Pro Ala Cys Gly Lys Ala
            115                 120                 125

Gly Cys Thr Thr Tyr Lys Trp Glu Thr Phe Leu Thr Ser Glu Leu Pro
130                 135                 140

Lys Trp Leu Ser Ala Asn Arg Ser Val Lys Ser Thr Gly Ser Ala Val
145                 150                 155                 160

Val Gly Leu Ser Met Ala Gly Ser Ser Ala Leu Ile Leu Ala Ala Tyr
                165                 170                 175

His Pro Asp Gln Phe Ile Tyr Ala Gly Ser Leu Ser Ala Leu Met Asp
            180                 185                 190

Ser Ser Gln Gly Ile Glu Pro Gln Leu Ile Gly Leu Ala Met Gly Asp
            195                 200                 205

Ala Gly Gly Tyr Lys Ala Ala Asp Met Trp Gly Pro Pro Asn Asp Pro
210                 215                 220

Ala Trp Gln Arg Asn Asp Pro Ile Leu Gln Ala Gly Lys Leu Val Ala
225                 230                 235                 240

Asn Asn Thr His Leu Trp Val Tyr Cys Gly Asn Gly Thr Pro Ser Glu
                245                 250                 255

Leu Gly Gly Thr Asn Val Pro Ala Glu Phe Leu Glu Asn Phe Val His
            260                 265                 270

Gly Ser Asn Leu Lys Phe Gln Asp Ala Tyr Asn Gly Ala Gly Gly His
            275                 280                 285

Asn Ala Val Phe Asn Leu Asn Ala Asp Gly Thr His Ser Trp Glu Tyr
290                 295                 300

Trp Gly Ala Gln Leu Asn Ala Met Lys Pro Asp Leu Gln Asn Thr Leu
305                 310                 315                 320

Met Ala Val Pro Arg Ser Gly
                325
```

(2) INFORMATION FOR SEQ ID NO:32:

(i) SEQUENCE CHARACTERISTICS:
      (A) LENGTH: 338 amino acids
      (B) TYPE: amino acid
      (C) STRANDEDNESS: single (D) TOPOLOGY: linear (ii) MOLECULE TYPE: protein (xi) SEQUENCE DESCRIPTION: SEQ ID NO:32:

Met Gln Leu Val Asp Arg Val Arg Gly Ala Val Thr Gly Met Ser Arg
 1               5                  10                  15

Arg Leu Val Val Gly Ala Val Gly Ala Ala Leu Val Ser Gly Leu Val
             20                  25                  30

Gly Ala Val Gly Gly Thr Ala Thr Ala Gly Ala Phe Ser Arg Pro Gly
         35                  40                  45

Leu Pro Val Glu Tyr Leu Gln Val Pro Ser Pro Ser Met Gly Arg Asp
     50                  55                  60

Ile Lys Val Gln Phe Gln Ser Gly Gly Ala Asn Ser Pro Ala Leu Tyr
65                  70                  75                  80

Leu Leu Asp Gly Leu Arg Ala Gln Asp Asp Phe Ser Gly Trp Asp Ile
                 85                  90                  95

Asn Thr Pro Ala Phe Glu Trp Tyr Asp Gln Ser Gly Leu Ser Val Val
             100                 105                 110

Met Pro Val Gly Gly Gln Ser Ser Phe Tyr Ser Asp Trp Tyr Gln Pro
         115                 120                 125

Ala Cys Gly Lys Ala Gly Cys Gln Thr Tyr Lys Trp Glu Thr Phe Leu
     130                 135                 140

Thr Ser Glu Leu Pro Gly Trp Leu Gln Ala Asn Arg His Val Lys Pro
145                 150                 155                 160

Thr Gly Ser Ala Val Val Gly Leu Ser Met Ala Ala Ser Ser Ala Leu
                165                 170                 175

Thr Leu Ala Ile Tyr His Pro Gln Gln Phe Val Tyr Ala Gly Ala Met
            180                 185                 190

Ser Gly Leu Leu Asp Pro Ser Gln Ala Met Gly Pro Thr Leu Ile Gly
        195                 200                 205

Leu Ala Met Gly Asp Ala Gly Gly Tyr Lys Ala Ser Asp Met Trp Gly
    210                 215                 220

Pro Lys Glu Asp Pro Ala Trp Gln Arg Asn Asp Pro Leu Leu Asn Val
225                 230                 235                 240

Gly Lys Leu Ile Ala Asn Asn Thr Arg Val Trp Val Tyr Cys Gly Asn
                245                 250                 255

Gly Lys Pro Ser Asp Leu Gly Gly Asn Asn Leu Pro Ala Lys Phe Leu
            260                 265                 270

Glu Gly Phe Val Arg Thr Ser Asn Ile Lys Phe Gln Asp Ala Tyr Asn
        275                 280                 285

Ala Gly Gly Gly His Asn Gly Val Phe Asp Phe Pro Asp Ser Gly Thr
    290                 295                 300

His Ser Trp Glu Tyr Trp Gly Ala Gln Leu Asn Ala Met Lys Pro Asp
305                 310                 315                 320

Leu Gln Arg Ala Leu Gly Ala Thr Pro Asn Thr Gly Pro Ala Pro Gln
                325                 330                 335

Gly Ala (2) INFORMATION FOR SEQ ID NO:33:

(i) SEQUENCE CHARACTERISTICS:
        (A) LENGTH: 325 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:33:

```
Met Thr Asp Val Ser Arg Lys Ile Arg Ala Trp Gly Arg Arg Leu Met
 1               5                  10                  15

Ile Gly Thr Ala Ala Val Val Leu Pro Gly Leu Val Gly Leu Ala
            20                  25                  30

Gly Gly Ala Ala Thr Ala Gly Ala Phe Ser Arg Pro Gly Leu Pro Val
            35                  40                  45

Glu Tyr Leu Gln Val Pro Ser Pro Ser Met Gly Arg Asp Ile Lys Val
            50                  55                  60

Gln Phe Gln Ser Gly Gly Asn Asn Ser Pro Ala Val Tyr Leu Leu Asp
 65                  70                  75                  80

Gly Leu Arg Ala Gln Asp Asp Tyr Asn Gly Trp Asp Ile Asn Thr Pro
                85                  90                  95

Ala Phe Glu Trp Tyr Tyr Gln Ser Gly Leu Ser Ile Val Met Pro Val
               100                 105                 110

Gly Gly Gln Ser Ser Phe Tyr Ser Asp Trp Tyr Ser Pro Ala Cys Gly
               115                 120                 125

Lys Ala Gly Cys Gln Thr Tyr Lys Trp Glu Thr Phe Leu Thr Ser Glu
           130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ser Ala Met Ile Leu Ala
                165                 170                 175

Ala Tyr His Pro Gln Gln Phe Ile Tyr Ala Gly Ser Leu Ser Ala Leu
            180                 185                 190

Leu Asp Pro Ser Gln Gly Met Gly Pro Ser Leu Ile Gly Leu Ala Met
            195                 200                 205

Gly Asp Ala Gly Gly Tyr Lys Ala Ala Asp Met Trp Gly Pro Ser Ser
    210                 215                 220

Asp Pro Ala Trp Glu Arg Asn Asp Pro Thr Gln Gln Ile Pro Lys Leu
225                 230                 235                 240

Val Ala Asn Asn Thr Arg Leu Trp Val Tyr Cys Gly Asn Gly Thr Pro
                245                 250                 255

Asn Glu Leu Gly Gly Ala Asn Ile Pro Ala Glu Phe Leu Glu Asn Phe
            260                 265                 270

Val Arg Ser Ser Asn Leu Lys Phe Gln Asp Ala Tyr Asn Ala Ala Gly
            275                 280                 285

Gly His Asn Ala Val Phe Asn Phe Pro Pro Asn Gly Thr His Ser Trp
    290                 295                 300

Glu Tyr Trp Gly Ala Gln Leu Asn Ala Met Lys Gly Asp Leu Gln Ser
305                 310                 315                 320

Ser Leu Gly Ala Gly
            325
```

(2) INFORMATION FOR SEQ ID NO:34:

(i) SEQUENCE CHARACTERISTICS:
        (A) LENGTH: 338 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:34:

```
Met Gln Leu Val Asp Arg Val Arg Gly Ala Val Thr Gly Met Ser Arg
  1               5                  10                  15

Arg Leu Val Val Gly Ala Val Gly Ala Ala Leu Val Ser Gly Leu Val
             20                  25                  30

Gly Ala Val Gly Gly Thr Ala Thr Ala Gly Ala Phe Ser Arg Pro Gly
         35                  40                  45

Leu Pro Val Glu Tyr Leu Gln Val Pro Ser Pro Ser Met Gly Arg Asp
     50                  55                  60

Ile Lys Val Gln Phe Gln Ser Gly Gly Ala Asn Ser Pro Ala Leu Tyr
 65                  70                  75                  80

Leu Leu Asp Gly Leu Arg Ala Gln Asp Asp Phe Ser Gly Trp Asp Ile
                 85                  90                  95

Asn Thr Pro Ala Phe Glu Trp Tyr Asp Gln Ser Gly Leu Ser Val Val
             100                 105                 110

Met Pro Val Gly Gly Gln Ser Ser Phe Tyr Ser Asp Trp Tyr Gln Pro
         115                 120                 125

Ala Cys Gly Lys Ala Gly Cys Gln Thr Tyr Lys Trp Glu Thr Phe Leu
    130                 135                 140

Thr Ser Glu Leu Pro Gly Trp Leu Gln Ala Asn Arg His Val Lys Pro
145                 150                 155                 160

Thr Gly Ser Ala Val Val Gly Leu Ser Met Ala Ala Ser Ser Ala Leu
                165                 170                 175

Thr Leu Ala Ile Tyr His Pro Gln Gln Phe Val Tyr Ala Gly Ala Met
            180                 185                 190

Ser Gly Leu Leu Asp Pro Ser Gln Ala Met Gly Pro Thr Leu Ile Gly
        195                 200                 205

Leu Ala Met Gly Asp Ala Gly Gly Tyr Lys Ala Ser Asp Met Trp Gly
210                 215                 220

Pro Lys Glu Asp Pro Ala Trp Gln Arg Asn Asp Pro Leu Leu Asn Val
225                 230                 235                 240

Gly Lys Leu Ile Ala Asn Asn Thr Arg Val Trp Val Tyr Cys Gly Asn
                245                 250                 255

Gly Lys Pro Ser Asp Leu Gly Gly Asn Asn Leu Pro Ala Lys Phe Leu
            260                 265                 270

Glu Gly Phe Val Arg Thr Ser Asn Ile Lys Phe Gln Asp Ala Tyr Asn
        275                 280                 285

Ala Gly Gly His Asn Gly Val Phe Asp Phe Pro Asp Ser Gly Thr
290                 295                 300

His Ser Trp Glu Tyr Trp Gly Ala Gln Leu Asn Ala Met Lys Pro Asp
305                 310                 315                 320

Leu Gln Arg Ala Leu Gly Ala Thr Pro Asn Thr Gly Pro Ala Pro Gln
                325                 330                 335

Gly Ala (2) INFORMATION FOR SEQ ID NO:35:

(i) SEQUENCE CHARACTERISTICS:
        (A) LENGTH: 323 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:35:

Met Thr Asp Val Ser Arg Lys Ile Arg Ala Trp Gly Arg Arg Leu Met
  1               5                  10                  15
```

```
Ile Gly Thr Ala Ala Ala Val Val Leu Pro Gly Leu Val Gly Leu Ala
            20                  25                  30

Gly Gly Ala Ala Thr Ala Gly Ala Phe Ser Arg Pro Gly Leu Pro Val
        35                  40                  45

Glu Tyr Leu Gln Val Pro Ser Pro Ser Met Gly Arg Asp Ile Lys Val
    50                  55                  60

Gln Phe Gln Ser Gly Gly Asn Asn Ser Pro Ala Val Tyr Leu Leu Asp
65                  70                  75                  80

Gly Leu Arg Ala Gln Asp Asp Tyr Asn Gly Trp Asp Ile Asn Thr Pro
                85                  90                  95

Ala Phe Glu Trp Tyr Tyr Gln Ser Gly Leu Ser Ile Val Met Pro Val
            100                 105                 110

Gly Gly Gln Ser Ser Phe Tyr Ser Asp Trp Tyr Ser Pro Ala Cys Gly
        115                 120                 125

Lys Ala Gly Cys Gln Thr Tyr Lys Trp Glu Thr Leu Leu Thr Ser Glu
130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ser Ala Met Ile Leu Ala
                165                 170                 175

Ala Tyr His Pro Gln Gln Phe Ile Tyr Ala Gly Ser Leu Ser Ala Leu
            180                 185                 190

Leu Asp Pro Ser Gln Gly Met Gly Leu Ile Gly Leu Ala Met Gly Asp
        195                 200                 205

Ala Gly Gly Tyr Lys Ala Ala Asp Met Trp Gly Pro Ser Ser Asp Pro
210                 215                 220

Ala Trp Glu Arg Asn Asp Pro Thr Gln Gln Ile Pro Lys Leu Val Ala
225                 230                 235                 240

Asn Asn Thr Arg Leu Trp Val Tyr Cys Gly Asn Gly Thr Pro Asn Glu
                245                 250                 255

Leu Gly Gly Ala Asn Ile Pro Ala Glu Phe Leu Glu Asn Phe Val Arg
            260                 265                 270

Ser Ser Asn Leu Lys Phe Gln Asp Ala Tyr Lys Pro Ala Gly Gly His
        275                 280                 285

Asn Ala Val Phe Asn Phe Pro Pro Asn Gly Thr His Ser Trp Glu Tyr
290                 295                 300

Trp Gly Ala Gln Leu Asn Ala Met Lys Gly Asp Leu Gln Ser Ser Leu
305                 310                 315                 320

Gly Ala Gly (2) INFORMATION FOR SEQ ID NO:36:

(i) SEQUENCE CHARACTERISTICS:
        (A) LENGTH: 333 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:36:

Met Lys Phe Leu Gln Gln Met Arg Lys Leu Phe Gly Leu Ala Ala Lys
1               5                   10                  15

Phe Pro Ala Arg Leu Thr Ile Ala Val Ile Gly Thr Ala Leu Leu Ala
            20                  25                  30
```

```
Gly Leu Val Gly Val Val Gly Asp Thr Ala Ile Ala Val Ala Phe Ser
        35                  40                  45
Lys Pro Gly Leu Pro Val Glu Tyr Leu Gln Val Pro Ser Pro Ser Met
 50                  55                  60
Gly His Asp Ile Lys Ile Gln Phe Gln Gly Gly Gln His Ala Val
 65                  70                  75                  80
Tyr Leu Leu Asp Gly Leu Arg Ala Gln Glu Asp Tyr Asn Gly Trp Asp
                 85                  90                  95
Ile Asn Thr Pro Ala Phe Glu Glu Tyr Tyr His Ser Gly Leu Ser Val
                100                 105                 110
Ile Met Pro Val Gly Gly Gln Ser Ser Phe Tyr Ser Asn Trp Tyr Gln
                115                 120                 125
Pro Ser Gln Gly Asn Gly Gln His Tyr Thr Tyr Lys Trp Glu Thr Phe
130                 135                 140
Leu Thr Gln Glu Met Pro Ser Trp Leu Gln Ala Asn Lys Asn Val Leu
145                 150                 155                 160
Pro Thr Gly Asn Ala Ala Val Gly Leu Ser Met Ser Gly Ser Ser Ala
                165                 170                 175
Leu Ile Leu Ala Ser Tyr Tyr Pro Gln Gln Phe Pro Tyr Ala Ala Ser
                180                 185                 190
Leu Ser Gly Phe Leu Asn Pro Ser Glu Gly Trp Trp Pro Thr Met Ile
                195                 200                 205
Gly Leu Ala Met Asn Asp Ser Gly Gly Tyr Asn Ala Asn Ser Met Trp
                210                 215                 220
Gly Pro Ser Thr Asp Pro Ala Trp Lys Arg Asn Asp Pro Met Val Gln
225                 230                 235                 240
Ile Pro Arg Leu Val Ala Asn Asn Thr Arg Ile Trp Val Tyr Cys Gly
                245                 250                 255
Asn Gly Ala Pro Asn Glu Leu Gly Gly Asp Asn Ile Pro Ala Lys Phe
                260                 265                 270
Leu Glu Ser Leu Thr Leu Ser Thr Asn Glu Ile Phe Gln Asn Thr Tyr
                275                 280                 285
Ala Ala Ser Gly Gly Arg Asn Gly Val Phe Asn Phe Pro Pro Asn Gly
290                 295                 300
Thr His Ser Trp Pro Tyr Trp Asn Gln Gln Leu Val Ala Met Lys Pro
305                 310                 315                 320
Asp Ile Gln Gln Ile Leu Asn Gly Ser Asn Asn Ala
                325                 330

(2) INFORMATION FOR SEQ ID NO:37:

(i) SEQUENCE CHARACTERISTICS:
        (A) LENGTH: 340 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:37:

Met Thr Phe Phe Glu Gln Val Arg Arg Leu Arg Ser Ala Ala Thr Thr
 1                   5                  10                  15
Leu Pro Arg Arg Val Ala Ile Ala Ala Met Gly Ala Val Leu Val Tyr
                 20                  25                  30
Gly Leu Val Gly Thr Phe Gly Gly Pro Ala Thr Ala Gly Ala Phe Ser
                 35                  40                  45
```

```
Arg Pro Gly Leu Pro Val Glu Tyr Leu Gln Val Pro Ser Ala Ser Met
 50                  55                  60

Gly Arg Asp Ile Lys Val Gln Phe Gln Gly Gly Pro His Ala Val
 65                  70                  75                  80

Tyr Leu Leu Asp Gly Leu Arg Ala Gln Asp Asp Tyr Asn Gly Trp Asp
                 85                  90                  95

Ile Asn Thr Pro Ala Phe Glu Glu Tyr Tyr Gln Ser Gly Leu Ser Val
                100                 105                 110

Ile Met Pro Val Gly Gly Gln Ser Ser Phe Tyr Thr Asp Trp Tyr Gln
                115                 120                 125

Pro Ser Gln Ser Asn Gly Gln Asn Tyr Thr Tyr Lys Trp Glu Thr Phe
                130                 135                 140

Leu Thr Arg Glu Met Pro Ala Trp Leu Gln Ala Asn Lys Gly Val Ser
145                 150                 155                 160

Pro Thr Gly Asn Ala Ala Val Gly Leu Ser Met Ser Gly Gly Ser Ala
                165                 170                 175

Leu Ile Leu Ala Ala Tyr Tyr Pro Gln Gln Phe Pro Tyr Ala Ala Ser
                180                 185                 190

Leu Ser Gly Phe Leu Asn Pro Ser Glu Gly Trp Trp Pro Thr Leu Ile
                195                 200                 205

Gly Leu Ala Met Asn Asp Ser Gly Gly Tyr Asn Ala Asn Ser Met Trp
210                 215                 220

Gly Pro Ser Ser Asp Pro Ala Trp Lys Arg Asn Asp Pro Met Val Gln
225                 230                 235                 240

Ile Pro Arg Leu Val Ala Asn Asn Thr Arg Ile Trp Val Tyr Cys Gly
                245                 250                 255

Asn Gly Thr Pro Ser Asp Leu Gly Gly Asp Asn Ile Pro Ala Lys Phe
                260                 265                 270

Leu Glu Gly Leu Thr Leu Arg Thr Asn Gln Thr Phe Arg Asp Thr Tyr
                275                 280                 285

Ala Ala Asp Gly Gly Arg Asn Gly Val Phe Asn Phe Pro Pro Asn Gly
290                 295                 300

Thr His Ser Trp Pro Tyr Trp Asn Glu Gln Leu Val Ala Met Lys Ala
305                 310                 315                 320

Asp Ile Gln His Val Leu Asn Gly Ala Thr Pro Pro Ala Pro Ala
                325                 330                 335

Ala Pro Ala Ala
                340

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:38:

AGCGGCTGGG ACATCAACAC                                                    20

(2) INFORMATION FOR SEQ ID NO:39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: Other (xi) SEQUENCE DESCRIPTION: SEQ ID NO:39:

```
CAGACGCGGG TGTTGTTGGC                                                  20
```

(2) INFORMATION FOR SEQ ID NO:40:

(i) SEQUENCE CHARACTERISTICS:
        (A) LENGTH: 1211 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:40:

```
GGTACCGGAA GCTGGAGGAT TGACGGTATG AGACTTCTTG ACAGGATTCG TGGGCCTTGG     60
GCACGCCGTT TCGGCGTCGT GGCTGTCGCG ACAGCGATGA TGCCTGCTTT GGTGGGCCTG    120
GCTGGAGGGT CGGCGACCGC CGGAGCATTC TCCCGGCCAG GTCTGCCGGT GGAGTACCTG    180
ATGGTGCCTT CGCCGTCGAT GGGGCGCGAC ATCAAGATCC AGTTCCAGAG CGGTGGCGAG    240
AACTCGCCGG CTCTCTACCT GCTCGACGGC CTGCGTGCGC AGGAGGACTT CAACGGCTGG    300
GACATCAACA CTCAGGCTTT CGAGTGGTTC CTCGACAGCG GCATCTCCGT GGTGATGCCG    360
GTCGGTGGCC AGTCCAGCTT CTACACCGAC TGGTACGCCC CCGCCCGTAA CAAGGGCCCG    420
ACCGTGACCT ACAAGTGGGA GACCTTCCTG ACCCAGGAGC TCCCGGGCTG GCTGCAGGCC    480
AACCGCGCGG TCAAGCCGAC CGGCAGCGGC CCTGTCGGTC TGTCGATGGC GGGTTCGGCC    540
GCGCTGAACC TGGCGACCTG GCACCCGGAG CAGTTCATCT ACGCGGGCTC GATGTCCGGC    600
TTCCTGAACC CCTCCGAGGG CTGGTGGCCG TTCCTGATCA ACATCTCGAT GGGTGACGCC    660
GGCGGCTTCA AGGCCGACGA CATGTGGGGC AAGACCGAGG GGATCCCAAC AGCGGTTGGA    720
CAGCGCAACG ATCCGATGCT GAACATCCCG ACCCTGGTCG CCAACAACAC CCGTATCTGG    780
GTCTACTGCG GTAACGGCCA GCCCACCGAG CTCGGCGGCG GCGACCTGCC CGCCACGTTC    840
CTCGAAGGTC TGACCATCCG CACCAACGAG ACCTTCCGCG ACAACTACAT CGCCGCGGGT    900
GGCCACAACG GTGTGTTCAA CTTCCCGGCC AACGGCACGC ACAACTGGGC GTACTGGGGT    960
CGCGAGCTGC AGGCGATGAA GCCTGACCTG CAGGCGCACC TTCTCTGACG GTTGCACGAA   1020
ACGAAGCCCC CGGCCGATTG CGGCCGAGGG TTTCGTCGTC CGGGGCTACT GTGGCCGACA   1080
TAACCGAAAT CAACGCGATG GTGGCTCATC AGGAACGCCG AGGGGGTCAT TGCGCTACGA   1140
CACGAGGTGG GCGAGCAATC CTTCCTGCCC GACGGAGAGG TCAACATCCA CGTCGAGTAC   1200
TCCAGCGTGA A                                                        1211
```

(2) INFORMATION FOR SEQ ID NO:41:

(i) SEQUENCE CHARACTERISTICS:
        (A) LENGTH: 485 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:41:

```
AGCGGCTGGG ACATCAACAC CGCCGCCTTC GAGTGGTACG TCGACTCGGG TCTCGCGGTG     60
ATCATGCCCG TCGGCGGGCA GTCCAGCTTC TACAGCGACT GGTACAGCCC GGCCTGCGGT    120
AAGGCCGGCT GCCAGACCTA CAAGTGGGAG ACGTTCCTGA CCCAGGAGCT GCCGGCCTAC    180
```

```
CTCGCCGCCA ACAAGGGGGT CGACCCGAAC CGCAACGCGG CCGTCGGTCT GTCCATGGCC      240

GGTTCGGCGG CGCTGACGCT GGCGATCTAC CACCCGCAGC AGTTCCAGTA CGCCGGGTCG      300

CTGTCGGGCT ACCTGAACCC GTCCGAGGGG TGGTGGCCGA TGCTGATCAA CATCTCGATG      360

GGTGACGCGG GCGGCTACAA GGCCAACGAC ATGTGGGGTC ACCGAAGGA CCCGAGCAGC       420

GCCTGGAAGC GCAACGACCC GATGGTCAAC ATCGGCAAGC TGGTGGCCAA CAACACCCCC      480

CTCTC                                                                  485
```

(2) INFORMATION FOR SEQ ID NO:42:

(i) SEQUENCE CHARACTERISTICS:
        (A) LENGTH: 1052 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:42:

```
GTTGATGAGA AAGGTGGGTT GTTTGCCGTT ATGAAGTTCA CAGAGAAGTG GCGGGGCTCC       60

GCAAAGGCGG CGATGCACCG GGTGGGCGTT GCCGATATGG CCGCCGTTGC GCTGCCCGGA      120

CTGATCGGCT TCGCCGGGGG TTCGGCAACG GCCGGGGCAT TCTCCCGGCC CGGTCTTCCT      180

GTCGAGTACC TCGACGTGTT CTCGCCGTCG ATGGGCCGCG ACATCCGGGT CCAGTTCCAG      240

GGTGGCGGTA CTCATGCGGT CTACCTGCTC GACGGTCTGC GTGCCCAGGA CGACTACAAC      300

GGCTGGGACA TCAACACCCC TGCGTTCGAG TGGTTCTACG AGTCCGGCTT GTCGACGATC      360

ATGCCGGTCG GCGGACAGTC CAGCTTCTAC AGCGACTGGT ACCAGCCGTC TCGGGCAAC       420

GGGCAGAACT ACACCTACAA GTGGGAGACG TTCCTGACCC AGGAGCTGCC GACGTGGCTG      480

GAGGCCAACC GCGGAGTGTC GCGCACCGGC AACGCGTTCG TCGGCCTGTC GATGGCGGGC      540

AGCGCGGCGC TGACCTACGC GATCCATCAC CCGCAGCAGT TCATCTACGC CTCGTCGCTG      600

TCAGGCTTCC TGAACCCGTC CGAGGGCTGG TGGCCGATGC TGATCGGGCT GGCGATGAAC      660

GACGCAGGCG GCTTCAACGC CGAGAGCATG TGGGGCCCGT CCTCGGACCC GGCGTGGAAG      720

CGCAACGACC CGATGGTCAA CATCAACCAG CTGGTGGCCA ACAACACCCG GATCTGGATC      780

TACTGCGGCA CCGGCACCCC GTCGGAGCTG GACACCGGGA CCCCGGGCCA GAACCTGATG      840

GCCGCGCAGT TCCTCGAAGG ATTCACGTTG CGGACCAACA TCGCCTTCCG TGACAACTAC      900

ATCGCAGCCG GCGGCACCAA CGGTGTCTTC AACTTCCCGG CCTCGGGCAC CCACAGCTGG      960

GGGTACTGGG GCAGCAGCT GCAGCAGATG AAGCCCGACA TCCAGCGGGT TCTGGGAGCT     1020

CAGGCCACCG CCTAGCCACC CACCCCACAC CC                                  1052
```

(2) INFORMATION FOR SEQ ID NO:43:

(i) SEQUENCE CHARACTERISTICS:
        (A) LENGTH: 326 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:43:

```
Met Arg Leu Leu Asp Arg Ile Arg Gly Pro Trp Ala Arg Arg Phe Gly
 1               5                  10                  15

Val Val Ala Val Ala Thr Ala Met Met Pro Ala Leu Val Gly Leu Ala
            20                  25                  30
```

```
Gly Gly Ser Ala Thr Ala Gly Ala Phe Ser Arg Pro Gly Leu Pro Val
          35                  40                  45

Glu Tyr Leu Met Val Pro Ser Pro Ser Met Gly Arg Asp Ile Lys Ile
 50                  55                  60

Gln Phe Gln Ser Gly Gly Glu Asn Ser Pro Ala Leu Tyr Leu Leu Asp
 65                  70                  75                  80

Gly Leu Arg Ala Gln Glu Asp Phe Asn Gly Trp Asp Ile Asn Thr Gln
                 85                  90                  95

Ala Phe Glu Trp Phe Leu Asp Ser Gly Ile Ser Val Val Met Pro Val
                100                 105                 110

Gly Gly Gln Ser Ser Phe Tyr Thr Asp Trp Tyr Ala Pro Ala Arg Asn
                115                 120                 125

Lys Gly Pro Thr Val Thr Tyr Lys Trp Glu Thr Phe Leu Thr Gln Glu
        130                 135                 140

Leu Pro Gly Trp Leu Gln Ala Asn Arg Ala Val Lys Pro Thr Gly Ser
145                 150                 155                 160

Gly Pro Val Gly Leu Ser Met Ala Gly Ser Ala Ala Leu Asn Leu Ala
                165                 170                 175

Thr Trp His Pro Glu Gln Phe Ile Tyr Ala Gly Ser Met Ser Gly Phe
                180                 185                 190

Leu Asn Pro Ser Glu Gly Trp Trp Pro Phe Leu Ile Asn Ile Ser Met
        195                 200                 205

Gly Asp Ala Gly Gly Phe Lys Ala Asp Asp Met Trp Gly Lys Thr Glu
        210                 215                 220

Gly Ile Pro Thr Ala Val Gly Gln Arg Asn Asp Pro Met Leu Asn Ile
225                 230                 235                 240

Pro Thr Leu Val Ala Asn Asn Thr Arg Ile Trp Val Tyr Cys Gly Asn
                245                 250                 255

Gly Gln Pro Thr Glu Leu Gly Gly Asp Leu Pro Ala Thr Phe Leu
                260                 265                 270

Glu Gly Leu Thr Ile Arg Thr Asn Glu Thr Phe Arg Asp Asn Tyr Ile
        275                 280                 285

Ala Ala Gly Gly His Asn Gly Val Phe Asn Phe Pro Ala Asn Gly Thr
        290                 295                 300

His Asn Trp Ala Tyr Trp Gly Arg Glu Leu Gln Ala Met Lys Pro Asp
305                 310                 315                 320

Leu Gln Ala His Leu Leu
                325

(2) INFORMATION FOR SEQ ID NO:44:

(i) SEQUENCE CHARACTERISTICS:
        (A) LENGTH: 161 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:44:

Ser Gly Trp Asp Ile Asn Thr Ala Ala Phe Glu Trp Tyr Val Asp Ser
 1                   5                  10                  15

Gly Leu Ala Val Ile Met Pro Val Gly Gly Gln Ser Ser Phe Tyr Ser
                 20                  25                  30

Asp Trp Tyr Ser Pro Ala Cys Gly Lys Ala Gly Cys Gln Thr Tyr Lys
         35                  40                  45
```

-continued

```
Trp Glu Thr Phe Leu Thr Gln Glu Leu Pro Ala Tyr Leu Ala Ala Asn
 50                  55                  60

Lys Gly Val Asp Pro Asn Arg Asn Ala Ala Val Gly Leu Ser Met Ala
 65                  70                  75                  80

Gly Ser Ala Ala Leu Thr Leu Ala Ile Tyr His Pro Gln Gln Phe Gln
                 85                  90                  95

Tyr Ala Gly Ser Leu Ser Gly Tyr Leu Asn Pro Ser Glu Gly Trp Trp
            100                 105                 110

Pro Met Leu Ile Asn Ile Ser Met Gly Asp Ala Gly Gly Tyr Lys Ala
            115                 120                 125

Asn Asp Met Trp Gly Pro Pro Lys Asp Pro Ser Ser Ala Trp Lys Arg
            130                 135                 140

Asn Asp Pro Met Val Asn Ile Gly Lys Leu Val Ala Asn Asn Thr Pro
145                 150                 155                 160

Leu
```

(2) INFORMATION FOR SEQ ID NO:45:

(i) SEQUENCE CHARACTERISTICS:
       (A) LENGTH: 334 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:45:

```
Met Lys Phe Thr Glu Lys Trp Arg Gly Ser Ala Lys Ala Ala Met His
  1               5                  10                  15

Arg Val Gly Val Ala Asp Met Ala Ala Val Ala Leu Pro Gly Leu Ile
                 20                  25                  30

Gly Phe Ala Gly Gly Ser Ala Thr Ala Gly Ala Phe Ser Arg Pro Gly
             35                  40                  45

Leu Pro Val Glu Tyr Leu Asp Val Phe Ser Pro Ser Met Gly Arg Asp
 50                  55                  60

Ile Arg Val Gln Phe Gln Gly Gly Thr His Ala Val Tyr Leu Leu
 65                  70                  75                  80

Asp Gly Leu Arg Ala Gln Asp Asp Tyr Asn Gly Trp Asp Ile Asn Thr
                 85                  90                  95

Pro Ala Phe Glu Trp Phe Tyr Glu Ser Gly Leu Ser Thr Ile Met Pro
            100                 105                 110

Val Gly Gly Gln Ser Ser Phe Tyr Ser Asp Trp Tyr Gln Pro Ser Arg
            115                 120                 125

Gly Asn Gly Gln Asn Tyr Thr Tyr Lys Trp Glu Thr Phe Leu Thr Gln
            130                 135                 140

Glu Leu Pro Thr Trp Leu Glu Ala Asn Arg Gly Val Ser Arg Thr Gly
145                 150                 155                 160

Asn Ala Phe Val Gly Leu Ser Met Ala Gly Ser Ala Ala Leu Thr Tyr
                165                 170                 175

Ala Ile His His Pro Gln Gln Phe Ile Tyr Ala Ser Ser Leu Ser Gly
                180                 185                 190

Phe Leu Asn Pro Ser Glu Gly Trp Trp Pro Met Leu Ile Gly Leu Ala
            195                 200                 205

Met Asn Asp Ala Gly Gly Phe Asn Ala Glu Ser Met Trp Gly Pro Ser
            210                 215                 220

Ser Asp Pro Ala Trp Lys Arg Asn Asp Pro Met Val Asn Ile Asn Gln
225                 230                 235                 240
```

```
Leu Val Ala Asn Asn Thr Arg Ile Trp Ile Tyr Cys Gly Thr Gly Thr
                245                 250                 255

Pro Ser Glu Leu Asp Thr Gly Thr Pro Gly Gln Asn Leu Met Ala Ala
            260                 265                 270

Gln Phe Leu Glu Gly Phe Thr Leu Arg Thr Asn Ile Ala Phe Arg Asp
        275                 280                 285

Asn Tyr Ile Ala Ala Gly Gly Thr Asn Gly Val Phe Asn Phe Pro Ala
        290                 295                 300

Ser Gly Thr His Ser Trp Gly Tyr Trp Gly Gln Gln Leu Gln Gln Met
305                 310                 315                 320

Lys Pro Asp Ile Gln Arg Val Leu Gly Ala Gln Ala Thr Ala
                325                 330
```

(2) INFORMATION FOR SEQ ID NO:46:

(i) SEQUENCE CHARACTERISTICS:
        (A) LENGTH: 795 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:46:

```
CTGCCGCGGG TTTGCCATCT CTTGGGTCCT GGGTCGGGAG GCCATGTTCT GGGTAACGAT    60

CCGGTACCGT CCGGCGATGT GACCAACATG CGAACAGCGA CAACGAAGCT AGGAGCGGCG   120

CTCGGCGCAG CAGCATTGGT GGCCGCCACG GGGATGGTCA GCGCGGCGAC GGCGAACGCC   180

CAGGAAGGGC ACCAGGTCCG TTACACGCTC ACCTCGGCCG GCGCTTACGA GTTCGACCTG   240

TTCTATCTGA CGACGCAGCC GCCGAGCATG CAGGCGTTCA ACGCCGACGC GTATGCGTTC   300

GCCAAGCGGG AGAAGGTCAG CCTCGCCCCG GGTGTGCCGT GGGTCTTCGA AACCACGATG   360

GCCGACCCGA ACTGGGCGAT CCTTCAGGTC AGCAGCACCA CCCGCGGTGG GCAGGCCGCC   420

CCGAACGCGC ACTGCGACAT CGCCGTCGAT GGCCAGGAGG TGCTCAGCCA GCACGACGAC   480

CCCTACAACG TGCGGTGCCA GCTCGGTCAG TGGTGAGTCA CCTCGCCGAG AGTCCGGCCA   540

GCGCCGGCGG CAGCGGCTCG CGGTGCAGCA CCCCGAGGCG CTGGGTCGCG CGGGTCAGCG   600

CGACGTAAAG ATCGCTGGCC CCGCGCGGCC CCTCGGCGAG GATCTGCTCC GGGTAGACCA   660

CCAGCACGGC GTCTAACTCC AGACCCTTGG TCTGCGTGGG TGCCACCGCG CCCGGGACAC   720

CGGGCGGGCC GATCACCACG CTGGTGCCCT CCCGGTCCGC CTCCGCACGC ACGAAATCGT   780

CGATGGCACC GGCGA                                                    795
```

(2) INFORMATION FOR SEQ ID NO:47:

(i) SEQUENCE CHARACTERISTICS:
        (A) LENGTH: 142 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:47:

```
Met Arg Thr Ala Thr Thr Lys Leu Gly Ala Ala Leu Gly Ala Ala Ala
1               5                   10                  15

Leu Val Ala Ala Thr Gly Met Val Ser Ala Ala Thr Ala Asn Ala Gln
            20                  25                  30
```

```
Glu Gly His Gln Val Arg Tyr Thr Leu Thr Ser Ala Gly Ala Tyr Glu
     35                  40                  45

Phe Asp Leu Phe Tyr Leu Thr Thr Gln Pro Pro Ser Met Gln Ala Phe
 50                  55                  60

Asn Ala Asp Ala Tyr Ala Phe Ala Lys Arg Glu Lys Val Ser Leu Ala
 65                  70                  75                  80

Pro Gly Val Pro Trp Val Phe Glu Thr Thr Met Ala Asp Pro Asn Trp
                 85                  90                  95

Ala Ile Leu Gln Val Ser Ser Thr Thr Arg Gly Gly Gln Ala Ala Pro
                100                 105                 110

Asn Ala His Cys Asp Ile Ala Val Asp Gly Gln Glu Val Leu Ser Gln
                115                 120                 125

His Asp Asp Pro Tyr Asn Val Arg Cys Gln Leu Gly Gln Trp
130                 135                 140
```

(2) INFORMATION FOR SEQ ID NO:48:

(i) SEQUENCE CHARACTERISTICS:
        (A) LENGTH: 300 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:48:

```
GCCAGTGCGC CAACGGTTTT CATCGATGCC GCACACAACC CCGGTGGGCC CTGCGCTTGC    60

CGAAGGCTGC GCGACGAGTT CGACTTCCGG TATCTCGTCG GCGTCGTCTC GGTGATGGGG   120

GACAAGGACG TGGACGGGAT CCGCCAGGAC CCGGGCGTGC CGGACGGGCG CGGTCTCGCA   180

CTGTTCGTCT CGGGCGACAA CCTTCGAAAG GGTGCGGCGC TCAACACGAT CCAGATCGCC   240

GAGCTGCTGG CCGCCCAGTT GTAAGTGTTC CGCCGAAATT GCATTCCACG CCGATAATCG   300
```

(2) INFORMATION FOR SEQ ID NO:49:

(i) SEQUENCE CHARACTERISTICS:
        (A) LENGTH: 563 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:49:

```
GGATCCTCGG CCGGCTCAAG AGTCCGCGCC GAGGTGGATG TGACGCTGGA CGGCTACGAG    60

TTCAGTCGGG CCTGCGAGGC GCTGTACCAC TTCGCCTGGG ACAGTTCTG CGACTGGTAT   120

GTCGAGCTTG CCAAAGTGCA ACTGGGTGAA GGTTTCTCGC ACACCACGGC CGTGTTGGCC   180

ACCGTGCTCG ATGTGCTGCT CAAGCTTCTG CACCCGGTCA TGCCGTTCGT CACCGAGGTG   240

CTGTGGAAGG CCCTGACCGG GCGGGCCGGC GCGAGCGAAC GTCTGGGAAA TGTGGAGTCA   300

CTGGTCGTCG CGGACTGGCC CACGCCCACC GGATACGCGC TGGATCAGGC TGCCGCACAA   360

CGGATCGCCG ACACCCAGAA GTTGATCACC GAGGTGCGCC GGTTCCGCAG CGATCAGGGT   420

CTGGCCGACC GCCAGCGGGT GCCTGCCCGG TTGTCCGGCA TCGACACCGC GGGTCTGGAC   480

GCCCATGTCC CGGCGGTGCG CGCGCTGGCC TGGCTTGACC GAGGGTGATG AGGGCTTCAC   540

CGCGTCCGAA TCGGTCGAGG TGC                                           563
```

(2) INFORMATION FOR SEQ ID NO:50:

```
    (i) SEQUENCE CHARACTERISTICS:
        (A) LENGTH: 434 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:50:

GGGCCGGGCC CGAGGATGAG CAAGTTCGAA GTCGTCACCG GGATGGCGTT CGCGGCTTTC        60

GCCGACGCGC CCATCGACGT CGCCGTCGTC GAGGTCGGGC TCGGTGGTCG CTGGGACGCG       120

ACGAACGTGG TGAACGCACC GGTCGCGGTC ATCACCCCGA TCGGGGTGGA CCACACCGAC       180

TACCTCGGTG ACACGATCGC CGAGATCGCC GGGGAGAAGG CCGGAAATCA TCACCCGCCA       240

GCCGACGACC TGGTGCCGAC CGACACCGTC GCCGTGCTGG CGCGGCAGGT TCCCGAGGCC       300

ATGGAGGTGC TGCTGGCCCA GGCGGTGCGC TCGGATGCGG CTGTAGCGCG CGAGGATTCG       360

GAGTGCGCGG TGCTGGGCCG TCAGGTCGCC ATCGGCGGCA GCTGCTCCGG TTGCAGGGGC       420

TCGGTGGCGT CTAC                                                        434

(2) INFORMATION FOR SEQ ID NO:51:

(i) SEQUENCE CHARACTERISTICS:
        (A) LENGTH: 438 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:51:

GGATCCCACT CCCGCGCCGG CGGCGGCCAG CTGGTACGGC CATTCCAGCG TGCTGATCGA        60

GGTCGACGGC TACCGCGTGC TGGCCGACCC GGTGTGGAGC AACAGATGTT CGCCCTCACG       120

GGCGGTCGGA CCGCAGCGCA TGCACGACGT CCCGGTGCCG CTGGAGGCGC TTCCCGCCGT       180

GGACGCGGTG GTGATCGCCA ACGACCACTA CGACCACCTC GACATCGACA CCATCGTCGC       240

GTTGGCGCAC ACCCAGCGGG CCCCGTTCGT GGTGCCGTTG GGCATCGGCG CACACCTGCG       300

CAAGTGGGGC GTCCCCGAGG CGCGGATCGT CGAGTTGGAC TGGCACGAAG CCCACCGCAT       360

CGACGACCTG ACGCTGGTCT GCACCCCCGC CCGGCACTTC TCCGGCCGGT TGTTCTCCCG       420

CGACTCGACG CTGTGGGC                                                    438

(2) INFORMATION FOR SEQ ID NO:52:

(i) SEQUENCE CHARACTERISTICS:
        (A) LENGTH: 87 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:52:

Ala Ser Ala Pro Thr Val Phe Ile Asp Ala Ala His Asn Pro Gly Gly
 1               5                  10                  15

Pro Cys Ala Cys Arg Arg Leu Arg Asp Glu Phe Asp Phe Arg Tyr Leu
                20                  25                  30

Val Gly Val Val Ser Val Met Gly Asp Lys Asp Val Asp Gly Ile Arg
            35                  40                  45

Gln Asp Pro Gly Val Pro Asp Gly Arg Gly Leu Ala Leu Phe Val Ser
        50                  55                  60
```

```
Gly Asp Asn Leu Arg Lys Gly Ala Ala Leu Asn Thr Ile Gln Ile Ala
 65                  70                  75                  80

Glu Leu Leu Ala Ala Gln Leu
                 85
```

(2) INFORMATION FOR SEQ ID NO:53:

(i) SEQUENCE CHARACTERISTICS:
        (A) LENGTH: 175 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:53:

```
Gly Ser Ser Ala Gly Ser Arg Val Arg Ala Glu Val Asp Val Thr Leu
 1               5                  10                  15

Asp Gly Tyr Glu Phe Ser Arg Ala Cys Glu Ala Leu Tyr His Phe Ala
             20                  25                  30

Trp Asp Glu Phe Cys Asp Trp Tyr Val Glu Leu Ala Lys Val Gln Leu
         35                  40                  45

Gly Glu Gly Phe Ser His Thr Thr Ala Val Leu Ala Thr Val Leu Asp
     50                  55                  60

Val Leu Leu Lys Leu Leu His Pro Val Met Pro Phe Val Thr Glu Val
 65                  70                  75                  80

Leu Trp Lys Ala Leu Thr Gly Arg Ala Gly Ala Ser Glu Arg Leu Gly
                 85                  90                  95

Asn Val Glu Ser Leu Val Val Ala Asp Trp Pro Thr Pro Thr Gly Tyr
             100                 105                 110

Ala Leu Asp Gln Ala Ala Ala Gln Arg Ile Ala Asp Thr Gln Lys Leu
         115                 120                 125

Ile Thr Glu Val Arg Arg Phe Arg Ser Asp Gln Gly Leu Ala Asp Arg
     130                 135                 140

Gln Arg Val Pro Ala Arg Leu Ser Gly Ile Asp Thr Ala Gly Leu Asp
145                 150                 155                 160

Ala His Val Pro Ala Val Arg Ala Leu Ala Trp Leu Asp Arg Gly
                 165                 170                 175
```

(2) INFORMATION FOR SEQ ID NO:54:

(i) SEQUENCE CHARACTERISTICS:
        (A) LENGTH: 144 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:54:

```
Gly Pro Gly Pro Arg Asn Ser Lys Phe Glu Val Val Thr Gly Met Ala
 1               5                  10                  15

Phe Ala Ala Phe Ala Asp Ala Pro Ile Asp Val Ala Val Val Glu Val
             20                  25                  30

Gly Leu Gly Gly Arg Trp Asp Ala Thr Asn Val Val Asn Ala Pro Val
         35                  40                  45

Ala Val Ile Thr Pro Ile Gly Val Asp His Thr Asp Tyr Leu Gly Asp
     50                  55                  60

Thr Ile Ala Glu Ile Ala Gly Glu Lys Ala Gly Asn His His Pro Pro
 65                  70                  75                  80
```

```
Ala Asp Asp Leu Val Pro Thr Asp Thr Val Ala Val Leu Ala Arg Gln
            85                  90                  95

Val Pro Glu Ala Asn Glu Val Leu Leu Ala Gln Ala Val Arg Ser Asp
        100                 105                 110

Ala Ala Val Ala Arg Glu Asp Ser Glu Cys Ala Val Leu Gly Arg Gln
            115                 120                 125

Val Ala Ile Gly Gly Ser Cys Ser Gly Cys Arg Gly Ser Val Ala Ser
130                 135                 140
```

(2) INFORMATION FOR SEQ ID NO:55:

(i) SEQUENCE CHARACTERISTICS:
        (A) LENGTH: 145 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:55:

```
Asp Pro Thr Pro Ala Pro Ala Ala Ala Ser Trp Tyr Gly His Ser Ser
1               5                   10                  15

Val Leu Ile Glu Val Asp Gly Tyr Arg Val Leu Ala Asp Pro Val Trp
            20                  25                  30

Ser Asn Arg Cys Ser Pro Ser Arg Ala Val Gly Pro Gln Arg Met His
        35                  40                  45

Asp Val Pro Val Pro Leu Glu Ala Leu Pro Ala Val Asp Ala Val Val
    50                  55                  60

Ile Ser Asn Asp His Tyr Asp His Leu Asp Ile Asp Thr Ile Val Ala
65                  70                  75                  80

Leu Ala His Thr Gln Arg Ala Pro Phe Val Val Pro Leu Gly Ile Gly
            85                  90                  95

Ala His Leu Arg Lys Trp Gly Val Pro Glu Ala Arg Ile Val Glu Leu
        100                 105                 110

Asp Trp His Glu Ala His Arg Ile Asp Asp Leu Thr Leu Val Cys Thr
    115                 120                 125

Pro Ala Arg His Phe Ser Gly Arg Leu Phe Ser Arg Asp Ser Thr Leu
    130                 135                 140

Trp
145
```

(2) INFORMATION FOR SEQ ID NO:56:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 1...1
        (D) OTHER INFORMATION: Residue can be either Gly, Ile, Leu or
            Val
        (A) NAME/KEY: Other
        (B) LOCATION: 2...2
        (D) OTHER INFORMATION: Residue can be either Ile, Leu, Gly or
            Ala (xi) SEQUENCE DESCRIPTION: SEQ ID NO:56:

```
Xaa Xaa Ala Pro Xaa Gly Asp Ala Xaa Arg
1               5                   10
```

(2) INFORMATION FOR SEQ ID NO:57:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 7...7
        (D) OTHER INFORMATION: Residue can be either Ile or Leu (xi) SEQUENCE DESCRIPTION: SEQ ID NO:57:

Pro Glu Ala Glu Ala Asn Xaa Arg
1               5

(2) INFORMATION FOR SEQ ID NO:58:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 4...4
        (D) OTHER INFORMATION: Residue can be either Gln or Gly
        (A) NAME/KEY: Other
        (B) LOCATION: 5...5
        (D) OTHER INFORMATION: Residue cn be either Gly or Gln (xi) SEQUENCE DESCRIPTION: SEQ ID NO:58:

Thr Ala Asn Xaa Xaa Glu Tyr Tyr Asp Asn Arg
1               5                   10

(2) INFORMATION FOR SEQ ID NO:59:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:59:

Asn Ser Pro Arg Ala Glu Ala Glu Ala Asn Leu Arg Gly Tyr Phe Thr
1               5                   10                 15

Ala Asn Pro Ala Glu Tyr Tyr Asp Leu Arg Gly Ile Leu Ala Pro Ile
             20                 25                 30

Gly Asp (2) INFORMATION FOR SEQ ID NO:60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:60:

```
CCGGTGGGCC CGGGCTGCGC                                              20
```

(2) INFORMATION FOR SEQ ID NO:61:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:61:

```
TGGCCGGCCA CCACGTGGTA                                              20
```

(2) INFORMATION FOR SEQ ID NO:62:

(i) SEQUENCE CHARACTERISTICS:
        (A) LENGTH: 313 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:62:

```
GCCGGTGGGC CCGGGCTGCG CGGAATACGC GGCAGCCAAT CCCACTGGGC CGGCCTCGGT    60
GCAGGGAATG TCGCAGGACC CGGTCGCGGT GGCGGCCTCG AACAATCCGG AGTTGACAAC   120
GCTGTACGGC TGCACTGTCG GGCCAGCTCA ATCCGCAAGT AAACCTGGTG GACACCCTCA   180
ACAGCGGTCA GTACACGGTG TTCGCACCGA CCAACGCGGC ATTTAGCAAG CTGCCGGCAT   240
CCACGATCGA CGAGCTCAAG ACCAATTCGT CACTGCTGAC CAGCATCCTG ACCTACCACG   300
TGGTGGCCGG CCA                                                      313
```

(2) INFORMATION FOR SEQ ID NO:63:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:63:

```
Glu Pro Ala Gly Pro Leu Pro Xaa Tyr Asn Glu Arg Leu His Thr Leu
 1               5                  10                  15
Xaa Gln
```

(2) INFORMATION FOR SEQ ID NO:64:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:64:

```
Gly Leu Asp Asn Glu Leu Ser Leu Val Asp Gly Gln Gly Arg Thr Leu
 1               5                  10                  15
Thr Val Gln Gln Xaa Asp Thr Phe Leu
                20                  25
```

(2) INFORMATION FOR SEQ ID NO:65:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:65:

```
Asp Pro Xaa Pro Asp Ile Glu Val Glu Phe Ala Arg Gly Thr Gly Ala
 1               5                  10                  15
Glu Pro Gly Leu Xaa Xaa Val Xaa Asp Ala
            20                  25
```

(2) INFORMATION FOR SEQ ID NO:66:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:66:

ACCGCCCTCG AGTTCTCCCG GCCAGGTCTG CC                    32

(2) INFORMATION FOR SEQ ID NO:67:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:67:

AAGCACGAGC TCAGTCTCTT CCACGCGGAC GT                    32

(2) INFORMATION FOR SEQ ID NO:68:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:68:

CATGGATCCA TTCTCCCGGC CCGGTCTTCC                      30

(2) INFORMATION FOR SEQ ID NO:69:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:69:

TTTGAATTCT AGGCGGTGGC CTGAGC                        26

(2) INFORMATION FOR SEQ ID NO:70:

(i) SEQUENCE CHARACTERISTICS:
    (A) LENGTH: 161 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:70:

Ser Gly Trp Asp Ile Asn Thr Ala Ala Phe Glu Trp Tyr Val Asp Ser
 1               5                  10                  15

Gly Leu Ala Val Ile Met Pro Val Gly Gly Gln Ser Ser Phe Tyr Ser
             20                  25                  30

Asp Trp Tyr Ser Pro Ala Cys Gly Lys Ala Gly Cys Gln Thr Tyr Lys
         35                  40                  45

Trp Glu Thr Phe Leu Thr Gln Glu Leu Pro Ala Tyr Leu Ala Ala Asn
 50                  55                  60

Lys Gly Val Asp Pro Asn Arg Asn Ala Ala Val Gly Leu Ser Met Ala
 65                  70                  75                  80

Gly Ser Ala Ala Leu Thr Leu Ala Ile Tyr His Pro Gln Gln Phe Gln
             85                  90                  95

Tyr Ala Gly Ser Leu Ser Gly Tyr Leu Asn Pro Ser Glu Gly Trp Trp
            100                 105                 110

Pro Met Leu Ile Asn Ile Ser Met Gly Asp Ala Gly Gly Tyr Lys Ala
            115                 120                 125

Asn Asp Met Trp Gly Arg Thr Glu Asp Pro Ser Ser Ala Trp Lys Arg
            130                 135                 140

Asn Asp Pro Met Val Asn Ile Gly Lys Leu Val Ala Asn Asn Thr Pro
145                 150                 155                 160

Leu (2) INFORMATION FOR SEQ ID NO:71:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:71:

GAGAGACTCG AGAACGCCCA GGAAGGGCAC CAG                                33

(2) INFORMATION FOR SEQ ID NO:72:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:72:

GAGAGACTCG AGTGACTCAC CACTGACCGA GC                                 32

(2) INFORMATION FOR SEQ ID NO:73:

(i) SEQUENCE CHARACTERISTICS:
        (A) LENGTH: 20 base pairs
        (B) TYPE: nucleic acid
        (C) STRANDEDNESS: single (D) TOPOLOGY: linear (ii) MOLECULE TYPE: Other (xi) SEQUENCE DESCRIPTION: SEQ ID NO:73:

GGNGCNGCNC ARGCNGARCC                                        20

(2) INFORMATION FOR SEQ ID NO:74:

(i) SEQUENCE CHARACTERISTICS:
    (A) LENGTH: 825 base pairs
    (B) TYPE: nucleic acid
    (C) STRANDEDNESS: single
    (D) TOPOLOGY: linear (ii) MOLECULE TYPE: Genomic DNA (xi) SEQUENCE DESCRIPTION: SEQ ID NO:74:

TTGGATCCCA CTCCCGCGCC GGCGGCGGCC AGCTGGTACG GCCATTCCAG CGTGCTGATC    60

GAGGTCGACG GCTACCGCGT GCTGGCCGAC CCGGTGTGGA GCAACAGATG TTCGCCCTCA   120

CGGGCGGTCG GACCGCAGCG CATGCACGAC GTCCCGGTGC CGCTGGAGGC GCTTCCCGCC   180

GTGGACGCGG TGGTGATCAG CCACGACCAC TACGACCACC TCGACATCGA CACCATCGTC   240

GCGTTGGCGC ACACCCAGCG GGCCCCGTTC GTGGTGCCGT TGGGCATCGG CGCACACCTG   300

CGCAAGTGGG GCGTCCCCGA GGCGCGGATC GTCGAGTTGG ACTGGCACGA AGCCCACCGC   360

ATAGACGACC TGACGCTGGT CTGCACCCCC GCCCGGCACT TCTCCGGACG GTTGTTCTCC   420

CGCGACTCGA CGCTGTGGGC GTCGTGGGTG GTCACCGGCT CGTCGCACAA GGCGTTCTTC   480

GGTGGCGACA CCGGATACAC GAAGAGCTTC GCCGAGATCG GCGACGAGTA CGGTCCGTTC   540

GATCTGACCC TGCTGCCGAT CGGGGCCTAC CATCCCGCGT TCGCCGACAT CCACATGAAC   600

CCCGAGGAGG CGGTGCGCGC CCATCTGGAC CTGACCGAGG TGGACAACAG CCTGATGGTG   660

CCCATCCACT GGGCGACATT CCGCCTCGCC CCGCATCCGT GGTCCGAGCC CGCCGAACGC   720

CTGCTGACCG CTGCCGACGC CGAGCGGGTA CGCCTGACCG TGCCGATTCC CGGTCAGCGG   780

GTGGACCCGG AGTCGACGTT CGACCCGTGG TGGCGGTTCT GAACC                   825

(2) INFORMATION FOR SEQ ID NO:75:

(i) SEQUENCE CHARACTERISTICS:
    (A) LENGTH: 273 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:75:

Leu Asp Pro Thr Pro Ala Pro Ala Ala Ser Trp Tyr Gly His Ser
 1               5                  10                  15

Ser Val Leu Ile Glu Val Asp Gly Tyr Arg Val Leu Ala Asp Pro Val
                20                  25                  30

Trp Ser Asn Arg Cys Ser Pro Ser Arg Ala Val Gly Pro Gln Arg Met
            35                  40                  45

His Asp Val Pro Val Pro Leu Glu Ala Leu Pro Ala Val Asp Ala Val
        50                  55                  60

Val Ile Ser His Asp His Tyr Asp His Leu Asp Ile Asp Thr Ile Val
65                  70                  75                  80

Ala Leu Ala His Thr Gln Arg Ala Pro Phe Val Val Pro Leu Gly Ile
                85                  90                  95

```
Gly Ala His Leu Arg Lys Trp Gly Val Pro Glu Ala Arg Ile Val Glu
            100                 105                 110

Leu Asp Trp His Glu Ala His Arg Ile Asp Asp Leu Thr Leu Val Cys
            115                 120                 125

Thr Pro Ala Arg His Phe Ser Gly Arg Leu Phe Ser Arg Asp Ser Thr
            130                 135                 140

Leu Trp Ala Ser Trp Val Val Thr Gly Ser Ser His Lys Ala Phe Phe
145                 150                 155                 160

Gly Gly Asp Thr Gly Tyr Thr Lys Ser Phe Ala Glu Ile Gly Asp Glu
            165                 170                 175

Tyr Gly Pro Phe Asp Leu Thr Leu Leu Pro Ile Gly Ala Tyr His Pro
            180                 185                 190

Ala Phe Ala Asp Ile His Met Asn Pro Glu Glu Ala Val Arg Ala His
            195                 200                 205

Leu Asp Leu Thr Glu Val Asp Asn Ser Leu Met Val Pro Ile His Trp
            210                 215                 220

Ala Thr Phe Arg Leu Ala Pro His Pro Trp Ser Glu Pro Ala Glu Arg
225                 230                 235                 240

Leu Leu Thr Ala Ala Asp Ala Glu Arg Val Arg Leu Thr Val Pro Ile
            245                 250                 255

Pro Gly Gln Arg Val Asp Pro Glu Ser Thr Phe Asp Pro Trp Trp Arg
            260                 265                 270

Phe (2) INFORMATION FOR SEQ ID NO:76:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:76:

Ala Lys Thr Ile Ala Tyr Asp Glu Glu Ala
1               5                   10

(2) INFORMATION FOR SEQ ID NO:77:

(i) SEQUENCE CHARACTERISTICS:
        (A) LENGTH: 337 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:77:

GATCCCTACA TCCTGCTGGT CAGCTCCAAG GTGTCGACCG TCAAGGATCT GCTCCCGCTG     60

CTGGAGAAGG TCATCCAGGC CGGCAAGCCG CTGCTGATCA TCGCCGAGGA CGTCGAGGGC    120

GAGGCCCTGT CCACGCTGGT GGTCAACAAG ATCCGCGGCA CCTTCAAGTC CGTCGCCGTC    180

AAGGCTCCGG GCTTCGGTGA CCGCCGCAAG GCGATGCTGC AGGACATGGC CATCCTCACC    240

GGTGGTCAGG TCGTCAGCGA AAGAGTCGGG CTGTCCCTGG AGACCGCCGA CGTCTCGCTG    300

CTGGGCCAGG CCCGCAAGGT CGTCGTCACC AAGGACA                             337

(2) INFORMATION FOR SEQ ID NO:78:

(i) SEQUENCE CHARACTERISTICS:
```

(A) LENGTH: 112 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:78:

Asp Pro Tyr Ile Leu Leu Val Ser Ser Lys Val Ser Thr Val Lys Asp
1               5                   10                  15

Leu Leu Pro Leu Leu Glu Lys Val Ile Gln Ala Gly Lys Pro Leu Leu
            20                  25                  30

Ile Ile Ala Glu Asp Val Glu Gly Glu Ala Leu Ser Thr Leu Val Val
        35                  40                  45

Asn Lys Ile Arg Gly Thr Phe Lys Ser Val Ala Val Lys Ala Pro Gly
    50                  55                  60

Phe Gly Asp Arg Arg Lys Ala Met Leu Gln Asp Met Ala Ile Leu Thr
65                  70                  75                  80

Gly Gly Gln Val Val Ser Glu Arg Val Gly Leu Ser Leu Glu Thr Ala
                85                  90                  95

Asp Val Ser Leu Leu Gly Gln Ala Arg Lys Val Val Thr Lys Asp
            100                 105                 110

(2) INFORMATION FOR SEQ ID NO:79:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:79:

CCGTACGAGA AGATCGGCGC TGAGCTGGTC AAAGAGGTCG CCAAGAAGAC CGACGACGTC        60

GCGGGCGACG GCACCACCAC CGCCACCGTG CTCGCTCAGG CTCTGGTTCG CGAAGGCCTG       120

CGCAACGTCG CAGCCGGCGC CAACCCGCTC GGCCTCAAGC GTGGCATCGA GAAGGCTGTC       180

GAGGCTGTCA CCCAGTCGCT GCTGAAGTCG CCAAGGAGG TCGAGACCAA GGAGCAGATT        240

TCTGCCACCG CGGCGATCTC CGCCGGCGAC ACCCAGATCG GCGAGCTCAT CGCCGAGGCC       300

ATGGACAAGG TCGGCAACGA GGGTGTCATC ACCGTCGAGG AGTCGAACAC CTTCGGCCTG       360

(2) INFORMATION FOR SEQ ID NO:80:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:80:

Pro Tyr Glu Lys Ile Gly Ala Glu Leu Val Lys Glu Val Ala Lys Lys
1               5                   10                  15

Thr Asp Asp Val Ala Gly Asp Gly Thr Thr Thr Ala Thr Val Leu Ala
            20                  25                  30

Gln Ala Leu Val Arg Glu Gly Leu Arg Asn Val Ala Ala Gly Ala Asn
        35                  40                  45

Pro Leu Gly Leu Lys Arg Gly Ile Glu Lys Ala Val Glu Ala Val Thr
    50                  55                  60

```
Gln Ser Leu Leu Lys Ser Ala Lys Glu Val Glu Thr Lys Glu Gln Ile
 65                  70                  75                  80

Ser Ala Thr Ala Ala Ile Ser Ala Gly Asp Thr Gln Ile Gly Glu Leu
                 85                  90                  95

Ile Ala Glu Ala Met Asp Lys Val Gly Asn Glu Gly Val Ile Thr Val
            100                 105                 110

Glu Glu Ser Asn Thr Phe Gly Leu
            115                 120
```

(2) INFORMATION FOR SEQ ID NO:81:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:81:

ACTGACGCTG AGGAGCGAAA GCGTGGGGAG CGAACAGGAT TAG                43

(2) INFORMATION FOR SEQ ID NO:82:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:82:

CGACAAGGAA CTTCGCTACC TTAGGACCGT CATAGTTACG GGC                43

(2) INFORMATION FOR SEQ ID NO:83:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:83:

AAAAAAAAAA AAAAAAAAAA                20

(2) INFORMATION FOR SEQ ID NO:84:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:84:

GGAAGGAAGC GGCCGCTTTT TTTTTTTTTT T                31

(2) INFORMATION FOR SEQ ID NO:85:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:85:

GAGAGAGAGC CCGGGCATGC TSCTSCTSCT S        31

(2) INFORMATION FOR SEQ ID NO:86:

(i) SEQUENCE CHARACTERISTICS:
        (A) LENGTH: 238 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:86:

```
CTCGATGAAC CGCTCGGAGC GCTCGACCTG AAGCTGCGCC ACGTCATGCA GTTCGAGCTC    60
AAGCGCATCC AGCGGGAGGT CGGGATCACG TTCATCTACG TGACCCACGA CCAGGAAGAG   120
GCGCTCACGA TGAGTGACCG CATCGCGGTG ATGAACGCCG GCAACGTCGA ACAGATCGGC   180
AGCCCGACCG AGATCTACGA CCGTCCCGCG ACGGTGTTCG TCGCCAGCTT CATCGAAT    238
```

(2) INFORMATION FOR SEQ ID NO:87:

(i) SEQUENCE CHARACTERISTICS:
        (A) LENGTH: 79 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:87:

```
Leu Asp Glu Pro Leu Gly Ala Leu Asp Leu Lys Leu Arg His Val Met
 1               5                  10                  15

Gln Phe Glu Leu Lys Arg Ile Gln Arg Glu Val Gly Ile Thr Phe Ile
            20                  25                  30

Tyr Val Thr His Asp Gln Glu Glu Ala Leu Thr Met Ser Asp Arg Ile
        35                  40                  45

Ala Val Met Asn Ala Gly Asn Val Glu Gln Ile Gly Ser Pro Thr Glu
    50                  55                  60

Ile Tyr Asp Arg Pro Ala Thr Val Phe Val Ala Ser Phe Ile Glu
65                  70                  75
```

(2) INFORMATION FOR SEQ ID NO:88:

(i) SEQUENCE CHARACTERISTICS:
        (A) LENGTH: 1518 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:88:

```
CACTCGCCAT GGGTGTTACA ATACCCCACC AGTTCCTCGA AGTAAACGAA CAGAACCGTG    60
ACATCCAGCT GAGAAAATAT TCACAGCGAC GAAGCCCGGC CGATGCCTGA TGGGGTCCGG   120
CATCAGTACA GCGCGCTTTC CTGCGCGGAT TCTATTGTCG AGTCCGGGGT GTGACGAAGG   180
AATCCATTGT CGAAATGTAA ATTCGTTGCG GAATCACTTG CATAGGTCCG TCAGATCCGC   240
GAAGGTTTAC CCCACAGCCA CGACGGCTGT CCCCGAGGAG GACCTGCCCT GACCGGCACA   300
CACATCACCG CTGCAGAACC TGCAGAACAG ACGGCGGATT CCGCGGCACC GCCCAAGGGC   360
```

```
GCGCCGGTGA TCGAGATCGA CCATGTCACG AAGCGCTTCG GCGACTACCT GGCCGTCGCG    420

GACGCAGACT TCTCCATCGC GCCCGGGGAG TTCTTCTCCA TGCTCGGCCC GTCCGGGTGT    480

GGGAAGACGA CCACGTTGCG CATGATCGCG GGATTCGAGA CCCCGACTGA AGGGGCGATC    540

CGCCTCGAAG GCGCCGACGT GTCGAGGACC CCACCCAACA AGCGCAACGT CAACACGGTG    600

TTCCAGCACT ACGCGCTGTT CCCGCACATG ACGGTCTGGG ACAACGTCGC GTACGGCCCG    660

CGCAGCAAGA AACTCGGCAA AGGCGAGGTC CGCAAGCGCG TCGACGAGCT GCTGGAGATC    720

GTCCGGCTGA CCGAATTTGC CGAGCGCAGG CCCGCCCAGC TGTCCGGCGG CAGCAGCAG    780

CGGGTGGCGT TGGCCCGGGC ACTGGTGAAC TACCCCAGCG CGCTGCTGCT CGATGAACCG    840

CTCGGAGCGC TCGACCTGAA GCTGCGCCAC GTCATGCAGT TCGAGCTCAA GCGCATCCAG    900

CGGGAGGTCG GGATCACGTT CATCTACGTG ACCCACGACC AGGAAGAGGC GCTCACGATG    960

AGTGACCGCA TCGCGGTGAT GAACGCCGGC AACGTCGAAC AGATCGGCAG CCCGACCGAG   1020

ATCTACGACC GTCCCGCGAC GGTGTTCGTC GCCAGCTTCA TCGGACAGGC CAACCTCTGG   1080

GCGGGCCGGT GCACCGGCCG CTCCAACCGC GATTACGTCG AGATCGACGT TCTCGGCTCG   1140

ACGCTGAAGG CACGCCCGGG CGAGACCACG ATCGAGCCCG GCGGGCACGC CACCCTGATG   1200

GTGCGTCCGG AACGCATCCG GGTCACCCCG GGCTCCCAGG ACGCGCCGAC CGGTGACGTC   1260

GCCTGCGTGC GTGCCACCGT CACCGACCTG ACCTTCCAAG GTCCGGTGGT GCGGCTCTCG   1320

CTGGCCGCTC CGGACGACTC GACCGTGATC GCCCACGTCG GCCCCGAGCA GGATCTGCCG   1380

CTGCTGCGCC CCGGCGACGA CGTGTACGTC AGCTGGGCAC CGGAAGCCTC CCTGGTGCTT   1440

CCCGGCGACG ACATCCCCAC CACCGAGGAC CTCGAAGAGA TGCTCGACGA CTCCTGAGTC   1500

ACGCTTCCCG ATTGCCGA                                                 1518
```

(2) INFORMATION FOR SEQ ID NO:89:

(i) SEQUENCE CHARACTERISTICS:
        (A) LENGTH: 376 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:89:

```
Val Ile Glu Ile Asp His Val Thr Lys Arg Phe Gly Asp Tyr Leu Ala
 1               5                  10                  15

Val Ala Asp Ala Asp Phe Ser Ile Ala Pro Gly Glu Phe Phe Ser Met
                20                  25                  30

Leu Gly Pro Ser Gly Cys Gly Lys Thr Thr Thr Leu Arg Met Ile Ala
            35                  40                  45

Gly Phe Glu Thr Pro Thr Glu Gly Ala Ile Arg Leu Glu Gly Ala Asp
        50                  55                  60

Val Ser Arg Thr Pro Pro Asn Lys Arg Asn Val Asn Thr Val Phe Gln
65                  70                  75                  80

His Tyr Ala Leu Phe Pro His Met Thr Val Trp Asp Asn Val Ala Tyr
                85                  90                  95

Gly Pro Arg Ser Lys Lys Leu Gly Lys Gly Glu Val Arg Lys Arg Val
            100                 105                 110

Asp Glu Leu Leu Glu Ile Val Arg Leu Thr Glu Phe Ala Glu Arg Arg
        115                 120                 125

Pro Ala Gln Leu Ser Gly Gly Gln Gln Arg Val Ala Leu Ala Arg
    130                 135                 140
```

```
Ala Leu Val Asn Tyr Pro Ser Ala Leu Leu Asp Glu Pro Leu Gly
145                 150                 155                 160

Ala Leu Asp Leu Lys Leu Arg His Val Met Gln Phe Glu Leu Lys Arg
                165                 170                 175

Ile Gln Arg Glu Val Gly Ile Thr Phe Ile Tyr Val Thr His Asp Gln
            180                 185                 190

Glu Glu Ala Leu Thr Met Ser Asp Arg Ile Ala Val Met Asn Ala Gly
            195                 200                 205

Asn Val Glu Gln Ile Gly Ser Pro Thr Glu Ile Tyr Asp Arg Pro Ala
        210                 215                 220

Thr Val Phe Val Ala Ser Phe Ile Gly Gln Ala Asn Leu Trp Ala Gly
225                 230                 235                 240

Arg Cys Thr Gly Arg Ser Asn Arg Asp Tyr Val Glu Ile Asp Val Leu
                245                 250                 255

Gly Ser Thr Leu Lys Ala Arg Pro Gly Glu Thr Thr Ile Glu Pro Gly
                260                 265                 270

Gly His Ala Thr Leu Met Val Arg Pro Glu Arg Ile Arg Val Thr Pro
            275                 280                 285

Gly Ser Gln Asp Ala Pro Thr Gly Asp Val Ala Cys Val Arg Ala Thr
        290                 295                 300

Val Thr Asp Leu Thr Phe Gln Gly Pro Val Val Arg Leu Ser Leu Ala
305                 310                 315                 320

Ala Pro Asp Asp Ser Thr Val Ile Ala His Val Gly Pro Glu Gln Asp
                325                 330                 335

Leu Pro Leu Leu Arg Pro Gly Asp Asp Val Tyr Val Ser Trp Ala Pro
                340                 345                 350

Glu Ala Ser Leu Val Leu Pro Gly Asp Ile Pro Thr Thr Glu Asp
            355                 360                 365

Leu Glu Glu Met Leu Asp Asp Ser
            370                 375

(2) INFORMATION FOR SEQ ID NO:90:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:90:

GAGAGACTCG AGGTGATCGA GATCGACCAT GTC                              33

(2) INFORMATION FOR SEQ ID NO:91:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:91:

AGAGACTCGA GCAATCGGGA AGCGTGACTC A                                31

(2) INFORMATION FOR SEQ ID NO:92:

(i) SEQUENCE CHARACTERISTICS:
```

(A) LENGTH: 323 base pairs
(B) TYPE: nucleic acid
(C) STRANDEDNESS: single
(D) TOPOLOGY: linear (ii) MOLECULE TYPE: Genomic DNA (xi) SEQUENCE DESCRIPTION: SEQ ID NO:92:

```
GTCGACTACA AAGAAGACTT CAACGACAAC GAGCAGTGGT TCGCCAAGGT CAAGGAGCCG      60
TTGTCGCGCA AGCAGGACAT AGGCGCCGAC CTGGTGATCC CCACCGAGTT CATGGCCGCG     120
CGCGTCAAGG GCCTGGGATG GCTCAATGAG ATCAGCGAAG CCGGCGTGCC CAATCGCAAG     180
AATCTGCGTC AGGACCTGTT GGACTCGAGC ATCGACGAGG GCCGCAAGTT CACCGCGCCG     240
TACATGACCG GCATGGTCGG TCTCGCCTAC AACAAGGCAG CCACCGGACG CGATATCCGC     300
ACCATCGACG ACCTCTGGGA TCC                                             323
```

(2) INFORMATION FOR SEQ ID NO:93:

(i) SEQUENCE CHARACTERISTICS:
(A) LENGTH: 1341 base pairs
(B) TYPE: nucleic acid
(C) STRANDEDNESS: single
(D) TOPOLOGY: linear (ii) MOLECULE TYPE: Genomic DNA (xi) SEQUENCE DESCRIPTION: SEQ ID NO:93:

```
CCCCACCCCC TTCCCTGGAG CCGACGAAAG GCACCCGCAC ATGTCCCGTG ACATCGATCC      60
CCACCTGCTG GCCCGAATGA CCGCACGCCG CACCTTGCGT CGCCGCTTCA TCGGCGGTGG     120
CGCCGCGGCC GCCGCGGGCC TGACCCTCGG TTCGTCGTTC CTGGCGGCGT GCGGGTCCGA     180
CAGTGGGACC TCGAGCACCA CGTCACAGGA CAGCGGCCCC GCCAGCGGCG CCCTGCGCGT     240
CTCCAACTGG CCGCTCTATA TGGCCGACGG TTTCATCGCA GCGTTCCAGA CCGCCTCGGG     300
CATCACGGTC GACTACAAAG AAGACTTCAA CGACAACGAG CAGTGGTTCG CCAAGGTCAA     360
GGAGCCGTTG TCGCGCAAGC AGGACATAGG CGCCGACCTG GTGATCCCCA CCGAGTTCAT     420
GGCCGCGCGC GTCAAGGGCC TGGGATGGCT CAATGAGATC AGCGAAGCCG GCGTGCCCAA     480
TCGCAAGAAT CTGCGTCAGG ACCTGTTGGA CTCGAGCATC GACGAGGGC GCAAGTTCAC      540
CGCGCCGTAC ATGACCGGCA TGGTCGGTCT CGCCTACAAC AAGGCAGCCA CCGGACGCGA     600
TATCCGCACC ATCGACGACC TCTGGGATCC CGCGTTCAAG GCCGCGTCA GTCTGTTCTC      660
CGACGTCCAG GACGGCCTCG GCATGATCAT GCTCTCGCAG GGCAACTCGC CGGAGAATCC     720
GACCACCGAG TCCATTCAGC AGGCGGTCGA TCTGGTCCGC GAACAGAACG CAGGGGGTC     780
AGATCCGTCG CTTCACCGGC AACGACTACG CCGACGACCT GGCCGCAGAA ACATCGCCAT     840
CGCGCAGGCG TACTCCGGTG ACGTCGTGCA GCTGCAGGCG GACAACCCCG ATCTGCAGTT     900
CATCGTTCCC GAATCCGGCG GCGACTGGTT CGTCGACACG ATGGTGATCC CGTACACCAC     960
GCAGAACCAG AAGGCCGCCG AGGCGTGGAT CGACTACATC TACGACCGAG CCAACTACGC    1020
CAAGCTGGTC GCGTTCACCC AGTTCGTGCC CGCACTCTCG GACATGACCG ACGAACTCGC    1080
CAAGGTCGAT CCTGCATCGG CGGAGAACCC GCTGATCAAC CCGTCGGCCG AGGTGCAGGC    1140
GAACCTGAAG TCGTGGGCGG CACTGACCGA CGAGCAGACG CAGGAGTTCA ACACTGCGTA    1200
CGCCGCCGTC ACCGGCGGCT GACGCGGTGG TAGTGCCGAT GCGAGGGGCA TAAATGGCCC    1260
TGCGGACGCG AGGAGCATAA ATGGCCGGTG TCGCCACCAG CAGCCGTCAG CGGACAAGGT    1320
CGCTCCGTAT CTGATGGTCC T                                              1341
```

(2) INFORMATION FOR SEQ ID NO:94:

(i) SEQUENCE CHARACTERISTICS:
        (A) LENGTH: 393 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:94:

```
Met Ser Arg Asp Ile Asp Pro His Leu Leu Ala Arg Met Thr Ala Arg
 1               5                  10                  15

Arg Thr Leu Arg Arg Arg Phe Ile Gly Gly Ala Ala Ala Ala
                20                  25                  30

Gly Leu Thr Leu Gly Ser Ser Phe Leu Ala Ala Cys Gly Ser Asp Ser
            35                  40                  45

Gly Thr Ser Ser Thr Thr Ser Gln Asp Ser Gly Pro Ala Ser Gly Ala
        50                  55                  60

Leu Arg Val Ser Asn Trp Pro Leu Tyr Met Ala Asp Gly Phe Ile Ala
65                  70                  75                  80

Ala Phe Gln Thr Ala Ser Gly Ile Thr Val Asp Tyr Lys Glu Asp Phe
                85                  90                  95

Asn Asp Asn Glu Gln Trp Phe Ala Lys Val Lys Glu Pro Leu Ser Arg
                100                 105                 110

Lys Gln Asp Ile Gly Ala Asp Leu Val Ile Pro Thr Glu Phe Met Ala
            115                 120                 125

Ala Arg Val Lys Gly Leu Gly Trp Leu Asn Glu Ile Ser Glu Ala Gly
        130                 135                 140

Val Pro Asn Arg Lys Asn Leu Arg Gln Asp Leu Leu Asp Ser Ser Ile
145                 150                 155                 160

Asp Glu Gly Arg Lys Phe Thr Ala Pro Tyr Met Thr Gly Met Val Gly
                165                 170                 175

Leu Ala Tyr Asn Lys Ala Ala Thr Gly Arg Asp Ile Arg Thr Ile Asp
            180                 185                 190

Asp Leu Trp Asp Pro Ala Phe Lys Gly Arg Val Ser Leu Phe Ser Asp
        195                 200                 205

Val Gln Asp Gly Leu Gly Met Ile Met Leu Ser Gln Gly Asn Ser Pro
210                 215                 220

Glu Asn Pro Thr Thr Glu Ser Ile Gln Gln Ala Val Asp Leu Val Arg
                225                 230                 235                 240

Glu Gln Asn Asp Arg Gly Ser Asp Pro Ser Leu His Arg Gln Arg Leu
            245                 250                 255

Arg Arg Arg Pro Gly Arg Arg Asn Ile Ala Ile Ala Gln Ala Tyr Ser
        260                 265                 270

Gly Asp Val Val Gln Leu Gln Ala Asp Asn Pro Asp Leu Gln Phe Ile
    275                 280                 285

Val Pro Glu Ser Gly Gly Asp Trp Phe Val Asp Thr Met Val Ile Pro
290                 295                 300

Tyr Thr Thr Gln Asn Gln Lys Ala Ala Glu Ala Trp Ile Asp Tyr Ile
305                 310                 315                 320

Tyr Asp Arg Ala Asn Tyr Ala Lys Leu Val Ala Phe Thr Gln Phe Val
            325                 330                 335

Pro Ala Leu Ser Asp Met Thr Asp Glu Leu Ala Lys Val Asp Pro Ala
        340                 345                 350
```

```
Ser Ala Glu Asn Pro Leu Ile Asn Pro Ser Ala Glu Val Gln Ala Asn
        355                 360                 365

Leu Lys Ser Trp Ala Ala Leu Thr Asp Glu Gln Thr Gln Glu Phe Asn
    370                 375                 380

Thr Ala Tyr Ala Ala Val Thr Gly Gly
385                 390
```

(2) INFORMATION FOR SEQ ID NO:95:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:95:

```
ATGTCCCGTG ACATCGATCC CC                                               22
```

(2) INFORMATION FOR SEQ ID NO:96:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:96:

```
ATCGGCACTA CCACCGCGTC A                                                21
```

(2) INFORMATION FOR SEQ ID NO:97:

(i) SEQUENCE CHARACTERISTICS:
        (A) LENGTH: 861 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:97:

```
GCCGGCGCTC GCATATCTCG CGATCTTCTT CCGTGGTGCC GTTCTTCTCG CTGGCACGCA        60

CCTCGTTGTC GGAGACCGGC GGCTCGGTGT TCATGCCGAC GCTGACGTTC GCCTGGGACT       120

TCGGCAACTA CGTCGACGCG TTCACGATGT ACCACGAGCA GATCTTCCGC TCGTTCGGCT       180

ACGCGTTCGT CGCCACGGTG CTGTGCCTGT TGCTGGCGTT CCCGCTGGCC TACGTCATCG       240

CGTTCAAGGC CGGCCGGTTC AAGAACCTGA TCCTGGGGCT GGTGATCCTG CCGTTCTTCG       300

TCACGTTCCT GATCCGCACC ATTGCGTGGA AGACGATCCT GGCCGACGAA GGCTGGGTGG       360

TCACCGCGCT GGGCGCCATC GGGCTGCTGC CTGACGAGGG CCGGCTGCTG TCCACCAGCT       420

GGGCGGTCAT CGGCGGTCTG ACCTACAACT GGATCATCTT CATGATCCTG CCGCTGTACG       480

TCAGCCTGGA GAAGATCGAC CCGCGTCTGC TGGAGGCCTC CCAGGACCTC TACTCGTCGG       540

CGCCGCGCAG CTTCGGCAAG GTGATCCTGC CGATGGCGAT GCCCGGGGTG CTGGCCGGGA       600

GCATGCTGGT GTTCATCCCG GCCGTCGGCG ACTTCATCAA CGCCGACTAT CTCGGCAGTA       660

CCCAGACCAC CATGATCGGC AACGTGATCC AGAAGCAGTT CCTGGTCGTC AAGGACTATC       720

CGGCGGCGGC CGCGCTGAGT CTGGGGCTGA TGTTGCTGAT CCTGATCGGC GTGCTCCTCT       780

ACACACGGGC GCTGGGTTCG GAGGATCTGG TATGACCACC CAGGCAGGCG CCGCACTGGC       840
```

CACCGCCGCC CAGCAGGATC C                                                              861

(2) INFORMATION FOR SEQ ID NO:98:

(i) SEQUENCE CHARACTERISTICS:
        (A) LENGTH: 259 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:98:

```
Val Val Pro Phe Phe Ser Leu Ala Arg Thr Ser Leu Ser Glu Thr Gly
 1               5                  10                  15
Gly Ser Val Phe Met Pro Thr Leu Thr Phe Ala Trp Asp Phe Gly Asn
                20                  25                  30
Tyr Val Asp Ala Phe Thr Met Tyr His Glu Gln Ile Phe Arg Ser Phe
             35                  40                  45
Gly Tyr Ala Phe Val Ala Thr Val Leu Cys Leu Leu Leu Ala Phe Pro
         50                  55                  60
Leu Ala Tyr Val Ile Ala Phe Lys Ala Gly Arg Phe Lys Asn Leu Ile
65                  70                  75                  80
Leu Gly Leu Val Ile Leu Pro Phe Phe Val Thr Phe Leu Ile Arg Thr
                85                  90                  95
Ile Ala Trp Thr Ile Leu Ala Asp Glu Gly Trp Val Val Thr Ala Leu
                100                 105                 110
Gly Ala Ile Gly Leu Leu Pro Asp Glu Gly Arg Leu Leu Ser Thr Ser
            115                 120                 125
Trp Ala Val Ile Gly Gly Leu Thr Tyr Asn Trp Ile Ile Phe Met Ile
130                 135                 140
Leu Pro Leu Tyr Val Ser Leu Glu Lys Ile Asp Pro Arg Leu Leu Glu
145                 150                 155                 160
Ala Ser Gln Asp Leu Tyr Ser Ser Ala Pro Arg Ser Phe Gly Lys Val
                165                 170                 175
Ile Leu Pro Met Ala Met Pro Gly Val Leu Ala Gly Ser Met Leu Val
                180                 185                 190
Phe Ile Pro Ala Val Gly Asp Phe Ile Asn Ala Asp Tyr Leu Gly Ser
            195                 200                 205
Thr Gln Thr Thr Met Ile Gly Asn Val Ile Gln Lys Gln Phe Leu Val
        210                 215                 220
Val Lys Asp Tyr Pro Ala Ala Ala Leu Ser Leu Gly Leu Met Leu
225                 230                 235                 240
Leu Ile Leu Ile Gly Val Leu Leu Tyr Thr Arg Ala Leu Gly Ser Glu
                245                 250                 255
Asp Leu Val
```

(2) INFORMATION FOR SEQ ID NO:99:

(i) SEQUENCE CHARACTERISTICS:
        (A) LENGTH: 277 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:99:

GTAATCTTTG CTGGAGCCCG TACGCCGGTA GGCAAACTCA TGGGTTCGCT CAAGGACTTC        60

```
AAGGGCAGCG ATCTCGGTGC CGTGGCGATC AAGGGCGCCC TGGAGAAAGC CTTCCCCGGC    120

GTCGACGACC CTGCTCGTCT CGTCGAGTAC GTGATCATGG GCCAAGTGCT CTCCGCCGGC    180

GCCGGCCAGA TGCCCGCCCG CCAGGCCGCC GTCGCCGCCG GCATCCCGTG GGACGTCGCC    240

TCGCTGACGA TCAACAAGAT GTGCCTGTCG GGCATCG                            277
```

(2) INFORMATION FOR SEQ ID NO:100:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:100:

```
Val Ile Phe Ala Gly Ala Arg Thr Pro Val Gly Lys Leu Met Gly Ser
 1               5                  10                  15

Leu Lys Asp Phe Lys Gly Ser Asp Leu Gly Ala Val Ala Ile Lys Gly
             20                  25                  30

Ala Leu Glu Lys Ala Phe Pro Gly Val Asp Asp Pro Ala Arg Leu Val
         35                  40                  45

Glu Tyr Val Ile Met Gly Gln Val Leu Ser Ala Gly Ala Gly Gln Met
 50                  55                  60

Pro Ala Arg Gln Ala Ala Val Ala Ala Gly Ile Pro Trp Asp Val Ala
65                  70                  75                  80

Ser Leu Thr Ile Asn Lys Met Cys Leu Ser Gly Ile
             85                  90
```

(2) INFORMATION FOR SEQ ID NO:101:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 1...1
        (D) OTHER INFORMATION: Residue can be either Glu or Pro
        (A) NAME/KEY: Other
        (B) LOCATION: 2...2
        (D) OTHER INFORMATION: Residue can be either Pro or Glu (xi) SEQUENCE DESCRIPTION: SEQ ID NO:101:

```
Xaa Xaa Ala Asp Arg Gly Xaa Ser Lys Tyr Arg Xaa
 1               5                  10
```

(2) INFORMATION FOR SEQ ID NO:102:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:102:

```
Xaa Ile Asp Glu Ser Leu Phe Asp Ala Glu Glu Lys Met Glu Lys Ala
 1               5                  10                  15
```

Val Ser Val Ala Arg Asp Ser Ala
            20

(2) INFORMATION FOR SEQ ID NO:103:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:103:

Xaa Xaa Ile Ala Pro Ala Thr Ser Gly Thr Leu Ser Glu Phe Xaa Ala
 1               5                  10                  15

Xaa Lys Gly Val Thr Met Glu
            20

(2) INFORMATION FOR SEQ ID NO:104:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:104:

Pro Asn Val Pro Asp Ala Phe Ala Val Leu Ala Asp Arg Val Gly
 1               5                  10                  15

(2) INFORMATION FOR SEQ ID NO:105:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:105:

Xaa Ile Arg Val Gly Val Asn Gly Phe
 1               5

(2) INFORMATION FOR SEQ ID NO:106:

(i) SEQUENCE CHARACTERISTICS:
        (A) LENGTH: 485 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:106:

AGCGGCTGGG ACATCAACAC CGCCGCCTTC GAGTGGTACG TCGACTCGGG TCTCGCGGTG      60

ATCATGCCCG TCGGCGGGCA GTCCAGCTTC TACAGCGACT GGTACAGCCC GGCCTGCGGT     120

AAGGCCGGCT GCCAGACCTA CAAGTGGGAG ACGTTCCTGA CCCAGGAGCT GCCGGCCTAC     180

CTCGCCGCCA ACAAGGGGGT CGACCCGAAC CGCAACGCGG CCGTCGGTCT GTCCATGGCC     240

GGTTCGGCGG CGCTGACGCT GGCGATCTAC CACCCGCAGC AGTTCCAGTA CGCCGGGTCG     300

CTGTCGGGCT ACCTGAACCC GTCCGAGGGG TGGTGGCCGA TGCTGATCAA CATCTCGATG     360

GGTGACGCGG GCGGCTACAA GGCCAACGAC ATGTGGGGTC GCACCGAGGA CCCGAGCAGC     420

```
GCCTGGAAGC GCAACGACCC GATGGTCAAC ATCGGCAAGC TGGTCGCCAA CAACACCCCC        480

CTCTC                                                                    485
```

(2) INFORMATION FOR SEQ ID NO:107:

(i) SEQUENCE CHARACTERISTICS:
        (A) LENGTH: 501 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:107:

```
ATGCCGGTGC GACGTGCGCG CAGTGCGCTT GCGTCCGTGA CCTTCGTCGC GGCCGCGTGC         60

GTGGGCGCTG AGGGCACCGC ACTGGCGGCG ACGCCGGACT GGAGCGGGCG CTACACGGTG        120

GTGACGTTCG CCTCCGACAA ACTCGGCACG AGTGTGGCCG CCCGCCAGCC AGAACCCGAC        180

TTCAGCGGTC AGTACACCTT CAGCACGTCC TGTGTGGGCA CCTGCGTGGC CACCGCGTCC        240

GACGGCCCGG CGCCGTCGAA CCCGACGATT CCGCAGCCCG CGCGCTACAC CTGGGACGGC        300

AGGCAGTGGG TGTTCAACTA CAACTGGCAG TGGGAGTGCT TCCGCGGCGC CGACGTCCCG        360

CGCGAGTACG CCGCCGCGCG TTCGCTGGTG TTCTACGCCC CGACCGCCGA CGGGTCGATG        420

TTCGGCACCT GGCGCACCGA NATCCTGGAN GGCCTCTGCA AGGGCACCGT GATCATGCCG        480

GTCGCGGCCT ATCCGGCGTA G                                                  501
```

(2) INFORMATION FOR SEQ ID NO:108:

(i) SEQUENCE CHARACTERISTICS:
        (A) LENGTH: 180 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:108:

```
ATGAACCAGC CGCGGCCCGA GGCCGAGGCG AACCTGCGGG GCTACTTCAC CGCCAACCCG         60

GCGGAGTACT ACGACCTGCG GGGCATCCTC GCCCCGATCG GTGACGCGCA GCGCAACTGC        120

AACATCACCG TGCTGCCGGT AGAGCTGCAG ACGGCCTACG ACACGTTCAT GGCCGGCTGA        180
```

(2) INFORMATION FOR SEQ ID NO:109:

(i) SEQUENCE CHARACTERISTICS:
        (A) LENGTH: 166 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:109:

```
Met Pro Val Arg Arg Ala Arg Ser Ala Leu Ala Ser Val Thr Phe Val
 1               5                  10                  15

Ala Ala Ala Cys Val Gly Ala Glu Gly Thr Ala Leu Ala Ala Thr Pro
                20                  25                  30

Asp Trp Ser Gly Arg Tyr Thr Val Val Thr Phe Ala Ser Asp Lys Leu
            35                  40                  45

Gly Thr Ser Val Ala Ala Arg Gln Pro Glu Pro Asp Phe Ser Gly Gln
        50                  55                  60
```

```
Tyr Thr Phe Ser Thr Ser Cys Val Gly Thr Cys Val Ala Thr Ala Ser
 65                  70                  75                  80

Asp Gly Pro Ala Pro Ser Asn Pro Thr Ile Pro Gln Pro Ala Arg Tyr
                 85                  90                  95

Thr Trp Asp Gly Arg Gln Trp Val Phe Asn Tyr Asn Trp Gln Trp Glu
            100                 105                 110

Cys Phe Arg Gly Ala Asp Val Pro Arg Glu Tyr Ala Ala Ala Arg Ser
            115                 120                 125

Leu Val Phe Tyr Ala Pro Thr Ala Asp Gly Ser Met Phe Gly Thr Trp
            130                 135                 140

Arg Thr Asp Ile Leu Asp Gly Leu Cys Lys Gly Thr Val Ile Met Pro
145                 150                 155                 160

Val Ala Ala Tyr Pro Ala
                165
```

(2) INFORMATION FOR SEQ ID NO:110:

(i) SEQUENCE CHARACTERISTICS:
        (A) LENGTH: 74 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:110:

```
Pro Arg Asp Thr His Pro Gly Ala Asn Gln Ala Val Thr Ala Ala Met
  1                5                  10                  15

Asn Gln Pro Arg Pro Glu Ala Glu Ala Asn Leu Arg Gly Tyr Phe Thr
                 20                  25                  30

Ala Asn Pro Ala Glu Tyr Tyr Asp Leu Arg Gly Ile Leu Ala Pro Ile
             35                  40                  45

Gly Asp Ala Gln Arg Asn Cys Asn Ile Thr Val Leu Pro Val Glu Leu
 50                  55                  60

Gln Thr Ala Tyr Asp Thr Phe Met Ala Gly
 65                  70
```

(2) INFORMATION FOR SEQ ID NO:111:

(i) SEQUENCE CHARACTERISTICS:
        (A) LENGTH: 503 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:111:

```
ATGCAGGTGC GGCGTGTTCT GGGCAGTGTC GGTGCAGCAG TCGCGGTTTC GGCCGCGTTA   60

TGGCAGACGG GGGTTTCGAT ACCGACCGCC TCAGCGGATC CGTGTCCGGA CATCGAGGTG  120

ATCTTCGCGC GCGGGACCGG TGCGGAACCC GGCCTCGGGT GGGTCGGTGA TGCGTTCGTC  180

AACGCGCTGC GGCCCAAGGT CGGTGAGCAG TCGGTGGGCA CCTACGCGGT GAACTACCCG  240

GCAGGATTCG GACTTCGACA AATCGGCGCC CATGGGCGCG GCCGACGCAT CGGGGCGGGT  300

GCAGTGGATG GCCGACAACT GCCCGGACAC CAAGCTTGTC CTGGGCGGCA TGTCGCANGG  360

CGCCGGCGTC ATCGACCTGA TCACCGTCGA TCCGCGACCG CTGGGCCGGT TCACCCCCAC  420

CCCGATGCCG CCCCGCGTCG CCGACCACGT GGCCGCCGTT GTGGTCTTCG GAAATCCGTT  480

GCGCGACATC CGTGGTGGCG GTC                                         503
```

(2) INFORMATION FOR SEQ ID NO:112:

(i) SEQUENCE CHARACTERISTICS:
        (A) LENGTH: 167 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:112:

```
Met Gln Val Arg Arg Val Leu Gly Ser Val Gly Ala Ala Val Ala Val
 1               5                  10                  15

Ser Ala Ala Leu Trp Gln Thr Gly Val Ser Ile Pro Thr Ala Ser Ala
                20                  25                  30

Asp Pro Cys Pro Asp Ile Glu Val Ile Phe Ala Arg Gly Thr Gly Ala
            35                  40                  45

Glu Pro Gly Leu Gly Trp Val Gly Asp Ala Phe Val Asn Ala Leu Arg
        50                  55                  60

Pro Lys Val Gly Glu Gln Ser Val Gly Thr Tyr Ala Val Asn Tyr Pro
65                  70                  75                  80

Ala Gly Phe Asp Phe Asp Lys Ser Ala Pro Met Gly Ala Ala Asp Ala
                85                  90                  95

Ser Gly Arg Val Gln Trp Met Ala Asp Asn Cys Pro Asp Thr Lys Leu
            100                 105                 110

Val Leu Gly Gly Met Ser Xaa Gly Ala Gly Val Ile Asp Leu Ile Thr
        115                 120                 125

Val Asp Pro Arg Pro Leu Gly Arg Phe Thr Pro Thr Pro Met Pro Pro
130                 135                 140

Arg Val Ala Asp His Val Ala Ala Val Val Phe Gly Asn Pro Leu
145                 150                 155                 160

Arg Asp Ile Arg Gly Gly Gly
                165
```

(2) INFORMATION FOR SEQ ID NO:113:

(i) SEQUENCE CHARACTERISTICS:
        (A) LENGTH: 1569 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:113:

```
ATGGCCAAGA CAATTGCGTA TGACGAAGAG GCCCGCCGTG GCCTCGAGCG GGGCCTCAAC    60

GCCCTCGCAG ACGCCGTAAA GGTGACGTTG GGCCCGAAGG GTCGCAACGT CGTGCTGGAG   120

AAGAAGTGGG GCGCCCCCAC GATCACCAAC GATGGTGTGT CCATCGCCAA GGAGATCGAG   180

CTGGAGGACC CGTACGAGAA GATCGGCGCT GAGCTGGTCA AGAGGTCGC CAAGAAGACC    240

GACGACGTCG CGGGCGACGG CACCACCACC GCCACCGTGC TCGCTCAGGC TCTGGTTCGC   300

GAAGGCCTGC GCAACGTCGC AGCCGGCGCC AACCCGCTCG GCCTCAAGCG TGGCATCGAG   360

AAGGCTGTCG AGGCTGTCAC CCAGTCGCTG CTGAAGTCGG CCAAGGAGGT CGAGACCAAG   420

GAGCAGATTT CTGCCACCGC GGCGATTTCC GCCGGCGACA CCCAGATCGG CGAGCTCATC   480

GCCGAGGCCA TGGACAAGGT CGGCAACGAG GGTGTCATCA CCGTCGAGGA GTCGAACACC   540

TTCGGCCTGC AGCTCGAGCT CACCGAGGGT ATGCGCTTCG ACAAGGGCTA CATCTCGGGT   600

TACTTCGTGA CCGACGCCGA GCGCCAGGAA GCCGTCCTGG AGGATCCCTA CATCCTGCTG   660
```

```
GTCAGCTCCA AGGTGTCGAC CGTCAAGGAT CTGCTCCCGC TGCTGGAGAA GGTCATCCAG    720

GCCGGCAAGC CGCTGCTGAT CATCGCCGAG GACGTCGAGG GCGAGGCCCT GTCCACGCTG    780

GTGGTCAACA AGATCCGCGG CACCTTCAAG TCCGTCGCCG TCAAGGCTCC GGGCTTCGGT    840

GACCGCCGCA AGGCGATGCT GCAGGACATG GCCATCCTCA CCGGTGGTCA GGTCGTCAGC    900

GAAAGAGTCG GGCTGTCCCT GGAGACCGCC GACGTCTCGC TGCTGGGCCA GGCCCGCAAG    960

GTCGTCGTCA CCAAGGACGA GACCACCATC GTCGAGGGCT CGGGCGATTC CGATGCCATC   1020

GCCGGCCGGG TGGCTCAGAT CCGCGCCGAG ATCGAGAACA GCGACTCCGA CTACGACCGC   1080

GAGAAGCTGC AGGAGCGCCT GGCCAAGCTG GCCGGCGGTG TTGCGGTGAT CAAGGCCGGA   1140

GCTGCCACCG AGGTGGAGCT CAAGGAGCGC AAGCACCGCA TCGAGGACGC CGTCCGCAAC   1200

GCGAAGGCTG CCGTCGAAGA GGGCATCGTC GCCGGTGGCG GCGTGGCTCT GCTGCAGTCG   1260

GCTCCTGCGC TGGACGACCT CGGCCTGACG GGCGACGAGG CCACCGGTGC CAACATCGTC   1320

CGCGTGGCGC TGTCGGCTCC GCTCAAGCAG ATCGCCTTCA ACGGCGGCCT GGAGCCCGGC   1380

GTCGTTGCCG AGAAGGTGTC CAACCTGCCC GCGGGTCACG GCCTCAACGC CGCGACCGGT   1440

GAGTACGAGG ACCTGCTCAA GGCCGGCGTC GCCGACCCGG TGAAGGTCAC CCGCTCGGCG   1500

CTGCAGAACG CGGCGTCCAT CGCGGCTCTG TTCCTCACCA CCGAGGCCGT CGTCGCCGAC   1560

AAGCCGGAG                                                          1569
```

(2) INFORMATION FOR SEQ ID NO:114:

(i) SEQUENCE CHARACTERISTICS:
        (A) LENGTH: 523 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:114:

```
Met Ala Lys Thr Ile Ala Tyr Asp Glu Glu Ala Arg Arg Gly Leu Glu
 1               5                  10                  15

Arg Gly Leu Asn Ala Leu Ala Asp Ala Val Lys Val Thr Leu Gly Pro
                20                  25                  30

Lys Gly Arg Asn Val Val Leu Glu Lys Lys Trp Gly Ala Pro Thr Ile
            35                  40                  45

Thr Asn Asp Gly Val Ser Ile Ala Lys Glu Ile Glu Leu Glu Asp Pro
        50                  55                  60

Tyr Glu Lys Ile Gly Ala Glu Leu Val Lys Glu Val Ala Lys Lys Thr
65                  70                  75                  80

Asp Asp Val Ala Gly Asp Gly Thr Thr Thr Ala Thr Val Leu Ala Gln
                85                  90                  95

Ala Leu Val Arg Glu Gly Leu Arg Asn Val Ala Ala Gly Ala Asn Pro
            100                 105                 110

Leu Gly Leu Lys Arg Gly Ile Glu Lys Ala Val Glu Ala Val Thr Gln
        115                 120                 125

Ser Leu Leu Lys Ser Ala Lys Glu Val Glu Thr Lys Glu Gln Ile Ser
    130                 135                 140

Ala Thr Ala Ala Ile Ser Ala Gly Asp Thr Gln Ile Gly Glu Leu Ile
145                 150                 155                 160

Ala Glu Ala Met Asp Lys Val Gly Asn Glu Gly Val Ile Thr Val Glu
                165                 170                 175
```

```
Glu Ser Asn Thr Phe Gly Leu Gln Leu Glu Leu Thr Glu Gly Met Arg
            180                 185                 190

Phe Asp Lys Gly Tyr Ile Ser Gly Tyr Phe Val Thr Asp Ala Glu Arg
        195                 200                 205

Gln Glu Ala Val Leu Glu Asp Pro Tyr Ile Leu Leu Val Ser Ser Lys
    210                 215                 220

Val Ser Thr Val Lys Asp Leu Leu Pro Leu Leu Glu Lys Val Ile Gln
225                 230                 235                 240

Ala Gly Lys Pro Leu Leu Ile Ile Ala Glu Asp Val Glu Gly Glu Ala
            245                 250                 255

Leu Ser Thr Leu Val Val Asn Lys Ile Arg Gly Thr Phe Lys Ser Val
            260                 265                 270

Ala Val Lys Ala Pro Gly Phe Gly Asp Arg Arg Lys Ala Met Leu Gln
        275                 280                 285

Asp Met Ala Ile Leu Thr Gly Gly Gln Val Val Ser Glu Arg Val Gly
    290                 295                 300

Leu Ser Leu Glu Thr Ala Asp Val Ser Leu Leu Gly Gln Ala Arg Lys
305                 310                 315                 320

Val Val Val Thr Lys Asp Glu Thr Thr Ile Val Glu Gly Ser Gly Asp
            325                 330                 335

Ser Asp Ala Ile Ala Gly Arg Val Ala Gln Ile Arg Ala Glu Ile Glu
            340                 345                 350

Asn Ser Asp Ser Asp Tyr Asp Arg Glu Lys Leu Gln Glu Arg Leu Ala
        355                 360                 365

Lys Leu Ala Gly Gly Val Ala Val Ile Lys Ala Gly Ala Ala Thr Glu
    370                 375                 380

Val Glu Leu Lys Glu Arg Lys His Arg Ile Glu Asp Ala Val Arg Asn
385                 390                 395                 400

Ala Lys Ala Ala Val Glu Glu Gly Ile Val Ala Gly Gly Val Ala
            405                 410                 415

Leu Leu Gln Ser Ala Pro Ala Leu Asp Asp Leu Gly Leu Thr Gly Asp
            420                 425                 430

Glu Ala Thr Gly Ala Asn Ile Val Arg Val Ala Leu Ser Ala Pro Leu
        435                 440                 445

Lys Gln Ile Ala Phe Asn Gly Gly Leu Glu Pro Gly Val Val Ala Glu
    450                 455                 460

Lys Val Ser Asn Leu Pro Ala Gly His Gly Leu Asn Ala Ala Thr Gly
465                 470                 475                 480

Glu Tyr Glu Asp Leu Leu Lys Ala Gly Val Ala Asp Pro Val Lys Val
            485                 490                 495

Thr Arg Ser Ala Leu Gln Asn Ala Ala Ser Ile Ala Ala Leu Phe Leu
            500                 505                 510

Thr Thr Glu Ala Val Val Ala Asp Lys Pro Glu
            515                 520

(2) INFORMATION FOR SEQ ID NO:115:

(i) SEQUENCE CHARACTERISTICS:
        (A) LENGTH: 647 base pairs
        (B) TYPE: nucleic acid
        (C) STRANDEDNESS: single
        (D) TOPOLOGY: linear (ii) MOLECULE TYPE: Genomic RNA (xi) SEQUENCE DESCRIPTION: SEQ ID NO:115:

ATGGCCAAGA CAATTGCGTA TGACGAAGAG GCCCGCCGTG GCCTCGAGCG GGGCCTCAAC     60
```

```
GCCCTCGCAG ACGCCGTAAA GGTGACGTTG GGCCCGAAGG GTCGCAACGT CGTGCTGGAG      120

AAGAAGTGGG GCGCCCCCAC GATCACCAAC GATGGTGTGT CCATCGCCAA GGAGATCGAG      180

CTGGAGGACC CGTACGAGAA GATCGGCGCT GAGCTGGTCA AAGAGGTCGC CAAGAAGACC      240

GACGACGTCG CGGGCGACGG CACCACCACC GCCACCGTGC TCGCTCAGGC TCTGGTTCGC      300

GAAGGCCTGC GCAACGTCGC AGCCGGCGCC AACCCGCTCG GCCTCAAGCG TGGCATCGAG      360

AAGGCTGTCG AGGCTGTCAC CCAGTCGCTG CTGAAGTCGG CCAAGGAGGT CGAGACCAAG      420

GAGCAGATTT CTGCCACCGC GGCGATTTCC GCCGGCGACA CCCAGATCGG CGAGCTCATC      480

GCCGAGGCCA TGGACAAGGT CGGCAACGAG GGTGTCATCA CCGTCGAGGA GTCGAACACC      540

TTCGGCCTGC AGCTCGAGCT CACCGAGGGT ATGCGCTTCG ACAAGGGCTA CATCTCGGGT      600

TACTTCGTGA CCGACGCCGA GCGCCAGGAA GCCGTCCTGG AGGATCC                   647
```

(2) INFORMATION FOR SEQ ID NO:116:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:116:

```
GATCCCTACA TCCTGCTGGT CAGCTCCAAG GTGTCGACCG TCAAGGATCT GCTCCCGCTG       60

CTGGAGAAGG TCATCCAGGC CGGCAAGCCG CTGCTGATCA TCGCCGAGGA CGTCGAGGGC      120

GAGGCCCTGT CCACGCTGGT GGTCAACAAG ATCCGCGGCA CCTTCAAGTC CGTCGCCGTC      180

AAGGCTCCGG GCTTCGGTGA CCGCCGCAAG GCGATGCTGC AGGACATGGC CATCCTCACC      240

GGTGGTCAGG TCGTCAGCGA AAGAGTCGGG CTGTCCCTGG AGACCGCCGA CGTCTCGCTG      300

CTGGGCCAGG CCCGCAAGGT CGTCGTCACC AAGGACGAGA CCACCATCGT CGAGGGCTCG      360

GGCGATTCCG ATGCCATCGC CGGCCGGGTG GCTCAGATCC GCGCCGAGAT CGAGAACAGC      420

GACTCCGACT ACGACCGCGA GAAGCTGCAG GAGCGCCTGG CCAAGCTGGC CGGCGGTGTT      480

GCGGTGATCA AGGCCGGAGC TGCCACCGAG GTGGAGCTCA AGGAGCGCAA GCACCGCATC      540

GAGGACGCCG TCCGCAACGC GAAGGCTGCC GTCGAAGAGG GCATCGTCGC CGGTGGCGGC      600

GTGGCTCTGC TGCAGTCGGC TCCTGCGCTG GACGACCTCG GCCTGACGGG CGACGAGGCC      660

ACCGGTGCCA ACATCGTCCG CGTGGCGCTG TCGGCTCCGC TCAAGCAGAT CGCCTTCAAC      720

GGCGGCCTGG AGCCCGGCGT CGTTGCCGAG AAGGTGTCCA ACCTGCCCGC GGGTCACGGC      780

CTCAACGCCG CGACCGGTGA GTACGAGGAC CTGCTCAAGG CCGGCGTCGC CGACCCGGTG      840

AAGGTCACCC GCTCGGCGCT GCAGAACGCG GCGTCCATCG CGGCTCTGTT CCTCACCACC      900

GAGGCCGTCG TCGCCGACAA GCCGGAG                                        927
```

(2) INFORMATION FOR SEQ ID NO:117:

(i) SEQUENCE CHARACTERISTICS:
        (A) LENGTH: 215 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:117:

Met Ala Lys Thr Ile Ala Tyr Asp Glu Glu Ala Arg Arg Gly Leu Glu
1               5                   10                  15

Arg Gly Leu Asn Ala Leu Ala Asp Ala Val Lys Val Thr Leu Gly Pro
                20                  25                  30

Lys Gly Arg Asn Val Val Leu Glu Lys Lys Trp Gly Ala Pro Thr Ile
        35                  40                  45

Thr Asn Asp Gly Val Ser Ile Ala Lys Glu Ile Glu Leu Glu Asp Pro
    50                  55                  60

Tyr Glu Lys Ile Gly Ala Glu Leu Val Lys Glu Val Ala Lys Lys Thr
65              70                  75                  80

Asp Asp Val Ala Gly Asp Gly Thr Thr Thr Ala Thr Val Leu Ala Gln
                85                  90                  95

Ala Leu Val Arg Glu Gly Leu Arg Asn Val Ala Ala Gly Ala Asn Pro
                100                 105                 110

Leu Gly Leu Lys Arg Gly Ile Glu Lys Ala Val Glu Ala Val Thr Gln
            115                 120                 125

Ser Leu Leu Lys Ser Ala Lys Glu Val Glu Thr Lys Glu Gln Ile Ser
    130                 135                 140

Ala Thr Ala Ala Ile Ser Ala Gly Asp Thr Gln Ile Gly Glu Leu Ile
145                 150                 155                 160

Ala Glu Ala Met Asp Lys Val Gly Asn Glu Gly Val Ile Thr Val Glu
                165                 170                 175

Glu Ser Asn Thr Phe Gly Leu Gln Leu Glu Leu Thr Glu Gly Met Arg
                180                 185                 190

Phe Asp Lys Gly Tyr Ile Ser Gly Tyr Phe Val Thr Asp Ala Glu Arg
            195                 200                 205

Gln Glu Ala Val Leu Glu Asp
    210                 215

(2) INFORMATION FOR SEQ ID NO:118:

(i) SEQUENCE CHARACTERISTICS:
        (A) LENGTH: 309 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:118:

Asp Pro Tyr Ile Leu Leu Val Ser Ser Lys Val Ser Thr Val Lys Asp
1               5                   10                  15

Leu Leu Pro Leu Leu Glu Lys Val Ile Gln Ala Gly Lys Pro Leu Leu
                20                  25                  30

Ile Ile Ala Glu Asp Val Glu Gly Glu Ala Leu Ser Thr Leu Val Val
        35                  40                  45

Asn Lys Ile Arg Gly Thr Phe Lys Ser Val Ala Val Lys Ala Pro Gly
    50                  55                  60

Phe Gly Asp Arg Arg Lys Ala Met Leu Gln Asp Met Ala Ile Leu Thr
65              70                  75                  80

Gly Gly Gln Val Val Ser Glu Arg Val Gly Leu Ser Leu Glu Thr Ala
                85                  90                  95

Asp Val Ser Leu Leu Gly Gln Ala Arg Lys Val Val Thr Lys Asp
                100                 105                 110

Glu Thr Thr Ile Val Glu Gly Ser Gly Asp Ser Asp Ala Ile Ala Gly
            115                 120                 125

```
Arg Val Ala Gln Ile Arg Ala Glu Ile Glu Asn Ser Asp Ser Asp Tyr
        130                 135                 140

Asp Arg Glu Lys Leu Gln Glu Arg Leu Ala Lys Leu Ala Gly Gly Val
145                 150                 155                 160

Ala Val Ile Lys Ala Gly Ala Ala Thr Glu Val Glu Leu Lys Glu Arg
            165                 170                 175

Lys His Arg Ile Glu Asp Ala Val Arg Asn Ala Lys Ala Ala Val Glu
                180                 185                 190

Glu Gly Ile Val Ala Gly Gly Val Ala Leu Leu Gln Ser Ala Pro
            195                 200                 205

Ala Leu Asp Asp Leu Gly Leu Thr Gly Asp Glu Ala Thr Gly Ala Asn
        210                 215                 220

Ile Val Arg Val Ala Leu Ser Ala Pro Leu Lys Gln Ile Ala Phe Asn
225                 230                 235                 240

Gly Gly Leu Glu Pro Gly Val Val Ala Glu Lys Val Ser Asn Leu Pro
            245                 250                 255

Ala Gly His Gly Leu Asn Ala Ala Thr Gly Glu Tyr Glu Asp Leu Leu
            260                 265                 270

Lys Ala Gly Val Ala Asp Pro Val Lys Val Thr Arg Ser Ala Leu Gln
        275                 280                 285

Asn Ala Ala Ser Ile Ala Ala Leu Phe Leu Thr Thr Glu Ala Val Val
        290                 295                 300

Ala Asp Lys Pro Glu
305
```

(2) INFORMATION FOR SEQ ID NO:119:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:119:

```
CTCGTACAGG CGACGGAGAT CTCCGACGAC GCCACGTCGG TACGGTTGGT CGCCACCCTG    60

TTCGGCGTCG TGTTGTTGAC GTTGGTGCTG TCCGGGCTCA ACGCCACCCT CATCCAGGGC   120

GCACCAGAAG ACAGCTGGCG CAGGCGGATT CCGTCGATCT TC                      162
```

(2) INFORMATION FOR SEQ ID NO:120:

(i) SEQUENCE CHARACTERISTICS:
        (A) LENGTH: 1366 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:120:

```
GATGAGCAGC GTGCTGAACT CGACCTGGTT GGCCTGGGCC GTCGCGGTCG CGGTCGGGTT    60

CCCGGTGCTG CTGGTCGTGC TGACCGAGGT GCACAACGCG TTGCGTCGGC GCGGCAGCGC   120

GCTGGCCCGC CCGGTGCAAC TCCTGCGTAC CTACATCCTG CCGCTGGGCG CGTTGCTGCT   180

CCTGCTGGTA CAGGCGATGG AGATCTCCGA CGACGCCACG TCGGTACGGT TGGTCGCCAC   240

CCTGTTCGGC GTCGTGTTGT TGACGTTGGT GCTGTCCGGG CTCAACGCCA CCCTCATCCA   300

GGGCGCACCA GAAGACAGCT GGCGCAGGCG GATTCCGTCG ATCTTCCTCG ACGTCGCGCG   360
```

```
CTTCGCGCTG ATCGCGGTCG GTATCACCGT GATCATGGCC TATGTCTGGG GCGCGAACGT    420

GGGGGGCCTG TTCACCGCAC TGGGCGTCAC TTCCATCGTT CTTGGCCTGG CTCTGCAGAA    480

TTCGGTCGGT CAGATCATCT CGGGTCTGCT GCTGCTGTTC GAGCAACCGT TCCGGCTCGG    540

CGACTGGATC ACCGTCCCCA CCGCGGCGGG CCGGCCGTCC GCCCACGGCC GCGTGGTGGA    600

AGTCAACTGG CGTGCAACAC ATATCGACAC CGGCGGCAAC CTGCTGGTAA TGCCCAACGC    660

CGAACTCGCC GGCGCGTCGT TCACCAATTA CAGCCGGCCC GTGGGAGAGC ACCGGCTGAC    720

CGTCGTCACC ACCTTCAACG CCGCGGACAC CCCCGATGAT GTCTGCGAGA TGCTGTCGTC    780

GGTCGCGGCG TCGCTGCCCG AACTGCGCAC CGACGGACAG ATCGCCACGC TCTATCTCGG    840

TGCGGCCGAA TACGAGAAGT CGATCCCGTT GCACACACCC GCGGTGGACG ACTCGGTCAG    900

GAGCACGTAC CTGCGATGGG TCTGGTACGC CGCGCGCCGG CAGGAACTTC GCCTNAACGG    960

CGTCGCCGAC GANTTCGACA CGCCGGAACG GATCGCCTCG GCCATGCGGG CTGTGGCGTC   1020

CACACTGCGC TTGGCAGACG ACGAACAGCA GGAGATCGCC GACGTGGTGC GTCTGGTCCG   1080

TTACGGCAAC GGGGAACGCC TCCAGCAGCC GGGTCAGGTA CCGACCGGGA TGAGGTTCAT   1140

CGTAGACGGC AGGGTGAGTC TGTCCGTGAT CGATCAGGAC GGCGACGTGA TCCCGGCGCG   1200

GGTGCTCGAG CGTGGCGACT TCCTGGGGCA GACCACGCTG ACGCGGGAAC CGGTACTGGC   1260

GACCGCGCAC GCGCTGGAGG AAGTCACCGT GCTGGAGATG GCCCGTGACG AGATCGAGCG   1320

CCTGGTGCAC CGAAAGCCGA TCCTGCTGCA CGTGATCGGG GCCGTG                  1366
```

(2) INFORMATION FOR SEQ ID NO:121:

(i) SEQUENCE CHARACTERISTICS:
        (A) LENGTH: 455 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:121:

```
Met Ser Ser Val Leu Asn Ser Thr Trp Leu Ala Trp Ala Val Ala Val
 1               5                  10                  15

Ala Val Gly Phe Pro Val Leu Leu Val Val Leu Thr Glu Val His Asn
             20                  25                  30

Ala Leu Arg Arg Arg Gly Ser Ala Leu Ala Arg Pro Val Gln Leu Leu
         35                  40                  45

Arg Thr Tyr Ile Leu Pro Leu Gly Ala Leu Leu Leu Leu Val Gln
     50                  55                  60

Ala Met Glu Ile Ser Asp Asp Ala Thr Ser Val Arg Leu Val Ala Thr
65                  70                  75                  80

Leu Phe Gly Val Val Leu Leu Thr Leu Val Leu Ser Gly Leu Asn Ala
                 85                  90                  95

Thr Leu Ile Gln Gly Ala Pro Glu Asp Ser Trp Arg Arg Arg Ile Pro
            100                 105                 110

Ser Ile Phe Leu Asp Val Ala Arg Phe Ala Leu Ile Ala Val Gly Ile
        115                 120                 125

Thr Val Ile Met Ala Tyr Val Trp Gly Ala Asn Val Gly Gly Leu Phe
    130                 135                 140

Thr Ala Leu Gly Val Thr Ser Ile Val Leu Gly Leu Ala Leu Gln Asn
145                 150                 155                 160

Ser Val Gly Gln Ile Ile Ser Gly Leu Leu Leu Phe Glu Gln Pro
                165                 170                 175
```

```
Phe Arg Leu Gly Asp Trp Ile Thr Val Pro Thr Ala Ala Gly Arg Pro
                180                 185                 190

Ser Ala His Gly Arg Val Val Glu Val Asn Trp Arg Ala Thr His Ile
        195                 200                 205

Asp Thr Gly Gly Asn Leu Leu Val Met Pro Asn Ala Glu Leu Ala Gly
    210                 215                 220

Ala Ser Phe Thr Asn Tyr Ser Arg Pro Val Gly Glu His Arg Leu Thr
225                 230                 235                 240

Val Val Thr Thr Phe Asn Ala Ala Asp Thr Pro Asp Asp Val Cys Glu
                245                 250                 255

Met Leu Ser Ser Val Ala Ala Ser Leu Pro Glu Leu Arg Thr Asp Gly
                260                 265                 270

Gln Ile Ala Thr Leu Tyr Leu Gly Ala Ala Glu Tyr Glu Lys Ser Ile
                275                 280                 285

Pro Leu His Thr Pro Ala Val Asp Asp Ser Val Arg Ser Thr Tyr Leu
            290                 295                 300

Arg Trp Val Trp Tyr Ala Ala Arg Arg Gln Glu Leu Arg Xaa Asn Gly
305                 310                 315                 320

Val Ala Asp Xaa Phe Asp Thr Pro Glu Arg Ile Ala Ser Ala Met Arg
                325                 330                 335

Ala Val Ala Ser Thr Leu Arg Leu Ala Asp Asp Glu Gln Gln Glu Ile
                340                 345                 350

Ala Asp Val Val Arg Leu Val Arg Tyr Gly Asn Gly Glu Arg Leu Gln
                355                 360                 365

Gln Pro Gly Gln Val Pro Thr Gly Met Arg Phe Ile Val Asp Gly Arg
            370                 375                 380

Val Ser Leu Ser Val Ile Asp Gln Asp Gly Asp Val Ile Pro Ala Arg
385                 390                 395                 400

Val Leu Glu Arg Gly Asp Phe Leu Gly Gln Thr Thr Leu Thr Arg Glu
                405                 410                 415

Pro Val Leu Ala Thr Ala His Ala Leu Glu Glu Val Thr Val Leu Glu
                420                 425                 430

Met Ala Arg Asp Glu Ile Glu Arg Leu Val His Arg Lys Pro Ile Leu
                435                 440                 445

Leu His Val Ile Gly Ala Val
            450                 455

(2) INFORMATION FOR SEQ ID NO:122:

(i) SEQUENCE CHARACTERISTICS:
        (A) LENGTH: 898 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:122:

ATGACAATTC TGCCCTGGAA TGCGCGAACG TCTGAACACC CGACGCGAAA AAGACGCGGG      60

CGCTACCACC TCCTGTCGCG GATGAGCATC CAGTCCAAGT TGCTGCTGAT GCTGCTTCTG     120

ACCAGCATTC TCTCGGCTGC GGTGGTCGGT TTCATCGGCT ATCAGTCCGG ACGGTCCTCG     180

CTGCGCGCAT CGGTGTTCGA CCGCCTCACC GACATCCGCG AGTCGCAGTC GCGCGGGTTG     240

GAGAATCAGT TCGCGGACCT GAAGAACTCG ATGGTGATTT ACTCGCGCGG CAGCACTGCC     300

ACGGAGGCGA TCGGCGCGTT CAGCGACGGT TTCCGTCAGC TCGGCGATGC GACGATCAAT     360

ACCGGGCAGG CGGCGTCATT GCGCCGTTAC TACGACCGGA CGTTCGCCAA CACCACCCTC     420
```

```
GACGACAGCG GAAACCGCGT CGACGTCCGC GCGCTCATCC CGAAATCCAA CCCCCAGCGC   480

TATCTGCAGG CGCTCTATAC CCCGCCGTTT CAGAACTGGG AGAAGGCGAT CGCGTTCGAC   540

GACGCGCGCG ACGGCAGCGC CTGGTCGGCC GCCAATGCCA GATTCAACGA GTTCTTCCGC   600

GAGATCGTGC ACCGCTTCAA CTTCGAGGAT CTGATGCTGC TCGACCTCGA GGGCAACGTG   660

GTGTACTCCG CCTACAAGGG GCCGGATCTC GGGACAAACA TCGTCAACGG CCCCTATCGC   720

AACCGGGAAC TGTCGGAAGC CTACGAGAAG GCGGTCGCGT CGAACTCGAT CGACTATGTC   780

GGTGTCACCG ACTTCGGGTG GTACCTGCCT GCCGAGGAAC CGACCGCCTG GTTCCTGTCC   840

CCGGTCGGGT TGAAGGACCG AGTCGACGGT GTGATGGCGG TCCAGTTCCC CGGAATTC    898
```

(2) INFORMATION FOR SEQ ID NO:123:

(i) SEQUENCE CHARACTERISTICS:
        (A) LENGTH: 1259 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:123:

```
CGCAATTGAT GACGGCGCGG GGACAGTGGC GTGACACCGG GATGGGAGAC ACCGGTGAGA    60

CCATCCTGGT CGGACCGGAC AATCTGATGC GCTCGGACTC CCGGCTGTTC CGCGAGAACC   120

GGGAGAAGTT CCTGGCCGAC GTCGTCGAGG GGGGAACCCC GCCGGAGGTC GCCGACGAAT   180

CGGTTGACCG CCGCGGCACC ACGCTGGTGC AGCCGGTGAC CACCCGCTCC GTCGAGGAGG   240

CCCAACGCGG CAACACCGGG ACGACGATCG AGGACGACTA TCTCGGCCAC GAGGCGTTAC   300

AGGCGTACTC ACCGGTGGAC CTGCCGGGAC TGCACTGGGT GATCGTGGCC AAGATCGACA   360

CCGACGAGGC GTTCGCCCCG GTGGCGCAGT TCACCAGGAC CCTGGTGCTG TCGACGGTGA   420

TCATCATCTT CGGCGTGTCG CTGGCGGCCA TGCTGCTGGC GCGGTTGTTC GTCCGTCCGA   480

TCCGGCGGTT GCAGGCCGGC GCCCAGCAGA TCAGCGGCGG TGACTACCGC CTCGCTCTGC   540

CGGTGTTGTC TCGTGACGAA TTCGGCGATC TGACAACAGC TTTCAACGAC ATGAGTCGCA   600

ATCTGTCGAT CAAGGACGAG CTGCTCGGCG AGGAGCGCGC CGAGAACCAA CGGCTGATGC   660

TGTCCCTGAT GCCCGAACCG GTGATGCAGC GCTACCTCGA CGGGGAGGAG ACGATCGCCC   720

AGGACCACAA GAACGTCACG GTGATCTTCG CCGACATGAT GGGCCTCGAC GAGTTGTCGC   780

GCATGTTGAC CTCCGAGGAA CTGATGGTGG TGGTCAACGA CCTGACCCGC CAGTTCGACG   840

CCGCCGCCGA GAGTCTCGGG GTCGACCACG TGCGGACGCT GCACGACGGG TACCTGGCCA   900

GCTGCGGGTT AGGCGTGCCG CGGCTGGACA ACGTCCGGCG CACGGTCAAT TTCGCGATCG   960

AAATGGACCG CATCATCGAC CGGCACGCCG CCGAGTCCGG GCACGACCTG CGGCTCCGCG  1020

CGGGCATCGA CACCGGGTCG GCGGCCAGCG GGCTGGTGGG GCGGTCCACG TTGGCGTACG  1080

ACATGTGGGG TTCGCGCGGTC GATGTCGCCT ACCAGGTGCA GCGCGGCTCC CCCCAGCCCG  1140

GCATCTACGT CACCTCGCGG GTGCACGAGG TCATGCAGGA AACTCTCGAC TTCGTCGCCG  1200

CCGGGGAGGT CGTCGGCGAG CGCGGCGTCG AGACGGTCTG GCGGTTGCAG GGCCACCCG   1259
```

(2) INFORMATION FOR SEQ ID NO:124:

(i) SEQUENCE CHARACTERISTICS:
        (A) LENGTH: 299 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:124:

```
Met Thr Ile Leu Pro Trp Asn Ala Arg Thr Ser Glu His Pro Thr Arg
 1               5                  10                  15

Lys Arg Arg Gly Arg Tyr His Leu Leu Ser Arg Met Ser Ile Gln Ser
                20                  25                  30

Lys Leu Leu Leu Met Leu Leu Leu Thr Ser Ile Leu Ser Ala Ala Val
            35                  40                  45

Val Gly Phe Ile Gly Tyr Gln Ser Gly Arg Ser Ser Leu Arg Ala Ser
 50                  55                  60

Val Phe Asp Arg Leu Thr Asp Ile Arg Glu Ser Gln Ser Arg Gly Leu
65                  70                  75                  80

Glu Asn Gln Phe Ala Asp Leu Lys Asn Ser Met Val Ile Tyr Ser Arg
                85                  90                  95

Gly Ser Thr Ala Thr Glu Ala Ile Gly Ala Phe Ser Asp Gly Phe Arg
            100                 105                 110

Gln Leu Gly Asp Ala Thr Ile Asn Thr Gly Gln Ala Ala Ser Leu Arg
        115                 120                 125

Arg Tyr Tyr Asp Arg Thr Phe Ala Asn Thr Thr Leu Asp Asp Ser Gly
    130                 135                 140

Asn Arg Val Asp Val Arg Ala Leu Ile Pro Lys Ser Asn Pro Gln Arg
145                 150                 155                 160

Tyr Leu Gln Ala Leu Tyr Thr Pro Pro Phe Gln Asn Trp Glu Lys Ala
                165                 170                 175

Ile Ala Phe Asp Asp Ala Arg Asp Gly Ser Ala Trp Ser Ala Ala Asn
            180                 185                 190

Ala Arg Phe Asn Glu Phe Phe Arg Glu Ile Val His Arg Phe Asn Phe
        195                 200                 205

Glu Asp Leu Met Leu Leu Asp Leu Glu Gly Asn Val Val Tyr Ser Ala
    210                 215                 220

Tyr Lys Gly Pro Asp Leu Gly Thr Asn Ile Val Asn Gly Pro Tyr Arg
225                 230                 235                 240

Asn Arg Glu Leu Ser Glu Ala Tyr Glu Lys Ala Val Ala Ser Asn Ser
                245                 250                 255

Ile Asp Tyr Val Gly Val Thr Asp Phe Gly Trp Tyr Leu Pro Ala Glu
            260                 265                 270

Glu Pro Thr Ala Trp Phe Leu Ser Pro Val Gly Leu Lys Asp Arg Val
        275                 280                 285

Asp Gly Val Met Ala Val Gln Phe Pro Gly Ile
    290                 295
```

(2) INFORMATION FOR SEQ ID NO:125:

(i) SEQUENCE CHARACTERISTICS:
        (A) LENGTH: 419 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:125:

```
Gln Leu Met Thr Ala Arg Gly Gln Trp Arg Asp Thr Gly Met Gly Asp
 1               5                  10                  15

Thr Gly Glu Thr Ile Leu Val Gly Pro Asp Asn Leu Met Arg Ser Asp
                20                  25                  30
```

-continued

Ser Arg Leu Phe Arg Glu Asn Arg Glu Lys Phe Leu Ala Asp Val Val
        35                  40                  45

Glu Gly Gly Thr Pro Pro Glu Val Ala Asp Glu Ser Val Asp Arg Arg
    50                  55                  60

Gly Thr Thr Leu Val Gln Pro Val Thr Thr Arg Ser Val Glu Glu Ala
65                  70                  75                  80

Gln Arg Gly Asn Thr Gly Thr Thr Ile Glu Asp Asp Tyr Leu Gly His
                85                  90                  95

Glu Ala Leu Gln Ala Tyr Ser Pro Val Asp Leu Pro Gly Leu His Trp
            100                 105                 110

Val Ile Val Ala Lys Ile Asp Thr Asp Glu Ala Phe Ala Pro Val Ala
            115                 120                 125

Gln Phe Thr Arg Thr Leu Val Leu Ser Thr Val Ile Ile Phe Gly
            130                 135                 140

Val Ser Leu Ala Ala Met Leu Leu Ala Arg Leu Phe Val Arg Pro Ile
145                 150                 155                 160

Arg Arg Leu Gln Ala Gly Ala Gln Gln Ile Ser Gly Gly Asp Tyr Arg
                165                 170                 175

Leu Ala Leu Pro Val Leu Ser Arg Asp Glu Phe Gly Asp Leu Thr Thr
            180                 185                 190

Ala Phe Asn Asp Met Ser Arg Asn Leu Ser Ile Lys Asp Glu Leu Leu
            195                 200                 205

Gly Glu Glu Arg Ala Glu Asn Gln Arg Leu Met Leu Ser Leu Met Pro
            210                 215                 220

Glu Pro Val Met Gln Arg Tyr Leu Asp Gly Glu Glu Thr Ile Ala Gln
225                 230                 235                 240

Asp His Lys Asn Val Thr Val Ile Phe Ala Asp Met Met Gly Leu Asp
                245                 250                 255

Glu Leu Ser Arg Met Leu Thr Ser Glu Glu Leu Met Val Val Val Asn
                260                 265                 270

Asp Leu Thr Arg Gln Phe Asp Ala Ala Ala Glu Ser Leu Gly Val Asp
            275                 280                 285

His Val Arg Thr Leu His Asp Gly Tyr Leu Ala Ser Cys Gly Leu Gly
            290                 295                 300

Val Pro Arg Leu Asp Asn Val Arg Arg Thr Val Asn Phe Ala Ile Glu
305                 310                 315                 320

Met Asp Arg Ile Ile Asp Arg His Ala Ala Glu Ser Gly His Asp Leu
                325                 330                 335

Arg Leu Arg Ala Gly Ile Asp Thr Gly Ser Ala Ala Ser Gly Leu Val
            340                 345                 350

Gly Arg Ser Thr Leu Ala Tyr Asp Met Trp Gly Ser Ala Val Asp Val
            355                 360                 365

Ala Tyr Gln Val Gln Arg Gly Ser Pro Gln Pro Gly Ile Tyr Val Thr
            370                 375                 380

Ser Arg Val His Glu Val Met Gln Glu Thr Leu Asp Phe Val Ala Ala
385                 390                 395                 400

Gly Glu Val Val Gly Glu Arg Gly Val Glu Thr Val Trp Arg Leu Gln
                405                 410                 415

Gly His Pro (2) INFORMATION FOR SEQ ID NO:126:

(i) SEQUENCE CHARACTERISTICS:
        (A) LENGTH: 27 base pairs (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:126:

CCGGATCCGA TGAGCAGCGT GCTGAAC                                              27

(2) INFORMATION FOR SEQ ID NO:127:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:127:

GCGGATCCCA CGGCCCCGAT CACGTG                                               26

(2) INFORMATION FOR SEQ ID NO:128:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:128:

CCGGATCCAA TGACATTTCT GCCCTGGAAT GCG                                       33

(2) INFORMATION FOR SEQ ID NO:129:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:129:

CCGGATCCAT TCGGTGGCCC TGCAACCGCC AG                                        32

(2) INFORMATION FOR SEQ ID NO:130:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:130:

CCGGATCCGG AGCAACCGTT CCGGCTC                                              27

(2) INFORMATION FOR SEQ ID NO:131:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:131:

CCGGATCCCG GCTATCAGTC CGGACGG                                                27

(2) INFORMATION FOR SEQ ID NO:132:

(i) SEQUENCE CHARACTERISTICS:
        (A) LENGTH: 844 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:132:

```
GAGCAACCGT TCCGGCTCGG CGACTGGATC ACCGTCCCCA CCGCGGCGGG CCGGCCGTCC    60

GCCCACGGCC GCGTGGTGGA AGTCAACTGG CGTGCAACAC ATATCGACAC CGGCGGCAAC   120

CTGCTGGTAA TGCCCAACGC CGAACTCGCC GGCGCGTCGT TCACCAATTA CAGCCGGCCC   180

GTGGGAGAGC ACCGGCTGAC CGTCGTCACC ACCTTCAACG CCGCGGACAC CCCCGATGAT   240

GTCTGCGAGA TGCTGTCGTC GGTCGCGGCG TCGCTGCCCG AACTGCGCAC CGACGGACAG   300

ATCGCCACGC TCTATCTCGG TGCGGCCGAA TACGAGAAGT CGATCCCGTT GCACACACCC   360

GCGGTGGACG ACTCGGTCAG GAGCACGTAC CTGCGATGGG TCTGGTACGC CGCGCGCCGG   420

CAGGAACTTC GCCTAACGGC GTCGCCGACG ATTCGACACG CCGGAACGGA TCGCCTCGGC   480

CATGCGGGCT GTGGCGTCCA CACTGCGCTT GGCAGACGAC GAACAGCAGG AGATCGCCGA   540

CGTGGTGCGT CTGGTCCGTT ACGGCAACGG GGAACGCCTC CAGCAGCCGG GTCAGGTACC   600

GACCGGGATG AGGTTCATCG TAGACGGCAG GGTGAGTCTG TCCGTGATCG ATCAGGACGG   660

CGACGTGATC CCGGCGCGGG TGCTCGAGCG TGGCGACTTC CTGGGGCAGA CCACGCTGAC   720

GCGGGAACCG GTACTGGCGA CCGCGCACGC GCTGGAGGAA GTCACCGTGC TGGAGATGGC   780

CCGTGACGAG ATCGAGCGCC TGGTGCACCG AAAGCCGATC CTGCTGCACG TGATCGGGGC   840

CGTG                                                                844
```

(2) INFORMATION FOR SEQ ID NO:133:

(i) SEQUENCE CHARACTERISTICS:
        (A) LENGTH: 742 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:133:

```
GGCTATCAGT CCGGACGGTC CTCGCTGCGC GCATCGGTGT TCGACCGCCT CACCGACATC    60

CGCGAGTCGC AGTCGCGCGG GTTGGAGAAT CAGTTCGCGG ACCTGAAGAA CTCGATGGTG   120

ATTTACTCGC GCGGCAGCAC TGCCACGGAG GCGATCGGCG CGTTCAGCGA CGGTTTCCGT   180

CAGCTCGGCG ATGCGACGAT CAATACCGGG CAGGCGGCGT CATTGCGCCG TTACTACGAC   240

CGGACGTTCG CCAACACCAC CCTCGACGAC AGCGGAAACC GCGTCGACGT CCGCGCGCTC   300

ATCCCGAAAT CCAACCCCCA GCGCTATCTG CAGGCGCTCT ATACCCCGCC GTTTCAGAAC   360

TGGGAGAAGG CGATCGCGTT CGACGACGCG CGCGACGGCA GCGCCTGGTC GGCCGCCAAT   420

GCCAGATTCA ACGAGTTCTT CCGCGAGATC GTGCACCGCT TCAACTTCGA GGATCTGATG   480

CTGCTCGACC TCGAGGGCAA CGTGGTGTAC TCCGCCTACA AGGGGCCGGA TCTCGGGACA   540

AACATCGTCA ACGGCCCCTA TCGCAACCGG GAACTGTCGG AAGCCTACGA GAAGGCGGTC   600
```

```
GCGTCGAACT CGATCGACTA TGTCGGTGTC ACCGACTTCG GGTGGTACCT GCCTGCCGAG    660

GAACCGACCG CCTGGTTCCT GTCCCCGGTC GGGTTGAAGG ACCGAGTCGA CGGTGTGATG    720

GCGGTCCAGT TCCCCGGAAT TC                                              742
```

(2) INFORMATION FOR SEQ ID NO:134:

(i) SEQUENCE CHARACTERISTICS:
        (A) LENGTH: 282 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:134:

```
Glu Gln Pro Phe Arg Leu Gly Asp Trp Ile Thr Val Pro Thr Ala Ala
  1               5                  10                  15

Gly Arg Pro Ser Ala His Gly Arg Val Glu Val Asn Trp Arg Ala
             20                  25                  30

Thr His Ile Asp Thr Gly Gly Asn Leu Leu Val Met Pro Asn Ala Glu
             35                  40                  45

Leu Ala Gly Ala Ser Phe Thr Asn Tyr Ser Arg Pro Val Gly Glu His
 50                  55                  60

Arg Leu Thr Val Val Thr Thr Phe Asn Ala Ala Asp Thr Pro Asp Asp
 65                  70                  75                  80

Val Cys Glu Met Leu Ser Ser Val Ala Ala Ser Leu Pro Glu Leu Arg
                 85                  90                  95

Thr Asp Gly Gln Ile Ala Thr Leu Tyr Leu Gly Ala Ala Glu Tyr Glu
                100                 105                 110

Lys Ser Ile Pro Leu His Thr Pro Ala Val Asp Asp Ser Val Arg Ser
                115                 120                 125

Thr Tyr Leu Arg Trp Val Trp Tyr Ala Ala Arg Arg Gln Glu Leu Arg
                130                 135                 140

Xaa Asn Gly Val Ala Asp Xaa Phe Asp Thr Pro Glu Arg Ile Ala Ser
145                 150                 155                 160

Ala Met Arg Ala Val Ala Ser Thr Leu Arg Leu Ala Asp Asp Glu Gln
                165                 170                 175

Gln Glu Ile Ala Asp Val Val Arg Leu Val Arg Tyr Gly Asn Gly Glu
                180                 185                 190

Arg Leu Gln Gln Pro Gly Gln Val Pro Thr Gly Met Arg Phe Ile Val
                195                 200                 205

Asp Gly Arg Val Ser Leu Ser Val Ile Asp Gln Asp Gly Asp Val Ile
                210                 215                 220

Pro Ala Arg Val Leu Glu Arg Gly Asp Phe Leu Gly Gln Thr Thr Leu
225                 230                 235                 240

Thr Arg Glu Pro Val Leu Ala Thr Ala His Ala Leu Glu Glu Val Thr
                245                 250                 255

Val Leu Glu Met Ala Arg Asp Glu Ile Glu Arg Leu Val His Arg Lys
                260                 265                 270

Pro Ile Leu Leu His Val Ile Gly Ala Val
                275                 280
```

(2) INFORMATION FOR SEQ ID NO:135:

(i) SEQUENCE CHARACTERISTICS:
        (A) LENGTH: 247 amino acids
        (B) TYPE: amino acid (C) STRANDEDNESS: single
(D) TOPOLOGY: linear (ii) MOLECULE TYPE: protein (xi) SEQUENCE DESCRIPTION: SEQ ID NO:135:

| | | | | | | | | | | | | | | |
|---|---|---|---|---|---|---|---|---|---|---|---|---|---|---|
| Gly | Tyr | Gln | Ser | Gly | Arg | Ser | Ser | Leu | Arg | Ala | Ser | Val | Phe | Asp | Arg |
| 1 | | | | 5 | | | | | 10 | | | | | 15 |

Leu Thr Asp Ile Arg Glu Ser Gln Ser Arg Gly Leu Glu Asn Gln Phe
            20                  25                  30

Ala Asp Leu Lys Asn Ser Met Val Ile Tyr Ser Arg Gly Ser Thr Ala
            35                  40                  45

Thr Glu Ala Ile Gly Ala Phe Ser Asp Gly Phe Arg Gln Leu Gly Asp
            50                  55                  60

Ala Thr Ile Asn Thr Gly Gln Ala Ala Ser Leu Arg Arg Tyr Tyr Asp
65                  70                  75                  80

Arg Thr Phe Ala Asn Thr Thr Leu Asp Asp Ser Gly Asn Arg Val Asp
                85                  90                  95

Val Arg Ala Leu Ile Pro Lys Ser Asn Pro Gln Arg Tyr Leu Gln Ala
                100                 105                 110

Leu Tyr Thr Pro Pro Phe Gln Asn Trp Glu Lys Ala Ile Ala Phe Asp
            115                 120                 125

Asp Ala Arg Asp Gly Ser Ala Trp Ser Ala Ala Asn Ala Arg Phe Asn
            130                 135                 140

Glu Phe Phe Arg Glu Ile Val His Arg Phe Asn Phe Glu Asp Leu Met
145                 150                 155                 160

Leu Leu Asp Leu Glu Gly Asn Val Val Tyr Ser Ala Tyr Lys Gly Pro
                165                 170                 175

Asp Leu Gly Thr Asn Ile Val Asn Gly Pro Tyr Arg Asn Arg Glu Leu
                180                 185                 190

Ser Glu Ala Tyr Glu Lys Ala Val Ala Ser Asn Ser Ile Asp Tyr Val
                195                 200                 205

Gly Val Thr Asp Phe Gly Trp Tyr Leu Pro Ala Glu Glu Pro Thr Ala
            210                 215                 220

Trp Phe Leu Ser Pro Val Gly Leu Lys Asp Arg Val Asp Gly Val Met
225                 230                 235                 240

Ala Val Gln Phe Pro Gly Ile
                245

(2) INFORMATION FOR SEQ ID NO:136:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:136:

ATGAGCGAAA TCGCCCGNCC CTGGCGGGTT CTGGCATGTG GCATC                45

(2) INFORMATION FOR SEQ ID NO:137:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:137:

```
GCCACCGGCG GCGCCGCCGC GGTGCCCGCC GGGGTGAGCG CCCCGGCGGT CGCGCCGGCC     60

CCCGCGATGC CGCCCGCCC GGTGTCCACG ATCGCGCCGG CGACCTCGGG CACGCTCAGC    120

GAGTTTTTCG CCGCCAAGGG CGTCACGATG GAGCCGCAGT CCAGCCGCGA CTTCCGCGCC   180

CTCAACATCG TGCTGCCGAA GCCGCGGGGC TGGGAGCACA TCCCGGACCC GAACGTGCCG   240

GACGCGTTCG CGGTGCTGGC CGACCGGGTC AGNGGTAAAG GTCAGNAGTC GACAAACGCC   300

CACGTGGTGG TCGACAAACA CGTAGGCGAG TTCGACGGCA                         340
```

(2) INFORMATION FOR SEQ ID NO:138:

(i) SEQUENCE CHARACTERISTICS:
        (A) LENGTH: 235 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:138:

```
GGTGACCACC AGCGTNGAAC AGGTCGTTGC CGAAGCCGCG GAGGCCACCG ACGCGATTGT     60

CAACGGCTTC AAGGTCAGCG TTCCGGGTCC GGGTCCGGCC GCACCGCCAC CTGCACCCGG   120

TGCCCCCGGT GTCCCGCCCG CCCCGGCGC CCCGGCGCTG CCGCTGGCCG TCGCACCACC    180

CCCGGCTCCC GCTGTTCCCG CCGTGGCGCC CGCGCCACAG CTGCTGGGAC TGCAG        235
```

(2) INFORMATION FOR SEQ ID NO:139:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:139:

```
Met Ser Glu Ile Ala Arg Pro Trp Arg Val Leu Ala Cys Gly Ile
 1               5                  10                  15
```

(2) INFORMATION FOR SEQ ID NO:140:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:140:

```
Ala Thr Gly Gly Ala Ala Ala Val Pro Ala Gly Val Ser Ala Pro Ala
 1               5                  10                  15

Val Ala Pro Ala Pro Ala Met Pro Ala Arg Pro Val Ser Thr Ile Ala
                20                  25                  30

Pro Ala Thr Ser Gly Thr Leu Ser Glu Phe Phe Ala Ala Lys Gly Val
                35                  40                  45

Thr Met Glu Pro Gln Ser Ser Arg Asp Phe Arg Ala Leu Asn Ile Val
                50                  55                  60

Leu Pro Lys Pro Arg Gly Trp Glu His Ile Pro Asp Pro Asn Val Pro
65                  70                  75                  80
```

Asp Ala Phe Ala Val Leu Ala Asp Arg Val Gly Gly Lys Gly Gln Xaa
            85                  90                  95

Ser Thr Asn Ala His Val Val Asp Lys His Val Gly Glu Phe Asp
            100                 105                 110

Gly (2) INFORMATION FOR SEQ ID NO:141:

(i) SEQUENCE CHARACTERISTICS:
        (A) LENGTH: 73 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:141:

Val Thr Thr Ser Val Glu Gln Val Val Ala Ala Asp Ala Thr Glu
1               5                   10                  15

Ala Ile Val Asn Gly Phe Lys Val Ser Val Pro Gly Pro Gly Pro Ala
            20                  25                  30

Ala Pro Pro Pro Ala Pro Gly Ala Pro Gly Val Pro Pro Ala Pro Gly
            35                  40                  45

Ala Pro Ala Leu Pro Leu Ala Val Ala Pro Pro Ala Pro Ala Val
50                  55                  60

Pro Ala Val Ala Pro Ala Pro Gln Leu
65                  70

(2) INFORMATION FOR SEQ ID NO:142:

(i) SEQUENCE CHARACTERISTICS:
        (A) LENGTH: 273 base pairs
        (B) TYPE: nucleic acid
        (C) STRANDEDNESS: single
        (D) TOPOLOGY: linear (xi) SEQUENCE DESCRIPTION: SEQ ID NO:142:

GCGACCTACG TGCAGGGGGG TCTCGGCCGC ATCGAGGCCC GGGTGGCCGA CAGCGGATAC      60

AGCAACGCCG CGGCCAAGGG CTACTTCCCG CTGAGCTTCA CCGTCGCCGG CATCGACCAG     120

AACGGTCCGA TCGTGACCGC CAACGTCACC GCGGCGGCCC CGACGGGCGC CGTGGCCACC    180

CAGCCGCTGA CGTTCATCGC CGGGCCGAGC CCGACCGGAT GGCAGCTGTC CAAGCAGTCC    240

GCACTGGCCC TGATGTCCGC GGTCATCGCC GCA                                 273

(2) INFORMATION FOR SEQ ID NO:143:

(i) SEQUENCE CHARACTERISTICS:
        (A) LENGTH: 91 amino acids
        (B) TYPE: amino acid
        (C) STRANDEDNESS: single
        (D) TOPOLOGY: linear (xi) SEQUENCE DESCRIPTION: SEQ ID NO:143:

Ala Thr Tyr Val Gln Gly Gly Leu Gly Arg Ile Glu Ala Arg Val Ala
1               5                   10                  15

Asp Ser Gly Tyr Ser Asn Ala Ala Ala Lys Gly Tyr Phe Pro Leu Ser
            20                  25                  30

Phe Thr Val Ala Gly Ile Asp Gln Asn Gly Pro Ile Val Thr Ala Asn
            35                  40                  45

Val Thr Ala Ala Ala Pro Thr Gly Ala Val Ala Thr Gln Pro Leu Thr
50                  55                  60

```
Phe Ile Ala Gly Pro Ser Pro Thr Gly Trp Gln Leu Ser Lys Gln Ser
 65                  70                  75                  80

Ala Leu Ala Leu Met Ser Ala Val Ile Ala Ala
                 85                  90
```

(2) INFORMATION FOR SEQ ID NO:144:

(i) SEQUENCE CHARACTERISTICS:
        (A) LENGTH: 554 base pairs
        (B) TYPE: nucleic acid
        (C) STRANDEDNESS: single
        (D) TOPOLOGY: linear (xi) SEQUENCE DESCRIPTION: SEQ ID NO:144:

```
GATGTCACGC CCGGAGAATG TAACGTTCGA CCGGAGAACG CCGTCGGCAC AACGAGTTAC    60

GTTTGAGCAC TTCAGATCTC GGTTACCTTG GATTTCAGGC GGGGGAAGCA GTAACCGATC   120

CAAGATTCGA AGGACCCAAA CAACATGAAA TTCACTGGAA TGACCGTGCG CGCAAGCCGC   180

GCGCCCTGGC CGGCGTCGGG GCGGCATGTC TGTTCGGCGG CGTGGCCGCG GCAACCGTGG   240

CGGCACAGAT GGCGGGCGCC CAGCCGGCCG AGTGCAACGC CAGCTCACTC ACCGGCACCG   300

TCAGCTCGGT GACCGGTCAG GCGCGTCAGT ACCTAGACAC CCACCCGGGC GCCAACCAGG   360

CCGTCACCGC GGCGATGAAC CAGCCGCGGC CCGAGGCCGA GGCGAACCTG CGGGGCTACT   420

TCACCGCCAA CCCGGCGGAG TACTACGACC TGCGGGGCAT CCTCGCCCCG ATCGGTGACG   480

CGCAGCGCAA CTGCAACATC ACCGTGCTGC CGGTAGAGCT GCAGACGGCC TACGACACGT   540

TCATGGCCGG CTGA                                                    554
```

(2) INFORMATION FOR SEQ ID NO:145:

(i) SEQUENCE CHARACTERISTICS:
        (A) LENGTH: 136 amino acids
        (B) TYPE: amino acid
        (C) STRANDEDNESS: single
        (D) TOPOLOGY: linear (xi) SEQUENCE DESCRIPTION: SEQ ID NO:145:

```
Met Lys Phe Thr Gly Met Thr Val Arg Ala Ser Arg Arg Ala Leu Ala
  1               5                  10                  15

Gly Val Gly Ala Ala Cys Leu Phe Gly Gly Val Ala Ala Thr Val
                 20                  25                  30

Ala Ala Gln Met Ala Gly Ala Gln Pro Ala Glu Cys Asn Ala Ser Ser
                 35                  40                  45

Leu Thr Gly Thr Val Ser Ser Val Thr Gly Gln Ala Arg Gln Tyr Leu
 50                  55                  60

Asp Thr His Pro Gly Ala Asn Gln Ala Val Thr Ala Ala Met Asn Gln
 65                  70                  75                  80

Pro Arg Pro Glu Ala Glu Ala Asn Leu Arg Gly Tyr Phe Thr Ala Asn
                 85                  90                  95

Pro Ala Glu Tyr Tyr Asp Leu Arg Gly Ile Leu Ala Pro Ile Gly Asp
                100                 105                 110

Ala Gln Arg Asn Cys Asn Ile Thr Val Leu Pro Val Glu Leu Gln Thr
                115                 120                 125

Ala Tyr Asp Thr Phe Met Ala Gly
                130                 135
```

(2) INFORMATION FOR SEQ ID NO:146:

(i) SEQUENCE CHARACTERISTICS:
        (A) LENGTH: 808 base pairs (B) TYPE: nucleic acid
        (C) STRANDEDNESS: single
        (D) TOPOLOGY: linear (xi) SEQUENCE DESCRIPTION: SEQ ID NO:146:

```
CCAAGTGTGA CGCGNGTGTG ACGGTAGACG TTCCGACCAA TCCAACGACG CCGCAGCTGG     60

GAATCACCCG TGTGCCAATT CAGTGCGGGC AACGGTGTCC GTCCACGAAG GGATTCAGGA    120

AATGATGACA ACTCGCCGGA AGTCAGCCGC AGTGGCGGGA ATCGCTGCGG TGGCCATCCT    180

CGGTGCGGCC GCATGTTCGA GTGAGGACGG TGGGAGCACG GCCTCGTCGG CCAGCAGCAC    240

GGCCTCCTCC GCGATGGAGT CCGCGACCGA CGAGATGACC ACGTCGTCGG CGGCCCCTTC    300

GGCCGACCCT GCGGCCAACC TGATCGGCTC CGGCTGCGCG GCCTACGCCG AGCAGGTCCC    360

CGAAGGTCCC GGGTCGGTGG CCGGGATGGC AGCCGATCCG GTGACGGTGG CGGCGTCGAA    420

CAACCCGATG CTGCAGACGC TGTCCCAGGC GCTGTCCGGC CAGCTCAATC CGCAGGTCAA    480

TCTCGTCGAC ACCCTCGACG GCGGTGAGTT CACCGTGTTC GCGCCGACCG ACGACGCGTT    540

CGCCAAGATC GATCCGGCCA CGCTGGAGAC CCTCAAGACG GACTCCGACA TGCTGACCAA    600

CATCCTGACC TACCACGTCG TGCCCGGCCA GGCCGCGCCC GATCAGGTGG TCGGCGAGCA    660

TGTGACGGTG GAGGGGGCGC CGGTCACGGT GTCCGGGATG GCCGACCAGC TCAAGGTCAA    720

CGACGCGTCG GTGGTGTGCG GTGGGGTGCA GACCGCCAAC GCGACGGTGT ATCTGATCGA    780

CACCGTGCTG ATGCCGCCGG CAGCGTAG                                      808
```

(2) INFORMATION FOR SEQ ID NO:147:

(i) SEQUENCE CHARACTERISTICS:
        (A) LENGTH: 228 amino acids
        (B) TYPE: amino acid
        (C) STRANDEDNESS: single
        (D) TOPOLOGY: linear (xi) SEQUENCE DESCRIPTION: SEQ ID NO:147:

```
Met Met Thr Thr Arg Arg Lys Ser Ala Ala Val Ala Gly Ile Ala Ala
 1               5                  10                  15

Val Ala Ile Leu Gly Ala Ala Ala Cys Ser Ser Glu Asp Gly Gly Ser
            20                  25                  30

Thr Ala Ser Ser Ala Ser Ser Thr Ala Ser Ser Ala Met Glu Ser Ala
        35                  40                  45

Thr Asp Glu Met Thr Thr Ser Ser Ala Ala Pro Ser Ala Asp Pro Ala
    50                  55                  60

Ala Asn Leu Ile Gly Ser Gly Cys Ala Ala Tyr Ala Glu Gln Val Pro
65                  70                  75                  80

Glu Gly Pro Gly Ser Val Ala Gly Met Ala Ala Asp Pro Val Thr Val
                85                  90                  95

Ala Ala Ser Asn Asn Pro Met Leu Gln Thr Leu Ser Gln Ala Leu Ser
            100                 105                 110

Gly Gln Leu Asn Pro Gln Val Asn Leu Val Asp Thr Leu Asp Gly Gly
        115                 120                 125

Glu Phe Thr Val Phe Ala Pro Thr Asp Asp Ala Phe Ala Lys Ile Asp
    130                 135                 140

Pro Ala Thr Leu Glu Thr Leu Lys Thr Asp Ser Asp Met Leu Thr Asn
145                 150                 155                 160

Ile Leu Thr Tyr His Val Val Pro Gly Gln Ala Ala Pro Asp Gln Val
                165                 170                 175

Val Gly Glu His Val Thr Val Glu Gly Ala Pro Val Thr Val Ser Gly
            180                 185                 190
```

```
Met Ala Asp Gln Leu Lys Val Asn Asp Ala Ser Val Val Cys Gly Gly
        195                 200                 205

Val Gln Thr Ala Asn Ala Thr Val Tyr Leu Ile Asp Thr Val Leu Met
    210                 215                 220

Pro Pro Ala Ala
225
```

(2) INFORMATION FOR SEQ ID NO:148:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:148:

```
GCSCCSGTSG GNCCGGNTGY GC                                        22
```

(2) INFORMATION FOR SEQ ID NO:149:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:149:

```
RTASGCSGCN GTNGCNACNG G                                         21
```

(2) INFORMATION FOR SEQ ID NO:150:

(i) SEQUENCE CHARACTERISTICS:
        (A) LENGTH: 102 base pairs
        (B) TYPE: nucleic acid
        (C) STRANDEDNESS: single
        (D) TOPOLOGY: linear (xi) SEQUENCE DESCRIPTION: SEQ ID NO:150:

```
GCCCCCGTCG GCCCCGGCTG TGCGGCCTAC GTGCAACAGG TGCCGGACGG GCCGGGATCG    60

GTGCAGGGCA TGGCGAGCTC GCCCGTAGCG ACCGCCGCGT AT                     102
```

(2) INFORMATION FOR SEQ ID NO:151:

(i) SEQUENCE CHARACTERISTICS:
        (A) LENGTH: 683 base pairs
        (B) TYPE: nucleic acid
        (C) STRANDEDNESS: single
        (D) TOPOLOGY: linear (xi) SEQUENCE DESCRIPTION: SEQ ID NO:151:

```
GCCCGCCAAC TAAAACCGCC GATCATCCAC TGCAGGAAGG AATCTCACGA TCATGAACAT    60

CAGCATGAAA ACTCTTGCCG GAGCGGGTTT CGCGATGACC GCCGCCGTCG GTCTGTCGCT   120

GGGTACCGCA GGCAGCGCCG CAGCCGCGCC GGTCGGACCG GGGTGTGCGG CCTACGTGCA   180

ACAGGTGCCG GACGGGCCGG GATCGGTGCA GGGCATGGCG AGCTCGCCGG TGGCCACCGC   240

GGCGGCCGAC AACCCGCTGC TCACCACGCT CTCGCAGGCG ATCTCGGGTC AGCTCAACCC   300

GAACGTCAAT CTCGTCGACA CGTTCAACGG CGGCCAGTTC ACCGTGTTCG CGCCGACCAA   360

TGACGCCTTC GCCAAGATCG ATCCGGCCAC GCTGGAGACC CTCAAGACCG ATTCCGACCT   420

GCTGACCAAG ATCCTCACCT ACCACGTCGT GCCCGGCCAG GCCGCGCCCC ATCAGGTGGT   480

CGGCGAGCAT GTGACGGTGG AGGGGGCGCC GGTCACGGTG TCCGGGATGG CCGACCAGCT   540
```

5,985,287

167

168

-continued

```
CAAGGTCAAC GACGCGTCGG TGGTGTGCGG TGGGGTGCAG ACCGCCAACG CGACGGTGTA      600

TCTGATCGAC ACCGTGCTGA TGCCGCCGGC AGCGTAGCCG GGCGGCACCA CAGAAGAGGG      660

TCCCCCGCAC CCGGCCTCCC CCG                                             683
```

(2) INFORMATION FOR SEQ ID NO:152:

(i) SEQUENCE CHARACTERISTICS:
        (A) LENGTH: 231 amino acids
        (B) TYPE: amino acid
        (C) STRANDEDNESS: single
        (D) TOPOLOGY: linear (xi) SEQUENCE DESCRIPTION: SEQ ID NO:152:

```
Asp Thr Val Leu Met Pro Pro Ala Asn Asn Arg Ser Ser Thr Ala
 1               5                  10                  15

Gly Arg Asn Leu Thr Ile Met Asn Ile Ser Met Lys Thr Leu Ala Gly
                20                  25                  30

Ala Gly Phe Ala Met Thr Ala Ala Val Gly Leu Ser Leu Gly Thr Ala
            35                  40                  45

Gly Ser Ala Ala Ala Ala Pro Val Gly Pro Gly Cys Ala Ala Tyr Val
        50                  55                  60

Gln Gln Val Pro Asp Gly Pro Gly Ser Val Gln Gly Met Ala Ser Ser
65                  70                  75                  80

Pro Val Ala Thr Ala Ala Ala Asp Asn Pro Leu Leu Thr Thr Leu Ser
                85                  90                  95

Gln Ala Ile Ser Gly Gln Leu Asn Pro Asn Val Asn Leu Val Asp Thr
            100                 105                 110

Phe Asn Gly Gly Gln Phe Thr Val Phe Ala Pro Thr Asn Asp Ala Phe
        115                 120                 125

Ala Lys Ile Asp Pro Ala Thr Leu Glu Thr Leu Lys Thr Asp Ser Asp
    130                 135                 140

Leu Leu Thr Lys Ile Leu Thr Tyr His Val Val Pro Gly Gln Ala Ala
145                 150                 155                 160

Pro Asp Gln Val Val Gly Glu His Val Thr Val Glu Gly Ala Pro Val
                165                 170                 175

Thr Val Ser Gly Met Ala Asp Gln Leu Lys Val Asn Asp Ala Ser Val
            180                 185                 190

Val Cys Gly Gly Val Gln Thr Ala Asn Ala Thr Val Tyr Leu Ile Asp
        195                 200                 205

Thr Val Leu Met Pro Pro Ala Ala Pro Gly Gly Thr Thr Glu Glu Gly
    210                 215                 220

Pro Pro His Pro Ala Ser Pro
225                 230
```

(2) INFORMATION FOR SEQ ID NO:153:

(i) SEQUENCE CHARACTERISTICS:
        (A) LENGTH: 1125 base pairs
        (B) TYPE: nucleic acid
        (C) STRANDEDNESS: single
        (D) TOPOLOGY: linear (xi) SEQUENCE DESCRIPTION: SEQ ID NO:153:

```
ATGCAGGTGC GGCGTGTTCT GGGCAGTGTC GGTGCAGCAG TCGCGGTTTC GGCCGCGTTA       60

TGGCAGACGG GGGTTTCGAT ACCGACCGCC TCAGCGGATC CGTGTCCGGA CATCGAGGTG      120

ATCTTCGCGC GCGGGACCGG TGCGGAACCC GGCCTCGGGT GGGTCGGTGA TGCGTTCGTC      180

AACGCGCTGC GGCCCAAGGT CGGTGAGCAG TCGGTGGGCA CCTACGCGGT GAACTACCCG      240
```

```
GCAGGATTCG GACTTCGACA AATCGGCGCC CATGGGCGCG GCCGACGCAT CGGGGCGGGT    300

GCAGTGGATG GCCGACAACT GCCCGGACAC CAAGCTTGTC CTGGGCGGCA TGTCGCANGG    360

CGCCGGCGTC ATCGACCTGA TCACCGTCGA TCCGCGACCG CTGGGCCGGT TCACCCCCAC    420

CCCGATGCCG CCCCGCGTCG CCGACCACGT GGCCGCCGTT GTGGTCTTCG GAAATCCGTT    480

GCGCGACATC CGTGGTGGCG GTCCGCTGCC GCAGATGAGC GGCACCTACG GGCCGAAGTC    540

GATCGATCTG TGTGCGCTCG ACGATCCGTT CTGCTCGCCC GGCTTCAACC TGCCGGCCCA    600

CTTCGCCTAC GCCGACAACG GCATGGTGGA GGAAGCCGCG AACTTCGCCC GCCTGGAACC    660

GGGCCAGAGC GTCGAGCTGC CCGAGGCGCC CTACCTGCAC CTGTTCGTCC CGCGGGGCGA    720

GGTAACGCTG GAGGACGCCG GACCGCTGCG CGAAGGCGAC GCAGTGCGTT CACCGCATC     780

GGGCGGCCAG CGGGTGACCG CCACCGCGCC CGCGGAGATC CTCGTCTGGG AGATGCATGC    840

GGGACTCGGT GCGGCATAAG CGAATAGGAG TCCTGCTGGC CGGCGCAGCA CTGCTCGCCG    900

GATGCACATC CGAACCTGGA CCCGGGCCGT CGGCGGCACC GGCCCCGACG AGCACAACCG    960

AGAGCGCACC CGGTCCCGGA CTCGTCCCGG TGACCGTCGC GGTCGACGAA CCTCTGGCCG   1020

ACGCGCCGTT CGACCAGCCC CGGGAGGCCC TGGTGCCGCA GGGTTGGACG CTGTCGGTGT   1080

GGGCGCGGAC CGCCCGGCCG CGGCTGGCCG CGTGGGCCCC GGACG                   1125
```

(2) INFORMATION FOR SEQ ID NO:154:

(i) SEQUENCE CHARACTERISTICS:
        (A) LENGTH: 748 amino acids
        (B) TYPE: amino acid
        (C) STRANDEDNESS: single
        (D) TOPOLOGY: linear (xi) SEQUENCE DESCRIPTION: SEQ ID NO:154:

```
Met Gln Val Arg Arg Val Leu Gly Ser Val Gly Ala Ala Val Ala Val
 1               5                  10                  15

Ser Ala Ala Leu Trp Gln Thr Gly Val Ser Ile Pro Thr Ala Ser Ala
                20                  25                  30

Asp Pro Cys Pro Asp Ile Glu Val Ile Phe Ala Arg Gly Thr Gly Ala
            35                  40                  45

Glu Pro Gly Leu Gly Trp Val Gly Asp Ala Phe Val Asn Ala Leu Arg
        50                  55                  60

Pro Lys Val Gly Glu Gln Ser Val Gly Thr Tyr Ala Val Asn Tyr Pro
65                  70                  75                  80

Ala Gly Phe Asp Phe Asp Lys Ser Ala Pro Met Gly Ala Ala Asp Ala
                85                  90                  95

Ser Gly Arg Val Gln Trp Met Ala Asp Asn Cys Pro Asp Thr Lys Leu
            100                 105                 110

Val Leu Gly Gly Met Ser Xaa Gly Ala Gly Val Ile Asp Leu Ile Thr
        115                 120                 125

Val Asp Pro Arg Pro Leu Gly Arg Phe Thr Pro Thr Pro Met Pro Pro
    130                 135                 140

Arg Val Ala Asp His Val Ala Ala Val Val Phe Gly Asn Pro Leu
145                 150                 155                 160

Arg Asp Ile Arg Gly Gly Pro Arg Leu Glu Pro Arg Gly Leu Asn
                165                 170                 175

Met Glu Thr Ser Glu Arg Gly Leu Tyr Thr His Arg Thr Tyr Arg Gly
            180                 185                 190

Leu Tyr Pro Arg Leu Tyr Ser Ser Glu Arg Ile Leu Glu Ala Ser Pro
        195                 200                 205
```

-continued

```
Leu Glu Cys Tyr Ser Ala Leu Ala Leu Glu Ala Ser Pro Ala Ser Pro
    210                 215                 220

Pro Arg Pro His Glu Cys Tyr Ser Ser Glu Arg Pro Arg Gly Leu Tyr
225                 230                 235                 240

Pro His Glu Ala Ser Asn Leu Glu Pro Arg Ala Leu Ala His Ile Ser
                245                 250                 255

Pro His Glu Ala Leu Ala Thr Tyr Arg Ala Leu Ala Ala Ser Pro Ala
            260                 265                 270

Ser Asn Gly Leu Tyr Met Glu Thr Val Ala Leu Gly Leu Gly Leu Ala
        275                 280                 285

Leu Ala Ala Leu Ala Ala Ser Asn Pro His Glu Ala Leu Ala Ala Arg
    290                 295                 300

Gly Leu Glu Gly Leu Pro Arg Gly Leu Tyr Gly Leu Asn Ser Glu Arg
305                 310                 315                 320

Val Ala Leu Gly Leu Leu Glu Pro Arg Gly Leu Ala Leu Ala Pro Arg
                325                 330                 335

Thr Tyr Arg Leu Glu His Ile Ser Leu Glu Pro His Glu Val Ala Leu
            340                 345                 350

Pro Arg Ala Arg Gly Gly Leu Tyr Gly Leu Val Ala Leu Thr His Arg
            355                 360                 365

Leu Glu Gly Leu Ala Ser Pro Ala Leu Ala Gly Leu Tyr Pro Arg Leu
    370                 375                 380

Glu Ala Arg Gly Gly Leu Gly Leu Tyr Ala Ser Pro Ala Leu Ala Val
385                 390                 395                 400

Ala Leu Ala Arg Gly Pro His Glu Thr His Arg Ala Leu Ala Ser Glu
                405                 410                 415

Arg Gly Leu Tyr Gly Leu Tyr Gly Leu Asn Ala Arg Gly Val Ala Leu
            420                 425                 430

Thr His Arg Ala Leu Ala Thr His Arg Ala Leu Ala Pro Arg Ala Leu
        435                 440                 445

Ala Gly Leu Ile Leu Glu Leu Glu Val Ala Leu Thr Arg Pro Gly Leu
    450                 455                 460

Met Glu Thr His Ile Ser Ala Leu Ala Gly Leu Tyr Leu Glu Gly Leu
465                 470                 475                 480

Tyr Ala Leu Ala Ala Leu Ala Ala Leu Ala Ala Ser Asn Ala Arg Gly
                485                 490                 495

Ser Glu Arg Pro Arg Ala Leu Ala Gly Leu Tyr Ala Arg Gly Ala Arg
            500                 505                 510

Gly Ser Glu Arg Thr His Arg Ala Leu Ala Ala Arg Gly Ala Arg Gly
        515                 520                 525

Met Glu Thr His Ile Ser Ile Leu Glu Ala Arg Gly Thr His Arg Thr
    530                 535                 540

Arg Pro Thr His Arg Ala Arg Gly Ala Leu Ala Val Ala Leu Gly Leu
545                 550                 555                 560

Tyr Gly Leu Tyr Thr His Arg Gly Leu Tyr Pro Arg Ala Ser Pro Gly
                565                 570                 575

Leu His Ile Ser Ala Ser Asn Ala Arg Gly Gly Leu Ala Arg Gly Thr
            580                 585                 590

His Arg Ala Arg Gly Ser Glu Arg Ala Arg Gly Thr His Arg Ala Arg
        595                 600                 605

Gly Pro Arg Gly Leu Tyr Ala Ser Pro Ala Arg Gly Ala Arg Gly Gly
    610                 615                 620
```

| | | | | | | | | | | | | | | |
|---|---|---|---|---|---|---|---|---|---|---|---|---|---|---|
|Leu|Tyr|Ala|Arg|Gly|Ala|Arg|Gly|Thr|His|Arg|Ser|Glu|Arg|Gly|Leu|
|625| | | | |630| | | | |635| | | | |640|

| | | | | | | | | | | | | | | |
|---|---|---|---|---|---|---|---|---|---|---|---|---|---|---|
|Tyr|Ala|Arg|Gly|Ala|Arg|Gly|Ala|Leu|Ala|Val|Ala|Leu|Ala|Arg|Gly|
| | | | |645| | | | |650| | | | |655| |

| | | | | | | | | | | | | | | |
|---|---|---|---|---|---|---|---|---|---|---|---|---|---|---|
|Pro|Arg|Ala|Leu|Ala|Pro|Arg|Gly|Leu|Tyr|Gly|Leu|Tyr|Pro|Arg|Gly|
| | | |660| | | | |665| | | | |670| | |

| | | | | | | | | | | | | | |
|---|---|---|---|---|---|---|---|---|---|---|---|---|---|
|Leu|Tyr|Ala|Leu|Ala|Ala|Leu|Ala|Gly|Leu|Tyr|Leu|Glu|Ala|Ser|Pro|
| | |675| | | | |680| | | | |685| | |

| | | | | | | | | | | | | | | |
|---|---|---|---|---|---|---|---|---|---|---|---|---|---|---|
|Ala|Leu|Ala|Val|Ala|Leu|Gly|Leu|Tyr|Val|Ala|Leu|Gly|Leu|Tyr|Ala|
| |690| | | | |695| | | | |700| | | | |

| | | | | | | | | | | | | | | |
|---|---|---|---|---|---|---|---|---|---|---|---|---|---|---|
|Leu|Ala|Ala|Ser|Pro|Ala|Arg|Gly|Pro|Arg|Ala|Leu|Ala|Ala|Leu|Ala|
|705| | | | |710| | | | |715| | | | |720|

| | | | | | | | | | | | | | | |
|---|---|---|---|---|---|---|---|---|---|---|---|---|---|---|
|Ala|Leu|Ala|Gly|Leu|Tyr|Ala|Arg|Gly|Val|Ala|Leu|Gly|Leu|Tyr|Pro|
| | | |725| | | | |730| | | | |735| | |

| | | | | | | | | |
|---|---|---|---|---|---|---|---|---|
|Arg|Gly|Leu|Tyr|Ala|Arg|Gly|Pro|Arg|Gly|Leu|Tyr|
| | | |740| | | | |745| | | |

(2) INFORMATION FOR SEQ ID NO:155:

(i) SEQUENCE CHARACTERISTICS:
        (A) LENGTH: 1012 base pairs
        (B) TYPE: nucleic acid
        (C) STRANDEDNESS: single
        (D) TOPOLOGY: linear (xi) SEQUENCE DESCRIPTION: SEQ ID NO:155:

```
ATGAAGGCAA ATCATTCGGG ATGCTACAAA TCCGCCGGCC CGATATGGTC GCATCCATCG     60

CCGCTTTGTT CGCCCGCACT GGCACCATCT CATGCAGGTC TGGACAATGA GCTGAGCCTG    120

GGCATCCACG GCCAGGGCCC GGAACGACTG ACCATTCAGC AGTGGGACAC CTTCCTCAAC    180

GGCGTCTTCC CGTTGGACCG CAACCGGTTG ACCCGGGAGT GGTTCCACTG GGGCAAGGCG    240

ACCTACGTCG TGGCCGGTGA AGGTGCCGAC GAGTTCGAGG GCACGCTGGA GCTGGGCTAC    300

CAGGTGGGCT TTCCGTGGTC GCTGGGCGTG GGCATCAACT TCAGCTACAC CACCCCGAAC    360

ATCACGTACG ACGGTTACGG CCTCAACTTC GCCGACCCGC TGCTGGGCTT CGGTGATTCC    420

ATCGTGACCC CGCCGCTGTT CCCGGGTGTC TCGATCACGG CGGACCTGGG CAACGGCCCC    480

GGCATCCAGG AGGTCGCGAC CTTCTCCGTG GACGTGGCCG GCCCCGGTGG TTCCGTGGTG    540

GTGTCCAACG CGCACGGCAC GGTCACCGGT GCTGCCGGTG GTGTGCTGCT GCGTCCGTTC    600

GCCCGCCTGA TCTCGTCGAC CGGCGACAGC GTCACCACCT ACGGCGCACC CTGCTGAAAC    660

ATGAACTGAC CACATCACGA TGGAGGCCCC CCGGCGTCAA CCGGGGCCCG CTTCACGCTG    720

GTCGGGAGGC GCCCGAGGTT CGATCGAAGT GGCCGACTGC GGCAAACGCC TGCGCGCGCG    780

ATTCTTCGAG TCTGACGCAG GGTCTGGTGG TAGTCGAATG TCATCCTGTG ACTCCACCTC    840

ATCGCCCGAG ACGCGACGGC CGGGGTTCCG GTGTGTGGGC GCCGGCCTTG GGCACGTACG    900

GGGGCGACCG ACGTCGTGAT GTGACGAGCG TCGCAGTGTT TGCCGGCAAC CCGGACGGCC    960

CGGCCGAGTC CCCGCATCCG TCCAGCGAAC CGGGGGATC CAAAGAATTC AG            1012
```

(2) INFORMATION FOR SEQ ID NO:156:

(i) SEQUENCE CHARACTERISTICS:
        (A) LENGTH: 336 amino acids
        (B) TYPE: amino acid
        (C) STRANDEDNESS: single
        (D) TOPOLOGY: linear (xi) SEQUENCE DESCRIPTION: SEQ ID NO:156:

```
Met Lys Ala Asn His Ser Gly Cys Tyr Lys Ser Ala Gly Pro Ile Trp
 1               5                  10                  15

Ser His Pro Ser Pro Leu Cys Ser Pro Ala Leu Ala Pro Ser His Ala
                20                  25                  30

Gly Leu Asp Asn Glu Leu Ser Leu Gly Val His Gly Gln Gly Pro Glu
            35                  40                  45

His Leu Thr Ile Gln Gln Trp Asp Thr Phe Leu Asn Gly Val Phe Pro
 50                  55                  60

Leu Asp Arg Asn Arg Leu Thr Arg Glu Trp Phe His Ser Gly Lys Ala
65                  70                  75                  80

Thr Tyr Val Val Ala Gly Glu Gly Ala Asp Glu Phe Glu Gly Thr Leu
                85                  90                  95

Glu Leu Gly Tyr His Val Gly Phe Pro Trp Ser Leu Gly Val Gly Ile
            100                 105                 110

Asn Phe Ser Tyr Thr Thr Pro Asn Ile Thr Tyr Asp Gly Tyr Gly Leu
            115                 120                 125

Asn Phe Ala Asp Pro Leu Leu Gly Phe Gly Asp Ser Ile Val Thr Pro
            130                 135                 140

Pro Leu Phe Pro Gly Val Ser Ile Thr Ala Asp Leu Gly Asn Gly Pro
145                 150                 155                 160

Gly Ile Gln Glu Val Ala Thr Phe Ser Val Asp Val Ala Gly Pro Gly
                165                 170                 175

Gly Ser Val Val Ser Asn Ala His Gly Thr Val Thr Gly Ala Ala
            180                 185                 190

Gly Gly Val Leu Leu Arg Pro Phe Ala Arg Leu Ile Ser Ser Thr Gly
            195                 200                 205

Asp Ser Val Thr Thr Tyr Gly Ala Pro Leu Lys His Glu Leu Thr Thr
        210                 215                 220

Ser Arg Trp Arg Pro Pro Gly Val Asn Arg Gly Pro Leu His Ala Gly
225                 230                 235                 240

Arg Glu Ala Pro Glu Val Arg Ser Lys Trp Pro Thr Ala Ala Asn Ala
                245                 250                 255

Cys Ala Arg Asp Ser Ser Ser Leu Thr Gln Gly Leu Val Val Val Glu
                260                 265                 270

Cys His Pro Val Thr Pro Pro His Arg Pro Arg Arg Asp Gly Arg Gly
                275                 280                 285

Ser Gly Val Trp Ala Pro Ala Leu Gly Thr Tyr Gly Gly Asp Arg Arg
        290                 295                 300

Arg Asp Val Thr Ser Val Ala Val Phe Ala Gly Asn Pro Asp Gly Pro
305                 310                 315                 320

Ala Glu Ser Pro His Pro Ser Ser Glu Pro Gly Gly Ser Lys Glu Phe
                325                 330                 335
```

(2) INFORMATION FOR SEQ ID NO:157:

(i) SEQUENCE CHARACTERISTICS:
        (A) LENGTH: 480 base pairs
        (B) TYPE: nucleic acid
        (C) STRANDEDNESS: single
        (D) TOPOLOGY: linear (xi) SEQUENCE DESCRIPTION: SEQ ID NO:157:

```
AACGGCTGGG ACATCAACAC CCCTGCGTTC GAGTGGTTCT ACGAGTCCGG CTTGTCGACG     60

ATCATGCCGG TCGGCGGACA GTCCAGCTTC TACAGCGACT GGTACCAGCC GTCTCGGGGC    120

AACGGGCAGA ACTACACCTA CAAGTGGGAG ACGTTCCTGA CCCAGGAGCT GCCGACGTGG    180
```

```
CTGGAGGCCA ACCGCGGAGT GTCGCGCACC GGCAACGCGT TCGTCGGCCT GTCGATGGCG      240

GGCAGCGCGG CGCTGACCTA CGCGATCCAT CACCCGCAGC AGTTCATCTA CGCCTCGTCG      300

CTGTCAGGCT TCCTGAACCC GTCCGAGGGC TGGTGGCCGA TGCTGATCGG GCTGGCGATG      360

AACGACGCAG GCGGCTTCAA CGCCGAGAGC ATGTGGGGCC CGTCCTCGGA CCCGGCGTGG      420

AAGCGCAACG ACCCGATGGT CAACATCAAC CAGCTGGTGG CCAACAACAC CCGGATCTGG      480
```

(2) INFORMATION FOR SEQ ID NO:158:

(i) SEQUENCE CHARACTERISTICS:
        (A) LENGTH: 161 amino acids
        (B) TYPE: amino acid
        (C) STRANDEDNESS: single
        (D) TOPOLOGY: linear (xi) SEQUENCE DESCRIPTION: SEQ ID NO:158:

```
Asn Gly Trp Asp Ile Asn Thr Pro Ala Phe Glu Trp Phe Tyr Glu Ser
 1               5                  10                  15

Gly Leu Ser Thr Ile Met Pro Val Gly Gly Gln Ser Ser Phe Tyr Ser
                20                  25                  30

Asp Trp Tyr Gln Pro Ser Arg Gly Asn Gly Gln Asn Tyr Thr Tyr Lys
            35                  40                  45

Trp Glu Thr Phe Leu Thr Gln Glu Leu Pro Thr Trp Leu Glu Ala Asn
50                  55                  60

Arg Gly Val Ser Arg Thr Gly Asn Ala Phe Val Gly Leu Ser Met Ala
65                  70                  75                  80

Gly Ser Ala Ala Leu Thr Tyr Ala Ile His His Pro Gln Gln Phe Ile
                85                  90                  95

Tyr Ala Ser Ser Leu Ser Gly Phe Leu Asn Pro Ser Glu Gly Trp Trp
            100                 105                 110

Pro Met Leu Ile Gly Leu Ala Met Asn Asp Ala Gly Gly Phe Asn Ala
        115                 120                 125

Glu Ser Met Trp Gly Pro Ser Ser Asp Pro Ala Trp Lys Arg Asn Asp
    130                 135                 140

Pro Met Val Asn Ile Asn Gln Leu Val Ala Asn Asn Thr Arg Ile Trp
145                 150                 155                 160

Ile
```

(2) INFORMATION FOR SEQ ID NO:159:

(i) SEQUENCE CHARACTERISTICS:
        (A) LENGTH: 1626 base pairs
        (B) TYPE: nucleic acid
        (C) STRANDEDNESS: single
        (D) TOPOLOGY: linear (xi) SEQUENCE DESCRIPTION: SEQ ID NO:159:

```
ATGGCCAAGA CAATTGCGTA TGACGAAGAG GCCCGCCGTG GCCTCGAGCG GGGCCTCAAC       60

GCCCTCGCAG ACGCCGTAAA GGTGACGTTG GCCCGAAGG GTCGCAACGC CGTGCTGGAG      120

AAGAAGTGGG GCGCCCCCAC GATCACCAAC GATGGTGTGT CCATCGCCAA GGAGATCGAG      180

CTGGAGGACC CGTACGAGAA GATCGGCGCT GAGCTGGTCA AGAGGTCGC CAAGAAGACC      240

GACGACGTCG CGGGCGACGG CACCACCACC GCCACCGTGC TCGCTCAGGC TCTGGTTCGC      300

GAAGGCCTGC GCAACGTCGC AGCCGGCGCC AACCCGCTCG GCCTCAAGCG TGGCATCGAG      360

AAGGCTGTCG AGGCTGTCAC CCAGTCGCTG CTGAAGTCGG CCAAGGAGGT CGAGACCAAG      420

GAGCAGATTT CTGCCACCGC GGCGATTTCC GCCGGCGACA CCCAGATCGG CGAGCTCATC      480
```

```
GCCGAGGCCA TGGACAAGGT CGGCAACGAG GGTGTCATCA CCGTCGAGGA GTCGAACACC      540

TTCGGCCTGC AGCTCGAGCT CACCGAGGGT ATGCGCTTCG ACAAGGGCTA CATCTCGGGT      600

TACTTCGTGA CCGACGCCGA GCGCCAGGAA GCCGTCCTGG AGGATCCCTA CATCCTGCTG      660

GTCAGCTCCA AGGTGTCGAC CGTCAAGGAT CTGCTCCCGC TGCTGGAGAA GGTCATCCAG      720

GCCGGCAAGC CGCTGCTGAT CATCGCCGAG GACGTCGAGG GCGAGGCCCT GTCCACGCTG      780

GTGGTCAACA GATCCGCGG CACCTTCAAG TCCGTCGCCG TCAAGGCTCC GGGCTTCGGT       840

GACCGCCGCA AGGCGATGCT GCAGGACATG GCCATCCTCA CCGGTGGTCA GGTCGTCAGC      900

GAAAGAGTCG GGCTGTCCCT GGAGACCGCC GACGTCTCGC TGCTGGGCCA GGCCCGCAAG      960

GTCGTCGTCA CCAAGGACGA GACCACCATC GTCGAGGGCT CGGGCGATTC CGATGCCATC     1020

GCCGGCCGGG TGGCTCAGAT CCGCGCCGAG ATCGAGAACA GCGACTCCGA CTACGACCGC     1080

GAGAAGCTGC AGGAGCGCCT GGCCAAGCTG GCCGGCGGTG TTGCGGTGAT CAAGGCCGGA     1140

GCTGCCACCG AGGTGGAGCT CAAGGAGCGC AAGCACCGCA TCGAGGACGC CGTCCGCAAC     1200

GCGAAGGCTG CCGTCGAAGA GGGCATCGTC GCCGGTGGCG GCGTGGCTCT GCTGCAGTCG     1260

GCTCCTGCGC TGGACGACCT CGGCCTGACG GGCGACGAGG CCACCGGTGC CAACATCGTC     1320

CGCGTGGCGC TGTCGGCTCC GCTCAAGCAG ATCGCCTTCA ACGGCGGCCT GGAGCCCGGC     1380

GTCGTTGCCG AGAAGGTGTC CAACCTGCCC GCGGGTCACG GCCTCAACGC CGCGACCGGT     1440

GAGTACGAGG ACCTGCTCAA GGCCGGCGTC GCCGACCCGG TGAAGGTCAC CCGCTCGGCG     1500

CTGCAGAACG CGGCGTCCAT CGCGGCTCTG TTCCTCACCA CCGAGGCCGT CGTCGCCGAC     1560

AAGCCGGAGA AGGCGTCCGC ACCCGCGGGC GACCCGACCG GTGGCATGGG CGGTATGGAC     1620

TTCTAA                                                                1626
```

(2) INFORMATION FOR SEQ ID NO:160:

(i) SEQUENCE CHARACTERISTICS:
        (A) LENGTH: 541 amino acids
        (B) TYPE: amino acid
        (C) STRANDEDNESS: single
        (D) TOPOLOGY: linear (xi) SEQUENCE DESCRIPTION: SEQ ID NO:160:

```
Met Ala Lys Thr Ile Ala Tyr Asp Glu Glu Ala Arg Arg Gly Leu Glu
 1               5                  10                  15

Arg Gly Leu Asn Ala Leu Ala Asp Ala Val Lys Val Thr Leu Gly Pro
                20                  25                  30

Lys Gly Arg Asn Val Val Leu Glu Lys Lys Trp Gly Ala Pro Thr Ile
            35                  40                  45

Thr Asn Asp Gly Val Ser Ile Ala Lys Glu Ile Glu Leu Glu Asp Pro
        50                  55                  60

Tyr Glu Lys Ile Gly Ala Glu Leu Val Lys Glu Val Ala Lys Lys Thr
65                  70                  75                  80

Asp Asp Val Ala Gly Asp Gly Thr Thr Thr Ala Thr Val Leu Ala Gln
                85                  90                  95

Ala Leu Val Arg Glu Gly Leu Arg Asn Val Ala Ala Gly Ala Asn Pro
            100                 105                 110

Leu Gly Leu Lys Arg Gly Ile Glu Lys Ala Val Glu Ala Val Thr Gln
        115                 120                 125

Ser Leu Leu Lys Ser Ala Lys Glu Val Glu Thr Lys Glu Gln Ile Ser
    130                 135                 140

Ala Thr Ala Ala Ile Ser Ala Gly Asp Thr Gln Ile Gly Glu Leu Ile
145                 150                 155                 160
```

```
Ala Glu Ala Met Asp Lys Val Gly Asn Glu Gly Val Ile Thr Val Glu
            165                 170                 175

Glu Ser Asn Thr Phe Gly Leu Gln Leu Glu Leu Thr Glu Gly Met Arg
            180                 185                 190

Phe Asp Lys Gly Tyr Ile Ser Gly Tyr Phe Val Thr Asp Ala Glu Arg
            195                 200                 205

Gln Glu Ala Val Leu Glu Asp Pro Tyr Ile Leu Leu Val Ser Ser Lys
            210                 215                 220

Val Ser Thr Val Lys Asp Leu Leu Pro Leu Glu Lys Val Ile Gln
225                 230                 235                 240

Ala Gly Lys Pro Leu Leu Ile Ile Ala Glu Asp Val Glu Gly Glu Ala
            245                 250                 255

Leu Ser Thr Leu Val Val Asn Lys Ile Arg Gly Thr Phe Lys Ser Val
            260                 265                 270

Ala Val Lys Ala Pro Gly Phe Gly Asp Arg Arg Lys Ala Met Leu Gln
            275                 280                 285

Asp Met Ala Ile Leu Thr Gly Gly Gln Val Val Ser Glu Arg Val Gly
            290                 295                 300

Leu Ser Leu Glu Thr Ala Asp Val Ser Leu Leu Gly Gln Ala Arg Lys
305                 310                 315                 320

Val Val Val Thr Lys Asp Glu Thr Thr Ile Val Glu Gly Ser Gly Asp
            325                 330                 335

Ser Asp Ala Ile Ala Gly Arg Val Ala Gln Ile Arg Ala Glu Ile Glu
            340                 345                 350

Asn Ser Asp Ser Asp Tyr Asp Arg Glu Lys Leu Gln Glu Arg Leu Ala
            355                 360                 365

Lys Leu Ala Gly Gly Val Ala Val Ile Lys Ala Gly Ala Ala Thr Glu
            370                 375                 380

Val Glu Leu Lys Glu Arg Lys His Arg Ile Glu Asp Ala Val Arg Asn
385                 390                 395                 400

Ala Lys Ala Ala Val Glu Glu Gly Ile Val Ala Gly Gly Val Ala
            405                 410                 415

Leu Leu Gln Ser Ala Pro Ala Leu Asp Asp Leu Gly Leu Thr Gly Asp
            420                 425                 430

Glu Ala Thr Gly Ala Asn Ile Val Arg Val Ala Leu Ser Ala Pro Leu
            435                 440                 445

Lys Gln Ile Ala Phe Asn Gly Gly Leu Glu Pro Gly Val Val Ala Glu
            450                 455                 460

Lys Val Ser Asn Leu Pro Ala Gly His Gly Leu Asn Ala Ala Thr Gly
465                 470                 475                 480

Glu Tyr Glu Asp Leu Leu Lys Ala Gly Val Ala Asp Pro Val Lys Val
            485                 490                 495

Thr Arg Ser Ala Leu Gln Asn Ala Ala Ser Ile Ala Ala Leu Phe Leu
            500                 505                 510

Thr Thr Glu Ala Val Val Ala Asp Lys Pro Glu Lys Ala Ser Ala Pro
            515                 520                 525

Ala Gly Asp Pro Thr Gly Gly Met Gly Gly Met Asp Phe
            530                 535                 540

(2) INFORMATION FOR SEQ ID NO:161:

(i) SEQUENCE CHARACTERISTICS:
        (A) LENGTH: 985 base pairs
        (B) TYPE: nucleic acid
        (C) STRANDEDNESS: single
```

(D) TOPOLOGY: linear (xi) SEQUENCE DESCRIPTION: SEQ ID NO:161:

```
GGATCCCTAC ATCCTGCTGG TCAGCTCCAA GGTGTCGACC GTCAAGGATC TGCTCCCGCT    60
GCTGGAGAAG GTCATCCAGG CCGGCAAGCC GCTGCTGATC ATCGCCGAGG ACGTCGAGGG   120
CGAGGCCCTG TCCACGCTGG TGGTCAACAA GATCCGCGGC ACCTTCAAGT CCGTCGCCGT   180
CAAGGCTCCG GGCTTCGGTG ACCGCCGCAA GGCGATGCTG CAGGACATGG CCATCCTCAC   240
CGGTGGTCAG GTCGTCAGCG AAAGAGTCGG GCTGTCCCTG GAGACCGCCG ACGTCTCGCT   300
GCTGGGCCAG GCCCGCAAGG TCGTCGTCAC CAAGGACGAG ACCACCATCG TCGAGGGCTC   360
GGGCGATTCC GATGCCATCG CCGGCCGGGT GGCTCAGATC CGCGCCGAGA TCGAGAACAG   420
CGACTCCGAC TACGACCGCG AGAAGCTGCA GGAGCGCCTG GCCAAGCTGG CCGGCGGTGT   480
TGCGGTGATC AAGGCCGGAG CTGCCACCGA GGTGGAGCTC AAGGAGCGCA AGCACCGCAT   540
CGAGGACGCC GTCCGCAACG CGAAGGCTGC CGTCGAAGAG GGCATCGTCG CCGGTGGCGG   600
CGTGGCTCTG CTGCAGTCGG CTCCTGCGCT GGACGACCTC GGCCTGACGG GCGACGAGGC   660
CACCGGTGCC AACATCGTCC GCGTGGCGCT GTCGGCTCCG CTCAAGCAGA TCGCCTTCAA   720
CGGCGGCCTG GAGCCCGGCG TCGTTGCCGA GAAGGTGTCC AACCTGCCCG CGGGTCACGG   780
CCTCAACGCC GCGACCGGTG AGTACGAGGA CCTGCTCAAG GCCGGCGTCG CCGACCCGGT   840
GAAGGTCACC CGCTCGGCGC TGCAGAACGC GGCGTCCATC GCGGCTCTGT TCCTCACCAC   900
CGAGGCCGTC GTCGCCGACA AGCCGGAGAA GGCGTCCGCA CCCGCGGGCG ACCCGACCGG   960
TGGCATGGGC GGTATGGGACT TCTAA                                       985
```

(2) INFORMATION FOR SEQ ID NO:162:

(i) SEQUENCE CHARACTERISTICS:
(A) LENGTH: 327 amino acids
(B) TYPE: amino acid
(C) STRANDEDNESS: single
(D) TOPOLOGY: linear (xi) SEQUENCE DESCRIPTION: SEQ ID NO:162:

```
Asp Pro Tyr Ile Leu Leu Val Ser Ser Lys Val Ser Thr Val Lys Asp
 1               5                  10                  15

Leu Leu Pro Leu Leu Glu Lys Val Ile Gln Ala Gly Lys Pro Leu Leu
                20                  25                  30

Ile Ile Ala Glu Asp Val Glu Gly Glu Ala Leu Ser Thr Leu Val Val
            35                  40                  45

Asn Lys Ile Arg Gly Thr Phe Lys Ser Val Ala Val Lys Ala Pro Gly
        50                  55                  60

Phe Gly Asp Arg Arg Lys Ala Met Leu Gln Asp Met Ala Ile Leu Thr
65                  70                  75                  80

Gly Gly Gln Val Val Ser Glu Arg Val Gly Leu Ser Leu Glu Thr Ala
                85                  90                  95

Asp Val Ser Leu Leu Gly Gln Ala Arg Lys Val Val Val Thr Lys Asp
                100                 105                 110

Glu Thr Thr Ile Val Glu Gly Ser Gly Asp Ser Asp Ala Ile Ala Gly
            115                 120                 125

Arg Val Ala Gln Ile Arg Ala Glu Ile Glu Asn Ser Asp Ser Asp Tyr
        130                 135                 140

Asp Arg Glu Lys Leu Gln Glu Arg Leu Ala Lys Leu Ala Gly Gly Val
145                 150                 155                 160
```

```
Ala Val Ile Lys Ala Gly Ala Ala Thr Glu Val Glu Leu Lys Glu Arg
            165                 170                 175

Lys His Arg Ile Glu Asp Ala Val Arg Asn Ala Lys Ala Ala Val Glu
            180                 185                 190

Glu Gly Ile Val Ala Gly Gly Val Ala Leu Leu Gln Ser Ala Pro
            195                 200                 205

Ala Leu Asp Asp Leu Gly Leu Thr Gly Asp Glu Ala Thr Gly Ala Asn
    210                 215                 220

Ile Val Arg Val Ala Leu Ser Ala Pro Leu Lys Gln Ile Ala Phe Asn
225                 230                 235                 240

Gly Gly Leu Glu Pro Gly Val Val Ala Glu Lys Val Ser Asn Leu Pro
                245                 250                 255

Ala Gly His Gly Leu Asn Ala Ala Thr Gly Glu Tyr Glu Asp Leu Leu
            260                 265                 270

Lys Ala Gly Val Ala Asp Pro Val Lys Val Thr Arg Ser Ala Leu Gln
            275                 280                 285

Asn Ala Ala Ser Ile Ala Ala Leu Phe Leu Thr Thr Glu Ala Val Val
            290                 295                 300

Ala Asp Lys Pro Glu Lys Ala Ser Ala Pro Ala Gly Asp Pro Thr Gly
305                 310                 315                 320

Gly Met Gly Gly Met Asp Phe
                325

(2) INFORMATION FOR SEQ ID NO:163:

(i) SEQUENCE CHARACTERISTICS:
        (A) LENGTH: 403 base pairs
        (B) TYPE: nucleic acid
        (C) STRANDEDNESS: single
        (D) TOPOLOGY: linear (xi) SEQUENCE DESCRIPTION: SEQ ID NO:163:

GGATCCGCGG CACCGGCTGG TGACGACCAA GTACAACCCG GCCCGCACCT GGACGGCCGA      60

GAACTCCGTC GGCATCGGCG GCGCGTACCT GTGCATCTAC GGGATGGAGG GCCCCGGCGG     120

CTATCAGTTC GTCGGCCGCA CCACCCAGGT GTGGAGTCGT TACCGCCACA CGGCGCCGTT     180

CGAACCCGGA AGTCCCTGGC TGCTGCGGTT TTTCGACCGA ATTTCGTGGT ATCCGGTGTC     240

GGCCGAGGAG CTGCTGGAAT TGCGAGCCGA CATGGCCGCA GGCCGGGGCT CGGTCGACAT     300

CACCGACGGC GTGTTCTCCC TCGCCGAGCA CGAACGGTTC CTGGCCGACA ACGCCGACGA     360

CATCGCCGCG TTCCGTTCCC GGCAGGCGGC CGCGTTCTCC GCC                      403

(2) INFORMATION FOR SEQ ID NO:164:

(i) SEQUENCE CHARACTERISTICS:
        (A) LENGTH: 336 base pairs
        (B) TYPE: nucleic acid
        (C) STRANDEDNESS: single
        (D) TOPOLOGY: linear (xi) SEQUENCE DESCRIPTION: SEQ ID NO:164:

CGGACCGCGT GGGCGGCCGC CGGCGAGTTC GACCGCGCCG AGAAAGCCGC GTCGAAGGCC      60

ACCGACGCCG ATACCGGGGA CCTGGTGCTC TACGACGGTG CGAGCGGGTC GACGCTCCGT     120

TCGCGTCGAG CGTGTGGAAG GTCGACGTCG CCGTCGGTGA CCGGGTGGTG GCCGGACAGC     180

CGTTGCTGGC GCTGGAGGCG ATGAAGATGG AGACCGTGCT GCGCGCCCCG GCCGACGGGG     240

TGGTCACCCA GATCCTGGTC TCCGCTGGGC ATCTCGTCGA TCCCGGCACC CCACTGGTCG     300

TGGTCGGCAC CGGAGTGCGC GCATGAGCGC CGTCGA                              336
```

(2) INFORMATION FOR SEQ ID NO:165:

(i) SEQUENCE CHARACTERISTICS:
        (A) LENGTH: 134 amino acids
        (B) TYPE: amino acid
        (C) STRANDEDNESS: single
        (D) TOPOLOGY: linear (xi) SEQUENCE DESCRIPTION: SEQ ID NO:165:

```
Asp Pro Arg His Arg Leu Val Thr Thr Lys Tyr Asn Pro Ala Arg Thr
 1               5                  10                  15

Trp Thr Ala Glu Asn Ser Val Gly Ile Gly Gly Ala Tyr Leu Cys Ile
            20                  25                  30

Tyr Gly Met Glu Gly Pro Gly Gly Tyr Gln Phe Val Gly Arg Thr Thr
        35                  40                  45

Gln Val Trp Ser Arg Tyr Arg His Thr Ala Pro Phe Glu Pro Gly Ser
    50                  55                  60

Pro Trp Leu Leu Arg Phe Phe Asp Arg Ile Ser Trp Tyr Pro Val Ser
65                  70                  75                  80

Ala Glu Glu Leu Leu Glu Leu Arg Ala Asp Met Ala Ala Gly Arg Gly
                85                  90                  95

Ser Val Asp Ile Thr Asp Gly Val Phe Ser Leu Ala Glu His Glu Arg
            100                 105                 110

Phe Leu Ala Asp Asn Ala Asp Asp Ile Ala Ala Phe Arg Ser Arg Gln
        115                 120                 125

Ala Ala Ala Phe Ser Ala
    130
```

(2) INFORMATION FOR SEQ ID NO:166:

(i) SEQUENCE CHARACTERISTICS:
        (A) LENGTH: 108 amino acids
        (B) TYPE: amino acid
        (C) STRANDEDNESS: single
        (D) TOPOLOGY: linear (xi) SEQUENCE DESCRIPTION: SEQ ID NO:166:

```
Arg Thr Ala Trp Ala Ala Ala Gly Glu Phe Asp Arg Ala Glu Lys Ala
 1               5                  10                  15

Ala Ser Lys Ala Thr Asp Ala Asp Thr Gly Asp Leu Val Leu Tyr Asp
            20                  25                  30

Gly Asp Glu Arg Val Asp Ala Pro Phe Ala Ser Ser Val Trp Lys Val
        35                  40                  45

Asp Val Ala Val Gly Asp Arg Val Val Ala Gly Gln Pro Leu Leu Ala
    50                  55                  60

Leu Glu Ala Met Lys Met Glu Thr Val Leu Arg Ala Pro Ala Asp Gly
65                  70                  75                  80

Val Val Thr Gln Ile Leu Val Ser Ala Gly His Leu Val Asp Pro Gly
                85                  90                  95

Thr Pro Leu Val Val Val Gly Thr Gly Val Arg Ala
            100                 105
```

(2) INFORMATION FOR SEQ ID NO:167:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:167:

ATAGAATTCG TCCGACAGTG GGACCTCGAG C                                   31

(2) INFORMATION FOR SEQ ID NO:168:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:168:

ATAGAATTCC CACCGCGTCA GCCGCCG                                        27

(2) INFORMATION FOR SEQ ID NO:169:

(i) SEQUENCE CHARACTERISTICS:
        (A) LENGTH: 1111 base pairs
        (B) TYPE: nucleic acid
        (C) STRANDEDNESS: single
        (D) TOPOLOGY: linear (xi) SEQUENCE DESCRIPTION: SEQ ID NO:169:

GTCCGACAGT GGGACCTCGA GCACCACGTC ACAGGACAGC GGCCCCGCCA GCGGCGCCCT     60

GCGCGTCTCC AACTGGCCGC TCTATATGGC CGACGGTTTC ATCGCAGCGT TCCAGACCGC    120

CTCGGGCATC ACGGTCGACT ACAAAGAAGA CTTCAACGAC AACGAGCAGT GGTTCGCCAA    180

GGTCAAGGAG CCGTTGTCGC GCAAGCAGGA CATAGGCGCC GACCTGGTGA TCCCCACCGA    240

GTTCATGGCC GCGCGCGTCA AGGGCCTGGG ATGGCTCAAT GAGATCAGCG AAGCCGGCGT    300

GCCCAATCGC AAGAATCTGC GTCAGGACCT GTTGGACTCG AGCATCGACG AGGGCCGCAA    360

GTTCACCGCG CCGTACATGA CCGGCATGGT CGGTCTCGCC TACAACAAGG CAGCCACCGG    420

ACGCGATATC CGCACCATCG ACGACCTCTG GGATCCCGCG TTCAAGGGCC GCGTCAGTCT    480

GTTCTCCGAC GTCCAGGACG GCCTCGGCAT GATCATGCTC TCGCAGGGCA ACTCGCCGGA    540

GAATCCGACC ACCGAGTCCA TTCAGCAGGC GGTCGATCTG GTCCGCGAAC AGAACGACAG    600

GGGGTCAGAT CCGTCGCTTC ACCGGCAACG ACTACGCCGA CGACCTGGCC GCAGAAACAT    660

CGCCATCGCG CAGGCGTACT CCGGTGACGT CGTGCAGCTG CAGGCGGACA ACCCCGATCT    720

GCAGTTCATC GTTCCCGAAT CCGGCGGCGA CTGGTTCGTC GACACGATGG TGATCCCGTA    780

CACCACGCAG AACCAGAAGG CCGCCGAGGC GTGGATCGAC TACATCTACG ACCGAGCCAA    840

CTACGCCAAG CTGGTCGCGT TCACCCAGTT CGTGCCCGCA CTCTCGGACA TGACCGACGA    900

ACTCGCCAAG GTCGATCCTG CATCGGCGGA GAACCCGCTG ATCAACCCGT CGGCCGAGGT    960

GCAGGCGAAC CTGAAGTCGT GGGCGGCACT GACCGACGAG CAGACGCAGG AGTTCAACAC   1020

TGCGTACGCC GCCGTCACCG GCGGCTGACG CGGTGGTAGT GCCGATGCGA GGGGCATAAA   1080

TGGCCCTGCG GACGCGAGGA GCATAAATGG C                                 1111

(2) INFORMATION FOR SEQ ID NO:170:

(i) SEQUENCE CHARACTERISTICS:
        (A) LENGTH: 348 amino acids
        (B) TYPE: amino acid
        (C) STRANDEDNESS: single
        (D) TOPOLOGY: linear (xi) SEQUENCE DESCRIPTION: SEQ ID NO:170:

Ser Asp Ser Gly Thr Ser Ser Thr Thr Ser Gln Asp Ser Gly Pro Ala
 1               5                  10                  15

```
Ser Gly Ala Leu Arg Val Ser Asn Trp Pro Leu Tyr Met Ala Asp Gly
            20                  25                  30

Phe Ile Ala Ala Phe Gln Thr Ala Ser Gly Ile Thr Val Asp Tyr Lys
            35                  40                  45

Glu Asp Phe Asn Asp Asn Glu Gln Trp Phe Ala Lys Val Lys Glu Pro
 50                  55                  60

Leu Ser Arg Lys Gln Asp Ile Gly Ala Asp Leu Val Ile Pro Thr Glu
 65                  70                  75                  80

Phe Met Ala Ala Arg Val Lys Gly Leu Gly Trp Leu Asn Glu Ile Ser
            85                  90                  95

Glu Ala Gly Val Pro Asn Arg Lys Asn Leu Arg Gln Asp Leu Leu Asp
            100                 105                 110

Ser Ser Ile Asp Glu Gly Arg Lys Phe Thr Ala Pro Tyr Met Thr Gly
            115                 120                 125

Met Val Gly Leu Ala Tyr Asn Lys Ala Ala Thr Gly Arg Asp Ile Arg
 130                 135                 140

Thr Ile Asp Asp Leu Trp Asp Pro Ala Phe Lys Gly Arg Val Ser Leu
145                 150                 155                 160

Phe Ser Asp Val Gln Asp Gly Leu Gly Met Ile Met Leu Ser Gln Gly
            165                 170                 175

Asn Ser Pro Glu Asn Pro Thr Thr Glu Ser Ile Gln Ala Val Asp
            180                 185                 190

Leu Val Arg Glu Gln Asn Asp Arg Gly Gln Ile Arg Arg Phe Thr Gly
            195                 200                 205

Asn Asp Tyr Ala Asp Asp Leu Ala Ala Gly Asn Ile Ala Ile Ala Gln
 210                 215                 220

Ala Tyr Ser Gly Asp Val Val Gln Leu Gln Ala Asp Asn Pro Asp Leu
225                 230                 235                 240

Gln Phe Ile Val Pro Glu Ser Gly Gly Asp Trp Phe Val Asp Thr Met
            245                 250                 255

Val Ile Pro Tyr Thr Thr Gln Asn Gln Lys Ala Ala Glu Ala Trp Ile
            260                 265                 270

Asp Tyr Ile Tyr Asp Arg Ala Asn Tyr Ala Lys Leu Val Ala Phe Thr
            275                 280                 285

Gln Phe Val Pro Ala Leu Ser Asp Met Thr Asp Glu Leu Ala Lys Val
            290                 295                 300

Asp Pro Ala Ser Ala Glu Asn Pro Leu Ile Asn Pro Ser Ala Glu Val
305                 310                 315                 320

Gln Ala Asn Leu Lys Ser Trp Ala Ala Leu Thr Asp Glu Gln Thr Gln
            325                 330                 335

Glu Phe Asn Thr Ala Tyr Ala Ala Val Thr Gly Gly
            340                 345
```

(2) INFORMATION FOR SEQ ID NO:171:

(i) SEQUENCE CHARACTERISTICS:
        (A) LENGTH: 1420 base pairs
        (B) TYPE: nucleic acid
        (C) STRANDEDNESS: single
        (D) TOPOLOGY: linear (xi) SEQUENCE DESCRIPTION: SEQ ID NO:171:

```
GATGAGCAGC GTGCTGAACT CGACCTGGTT GGCCTGGGCC GTCGCGGTCG CGGTCGGGTT    60

CCCGGTGCTG CTGGTCGTGC TGACCGAGGT GCACAACGCG TTGCGTCGGC GCGGCAGCGC   120

GCTGGCCCGC CCGGTGCAAC TCCTGCGTAC CTACATCCTG CCGCTGGGCG CGTTGCTGCT   180
```

```
CCTGCTGGTA CAGGCGATGG AGATCTCCGA CGACGCCACG TCGGTACGGT TGGTCGCCAC    240

CCTGTTCGGC GTCGTGTTGT TGACGTTGGT GCTGTCCGGG CTCAACGCCA CCCTCATCCA    300

GGGCGCACCA GAAGACAGCT GGCGCAGGCG GATTCCGTCG ATCTTCCTCG ACGTCGCGCG    360

CTTCGCGCTG ATCGCGGTCG GTATCACCGT GATCATGGCC TATGTCTGGG GCGCGAACGT    420

GGGGGGCCTG TTCACCGCAC TGGGCGTCAC TTCCATCGTT CTTGGCCTGG CTCTGCAGAA    480

TTCGGTCGGT CAGATCATCT CGGGTCTGCT GCTGCTGTTC GAGCAACCGT TCCGGCTCGG    540

CGACTGGATC ACCGTCCCCA CCGCGGCGGG CCGGCCGTCC GCCCACGGCC GCGTGGTGGA    600

AGTCAACTGG CGTGCAACAC ATATCGACAC CGGCGGCAAC CTGCTGGTAA TGCCCAACGC    660

CGAACTCGCC GGCGCGTCGT TCACCAATTA CAGCCGGCCC GTGGGAGAGC ACCGGCTGAC    720

CGTCGTCACC ACCTTCAACG CCGCGGACAC CCCCGATGAT GTCTGCGAGA TGCTGTCGTC    780

GGTCGCGGCG TCGCTGCCCG AACTGCGCAC CGACGGACAG ATCGCCACGC TCTATCTCGG    840

TGCGGCCGAA TACGAGAAGT CGATCCCGTT GCACACACCC GCGGTGGACG ACTCGGTCAG    900

GAGCACGTAC CTGCCGATGGG TCTGGTACGC CGCGCGCCGG CAGGAACTTC GCCTNAACGG    960

CGTCGCCGAC GANTTCGACA CGCCGGAACG GATCGCCTCG GCCATGCGGG CTGTGGCGTC    1020

CACACTGCGC TTGGCAGACG ACGAACAGCA GGAGATCGCC GACGTGGTGC GTCTGGTCCG    1080

TTACGGCAAC GGGGAACGCC TCCAGCAGCC GGGTCAGGTA CCGACCGGGA TGAGGTTCAT    1140

CGTAGACGGC AGGGTGAGTC TGTCCGTGAT CGATCAGGAC GGCGACGTGA TCCCGGCGCG    1200

GGTGCTCGAG CGTGGCGACT TCCTGGGGCA GACCACGCTG ACGCGGGAAC CGGTACTGGC    1260

GACCGCGCAC GCGCTGGAGG AAGTCACCGT GCTGGAGATG GCCCGTGACG AGATCGAGCG    1320

CCTGGTGCAC CGAAAGCCGA TCCTGCTGCA CGTGATCGGG GCCGTGATCG CCGACCGGCG    1380

CGCGCACGAA CTTCGGTTGA TGGCGGACTC GCAGGACTGA                           1420

(2) INFORMATION FOR SEQ ID NO:172:

(i) SEQUENCE CHARACTERISTICS:
        (A) LENGTH: 471 amino acids
        (B) TYPE: amino acid
        (C) STRANDEDNESS: single
        (D) TOPOLOGY: linear (xi) SEQUENCE DESCRIPTION: SEQ ID NO:172:

Met Ser Ser Val Leu Asn Ser Thr Trp Leu Ala Trp Ala Val Ala Val
 1               5                  10                  15

Ala Val Gly Phe Pro Val Leu Leu Val Leu Thr Glu Val His Asn
            20                  25                  30

Ala Leu Arg Arg Arg Gly Ser Ala Leu Ala Arg Pro Val Gln Leu Leu
        35                  40                  45

Arg Thr Tyr Ile Leu Pro Leu Gly Ala Leu Leu Leu Leu Val Gln
    50                  55                  60

Ala Met Glu Ile Ser Asp Asp Ala Thr Ser Val Arg Leu Val Ala Thr
65                  70                  75                  80

Leu Phe Gly Val Val Leu Leu Thr Leu Val Leu Ser Gly Leu Asn Ala
                85                  90                  95

Thr Leu Ile Gln Gly Ala Pro Glu Asp Ser Trp Arg Arg Ile Pro
           100                 105                 110

Ser Ile Phe Leu Asp Val Ala Arg Phe Ala Leu Ile Ala Val Gly Ile
           115                 120                 125

Thr Val Ile Met Ala Tyr Val Trp Gly Ala Asn Val Gly Gly Leu Phe
           130                 135                 140
```

```
Thr Ala Leu Gly Val Thr Ser Ile Val Leu Gly Leu Ala Leu Gln Asn
145                 150                 155                 160

Ser Val Gly Gln Ile Ile Ser Gly Leu Leu Leu Phe Glu Gln Pro
            165                 170                 175

Phe Arg Leu Gly Asp Trp Ile Thr Val Pro Thr Ala Ala Gly Arg Pro
            180                 185                 190

Ser Ala His Gly Arg Val Val Glu Val Asn Trp Arg Ala Thr His Ile
            195                 200                 205

Asp Thr Gly Gly Asn Leu Leu Val Met Pro Asn Ala Glu Leu Ala Gly
            210                 215                 220

Ala Ser Phe Thr Asn Tyr Ser Arg Pro Val Gly Glu His Arg Leu Thr
225                 230                 235                 240

Val Val Thr Thr Phe Asn Ala Ala Asp Thr Pro Asp Asp Val Cys Glu
                245                 250                 255

Met Leu Ser Ser Val Ala Ala Ser Leu Pro Glu Leu Arg Thr Asp Gly
            260                 265                 270

Gln Ile Ala Thr Leu Tyr Leu Gly Ala Ala Glu Tyr Glu Lys Ser Ile
            275                 280                 285

Pro Leu His Thr Pro Ala Val Asp Asp Ser Val Arg Ser Thr Tyr Leu
290                 295                 300

Arg Trp Val Trp Tyr Ala Ala Arg Arg Gln Glu Leu Arg Xaa Asn Gly
305                 310                 315                 320

Val Ala Asp Xaa Phe Asp Thr Pro Glu Arg Ile Ala Ser Ala Met Arg
                325                 330                 335

Ala Val Ala Ser Thr Leu Arg Leu Ala Asp Asp Glu Gln Gln Glu Ile
            340                 345                 350

Ala Asp Val Val Arg Leu Val Arg Tyr Gly Asn Gly Glu Arg Leu Gln
            355                 360                 365

Gln Pro Gly Gln Val Pro Thr Gly Met Arg Phe Ile Val Asp Gly Arg
370                 375                 380

Val Ser Leu Ser Val Ile Asp Gln Asp Gly Asp Val Ile Pro Ala Arg
385                 390                 395                 400

Val Leu Glu Arg Gly Asp Phe Leu Gly Gln Thr Thr Leu Thr Arg Glu
            405                 410                 415

Pro Val Leu Ala Thr Ala His Ala Leu Glu Glu Val Thr Val Leu Glu
            420                 425                 430

Met Ala Arg Asp Glu Ile Glu Arg Leu Val His Arg Lys Pro Ile Leu
435                 440                 445

Leu His Val Ile Gly Ala Val Ile Ala Asp Arg Arg Ala His Glu Leu
        450                 455                 460

Arg Leu Met Asp Ser Gln Asp
465                 470

(2) INFORMATION FOR SEQ ID NO:173:

(i) SEQUENCE CHARACTERISTICS:
        (A) LENGTH: 2172 base pairs
        (B) TYPE: nucleic acid
        (C) STRANDEDNESS: single
        (D) TOPOLOGY: linear (xi) SEQUENCE DESCRIPTION: SEQ ID NO:173:

TAGATGACAA TTCTGCCCTG AATGCGCGA ACGTCTGAAC ACCCGACGCG AAAAAGACGC    60

GGGCGCTACC ACCTCCTGTC GCGGATGAGC ATCCAGTCCA AGTTGCTGCT GATGCTGCTT  120

CTGACCAGCA TTCTCTCGGC TGCGGTGGTC GGTTTCATCG GCTATCAGTC CGGACGGTCC  180
```

-continued

```
TCGCTGCGCG CATCGGTGTT CGACCGCCTC ACCGACATCC GCGAGTCGCA GTCGCGCGGG      240

TTGGAGAATC AGTTCGCGGA CCTGAAGAAC TCGATGGTGA TTTACTCGCG CGGCAGCACT      300

GCCACGGAGG CGATCGGCGC GTTCAGCGAC GGTTTCCGTC AGCTCGGCGA TGCGACGATC      360

AATACCGGGC AGGCGGCGTC ATTGCGCCGT TACTACGACC GGACGTTCGC CAACACCACC      420

CTCGACGACA GCGGAAACCG CGTCGACGTC CGCGCGCTCA TCCCGAAATC CAACCCCCAG      480

CGCTATCTGC AGGCGCTCTA TACCCCGCCG TTTCAGAACT GGGAGAAGGC GATCGCGTTC      540

GACGACGCGC GCGACGGCAG CGCCTGGTCG GCCGCCAATG CCAGATTCAA CGAGTTCTTC      600

CGCGAGATCG TGCACCGCTT CAACTTCGAG GATCTGATGC TGCTCGACCT CGAGGGCAAC      660

GTGGTGTACT CCGCCTACAA GGGGCCGGAT CTCGGGACAA ACATCGTCAA CGGCCCCTAT      720

CGCAACCGGG AACTGTCGGA AGCCTACGAG AAGGCGGTCG CGTCGAACTC GATCGACTAT      780

GTCGGTGTCA CCGACTTCGG GTGGTACCTG CCTGCCGAGG AACCGACCGC CTGGTTCCTG      840

TCCCCGGTCG GGTTGAAGGA CCGAGTCGAC GGTGTGATGG CGGTCCAGTT CCCGATCGCG      900

CGGATCAACG AATTGATGAC GGCGCGGGGA CAGTGGCGTG ACACCGGGAT GGGAGACACC      960

GGTGAGACCA TCCTGGTCGG ACCGGACAAT CTGATGCGCT CGGACTCCCG GCTGTTCCGC     1020

GAGAACCGGG AGAAGTTCCT GGCCGACGTC GTCGAGGGGG AACCCCGCC GGAGGTCGCC      1080

GACGAATCGG TTGACCGCCG CGGCACCACG CTGGTGCAGC CGGTGACCAC CCGCTCCGTC     1140

GAGGAGGCCC AACGCGGCAA CACCGGGACG ACGATCGAGG ACGACTATCT CGGCCACGAG     1200

GCGTTACAGG CGTACTCACC GGTGGACCTG CCGGGACTGC ACTGGGTGAT CGTGGCCAAG     1260

ATCGACACCG ACGAGGCGTT CGCCCCGGTG GCGCAGTTCA CCAGGACCCT GGTGCTGTCG     1320

ACGGTGATCA TCATCTTCGG CGTGTCGCTG GCGGCCATGC TGCTGGCGCG GTTGTTCGTC     1380

CGTCCGATCC GGCGGTTGCA GGCCGGCGCC CAGCAGATCA GCGGCGGTGA CTACCGCCTC     1440

GCTCTGCCGG TGTTGTCTCG TGACGAATTC GGCGATCTGA CAACAGCTTT CAACGACATG     1500

AGTCGCAATC TGTCGATCAA GGACGAGCTG CTCGGCGAGG AGCGCGCCGA GAACCAACGG     1560

CTGATGCTGT CCCTGATGCC CGAACCGGTG ATGCAGCGCT ACCTCGACGG GGAGGAGACG     1620

ATCGCCCAGG ACCACAAGAA CGTCACGGTG ATCTTCGCCG ACATGATGGG CCTCGACGAG     1680

TTGTCGCGCA TGTTGACCTC CGAGGAACTG ATGGTGGTGG TCAACGACCT GACCCGCCAG     1740

TTCGACGCCG CCGCCGAGAG TCTCGGGGTC GACCACGTGC GGACGCTGCA CGACGGGTAC     1800

CTGGCCAGCT GCGGGTTAGG CGTGCCGCGG CTGGACAACG TCCGGCGCAC GGTCAATTTC     1860

GCGATCGAAA TGGACCGCAT CATCGACCGG CACGCCGCCG AGTCCGGGCA CGACCTGCGG     1920

CTCCGCGCGG GCATCGACAC CGGGTCGGCG GCCAGCGGGC TGGTGGGGCG GTCCACGTTG     1980

GCGTACGACA TGTGGGGTTC GGCGGTCGAT GTCGCTAACC AGGTGCAGCG CGGCTCCCCC     2040

CAGCCCGGCA TCTACGTCAC CTCGCGGGTG CACGAGGTCA TGCAGGAAAC TCTCGACTTC     2100

GTCGCCGCCG GGGAGGTCGT CGGCGAGCGC GGCGTCGAGA CGGTCTGGCG GTTGCAGGGC     2160

CACCGGCGAT GA                                                        2172
```

(2) INFORMATION FOR SEQ ID NO:174:

(i) SEQUENCE CHARACTERISTICS:
        (A) LENGTH: 722 amino acids
        (B) TYPE: amino acid
        (C) STRANDEDNESS: single
        (D) TOPOLOGY: linear (xi) SEQUENCE DESCRIPTION: SEQ ID NO:174:

```
Met Thr Ile Leu Pro Trp Asn Ala Arg Thr Ser Glu His Pro Thr Arg
 1               5                  10                  15

Lys Arg Arg Gly Arg Tyr His Leu Leu Ser Arg Met Ser Ile Gln Ser
            20                  25                  30

Lys Leu Leu Leu Met Leu Leu Leu Thr Ser Ile Leu Ser Ala Ala Val
        35                  40                  45

Val Gly Phe Ile Gly Tyr Gln Ser Gly Arg Ser Ser Leu Arg Ala Ser
    50                  55                  60

Val Phe Asp Arg Leu Thr Asp Ile Arg Glu Ser Gln Ser Arg Gly Leu
65                  70                  75                  80

Glu Asn Gln Phe Ala Asp Leu Lys Asn Ser Met Val Ile Tyr Ser Arg
                85                  90                  95

Gly Ser Thr Ala Thr Glu Ala Ile Gly Ala Phe Ser Asp Gly Phe Arg
            100                 105                 110

Gln Leu Gly Asp Ala Thr Ile Asn Thr Gly Gln Ala Ala Ser Leu Arg
        115                 120                 125

Arg Tyr Tyr Asp Arg Thr Phe Ala Asn Thr Thr Leu Asp Asp Ser Gly
    130                 135                 140

Asn Arg Val Asp Val Arg Ala Leu Ile Pro Lys Ser Asn Pro Gln Arg
145                 150                 155                 160

Tyr Leu Gln Ala Leu Tyr Thr Pro Pro Phe Gln Asn Trp Glu Lys Ala
                165                 170                 175

Ile Ala Phe Asp Asp Ala Arg Asp Gly Ser Ala Trp Ser Ala Ala Asn
            180                 185                 190

Ala Arg Phe Asn Glu Phe Phe Arg Glu Ile Val His Arg Phe Asn Phe
        195                 200                 205

Glu Asp Leu Met Leu Leu Asp Leu Gly Asn Val Val Tyr Ser Ala
    210                 215                 220

Tyr Lys Gly Pro Asp Leu Gly Thr Asn Ile Val Asn Gly Pro Tyr Arg
225                 230                 235                 240

Asn Arg Glu Leu Ser Glu Ala Tyr Glu Lys Ala Val Ala Ser Asn Ser
                245                 250                 255

Ile Asp Tyr Val Gly Val Thr Asp Phe Gly Trp Tyr Leu Pro Ala Glu
            260                 265                 270

Glu Pro Thr Ala Trp Phe Leu Ser Pro Val Gly Leu Lys Asp Arg Val
        275                 280                 285

Asp Gly Val Met Ala Val Gln Phe Pro Ile Ala Arg Ile Asn Glu Leu
    290                 295                 300

Met Thr Ala Arg Gly Gln Trp Arg Asp Thr Gly Met Gly Asp Thr Gly
305                 310                 315                 320

Glu Thr Ile Leu Val Gly Pro Asp Asn Leu Met Arg Ser Asp Ser Arg
                325                 330                 335

Leu Phe Arg Glu Asn Arg Glu Lys Phe Leu Ala Asp Val Val Glu Gly
            340                 345                 350

Gly Thr Pro Pro Glu Val Ala Asp Glu Ser Val Asp Arg Arg Gly Thr
        355                 360                 365

Thr Leu Val Gln Pro Val Thr Thr Arg Ser Val Glu Ala Gln Arg
    370                 375                 380

Gly Asn Thr Gly Thr Thr Ile Glu Asp Asp Tyr Leu Gly His Glu Ala
385                 390                 395                 400

Leu Gln Ala Tyr Ser Pro Val Asp Leu Pro Gly Leu His Trp Val Ile
                405                 410                 415

Val Ala Lys Ile Asp Thr Asp Glu Ala Phe Ala Pro Val Ala Gln Phe
            420                 425                 430
```

```
Thr Arg Thr Leu Val Leu Ser Thr Val Ile Ile Phe Gly Val Ser
        435                 440                 445

Leu Ala Ala Met Leu Leu Ala Arg Leu Phe Val Arg Pro Ile Arg Arg
    450                 455                 460

Leu Gln Ala Gly Ala Gln Gln Ile Ser Gly Gly Asp Tyr Arg Leu Ala
465                 470                 475                 480

Leu Pro Val Leu Ser Arg Asp Glu Phe Gly Asp Leu Thr Thr Ala Phe
                485                 490                 495

Asn Asp Met Ser Arg Asn Leu Ser Ile Lys Asp Glu Leu Leu Gly Glu
            500                 505                 510

Glu Arg Ala Glu Asn Gln Arg Leu Met Leu Ser Leu Met Pro Glu Pro
        515                 520                 525

Val Met Gln Arg Tyr Leu Asp Gly Glu Glu Thr Ile Ala Gln Asp His
    530                 535                 540

Lys Asn Val Thr Val Ile Phe Ala Asp Met Met Gly Leu Asp Glu Leu
545                 550                 555                 560

Ser Arg Met Leu Thr Ser Glu Glu Leu Met Val Val Asn Asp Leu
                565                 570                 575

Thr Arg Gln Phe Asp Ala Ala Ala Glu Ser Leu Gly Val Asp His Val
            580                 585                 590

Arg Thr Leu His Asp Gly Tyr Leu Ala Ser Cys Gly Leu Gly Val Pro
        595                 600                 605

Arg Leu Asp Asn Val Arg Arg Thr Val Asn Phe Ala Ile Glu Met Asp
    610                 615                 620

Arg Ile Ile Asp Arg His Ala Ala Glu Ser Gly His Asp Leu Arg Leu
625                 630                 635                 640

Arg Ala Gly Ile Asp Thr Gly Ser Ala Ala Ser Gly Leu Val Gly Arg
                645                 650                 655

Ser Thr Leu Ala Tyr Asp Met Trp Gly Ser Ala Val Asp Val Ala Asn
            660                 665                 670

Gln Val Gln Arg Gly Ser Pro Gln Pro Gly Ile Tyr Val Thr Ser Arg
        675                 680                 685

Val His Glu Val Met Gln Glu Thr Leu Asp Phe Val Ala Ala Gly Glu
    690                 695                 700

Val Val Gly Glu Arg Gly Val Glu Thr Val Trp Arg Leu Gln Gly His
705                 710                 715                 720

Arg Arg
```

(2) INFORMATION FOR SEQ ID NO:175:

(i) SEQUENCE CHARACTERISTICS:
        (A) LENGTH: 898 base pairs
        (B) TYPE: nucleic acid
        (C) STRANDEDNESS: single
        (D) TOPOLOGY: linear (xi) SEQUENCE DESCRIPTION: SEQ ID NO:175:

```
GAGCAACCGT TCCGGCTCGG CGACTGGATC ACCGTCCCCA CCGCGGCGGG CCGGCCGTCC      60

GCCCACGGCC GCGTGGTGGA AGTCAACTGG CGTGCAACAC ATATCGACAC CGGCGGCAAC     120

CTGCTGGTAA TGCCCAACGC CGAACTCGCC GGCGCGTCGT TCACCAATTA CAGCCGGCCC     180

GTGGGAGAGC ACCGGCTGAC CGTCGTCACC ACCTTCAACG CCGCGGACAC CCCCGATGAT     240

GTCTGCGAGA TGCTGTCGTC GGTCGCGGCG TCGCTGCCCG AACTGCGCAC CGACGGACAG     300

ATCGCCACGC TCTATCTCGG TGCGGCCGAA TACGAGAAGT CGATCCCGTT GCACACACCC     360
```

```
GCGGTGGACG ACTCGGTCAG GAGCACGTAC CTGCGATGGG TCTGGTACGC CGCGCGCCGG    420

CAGGAACTTC GCCTAACGGC GTCGCCGACG ATTCGACACG CCGGAACGGA TCGCCTCGGC    480

CATGCGGGCT GTGGCGTCCA CACTGCGCTT GGCAGACGAC GAACAGCAGG AGATCGCCGA    540

CGTGGTGCGT CTGGTCCGTT ACGGCAACGG GGAACGCCTC CAGCAGCCGG GTCAGGTACC    600

GACCGGGATG AGGTTCATCG TAGACGGCAG GGTGAGTCTG TCCGTGATCG ATCAGGACGG    660

CGACGTGATC CCGGCGCGGG TGCTCGAGCG TGGCGACTTC CTGGGGCAGA CCACGCTGAC    720

GCGGGAACCG GTACTGGCGA CCGCGCACGC GCTGGAGGAA GTCACCGTGC TGGAGATGGC    780

CCGTGACGAG ATCGAGCGCC TGGTGCACCG AAAGCCGATC CTGCTGCACG TGATCGGGGC    840

CGTGATCGCC GACCGGCGCG CGCACGAACT TCGGTTGATG GCGGACTCGC AGGACTGA     898
```

(2) INFORMATION FOR SEQ ID NO:176:

(i) SEQUENCE CHARACTERISTICS:
        (A) LENGTH: 2013 base pairs
        (B) TYPE: nucleic acid
        (C) STRANDEDNESS: single
        (D) TOPOLOGY: linear (xi) SEQUENCE DESCRIPTION: SEQ ID NO:176:

```
GGCTATCAGT CCGGACGGTC CTCGCTGCGC GCATCGGTGT TCGACCGCCT CACCGACATC     60

CGCGAGTCGC AGTCGCGCGG GTTGGAGAAT CAGTTCGCGG ACCTGAAGAA CTCGATGGTG    120

ATTTACTCGC GCGGCAGCAC TGCCACGGAG GCGATCGGCG CGTTCAGCGA CGGTTTCCGT    180

CAGCTCGGCG ATGCGACGAT CAATACCGGG CAGGCGGCGT CATTGCGCCG TTACTACGAC    240

CGGACGTTCG CCAACACCAC CCTCGACGAC AGCGGAAACC GCGTCGACGT CCGCGCGCTC    300

ATCCCGAAAT CCAACCCCCA GCGCTATCTG CAGGCGCTCT ATACCCCGCC GTTTCAGAAC    360

TGGGAGAAGG CGATCGCGTT CGACGACGCG CGCGACGGCA GCGCCTGGTC GGCCGCCAAT    420

GCCAGATTCA ACGAGTTCTT CCGCGAGATC GTGCACCGCT TCAACTTCGA GGATCTGATG    480

CTGCTCGACC TCGAGGGCAA CGTGGTGTAC TCCGCCTACA AGGGGCCGGA TCTCGGGACA    540

AACATCGTCA ACGGCCCCTA TCGCAACCGG GAACTGTCGG AAGCCTACGA GAAGGCGGTC    600

GCGTCGAACT CGATCGACTA TGTCGGTGTC ACCGACTTCG GGTGGTACCT GCCTGCCGAG    660

GAACCGACCG CCTGGTTCCT GTCCCCGGTC GGGTTGAAGG ACCGAGTCGA CGGTGTGATG    720

GCGGTCCAGT TCCCGATCGC GCGGATCAAC GAATTGATGA CGGCGCGGGG ACAGTGGCGT    780

GACACCGGGA TGGGAGACAC CGGTGAGACC ATCCTGGTCG GACCGGACAA TCTGATGCGC    840

TCGGACTCCC GGCTGTTCCG CGAGAACCGG GAGAAGTTCC TGGCCGACGT CGTCGAGGGG    900

GGAACCCCGC CGGAGGTCGC CGACGAATCG GTTGACCGCC GCGGCACCAC GCTGGTGCAG    960

CCGGTGACCA CCCGCTCCGT CGAGGAGGCC CAACGCGGCA ACACCGGGAC GACGATCGAG   1020

GACGACTATC TCGGCCACGA GGCGTTACAG GCGTACTCAC CGGTGGACCT GCCGGGACTG   1080

CACTGGGTGA TCGTGGCCAA GATCGACACC GACGAGGCGT TCGCCCCGGT GGCGCAGTTC   1140

ACCAGGACCC TGGTGCTGTC GACGGTGATC ATCATCTTCG GCGTGTCGCT GGCGGCCATG   1200

CTGCTGGCGC GGTTGTTCGT CCGTCCGATC CGGCGGTTGC AGGCCGGCGC CCAGCAGATC   1260

AGCGGCGGTG ACTACCGCCT CGCTCTGCCG GTGTTGTCTC GTGACGAATT CGGCGATCTG   1320

ACAACAGCTT TCAACGACAT GAGTCGCAAT CTGTCGATCA AGGACGAGCT GCTCGGCGAG   1380

GAGCGCGCCG AGAACCAACG GCTGATGCTG TCCCTGATGC CCGAACCGGT GATGCAGCGC   1440

TACCTCGACG GGGAGGAGAC GATCGCCCAG GACCACAAGA ACGTCACGGT GATCTTCGCC   1500

GACATGATGG GCCTCGACGA GTTGTCGCGC ATGTTGACCT CCGAGGAACT GATGGTGGTG   1560
```

```
GTCAACGACC TGACCCGCCA GTTCGACGCC GCCGCCGAGA GTCTCGGGGT CGACCACGTG    1620

CGGACGCTGC ACGACGGGTA CCTGGCCAGC TGCGGGTTAG GCGTGCCGCG GCTGGACAAC    1680

GTCCGGCGCA CGGTCAATTT CGCGATCGAA ATGGACCGCA TCATCGACCG CACGCCGCC     1740

GAGTCCGGGC ACGACCTGCG GCTCCGCGCG GGCATCGACA CCGGGTCGGC GGCCAGCGGG    1800

CTGGTGGGGC GGTCCACGTT GGCGTACGAC ATGTGGGGTT CGGCGGTCGA TGTCGCTAAC    1860

CAGGTGCAGC GCGGCTCCCC CCAGCCCGGC ATCTACGTCA CCTCGCGGGT GCACGAGGTC    1920

ATGCAGGAAA CTCTCGACTT CGTCGCCGCC GGGGAGGTCG TCGGCGAGCG CGGCGTCGAG    1980

ACGGTCTGGC GGTTGCAGGG CCACCGGCGA TGA                                 2013
```

(2) INFORMATION FOR SEQ ID NO:177:

(i) SEQUENCE CHARACTERISTICS:
        (A) LENGTH: 297 amino acids
        (B) TYPE: amino acid
        (C) STRANDEDNESS: single
        (D) TOPOLOGY: linear (xi) SEQUENCE DESCRIPTION: SEQ ID NO:177:

```
Glu Gln Pro Phe Arg Leu Gly Asp Trp Ile Thr Val Pro Thr Ala Ala
 1               5                  10                  15

Gly Arg Pro Ser Ala His Gly Arg Val Glu Val Asn Trp Arg Ala
            20                  25                  30

Thr His Ile Asp Thr Gly Gly Asn Leu Leu Val Met Pro Asn Ala Glu
         35                  40                  45

Leu Ala Gly Ala Ser Phe Thr Asn Tyr Ser Arg Pro Val Gly Glu His
     50                  55                  60

Arg Leu Thr Val Val Thr Thr Phe Asn Ala Ala Asp Thr Pro Asp Asp
 65                  70                  75                  80

Val Cys Glu Met Leu Ser Ser Val Ala Ala Ser Leu Pro Glu Leu Arg
                 85                  90                  95

Thr Asp Gly Gln Ile Ala Thr Leu Tyr Leu Gly Ala Ala Glu Tyr Glu
            100                 105                 110

Lys Ser Ile Pro Leu His Thr Pro Ala Val Asp Asp Ser Val Arg Ser
        115                 120                 125

Thr Tyr Leu Arg Trp Val Trp Tyr Ala Ala Arg Arg Gln Glu Leu Arg
    130                 135                 140

Xaa Asn Gly Val Ala Asp Xaa Phe Asp Thr Pro Glu Arg Ile Ala Ser
145                 150                 155                 160

Ala Met Arg Ala Val Ala Ser Thr Leu Arg Leu Ala Asp Asp Glu Gln
                165                 170                 175

Gln Glu Ile Ala Asp Val Val Arg Leu Val Arg Tyr Gly Asn Gly Glu
            180                 185                 190

Arg Leu Gln Gln Pro Gly Gln Val Pro Thr Gly Met Arg Phe Ile Val
        195                 200                 205

Asp Gly Arg Val Ser Leu Ser Val Ile Asp Gln Asp Gly Asp Val Ile
    210                 215                 220

Pro Ala Arg Val Leu Glu Arg Gly Asp Phe Leu Gly Gln Thr Thr Leu
225                 230                 235                 240

Thr Arg Glu Pro Val Leu Ala Thr Ala His Ala Leu Glu Glu Val Thr
                245                 250                 255

Val Leu Glu Met Ala Arg Asp Glu Ile Glu Arg Leu Val His Arg Lys
            260                 265                 270

Pro Ile Leu Leu His Val Ile Gly Ala Val Ala Asp Arg Arg Ala His
        275                 280                 285
```

```
Glu Leu Arg Leu Met Asp Ser Gln Asp
    290                 295
```

(2) INFORMATION FOR SEQ ID NO:178:

(i) SEQUENCE CHARACTERISTICS:
        (A) LENGTH: 670 amino acids
        (B) TYPE: amino acid
        (C) STRANDEDNESS: single
        (D) TOPOLOGY: linear (xi) SEQUENCE DESCRIPTION: SEQ ID NO:178:

```
Gly Tyr Gln Ser Gly Arg Ser Ser Leu Arg Ala Ser Val Phe Asp Arg
1               5                   10                  15

Leu Thr Asp Ile Arg Glu Ser Gln Ser Arg Gly Leu Glu Asn Gln Phe
            20                  25                  30

Ala Asp Leu Lys Asn Ser Met Val Ile Tyr Ser Arg Gly Ser Thr Ala
            35                  40                  45

Thr Glu Ala Ile Gly Ala Phe Ser Asp Gly Phe Arg Gln Leu Gly Asp
        50                  55                  60

Ala Thr Ile Asn Thr Gly Gln Ala Ala Ser Leu Arg Arg Tyr Tyr Asp
65                  70                  75                  80

Arg Thr Phe Ala Asn Thr Thr Leu Asp Asp Ser Gly Asn Arg Val Asp
            85                  90                  95

Val Arg Ala Leu Ile Pro Lys Ser Asn Pro Gln Arg Tyr Leu Gln Ala
            100                 105                 110

Leu Tyr Thr Pro Pro Phe Gln Asn Trp Glu Lys Ala Ile Ala Phe Asp
            115                 120                 125

Asp Ala Arg Asp Gly Ser Ala Trp Ser Ala Ala Asn Ala Arg Phe Asn
            130                 135                 140

Glu Phe Phe Arg Glu Ile Val His Arg Phe Asn Phe Glu Asp Leu Met
145                 150                 155                 160

Leu Leu Asp Leu Glu Gly Asn Val Val Tyr Ser Ala Tyr Lys Gly Pro
            165                 170                 175

Asp Leu Gly Thr Asn Ile Val Asn Gly Pro Tyr Arg Asn Arg Glu Leu
            180                 185                 190

Ser Glu Ala Tyr Glu Lys Ala Val Ala Ser Asn Ser Ile Asp Tyr Val
            195                 200                 205

Gly Val Thr Asp Phe Gly Trp Tyr Leu Pro Ala Glu Glu Pro Thr Ala
        210                 215                 220

Trp Phe Leu Ser Pro Val Gly Leu Lys Asp Arg Val Asp Gly Val Met
225                 230                 235                 240

Ala Val Gln Phe Pro Ile Ala Arg Ile Asn Glu Leu Met Thr Ala Arg
            245                 250                 255

Gly Gln Trp Arg Asp Thr Gly Met Gly Asp Thr Gly Glu Thr Ile Leu
            260                 265                 270

Val Gly Pro Asp Asn Leu Met Arg Ser Asp Ser Arg Leu Phe Arg Glu
        275                 280                 285

Asn Arg Glu Lys Phe Leu Ala Asp Val Val Glu Gly Gly Thr Pro Pro
290                 295                 300

Glu Val Ala Asp Glu Ser Val Asp Arg Arg Gly Thr Thr Leu Val Gln
305                 310                 315                 320

Pro Val Thr Thr Arg Ser Val Glu Glu Ala Gln Arg Gly Asn Thr Gly
            325                 330                 335

Thr Thr Ile Glu Asp Asp Tyr Leu Gly His Glu Ala Leu Gln Ala Tyr
            340                 345                 350
```

```
Ser Pro Val Asp Leu Pro Gly Leu His Trp Val Ile Val Ala Lys Ile
        355                 360                 365

Asp Thr Asp Glu Ala Phe Ala Pro Val Ala Gln Phe Thr Arg Thr Leu
    370                 375                 380

Val Leu Ser Thr Val Ile Ile Phe Gly Val Ser Leu Ala Ala Met
385                 390                 395                 400

Leu Leu Ala Arg Leu Phe Val Arg Pro Ile Arg Arg Leu Gln Ala Gly
            405                 410                 415

Ala Gln Gln Ile Ser Gly Gly Asp Tyr Arg Leu Ala Leu Pro Val Leu
            420                 425                 430

Ser Arg Asp Glu Phe Gly Asp Leu Thr Thr Ala Phe Asn Asp Met Ser
        435                 440                 445

Arg Asn Leu Ser Ile Lys Asp Glu Leu Leu Gly Glu Arg Ala Glu
    450                 455                 460

Asn Gln Arg Leu Met Leu Ser Leu Met Pro Glu Pro Val Met Gln Arg
465                 470                 475                 480

Tyr Leu Asp Gly Glu Glu Thr Ile Ala Gln Asp His Lys Asn Val Thr
                485                 490                 495

Val Ile Phe Ala Asp Met Met Gly Leu Asp Glu Leu Ser Arg Met Leu
                500                 505                 510

Thr Ser Glu Glu Leu Met Val Val Val Asn Asp Leu Thr Arg Gln Phe
        515                 520                 525

Asp Ala Ala Ala Glu Ser Leu Gly Val Asp His Val Arg Thr Leu His
        530                 535                 540

Asp Gly Tyr Leu Ala Ser Cys Gly Leu Gly Val Pro Arg Leu Asp Asn
545                 550                 555                 560

Val Arg Arg Thr Val Asn Phe Ala Ile Glu Met Asp Arg Ile Ile Asp
                565                 570                 575

Arg His Ala Ala Glu Ser Gly His Asp Leu Arg Leu Arg Ala Gly Ile
                580                 585                 590

Asp Thr Gly Ser Ala Ala Ser Gly Leu Val Gly Arg Ser Thr Leu Ala
        595                 600                 605

Tyr Asp Met Trp Gly Ser Ala Val Asp Val Ala Asn Gln Val Gln Arg
    610                 615                 620

Gly Ser Pro Gln Pro Gly Ile Tyr Val Thr Ser Arg Val His Glu Val
625                 630                 635                 640

Met Gln Glu Thr Leu Asp Phe Val Ala Ala Gly Glu Val Val Gly Glu
                645                 650                 655

Arg Gly Val Glu Thr Val Trp Arg Leu Gln Gly His Arg Arg
                660                 665                 670

(2) INFORMATION FOR SEQ ID NO:179:

(i) SEQUENCE CHARACTERISTICS:
        (A) LENGTH: 520 base pairs
        (B) TYPE: nucleic acid
        (C) STRANDEDNESS: single
        (D) TOPOLOGY: linear (xi) SEQUENCE DESCRIPTION: SEQ ID NO:179:

GTGATCGACG AAACCCTCTT CCATGCCGAG GAGAAGATGG AGAAGGCCGT CTCGGTGGCA    60

CCCGACGACC TGGCGTCGAT TCGTACCGGC CGCGCGAACC CCGGCATGTT CAACCGGATC   120

AACATCGACT ACTACGGCGC CTCCACCCCG ATCACGCAGC TGTCCAGCAT CAACGTGCCC   180

GAGGCGCGCA TGGTGGTGAT CAAGCCCTAC GAGGCGAGCC AGCTGCGCCT CATCGAGGAT   240
```

```
GCGATCCGCA ACTCCGACCT CGGCGTCAAT CCGACCAACG ACGGCAACAT CATCCGGGTG      300

TCGATCCCGC AGCTCACCGA GGAGCGCCGC CGCGACCTGG TCAAGCAGGC CAAGGCCAAG      360

GGCGAGGACG CCAAGGTGTC GGTGCGCAAC ATCCGTCGCA ACGATATGAA CACCTTTCGC      420

ATCGCACCGG TACGGCTGCC GACGCCACCG CCGTCGTAGA AGCGACAGAG GATCGCAGGT      480

AACGGTATTG GCCACGCCTT CTGTGGCGGG CCGACACCAC                            520
```

(2) INFORMATION FOR SEQ ID NO:180:

(i) SEQUENCE CHARACTERISTICS:
        (A) LENGTH: 1071 base pairs
        (B) TYPE: nucleic acid
        (C) STRANDEDNESS: single
        (D) TOPOLOGY: linear (xi) SEQUENCE DESCRIPTION: SEQ ID NO:180:

```
CGTGGGGAAG GATTGCACTC TATGAGCGAA ATCGCCCGTC CCTGGCGGGT TCTGGCAGGT       60

GGCATCGGTG CCTGCGCCGC GGGTATCGCC GGGGTGCTGA GCATCGCGGT CACCACGGCG      120

TCGGCCCAGC CGGGCCTCCC GCAGCCCCCG CTGCCCGCCC CTGCCACAGT GACGCAAACC      180

GTCACGGTTG CGCCCAACGC CGCGCCACAA CTCATCCCGC GCCCCGGTGT GACGCCTGCC      240

ACCGGCGGCG CCGCCGCGGT GCCCGCCGGG GTGAGCGCCC CGGCGGTCGC GCCGGCCCCC      300

GCGCTGCCCG CCCGCCCGGT GTCCACGATC GCCCCGGCCA CCTCGGGCAC GCTCAGCGAG      360

TTCTTCGCCG CCAAGGGCGT CACGATGGAG CCGCAGTCCA GCCGCGACTT CCGCGCCCTC      420

AACATCGTGC TGCCGAAGCC GCGGGGCTGG GAGCACATCC CGGACCCGAA CGTGCCGGAC      480

GCGTTCGCGG TGCTGGCCGA CCGGGTCGGC GGCAACGGCC TGTACTCGTC GAACGCCCAG      540

GTGGTGGTCT ACAAACTCGT CGGCGAGTTC GACCCCAAGG AAGCGATCAG CCACGGCTTC      600

GTCGACAGCC AGAAGCTGCC GGCGTGGCGT TCCACCGACG CGTCGCTGGC CGACTTCGGC      660

GGAATGCCGT CCTCGCTGAT CGAGGGCACC TACCGCGAGA ACAACATGAA GCTGAACACG      720

TCCCGGCGCC ACGTCATTGC CACCGCGGGG CCCGACCACT ACCTGGTGTC GCTGTCGGTG      780

ACCACCAGCG TCGAACAGGC CGTGGCCGAA GCCGCGGAGG CCACCGACGC GATTGTCAAC      840

GGCTTCAAGG TCAGCGTTCC GGGTCCGGGT CCGGCCGCAC CGCCACCTGC ACCCGGTGCC      900

CCCGGTGTCC CGCCCGCCCC CGGCGCCCCG GCGCTGCCGC TGGCCGTCGC ACCACCCCCG      960

GCTCCCGCTG TTCCCGCCGT GGCGCCCGCG CCACAGCTGC TGGGACTGCA GGGATAGACG     1020

TCGTCGTCCC CCGGGCGAAG CCTGGCGCCC GGGGACGAC GGCCCCTTTC T              1071
```

(2) INFORMATION FOR SEQ ID NO:181:

(i) SEQUENCE CHARACTERISTICS:
        (A) LENGTH: 152 amino acids
        (B) TYPE: amino acid
        (C) STRANDEDNESS: single
        (D) TOPOLOGY: linear (xi) SEQUENCE DESCRIPTION: SEQ ID NO:181:

```
Val Ile Asp Glu Thr Leu Phe His Ala Glu Glu Lys Met Glu Lys Ala
  1               5                  10                  15

Val Ser Val Ala Pro Asp Asp Leu Ala Ser Ile Arg Thr Gly Arg Ala
                 20                  25                  30

Asn Pro Gly Met Phe Asn Arg Ile Asn Ile Asp Tyr Tyr Gly Ala Ser
             35                  40                  45

Thr Pro Ile Thr Gln Leu Ser Ser Ile Asn Val Pro Glu Ala Arg Met
         50                  55                  60
```

```
Val Val Ile Lys Pro Tyr Glu Ala Ser Gln Leu Arg Leu Ile Glu Asp
 65                  70                  75                  80

Ala Ile Arg Asn Ser Asp Leu Gly Val Asn Pro Thr Asn Asp Gly Asn
                 85                  90                  95

Ile Ile Arg Val Ser Ile Pro Gln Leu Thr Glu Arg Arg Arg Arg Asp
                100                 105                 110

Leu Val Lys Gln Ala Lys Ala Lys Gly Glu Asp Ala Lys Val Ser Val
            115                 120                 125

Arg Asn Ile Arg Arg Asn Asp Met Asn Thr Phe Arg Ile Ala Pro Val
    130                 135                 140

Arg Leu Pro Thr Pro Pro Pro Ser
145                 150
```

(2) INFORMATION FOR SEQ ID NO:182:

(i) SEQUENCE CHARACTERISTICS:
        (A) LENGTH: 331 amino acids
        (B) TYPE: amino acid
        (C) STRANDEDNESS: single
        (D) TOPOLOGY: linear (xi) SEQUENCE DESCRIPTION: SEQ ID NO:182:

```
Met Ser Glu Ile Ala Arg Pro Trp Arg Val Leu Ala Gly Gly Ile Gly
  1               5                  10                  15

Ala Cys Ala Ala Gly Ile Ala Gly Val Leu Ser Ile Ala Val Thr Thr
                 20                  25                  30

Ala Ser Ala Gln Pro Gly Leu Pro Gln Pro Leu Pro Ala Pro Ala
             35                  40                  45

Thr Val Thr Gln Thr Val Thr Val Ala Pro Asn Ala Ala Pro Gln Leu
 50                  55                  60

Ile Pro Arg Pro Gly Val Thr Pro Ala Thr Gly Gly Ala Ala Ala Val
 65                  70                  75                  80

Pro Ala Gly Val Ser Ala Pro Ala Val Ala Pro Ala Pro Ala Leu Pro
                 85                  90                  95

Ala Arg Pro Val Ser Thr Ile Ala Pro Ala Thr Ser Gly Thr Leu Ser
                100                 105                 110

Glu Phe Phe Ala Ala Lys Gly Val Thr Met Glu Pro Gln Ser Ser Arg
            115                 120                 125

Asp Phe Arg Ala Leu Asn Ile Val Leu Pro Lys Pro Arg Gly Trp Glu
    130                 135                 140

His Ile Pro Asp Pro Asn Val Pro Asp Ala Phe Ala Val Leu Ala Asp
145                 150                 155                 160

Arg Val Gly Gly Asn Gly Leu Tyr Ser Ser Asn Ala Gln Val Val Val
                165                 170                 175

Tyr Lys Leu Val Gly Glu Phe Asp Pro Lys Glu Ala Ile Ser His Gly
            180                 185                 190

Phe Val Asp Ser Gln Lys Leu Pro Ala Trp Arg Ser Thr Asp Ala Ser
    195                 200                 205

Leu Ala Asp Phe Gly Gly Met Pro Ser Ser Leu Ile Glu Gly Thr Tyr
210                 215                 220

Arg Glu Asn Asn Met Lys Leu Asn Thr Ser Arg Arg His Val Ile Ala
225                 230                 235                 240

Thr Ala Gly Pro Asp His Tyr Leu Val Ser Leu Ser Val Thr Thr Ser
                245                 250                 255

Val Glu Gln Ala Val Ala Glu Ala Ala Glu Ala Thr Asp Ala Ile Val
                260                 265                 270
```

```
Asn Gly Phe Lys Val Ser Val Pro Gly Pro Gly Pro Ala Ala Pro Pro
            275                 280                 285

Pro Ala Pro Gly Ala Pro Gly Val Pro Pro Ala Pro Gly Ala Pro Ala
        290                 295                 300

Leu Pro Leu Ala Val Ala Pro Pro Pro Ala Pro Ala Val Pro Ala Val
305                 310                 315                 320

Ala Pro Ala Pro Gln Leu Leu Gly Leu Gln Gly
            325                 330
```

(2) INFORMATION FOR SEQ ID NO:183:

(i) SEQUENCE CHARACTERISTICS:
        (A) LENGTH: 207 base pairs
        (B) TYPE: nucleic acid
        (C) STRANDEDNESS: single
        (D) TOPOLOGY: linear (xi) SEQUENCE DESCRIPTION: SEQ ID NO:183:

```
ACCTACGAGT TCGAGAACAA GGTCACGGGC GGCCGCATCC CGCGCGAGTA CATCCCGTCG     60

GTGGATGCCG GCGCGCAGGA CGCCATGCAG TACGGCGTGC TGGCCGGCTA CCCGCTGGTT    120

AACGTCAAGC TGACGCTGCT CGACGGTGCC TACCACGAAG TCGACTCGTC GGAAATGGCA    180

TTCAAGGTTG CCGGCTCCCA GGTCATA                                       207
```

(2) INFORMATION FOR SEQ ID NO:184:

(i) SEQUENCE CHARACTERISTICS:
        (A) LENGTH: 69 amino acids
        (B) TYPE: amino acid
        (C) STRANDEDNESS: single
        (D) TOPOLOGY: linear (xi) SEQUENCE DESCRIPTION: SEQ ID NO:184:

```
Thr Tyr Glu Phe Glu Asn Lys Val Thr Gly Gly Arg Ile Pro Arg Glu
1               5                   10                  15

Tyr Ile Pro Ser Val Asp Ala Gly Ala Gln Asp Ala Met Gln Tyr Gly
            20                  25                  30

Val Leu Ala Gly Tyr Pro Leu Val Asn Val Lys Leu Thr Leu Leu Asp
        35                  40                  45

Gly Ala Tyr His Glu Val Asp Ser Ser Glu Met Ala Phe Lys Val Ala
    50                  55                  60

Gly Ser Gln Val Ile
65
```

(2) INFORMATION FOR SEQ ID NO:185:

(i) SEQUENCE CHARACTERISTICS:
        (A) LENGTH: 898 base pairs
        (B) TYPE: nucleic acid
        (C) STRANDEDNESS: single
        (D) TOPOLOGY: linear (xi) SEQUENCE DESCRIPTION: SEQ ID NO:185:

```
CGACCTCCAC CCGGGCGTGA GGCCAACCAC TAGGCTGGTC ACCAGTAGTC GACGGCACAC     60

TTCACCGAAA AAATGAGGAC AGAGGAGACA CCCGTGACGA TCCGTGTTGG TGTGAACGGC    120

TTCGGCCGTA TCGGACGCAA CTTCTTCCGC GCGCTGGACG CGCAGAAGGC CGAAGGCAAG    180

AACAAGGACA TCGAGATCGT CGCGGTCAAC GACCTCACCG ACAACGCCAC GCTGGCGCAC    240

CTGCTGAAGT TCGACTCGAT CCTGGGCCGG CTGCCCTACG ACGTGAGCCT CGAAGGCGAG    300

GACACCATCG TCGTCGGCAG CACCAAGATC AAGGCGCTCG AGGTCAAGGA AGGCCCGGCG    360
```

-continued

```
GCGCTGCCCT GGGGCGACCT GGGCGTCGAC GTCGTCGTCG AGTCCACCGG CATCTTCACC      420

AAGCGCGACA AGGCCCAGGG CCACCTCGAC GCGGGCGCCA AGAAGGTCAT CATCTCCGCG      480

CCGGCCACCG ATGAGGACAT CACCATCGTG CTCGGCGTCA ACGACGACAA GTACGACGGC      540

AGCCAGAACA TCATCTCCAA CGCGTCGTGC ACCACGAACT GCCTCGGCCC GCTGGCGAAG      600

GTCATCAACG ACGAGTTCGG CATCGTCAAG GGCCTGNTGA CCACCATCCA CGCCTACACC      660

CNGGTCCAGA ACCTGCAGGA CGGCCCGCAC AAGGATCTGC GCCGGGCCCG CGCCGCCGCG      720

CTGAACATCG TGCCGACCTC CACCGGTGCC GCCAAGGCCA TCGGACTGGT GCTGCCCGAG      780

CTGAAGGGCA AGCTCGACGG CTACGCGCTG CGGGTGCCGA TCCCCACCGG CTCGGTCACC      840

GACCTGACCG CCGAGCTGGG CAAGTCGGCC ACCGTGGACG AGATCAACGC CGCGATGA       898
```

(2) INFORMATION FOR SEQ ID NO:186:

(i) SEQUENCE CHARACTERISTICS:
      (A) LENGTH: 268 amino acids
      (B) TYPE: amino acid
      (C) STRANDEDNESS: single
      (D) TOPOLOGY: linear (xi) SEQUENCE DESCRIPTION: SEQ ID NO:186:

```
Val Thr Ile Arg Val Gly Val Asn Gly Phe Gly Arg Ile Gly Arg Asn
 1               5                  10                  15

Phe Phe Arg Ala Leu Asp Ala Gln Lys Ala Glu Gly Lys Asn Lys Asp
            20                  25                  30

Ile Glu Ile Val Ala Val Asn Asp Leu Thr Asp Asn Ala Thr Leu Ala
        35                  40                  45

His Leu Leu Lys Phe Asp Ser Ile Leu Gly Arg Leu Pro Tyr Asp Val
    50                  55                  60

Ser Leu Glu Gly Glu Asp Thr Ile Val Val Gly Ser Thr Lys Ile Lys
65                  70                  75                  80

Ala Leu Glu Val Lys Glu Gly Pro Ala Ala Leu Pro Trp Gly Asp Leu
                85                  90                  95

Gly Val Asp Val Val Glu Ser Thr Gly Ile Phe Thr Lys Arg Asp
            100                 105                 110

Lys Ala Gln Gly His Leu Asp Ala Gly Ala Lys Val Ile Ile Ser
        115                 120                 125

Ala Pro Ala Thr Asp Glu Asp Ile Thr Ile Val Leu Gly Val Asn Asp
    130                 135                 140

Asp Lys Tyr Asp Gly Ser Gln Asn Ile Ile Ser Asn Ala Ser Cys Thr
145                 150                 155                 160

Thr Asn Cys Leu Gly Pro Leu Ala Lys Val Ile Asn Asp Glu Phe Gly
                165                 170                 175

Ile Val Lys Gly Leu Xaa Thr Thr Ile His Ala Tyr Thr Xaa Val Gln
            180                 185                 190

Asn Leu Gln Asp Gly Pro His Lys Asp Leu Arg Arg Ala Arg Ala Ala
        195                 200                 205

Ala Leu Asn Ile Val Pro Thr Ser Thr Gly Ala Ala Lys Ala Ile Gly
    210                 215                 220

Leu Val Leu Pro Glu Leu Lys Gly Lys Leu Asp Gly Tyr Ala Leu Arg
225                 230                 235                 240

Val Pro Ile Pro Thr Gly Ser Val Thr Asp Leu Thr Ala Glu Leu Gly
                245                 250                 255

Lys Ser Ala Thr Val Asp Glu Ile Asn Ala Ala Met
            260                 265
```

(2) INFORMATION FOR SEQ ID NO:187:

(i) SEQUENCE CHARACTERISTICS:
        (A) LENGTH: 41 amino acids
        (B) TYPE: amino acid
        (C) STRANDEDNESS: single
        (D) TOPOLOGY: linear (xi) SEQUENCE DESCRIPTION: SEQ ID NO:187:

```
Met Asn Lys Ala Glu Leu Ile Asp Val Leu Thr Glu Lys Leu Gly Ser
 1               5                  10                  15

Asp Arg Arg Gln Ala Thr Ala Ala Val Glu Asn Val Val Asp Thr Ile
             20                  25                  30

Val Ala Ala Val Pro Lys Xaa Val Val
         35                  40
```

(2) INFORMATION FOR SEQ ID NO:188:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:188:

ATGAAYAARG CNGARCTSAT YGAYGT                                   26

(2) INFORMATION FOR SEQ ID NO:189:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:189:

ATSGTRTGVA CVACGTTYTC                                         20

(2) INFORMATION FOR SEQ ID NO:190:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (xi) SEQUENCE DESCRIPTION: SEQ ID NO:190:

GNACTCATTG ACGTACTCAC TGAGAAGCTG GGCTCGGATT GTCGGCAAGC GACTGCGGCA    60

ATGGAGAACG TGGTCCACAC CATA                                         84

(2) INFORMATION FOR SEQ ID NO:191:

(i) SEQUENCE CHARACTERISTICS:
        (A) LENGTH: 337 base pairs
        (B) TYPE: nucleic acid
        (C) STRANDEDNESS: single
        (D) TOPOLOGY: linear (xi) SEQUENCE DESCRIPTION: SEQ ID NO:191:

GNACTCATTG ACGTACTCAC TGAGAAGCTG GGCTCGGATT GTCGGCAAGC GACTGCGGCG    60

GTGGAGAATG TTGTCGACAC CATCGTGCGC GCCGTGCACA AGGGTGAGAG CGTCACCATC   120

ACGGGCTTCG GTGTTTTCGA GCAGCGTCGT CGCGCAGCAC GCGTGGCACG CAATCCGCGC   180

ACCGGCGAGA CCGTGAAGGT CAAGCCCACC TCAGTCCCGG CATTCCGTCC CGGCGCTCAG   240

```
TTCAAGGCTG TTGTCTCTGG CGCACAGAAG CTTCCGGCCG AGGGTCCGGC GGTCAAGCGC    300

GGTGTGACCG CGACGAGCAC CGCCCGCAAG GCAGCCA                              337
```

(2) INFORMATION FOR SEQ ID NO:192:

(i) SEQUENCE CHARACTERISTICS:
        (A) LENGTH: 111 amino acids
        (B) TYPE: amino acid
        (C) STRANDEDNESS: single
        (D) TOPOLOGY: linear (xi) SEQUENCE DESCRIPTION: SEQ ID NO:192:

```
Xaa Leu Ile Asp Val Leu Thr Glu Lys Leu Gly Ser Asp Arg Gln Ala
 1               5                  10                  15

Thr Ala Ala Val Glu Asn Val Val Asp Thr Ile Val Arg Ala Val His
            20                  25                  30

Lys Gly Glu Ser Val Thr Ile Thr Gly Phe Gly Val Phe Glu Gln Arg
        35                  40                  45

Arg Arg Ala Ala Arg Val Ala Arg Asn Pro Arg Thr Gly Glu Thr Val
    50                  55                  60

Lys Val Lys Pro Thr Ser Val Pro Ala Phe Arg Pro Gly Ala Gln Phe
65                  70                  75                  80

Lys Ala Val Val Ser Gly Ala Gln Lys Leu Pro Ala Glu Gly Pro Ala
                85                  90                  95

Val Lys Arg Gly Val Thr Ala Thr Ser Thr Ala Arg Lys Ala Ala
            100                 105                 110
```

(2) INFORMATION FOR SEQ ID NO:193:

(i) SEQUENCE CHARACTERISTICS:
        (A) LENGTH: 1164 base pairs
        (B) TYPE: nucleic acid
        (C) STRANDEDNESS: single
        (D) TOPOLOGY: linear (xi) SEQUENCE DESCRIPTION: SEQ ID NO:193:

```
GGTGGCGCGC ATCGAGAAGC GCCCGCCCCG GTTCACGGGC GCCTGATCAT GGTGCGGGCG     60

GCGCTGCGCT ACGGCTTCGG GACGGCCTCA CTGCTGGCCG GCGGGTTCGT GCTGCGCGCC    120

CTGCAGGGCA CGCCTGCCGC CCTCGGCGCG ACTCCGGGCG AGGTCGCGCC GGTGGCGCGC    180

CGCTCGCCGA ACTACCGCGA CGGCAAGTTC GTCAACCTGG AGCCCCCGTC GGGCATCACG    240

ATGGATCGCG ACCTGCAGCG GATGCTGTTG CGCGATCTGG CCAACGCCGC ATCCCAGGGC    300

AAGCCGCCCG GACCGATCCC GCTGGCCGAG CCGCCGAAGG GGGATCCCAC TCCCGCGCCG    360

GCGGCGGCCA GCTGGTACGG CCATTCCAGC GTGCTGATCG AGGTCGACGG CTACCGCGTG    420

CTGGCCGACC CGGTGTGGAG CAACAGATGT TCGCCCTCAC GGGCGGTCGG ACCGCAGCGC    480

ATGCACGACG TCCCGGTGCC GCTGGAGGCG CTTCCCGCCG TGGACGCGGT GGTGATCAGC    540

CACGACCACT ACGACCACCT CGACATCGAC ACCATCGTCG CGTTGGCGCA CACCCAGCGG    600

GCCCCGTTCG TGGTGCCGTT GGGCATCGGC GCACACCTGC GCAAGTGGGG CGTCCCCGAG    660

GCGCGGATCG TCGAGTTGGA CTGGCACGAA GCCCACCGCA TAGACGACCT GACGCTGGTC    720

TGCACCCCCG CCCGGCACTT CTCCGGACGG TTGTTCTCCC GCGACTCGAC GCTGTGGGCG    780

TCGTGGGTGG TCACCGGCTC GTCGCACAAG GCGTTCTTCG GTGGCGACAC CGGATACACG    840

AAGAGCTTCG CCGAGATCGG CGACGAGTAC GGTCCGTTCG ATCTGACCCT GCTGCCGATC    900

GGGGCCTACC ATCCCGCGTT CGCCGACATC CACATGAACC CCGAGGAGGC GGTGCGCGCC    960

CATCTGGACC TGACCGAGGT GGACAACAGC CTGATGGTGC CCATCCACTG GGCGACATTC   1020
```

```
CGCCTCGCCC CGCATCCGTG GTCCGAGCCC GCCGAACGCC TGCTGACCGC TGCCGACGCC    1080

GAGCGGGTAC GCCTGACCGT GCCGATTCCC GGTCAGCGGG TGGACCCGGA GTCGACGTTC    1140

GACCCGTGGT GGCGGTTCTG AACC                                          1164
```

(2) INFORMATION FOR SEQ ID NO:194:

(i) SEQUENCE CHARACTERISTICS:
        (A) LENGTH: 370 amino acids
        (B) TYPE: amino acid
        (C) STRANDEDNESS: single
        (D) TOPOLOGY: linear (xi) SEQUENCE DESCRIPTION: SEQ ID NO:194:

```
Met Val Arg Ala Ala Leu Arg Tyr Gly Phe Gly Thr Ala Ser Leu Leu
 1               5                  10                  15

Ala Gly Gly Phe Val Leu Arg Ala Leu Gln Gly Thr Pro Ala Ala Leu
                20                  25                  30

Gly Ala Thr Pro Gly Glu Val Ala Pro Val Ala Arg Arg Ser Pro Asn
            35                  40                  45

Tyr Arg Asp Gly Lys Phe Val Asn Leu Glu Pro Ser Gly Ile Thr
 50                  55                  60

Met Asp Arg Asp Leu Gln Arg Met Leu Leu Arg Asp Leu Ala Asn Ala
65                  70                  75                  80

Ala Ser Gln Gly Lys Pro Pro Gly Pro Ile Pro Leu Ala Glu Pro Pro
                85                  90                  95

Lys Gly Asp Pro Thr Pro Ala Pro Ala Ala Ser Trp Tyr Gly His
            100                 105                 110

Ser Ser Val Leu Ile Glu Val Asp Gly Tyr Arg Val Leu Ala Asp Pro
            115                 120                 125

Val Trp Ser Asn Arg Cys Ser Pro Ser Arg Ala Val Gly Pro Gln Arg
130                 135                 140

Met His Asp Val Pro Val Pro Leu Glu Ala Leu Pro Ala Val Asp Ala
145                 150                 155                 160

Val Val Ile Ser His Asp His Tyr Asp His Leu Asp Ile Asp Thr Ile
                165                 170                 175

Val Ala Leu Ala His Thr Gln Arg Ala Pro Phe Val Val Pro Leu Gly
            180                 185                 190

Ile Gly Ala His Leu Arg Lys Trp Gly Val Pro Glu Ala Arg Ile Val
            195                 200                 205

Glu Leu Asp Trp His Glu Ala His Arg Ile Asp Asp Leu Thr Leu Val
210                 215                 220

Cys Thr Pro Ala Arg His Phe Ser Gly Arg Leu Phe Ser Arg Asp Ser
225                 230                 235                 240

Thr Leu Trp Ala Ser Trp Val Val Thr Gly Ser Ser His Lys Ala Phe
                245                 250                 255

Phe Gly Gly Asp Thr Gly Tyr Thr Lys Ser Phe Ala Glu Ile Gly Asp
            260                 265                 270

Glu Tyr Gly Pro Phe Asp Leu Thr Leu Leu Pro Ile Gly Ala Tyr His
            275                 280                 285

Pro Ala Phe Ala Asp Ile His Met Asn Pro Glu Glu Ala Val Arg Ala
        290                 295                 300

His Leu Asp Leu Thr Glu Val Asp Asn Ser Leu Met Val Pro Ile His
305                 310                 315                 320

Trp Ala Thr Phe Arg Leu Ala Pro His Pro Trp Ser Glu Pro Ala Glu
                325                 330                 335
```

-continued

```
Arg Leu Leu Thr Ala Ala Asp Ala Glu Arg Val Arg Leu Thr Val Pro
            340                 345                 350

Ile Pro Gly Gln Arg Val Asp Pro Glu Ser Thr Phe Asp Pro Trp Trp
            355                 360                 365

Arg Phe
    370
```

COMPOUNDS AND METHODS FOR TREATMENT AND DIAGNOSIS OF MYCOBACTERIAL INFECTIONS

REFERENCE TO RELATED APPLICATIONS

This application is a continuation-in-part of U.S. patent application Ser. No. 08/873,970, filed Jun. 12, 1997, which is a continuation-in-part of U.S. patent application Ser. No. 08/705,347, filed Aug. 29, 1996.

TECHNICAL FIELD

The present invention relates generally to the detection, treatment and prevention of infectious diseases. In particular, the invention is related to compounds and methods for the treatment of mycobacterial infections including *Mycobacterium tuberculosis* and *Mycobacterium avium*. The invention is further related to compounds that function as non-specific immune response amplifiers, and the use of such non-specific immune response amplifiers as adjuvants in vaccination or immunotherapy against infectious disease, and in certain treatments for immune disorders and cancer.

BACKGROUND OF THE INVENTION

Tuberculosis is a chronic, infectious disease, that is caused by infection with *Mycobacterium tuberculosis* (*M. tuberculosis*). It is a major disease in developing countries, as well as an increasing problem in developed areas of the world, with about 8 million new cases and 3 million deaths each year. Although the infection may be asymptomatic for a considerable period of time, the disease is most commonly manifested as a chronic inflammation of the lungs, resulting in fever and respiratory symptoms. If left untreated, significant morbidity and death may result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behaviour is difficult to monitor. Some patients do not complete the course of treatment, which can lead to ineffective treatment and the development of drug resistant mycobacteria.

Inhibiting the spread of tuberculosis requires effective vaccination and accurate, early diagnosis of the disease. Currently, vaccination with live bacteria is the most efficient method for inducing protective immunity. The most common mycobacterium employed for this purpose is Bacillus Calmette-Guerin (BCG), an avirulent strain of *Mycobacterium bovis*. However, the safety and efficacy of BCG is a source of controversy and some countries, such as the United States, do not vaccinate the general public. Diagnosis of *M. tuberculosis* infection is commonly achieved using a skin test, which involves intradermal exposure to tuberculin PPD (protein-purified derivative). Antigen-specific T cell responses result in measurable induration at the injection site by 48–72 hours after injection, thereby indicating exposure to mycobacterial antigens. Sensitivity and specificity have, however, been a problem with this test, and individuals vaccinated with BCG cannot be distinguished from infected individuals.

A less well-known mycobacterium that has been used for immunotherapy for tuberculosis, and also leprosy, is *Mycobacterium vaccae*, which is non-pathogenic in humans. However, there is less information on the efficacy of *M. vaccae* compared with BCG, and it has not been used widely to vaccinate the general public. *M. bovis* BCG and *M. vaccae* are believed to contain antigenic compounds that are recognised by the immune system of individuals exposed to infection with *M. tuberculosis*.

Several patents and other publications disclose treatment of various conditions by administering mycobacteria, including *M. vaccae*, or certain mycobacterial fractions. International Patent Publication WO 91/02542 discloses treatment of chronic inflammatory disorders in which a patient demonstrates an abnormally high release of IL-6 and/or TNF or in which the patient's IgG shows an abnormally high proportion of agalactosyl IgG. Among the disorders mentioned in this publication are psoriasis, rheumatoid arthritis, mycobacterial disease, Crohn's disease, primary biliary cirrhosis, sarcoidosis, ulcerative colitis, systemic lupus erythematosus, multiple sclerosis, Guillain-Barre syndrome, primary diabetes mellitus, and some aspects of graft rejection. The therapeutic agent preferably comprises autoclaved *M. vaccae* administered by injection in a single dose.

U.S. Pat. No. 4,716,038 discloses diagnosis of, vaccination against and treatment of autoimmune diseases of various types, including arthritic diseases, by administering mycobacteria, including *M. vaccae*. U.S. Pat. No. 4,724,144 discloses an immunotherapeutic agent comprising antigenic material derived from *M. vaccae* for treatment of mycobacterial diseases, especially tuberculosis and leprosy, and as an adjuvant to chemotherapy. International Patent Publication WO 91/01751 discloses the use of antigenic and/or immunoregulatory material from *M. vaccae* as an immunoprophylactic to delay and/or prevent the onset of AIDS. International Patent Publication WO 94/06466 discloses the use of antigenic and/or immunoregulatory material derived from *M. vaccae* for therapy of HIV infection, with or without AIDS and with or without associated tuberculosis.

U.S. Pat. No. 5,599,545 discloses the use of mycobacteria, especially whole, inactivated *M. vaccae*, as an adjuvant for administration with antigens which are not endogenous to *M. vaccae*. This publication theorises that the beneficial effect as an adjuvant may be due to heat shock protein 65 (hsp 65). International Patent Publication WO 92/08484 discloses the use of antigenic and/or immunoregulatory material derived from *M. vaccae* for the treatment of uveitis. International Patent Publication WO 93/16727 discloses the use of antigenic and/or immunoregulatory material derived from *M. vaccae* for the treatment of mental diseases associated with an autoimmune reaction initiated by an infection. International Patent Publication WO 95/26742 discloses the use of antigenic and/or immunoregulatory material derived from *M. vaccae* for delaying or preventing the growth or spread of tumors.

There remains a need in the art for effective compounds and methods for preventing, treating and detecting tuberculosis.

SUMMARY OF THE INVENTION

Briefly stated, the present invention provides compounds and methods for the prevention, treatment and diagnosis of mycobacterial infection, together with adjuvants for use in vaccines or immunotherapy of infectious diseases and cancers.

In a first aspect, polypeptides derived from *Mycobacterium vaccae* are provided comprising an immunogenic portion of an antigen, or a variant of such an antigen. In one embodiment, the antigen includes an amino acid sequence selected from the group consisting of: (a) sequences recited in SEQ ID NOS: 70, 75, 89, 94, 100, 105, 109, 110, 112, 121, 124, 125, 134, 135, 140, 141, 143, 145, 147, 152, 154 156, 158, 160, 165, 166, 170, 172, 174, 177, 178, 181, 182, 184, 186, 187, 192 and 194; and (b) sequences having at least about a 99% probability of being the same as a sequence recited in SEQ ID NOS: 70, 75, 89, 94, 100, 105, 109, 110, 112, 121, 124, 125, 134, 135, 140, 141, 143, 145, 147, 152, 154 156, 158, 160, 165, 166, 170, 172, 174, 177, 178, 181, 182, 184, 186, 187, 192 and 194 as measured by the computer algorithm BLASTP.

In a second aspect, the invention provides polypeptides comprising an immunogenic portion of an *M. vaccae* antigen wherein the antigen comprises an amino acid sequence encoded by a DNA molecule selected from the group consisting of: (a) sequences recited in SEQ ID NOS: 74, 88, 93, 97, 99, 106–108, 111, 120, 122, 123, 132, 133, 136–138, 142, 144, 146, 151, 153, 155, 157, 159, 161, 162, 163, 164, 169, 171, 173, 175, 176, 179, 180, 183, 185, 191 and 193; (b) complements of the sequences recited in SEQ ID NOS: 74, 88, 93, 97, 99, 106–108, 111, 120, 122, 123, 132, 133, 136–138, 142, 144, 146, 151, 153, 155, 157, 159, 161, 162, 163, 164, 169, 171, 173, 175, 176, 179, 180, 183, 185, 191 and 193; and (c) sequences having at least about a 99% probability of being the same as a sequence of (a) or (b) as measured by the computer algorithm FASTA.

DNA sequences encoding the inventive polypeptides, expression vectors comprising these DNA sequences, and host cells transformed or transfected with such expression vectors are also provided.

In another aspect, the present invention provides fusion proteins comprising a first and a second inventive polypeptide or, alternatively, an inventive polypeptide and a known *M. tuberculosis* antigen.

Within other aspects, the present invention provides pharmaceutical compositions that comprise at least one of the inventive polypeptides, or a DNA molecule encoding such a polypeptide, and a physiologically acceptable carrier. The invention also provides vaccines comprising at least one of the above polypeptides and a non-specific immune response amplifier, together with vaccines comprising at least one DNA sequence encoding such polypeptides and a non-specific immune response amplifier.

In yet another aspect, methods are provided for inducing protective immunity in a patient, comprising administering to a patient an effective amount of one or more of the above polypeptides together with an immune response amplifier.

In further aspects of this invention, methods and diagnostic kits are provided for detecting tuberculosis in a patient. In a first embodiment, the method comprises contacting dermal cells of a patient with one or more of the above polypeptides and detecting an immune response on the patient's skin. In a second embodiment, the method comprises contacting a biological sample with at least one of the above polypeptides; and detecting in the sample the presence of antibodies that bind to the polypeptide or polypeptides, thereby detecting *M. tuberculosis* infection in the biological sample. Suitable biological samples include whole blood, sputum, serum, plasma, saliva, cerebrospinal fluid and urine.

Diagnostic kits comprising one or more of the above polypeptides in combination with an apparatus sufficient to contact the polypeptide with the dermal cells of a patient are provided. The present invention also provides diagnostic kits comprising one or more of the inventive polypeptides in combination with a detection reagent.

In yet another aspect, the present invention provides antibodies, both polyclonal and monoclonal, that bind to the polypeptides described above, as well as methods for their use in the detection of *M. tuberculosis* infection.

The present invention also provides methods for enhancing a non-specific immune response to an antigen. In one embodiment, such methods comprise administering a composition comprising a component selected from the group consisting of: (a) delipidated *M. vaccae* cells, (b) deglycolipidated *M. vaccae* cells; (c) delipidated and deglycolipidated *M. vaccae* cells and (d) *M. vaccae* culture filtrate. In a second embodiment, such methods comprise administering a polypeptide, the polypeptide comprising an immunogenic portion of an antigen, wherein said antigen includes a sequence selected from the group consisting of: (a) sequences recited in SEQ ID NOS: 114, 117 and 118; and (b) sequences having at least about 97% identity to a sequence recited in SEQ ID NOS: 114, 117 and 118.

In yet a further aspect, compositions comprising a component selected from the group consisting of delipidated *M. vaccae* cells, deglycolipidated *M. vaccae* cells, and delipidated and deglycolipidated *M. vaccae* cells are provided, together with vaccines comprising such components and methods of using such compositions and vaccines to induce protective immunity in a patient.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 3 is a comparison of the Antigen 85A protein sequence obtained from *M. vaccae* with those from *M. bovis, M. tuberculosis* and *M. leprae*.

FIG. 4C(ii) illustrates the non-specific immune amplifying effects of soluble *M. vaccae* proteins extracted with SDS from delipidated and deglycolipidated *M. vaccae*.

FIG. 4C(iii) illustrates that the non-specific amplifying effects of the preparation of FIG. 4C(ii) are destroyed by treatment with the proteolytic enzyme Pronase.

DETAILED DESCRIPTION OF THE INVENTION

Figure 1A:
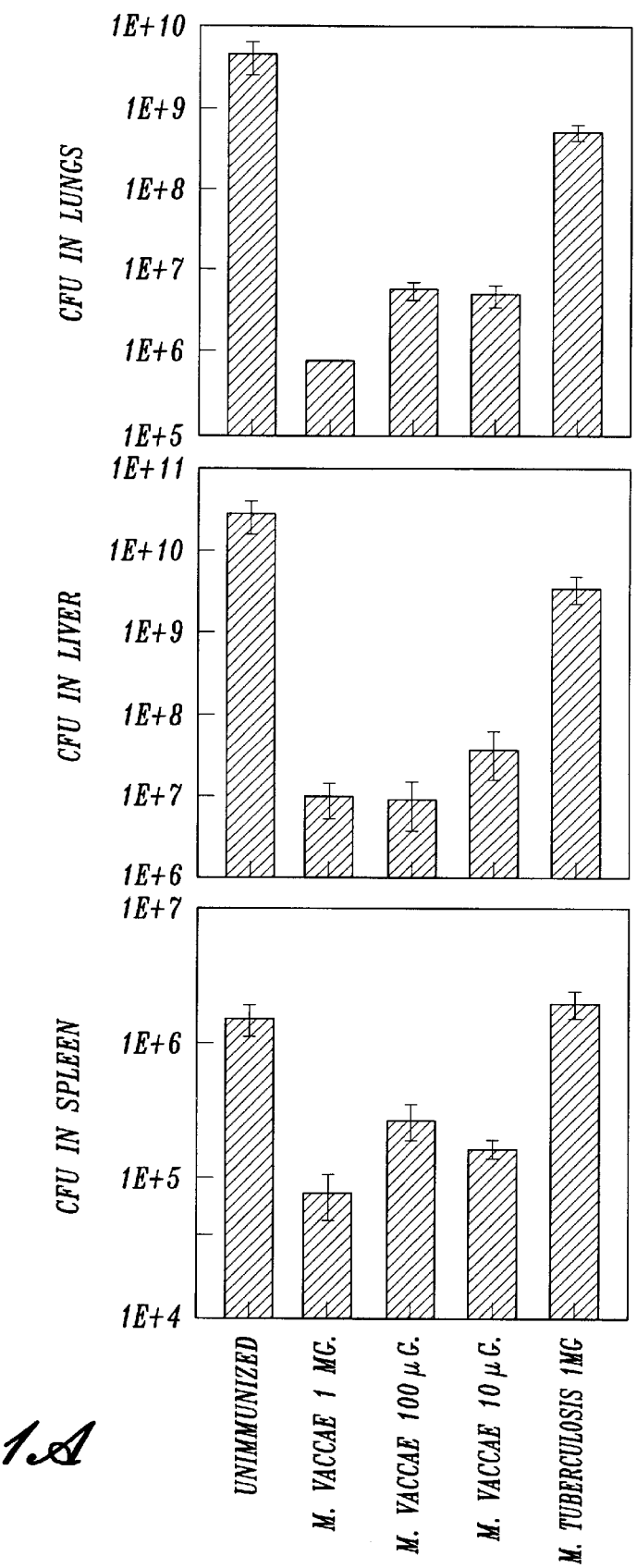
FIGS. 1A and 1B illustrate the protective effects of immunizing mice with autoclaved *M. vaccae* or unfractionated *M. vaccae* culture filtrates, respectively, prior to infection with live *M. tuberculosis* H37Rv.

As noted above, the present invention is generally directed to compositions and methods for preventing, treating and diagnosing mycobacterial infections, including *M. tuberculosis* and *M. avium* infections.

Considerable research efforts have been directed towards elucidating the mechanism of immune response to mycobacterial infection, in particular *M. tuberculosis* infection. While macrophages have been shown to act as the principal effectors of *M. tuberculosis* immunity, T cells are the predominant inducers of such immunity. The essential role of T cells in protection against *M. tuberculosis* infection is illustrated by the frequent occurrence of *M. tuberculosis* in AIDS patients, due to the depletion of CD4 T cells associated with human immunodeficiency virus (HIV) infection. Mycobacterium-reactive CD4 T cells have been shown to be potent producers of gamma-interferon (IFN-γ), which, in turn, has been shown to trigger the anti-mycobacterial effects of macrophages in mice. While the role of IFN-γ in humans is less clear, studies have shown that 1,25-dihydroxy-vitamin D3, either alone or in combination with IFN-γ or tumor necrosis factor-alpha, activates human macrophages to inhibit *M. tuberculosis* infection. Furthermore, it is known that IFN-γ stimulates human macrophages to make 1,25-dihydroxy-vitamin D3. Similarly, IL-12 has been shown to play a role in stimulating resistance to *M. tuberculosis* infection. Another property of CD4$^+$ T cells and macrophages is their ability to activate CD8$^+$ cytotoxic T cells which are capable of killing pathogen-infected cells. CD8$^+$ T cells have been shown to kill macrophages and other cells that harbour *M. tuberculosis*. For a review of the immunology of *M. tuberculosis* infection see Chan and Kaufmann in *Tuberculosis: Pathogenesis, Protection and Control*, Bloom (ed.), ASM Press, Washington, DC, 1994.

The compositions of the present invention include polypeptides that comprise at least one immunogenic portion of a*M. vaccae* antigen, or a variant thereof. Such polypeptides stimulate T cell proliferation, and/or, interferon gamma secretion from T cells of individuals exposed to *M. tuberculosis*. In certain embodiments, the inventive polypeptides comprise at least an immunogenic portion of a soluble *M. vaccae* antigen. A "soluble *M. vaccae* antigen" is a protein of *M. vaccae* origin that is present in *M. vaccae* culture filtrate. As used herein, the term "polypeptide" encompasses amino acid chains of any length, including full length proteins (i.e., antigens), wherein the amino acid residues are linked by covalent peptide bonds. Thus, a polypeptide comprising an immunogenic portion of one of the above antigens may consist entirely of the immunogenic portion, or may contain additional sequences. The additional sequences may be derived from the native *M. vaccae* antigen or may be heterologous, and such sequences may (but need not) be immunogenic.

"Immunogenic," as used herein, refers to the ability to elicit an immune response in a patient, such as a human, or in a biological sample. In particular, immunogenic antigens are capable of stimulating cell proliferation, interleukin-12 production or interferon-γ production in biological samples comprising one or more cells selected from the group of T cells, NK cells, B cells and macrophages, where the cells are derived from an *M. tuberculosis*-immune individual. Polypeptides comprising at least an immunogenic portion of one or more *M. vaccae* antigens may generally be used to detect tuberculosis or to induce protective immunity against tuberculosis in a patient.

The compositions and methods of this invention also encompass variants of the above polypeptides. As used herein, the term "variant" covers any sequence which exhibits at least about 50%, more preferably at least about 70% and more preferably yet, at least about 90% identity to a sequence of the present invention. Most preferably, a "variant" is any sequence which has at least about a 99% probability of being the same as the inventive sequence. The probability for DNA sequences is measured by the computer algorithm FASTA (version 2.0u4, February 1996; Pearson W. R. et al., *Proc. Natl. Acad. Sci.*, 85:2444–2448, 1988), the probability for translated DNA sequences is measured by the computer algorithm TBLASTX and that for protein sequences is measured by the computer algorithm BLASTP (Altschul, S. F. et al. *J. Mol. Biol.*, 215:403–410, 1990). The term "variants" thus encompasses sequences wherein the probability of finding a match by chance (smallest sum probability), is less than about 1% as measured by any of the above tests.

A polypeptide of the present invention may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

In general, *M. vaccae* antigens, and DNA sequences encoding such antigens, may be prepared using any of a variety of procedures. For example, soluble antigens may be isolated from *M. vaccae* culture filtrate as described below. Antigens may also be produced recombinantly by inserting a DNA sequence that encodes the antigen into an expression vector and expressing the antigen in an appropriate host. Any of a variety of expression vectors known to those of ordinary skill in the art may be employed. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, mycobacteria, insect, yeast or a mammalian cell line such as COS or CHO. The DNA sequences expressed in this manner may encode naturally occurring antigens, portions of naturally occurring antigens, or other variants thereof.

DNA sequences encoding *M. vaccae* antigens may be obtained by screening an appropriate *M. vaccae* cDNA or genomic DNA library for DNA sequences that hybridize to degenerate oligonucleotides derived from partial amino acid sequences of isolated soluble antigens. Suitable degenerate oligonucleotides may be designed and synthesized, and the screen may be performed as described, for example in Maniatis et al., *Molecular Cloning: A Laboratory Manual*, Cold Spring Harbor Laboratories, Cold Spring Harbor, N.Y., 1989. As described below, polymerase chain reaction (PCR) may be employed to isolate a nucleic acid probe from genomic DNA, or a cDNA or genomic DNA library. The library screen may then be performed using the isolated probe.

DNA molecules encoding *M. vaccae* antigens may also be isolated by screening an appropriate *M. vaccae* expression library with anti-sera (e.g., rabbit or monkey) raised specifically against *M. vaccae* antigens.

Regardless of the method of preparation, the antigens described herein have the ability to induce an immunogenic response. More specifically, the antigens have the ability to induce cell proliferation and/or cytokine production (for example, interferon-γ and/or interleukin-12 production) in T cells, NK cells, B cells or macrophages derived from an *M. tuberculosis*-immune individual. An *M. tuberculosis*-immune individual is one who is considered to be resistant to the development of tuberculosis by virtue of having mounted an effective T cell response to *M. tuberculosis*. Such individuals may be identified based on a strongly positive (i.e., greater than about 10 mm diameter induration) intradermal skin test response to tuberculosis proteins (PPD), and an absence of any symptoms of tuberculosis infection.

The selection of cell type for use in evaluating an immunogenic response to an antigen will depend on the desired response. For example, interleukin-12 production is most readily evaluated using preparations containing T cells, NK cells, B cells and macrophages derived from *M. tuberculosis*-immune individuals may be prepared using methods well known in the art. For example, a preparation of peripheral blood mononuclear cells (PBMCs) may be employed without further separation of component cells. PBMCs may be prepared, for example, using density centrifugation through Ficoll™ (Winthrop Laboratories, NY). T cells for use in the assays described herein may be purified directly from PBMCs. Alternatively, an enriched T cell line reactive against mycobacterial proteins, or T cell clones reactive to individual mycobacterial proteins, may be employed. Such T cell clones may be generated by, for example, culturing PBMCs from *M. tuberculosis*-immune individuals with mycobacterial proteins for a period of 2–4 weeks. This allows expansion of only the mycobacterial protein-specific T cells, resulting in a line composed solely of such cells. These cells may then be cloned and tested with individual proteins, using methods well known in the art, to more accurately define individual T cell specificity. Assays for cell proliferation or cytokine production in T cells, NK cells, B cells or macrophages may be performed, for example, using the procedures described below.

In general, immunogenic antigens are those antigens that stimulate proliferation or cytokine production (i.e., interferon-γ and/or interleukin-12 production) in T cells, NK cells, B cells or macrophages derived from at least about 25% of *M. tuberculosis*-immune individuals. Among these immunogenic antigens, polypeptides having superior therapeutic properties may be distinguished based on the magnitude of the responses in the above assays and based on the percentage of individuals for which a response is observed. In addition, antigens having superior therapeutic properties will not stimulate cell proliferation or cytokine production in vitro in cells derived from more than about 25% of individuals that are not *M. tuberculosis*-immune, thereby eliminating responses that are not specifically due to *M. tuberculosis*-responsive cells. Thus, those antigens that induce a response in a high percentage of T cell, NK cell, B cell or macrophage preparations from *M. tuberculosis*-immune individuals (with a low incidence of responses in cell preparations from other individuals) have superior therapeutic properties.

Antigens with superior therapeutic properties may also be identified based on their ability to diminish the severity of *M. tuberculosis* infection, or other mycobacterial infection, in experimental animals, when administered as a vaccine. Suitable vaccine preparations for use in experimental animals are described in detail below.

Antigens having superior diagnostic properties may generally be identified based on the ability to elicit a response in an intradermal skin test performed on an individual with active tuberculosis, but not in a test performed on an individual who is not infected with *M. tuberculosis*. Skin tests may generally be performed as described below, with a response of at least about 5 mm induration considered positive.

Immunogenic portions of the antigens described herein may be prepared and identified using well known techniques, such as those summarized in Paul, *Fundamental Immunology*, 3d ed., Raven Press, 1993, pp. 243–247. Such techniques include screening polypeptide portions of the native antigen for immunogenic properties. The representative proliferation and cytokine production assays described herein may be employed in these screens. An immunogenic portion of a polypeptide is a portion that, within such representative assays, generates an immune response (e.g., cell proliferation, interferon-γ production or interleukin-12 production) that is substantially similar to that generated by the full-length antigen. In other words, an immunogenic portion of an antigen may generate at least about 20%, preferably about 65%, and most preferably about 100%, of the proliferation induced by the full-length antigen in the model proliferation assay described herein. An immunogenic portion may also, or alternatively, stimulate the production of at least about 20%, preferably about 65% and most preferably about 100%, of the interferon-γ and/or interleukin-12 induced by the full length antigen in the model assay described herein.

Portions and other variants of *M. vaccae* antigens may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems, Inc. (Foster City, Calif.), and may be operated according to the manufacturer's instructions. Variants of a native antigen may be prepared using standard mutagenesis techniques, such as oligonucleotide-directed site-specific mutagenesis. Sections of the DNA sequence may also be removed using standard techniques to permit preparation of truncated polypeptides.

In general, regardless of the method of preparation, the polypeptides disclosed herein are prepared in substantially pure form. Preferably, the polypeptides are at least about 80% pure, more preferably at least about 90% pure and most preferably at least about 99% pure. In certain preferred embodiments, described in detail below, the substantially pure polypeptides are incorporated into pharmaceutical compositions or vaccines for use in one or more of the methods disclosed herein.

The present invention also provides fusion proteins comprising a first and a second inventive polypeptide or, alternatively, a polypeptide of the present invention and a known *M. tuberculosis* antigen, such as the 38 kDa antigen described in Andersen and Hansen, *Infect. Immun.* 57:2481–2488, 1989, together with variants of such fusion proteins. The fusion proteins of the present invention may also include a linker peptide between the first and second polypeptides.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci USA* 83:8258–8262, 1986; U.S. Pat. No. 4,935,233 and U.S. Pat. No. 4,751,180. The linker sequence may be from 1 to about 50 amino acids in length. Peptide linker sequences are not required when the first and second polypeptides have non-essential N-terminal amino acid regions that can be used to separate the functional domains and prevent steric interference.

The ligated DNA sequences encoding the fusion proteins are cloned into suitable expression systems using techniques known to those of ordinary skill in the art.

In another aspect, the present invention provides methods for using one or more of the inventive polypeptides or fusion proteins (or DNA molecules encoding such polypeptides or fusion proteins) to induce protective immunity against tuberculosis in a patient. As used herein, a "patient" refers to any warm-blooded animal, preferably a human. A patient may be afflicted with a disease, or may be free of detectable disease or infection. In other words, protective immunity may be induced to prevent or treat tuberculosis.

In this aspect, the polypeptide, fusion protein or DNA molecule is generally present within a pharmaceutical composition or a vaccine. Pharmaceutical compositions may comprise one or more polypeptides, each of which may contain one or more of the above sequences (or variants thereof, and a physiologically acceptable carrier. Vaccines may comprise one or more of the above polypeptides and a non-specific immune response amplifier, such as an adjuvant or a liposome, into which the polypeptide is incorporated. Such pharmaceutical compositions and vaccines may also contain other mycobacterial antigens, either, as discussed above, incorporated into a fusion protein or present within a separate polypeptide.

Alternatively, a vaccine of the present invention may contain DNA encoding one or more polypeptides as described above, such that the polypeptide is generated in situ. In such vaccines, the DNA may be present within any of a variety of delivery systems known to those of ordinary skill in the art, including nucleic acid expression systems, bacterial and viral expression systems. Appropriate nucleic acid expression systems contain the necessary DNA sequences for expression in the patient (such as a suitable promoter and terminator signal). Bacterial delivery systems involve the administration of a bacterium (such as Bacillus-Calmette-Guerin) that expresses an immunogenic portion of the polypeptide on its cell surface. In a preferred embodiment, the DNA may be introduced using a viral expression system (e.g., vaccinia or other poxvirus, retrovirus, or adenovirus), which may involve the use of a non-pathogenic, or defective, replication competent virus. Techniques for incorporating DNA into such expression systems are well known in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

A DNA vaccine as described above may be administered simultaneously with or sequentially to either a polypeptide of the present invention or a known mycobacterial antigen, such as the 38 kDa antigen described above. For example, administration of DNA encoding a polypeptide of the present invention, may be followed by administration of an antigen in order to enhance the protective immune effect of the vaccine.

Routes and frequency of administration, as well as dosage, will vary from individual to individual and may parallel those currently being used in immunization using BCG. In general, the pharmaceutical compositions and vaccines may be administered by injection (e.g., intradermal, intramuscular, intravenous or subcutaneous), intranasally (e.g., by aspiration) or orally. Between 1 and 3 doses may be administered for a 1–36 week period. Preferably, 3 doses are administered, at intervals of 3–4 months, and booster vaccinations may be given periodically thereafter. Alternate protocols may be appropriate for individual patients. A suitable dose is an amount of polypeptide or DNA that, when administered as described above, is capable of raising an immune response in a patient sufficient to protect the patient from mycobacterial infection for at least 1–2 years. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 $\mu$g. Suitable dose sizes will vary with the size of the patient, but will typically range from about 0.1 ml to about 5 ml.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the vaccines of this invention to non-specifically enhance the immune response. Most adjuvants contain a substance designed to protect the antigen from rapid catabolism, such as aluminum hydroxide or mineral oil, and a non-specific stimulator of immune responses, such as lipid A, *Bordetella pertussis, M. tuberculosis,* or, as discussed below, *M. vaccae.* Suitable adjuvants are commercially available as, for example, Freund's Incomplete Adjuvant and Freund's Complete Adjuvant (Difco Laboratories, Detroit, Mich.), and Merck Adjuvant 65 (Merck and Company, Inc., Rahway, N.J.). Other suitable adjuvants include alum, biodegradable microspheres, monophosphoryl lipid A and Quil A.

In another aspect, this invention provides methods for using one or more of the polypeptides described above to diagnose tuberculosis using a skin test. As used herein, a "skin test" is any assay performed directly on a patient in which a delayed-type hypersensitivity (DTH) reaction (such as swelling, reddening or dermatitis) is measured following intradermal injection of one or more polypeptides as described above. Preferably, the reaction is measured at least 48 hours after injection, more preferably 48–72 hours.

The DTH reaction is a cell-mediated immune response, which is greater in patients that have been exposed previously to the test antigen (i.e., the immunogenic portion of the polypeptide employed, or a variant thereof). The response may be measured visually, using a ruler. In general, a response that is greater than about 0.5 cm in diameter, preferably greater than about 1.0 cm in diameter, is a positive response, indicative of tuberculosis infection.

For use in a skin test, the polypeptides of the present invention are preferably formulated, as pharmaceutical compositions containing a polypeptide and a physiologically acceptable carrier, as described above. Such compositions typically contain one or more of the above polypeptides in an amount ranging from about 1 µg to about 100 µg, preferably from about 10 µg to about 50 µg in a volume of 0.1 ml. Preferably, the carrier employed in such pharmaceutical compositions is a saline solution with appropriate preservatives, such as phenol and/or Tween 80™.

In a preferred embodiment, a polypeptide employed in a skin test is of sufficient size such that it remains at the site of injection for the duration of the reaction period. In general, a polypeptide that is at least 9 amino acids in length is sufficient. The polypeptide is also preferably broken down by macrophages or dendritic cells within hours of injection to allow presentation to T-cells. Such polypeptides may contain repeats of one or more of the above sequences or other immunogenic or nonimmunogenic sequences.

In another aspect, methods are provided for detecting mycobacterial infection in a biological sample, using one or more of the above polypeptides, either alone or in combination. In embodiments in which multiple polypeptides are employed, polypeptides other than those specifically described herein, such as the 38 kDa antigen described above, may be included. As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient or a blood supply. The polypeptide (s) are used in an assay, as described below, to determine the presence or absence of antibodies to the polypeptide(s) in the sample, relative to a predetermined cut-off value. The presence of such antibodies indicates the presence of mycobacterial infection.

In embodiments in which more than one polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with a Mycobacterium. After determining which samples test positive (as described below) with each polypeptide, combinations of two or more polypeptides may be formulated that are capable of detecting infection in most, or all, of the samples tested. For example, approximately 25–30% of sera from tuberculosis-infected individuals are negative for antibodies to any single protein, such as the 38 kDa antigen mentioned above. Complementary polypeptides may, therefore, be used in combination with the 38 kDa antigen to improve sensitivity of a diagnostic test.

A variety of assay formats employing one or more polypeptides to detect antibodies in a sample are well known in the art. See, e.g., Harlow and Lane, *Antibodies: A Laboratory Manual,* Cold Spring Harbor Laboratory, 1988. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labelled with a reporter group (e.g., in a semi-competitive assay). Alternatively, a competitive assay may be utilized, in which an antibody that binds to the polypeptide is labelled with a reporter group and allowed to bind to the immobilized antigen after incubation of the antigen with the sample. The extent to which components of the sample inhibit the binding of the labelled antibody to the polypeptide is indicative of the reactivity of the sample with the immobilized polypeptide.

The solid support may be any solid material to which the antigen may be attached. Suitable materials are well known in the art. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques well known in the art. In the context of the present invention, the term "bound" refers to both noncovalent association, such as adsorption, and covalent attachment, which may be a direct linkage between the antigen and functional groups on the support or a linkage by way of a cross-linking agent. Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 μg, and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, 1991, at A12–A13).

In certain embodiments, the assay is an enzyme-linked immunosorbent assay (ELISA). This assay may be performed by first contacting a polypeptide antigen that has been immobilized on a solid support, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.) may be employed. The immobilized polypeptide is then incubated with the sample, and antibody is allowed to bind to the antigen. The sample may be diluted with a suitable diluent, such as phosphate-buffered saline (PBS) prior to incubation. In general, an appropriate contact time, or incubation time, is that period of time that is sufficient to detect the presence of antibody within a *M. tuberculosis*-infected sample. Preferably, the contact time is sufficient to achieve a level of binding that is at least 95% of that achieved at equilibrium between bound and unbound antibody. The time necessary to achieve equilibrium may be readily determined by assaying the level of binding that occurs over a period of time. At room temperature, an incubation time of about 30 minutes is generally sufficient.

Unbound sample may be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known in the art. Common binding agents may also be purchased conjugated to a variety of reporter groups from many commercial sources (e.g., Zymed Laboratories, San Francisco, Calif., and Pierce, Rockford, Ill.).

The detection reagent is incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may be detected by the addition of substrate (generally for a specific period of time), followed by spectroscopic or other analysis of the reaction products.

To determine the presence or absence of anti-mycobacterial antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, pp. 106–107. In general, signals higher than the predetermined cut-off value are considered to be positive for mycobacterial infection.

The assay may also be performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-mycobacterial antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 1 μg, and more preferably from about 50 ng to about 500 ng. Such tests can typically be performed with a very small amount (e.g., one drop) of patient serum or blood.

Numerous other assay protocols exist that are suitable for use with the polypeptides of the present invention. The above descriptions are intended to be exemplary only.

The present invention also provides antibodies to the inventive polypeptides. Antibodies may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells may then be immortalized by fusion with a myeloma cell fusion partner, preferably one that is syngeneic with the immunized animal, using one of a variety of techniques well known in the art.

Monoclonal antibodies may be isolated from the supernatants of the resulting hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood.

Antibodies may be used in diagnostic tests to detect the presence of mycobacterial antigens using assays similar to those detailed above and other techniques well known to those of skill in the art, thereby providing a method for detecting mycobacterial infection, such as *M. tuberculosis* infection, in a patient.

Diagnostic reagents of the present invention may also comprise DNA sequences encoding one or more of the above polypeptides, or one or more portions thereof For example, primers comprising at least 10 contiguous oligonucleotides of the subject DNA sequences may be used in polymerase chain reaction (PCR) based tests. Similarly, probes comprising at least 18 contiguous oligonucleotides of the subject DNA sequences may be used for hybridizing to specific sequences. Techniques for both PCR based tests and hybridization tests are well known in the art. Primers or probes may thus be used to detect *M. tuberculosis* and other mycobacterial infections in biological samples, preferably sputum, blood, serum, saliva, cerebrospinal fluid or urine. DNA probes or primers comprising oligonucleotide sequences described above may be used alone, in combination with each other, or with previously identified sequences, such as the 38 kDa antigen discussed above.

As discussed above, effective vaccines contain at least two different components. The first is a polypeptide comprising an antigen, which is processed by macrophages and other antigen-presenting cells and displayed for $CD4^+$ T cells or for $CD8^+$ T cells. This antigen forms the "specific" target of an immune response. The second component of a vaccine is a non-specific immune response amplifier, such as an adjuvant or a liposome, into which the antigen is incorporated. An adjuvant amplifies immune responses to a structurally unrelated compound or polypeptide. Several adjuvants are prepared from microbes such as *Bordetella pertussis, M. tuberculosis* and *M. bovis* BCG. Adjuvants may also contain components designed to protect polypeptide antigens from degradation, such as aluminum hydroxide or mineral oil.

While the antigenic component of a vaccine contains polypeptides that direct the immune attack against a specific pathogen, such as *M. tuberculosis,* the adjuvant is often capable of broad use in many different vaccine formulations. Certain pathogens, such as *M. tuberculosis,* as well as certain cancers, are effectively contained by an immune attack directed by T cells, known as cell-mediated immunity. Other pathogens, such as poliovirus, also require antibodies produced by B cells for containment. These different classes of immune attack (T cell or B cell) are controlled by different subpopulations of $CD4^+$ T cells, commonly referred to as Th1 and Th2 cells. A desirable property of an adjuvant is the ability to selectively amplify the function of either Th1 or Th2 populations of $CD4^+$ T cells. As shown below in Example 6, *M. vaccae* and a modified form of autoclaved *M. vaccae* have been found to have adjuvant properties. As used herein, the term "modified *M. vaccae*" includes delipidated *M. vaccae* cells, deglycolipidated *M. vaccae* cells and *M. vaccae* cells that have been both delipidated and deglycolipidated (hereinafter referred to as DD-*M. vaccae*). Furthermore, it has been found that *M. vaccae* produces compounds which amplify the immune response to *M. vaccae* antigens, as well as to antigens from other sources. The present invention thus provides methods for enhancing immune responses to an antigen comprising administering killed *M. vaccae* cells, *M. vaccae* culture filtrate or modified *M. vaccae* cells. As detailed below, further studies have demonstrated that this non-specific immune amplifying effect is due, at least in part, to an *M. vaccae* polypeptide having homology to heat shock protein 65 (GroEL), previously identified in *M. tuberculosis.*

As described below in Example 10, it has also been found that heat-killed *M. vaccae* and *M. vaccae* constituents have cytokine stimulation properties. In particular, it has been found that heat-killed *M. vaccae,* lyophilised *M. vaccae* and DD-*M. vaccae* stimulate the production of interleukin 12 (IL-12) from macrophages. Production of IL-12 from macrophages is known to enhance stimulation of a Th1 immune response.

The following examples are offered by way of illustration and not by way of limitation.

EXAMPLE 1

Effect of Immunization of Mice with *M. vaccae* on Tuberculosis

This example illustrates the effect of immunization with *M. vaccae* or *M. vaccae* culture filtrate in mice prior to challenge with live *M. tuberculosis.*

*M. vaccae* (ATCC Number 15483) was cultured in sterile Medium 90 (yeast extract, 2.5 g/l; tryptone, 5 g/l; glucose, 1 g/l) at 37° C. The cells were harvested by centrifugation, and transferred into sterile Middlebrook 7H9 medium (Difco Laboratories, Detroit, Mich., USA) with glucose at 37° C. for one day. The medium was then centrifuged to pellet the bacteria, and the culture filtrate removed. The bacterial pellet was resuspended in phosphate buffered saline at a concentration of 10 mg/ml, equivalent to $10^{10}$ *M. vaccae* organisms per ml. The cell suspension was then autoclaved for 15 min at 120° C. The culture filtrate was passaged through a 0.45 μm filter into sterile bottles.

As shown in FIG. 1A, when mice were immunized with 1 mg, 100 μg or 10 μg of *M. vaccae* and infected three weeks later with 5×10⁵ colony forming units (CFU) of live *M. tuberculosis* H37Rv, significant protection from infection was seen. In this example, spleen, liver and lung tissue was harvested from mice three weeks after infection, and live bacilli determined (expressed as CFU). The reduction in bacilli numbers, when compared to tissue from non-immunized control mice, exceeded 2 logs in liver and lung tissue, and 1 log in spleen tissue. Immunization of mice with heat-killed *M. tuberculosis* H37Rv had no significant protective effects on mice subsequently infected with live M tuberculosis H37Rv.

Figure 1B:
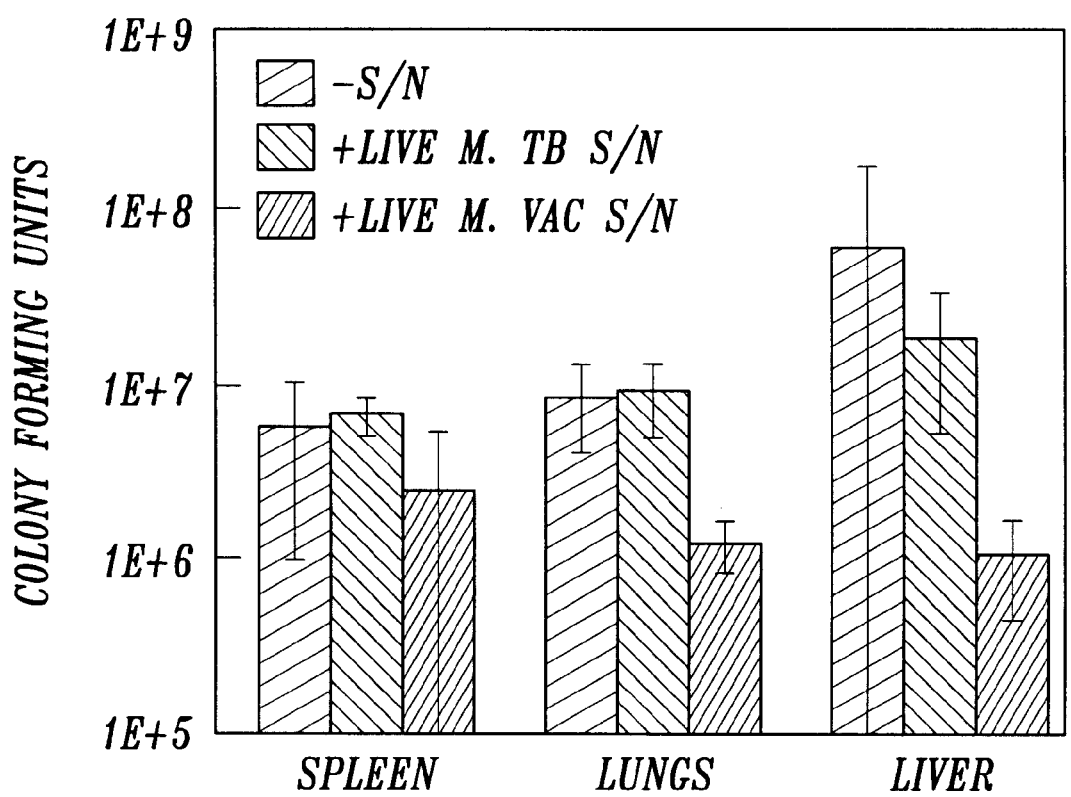

FIG. 1B shows that when mice were immunized with 100 μg of *M. vaccae* culture filtrate, and infected three weeks later with 5×10⁵ CFU of *M. tuberculosis* H37Rv, significant protection was also seen. When spleen, liver and lung tissue was harvested from mice three weeks after infection, and live bacilli numbers (CFU) determined, a 1–2 log reduction in numbers, as compared to non-immunized control mice, was observed.

EXAMPLE 2

Purification and Characterization of Polypeptides from *M. vaccae* Culture Filtrate This example illustrates the preparation of *M. vaccae* soluble proteins from culture filtrate. Unless otherwise noted, all percentages in the following example are weight per volume.

*M. vaccae* (ATCC Number 15483) was cultured in sterile Medium 90 at 37° C. The cells were harvested by centrifugation, and transferred into sterile Middlebrook 7H9 medium with glucose at 37° C. for one day. The medium was then centrifuged (leaving the bulk of the cells) and filtered through a 0.45 μm filter into sterile bottles.

The culture filtrate was concentrated by lyophilization, and redissolved in MilliQ water. A small amount of insoluble material was removed by filtration through a 0.45 μm membrane. The culture filtrate was desalted by membrane filtration in a 400 ml Amicon stirred cell which contained a 3 kDa molecular weight cut-off (MWCO) membrane. The pressure was maintained at 50 psi using nitrogen gas. The culture filtrate was repeatedly concentrated by membrane filtration and diluted with water until the conductivity of the sample was less than 1.0 mS. This procedure reduced the 20 1 volume to approximately 50 ml. Protein concentrations were determined by the Bradford protein assay (Bio-Rad, Hercules, Calif., USA).

The desalted culture filtrate was fractionated by ion exchange chromatography on a column of Q-Sepharose (Pharmacia Biotech, Uppsala, Sweden) (16×100 mm) equilibrated with 10 mM Tris HCl buffer pH 8.0. Polypeptides were eluted with a linear gradient of NaCl from 0 to 1.0 M in the above buffer system. The column eluent was monitored at a wavelength of 280 nm.

The pool of polypeptides eluting from the ion exchange column was concentrated in a 400 ml Amicon stirred cell which contained a 3 kDa MWCO membrane. The pressure was maintained at 50 psi using nitrogen gas. The polypeptides were repeatedly concentrated by membrane filtration and diluted with 1% glycine until the conductivity of the sample was less than 0.1 mS.

The purified polypeptides were then fractionated by preparative isoelectric focusing in a Rotofor device (Bio-Rad, Hercules, Calif., USA). The pH gradient was established with a mixture of Ampholytes (Pharmacia Biotech) comprising 1.6% pH 3.5–5.0 Ampholytes and 0.4% pH 5.0–7.0 Ampholytes. Acetic acid (0.5 M) was used as the anolyte, and 0.5 M ethanolamine as the catholyte. Isoelectric focusing was carried out at 12W constant power for 6 hours, following the manufacturer's instructions. Twenty fractions were obtained.

Fractions from isoelectric focusing were combined, and the polypeptides were purified on a Vydac C4 column (Separations Group, Hesperia, Calif., USA) 300 Angstrom pore size, 5 micron particle size (10×250 mm). The polypeptides were eluted from the column with a linear gradient of acetonitrile (0–80% v/v) in 0.05% (v/v) trifluoroacetic acid (TFA). The flow-rate was 2.0 ml/min and the HPLC eluent was monitored at 220 nm. Fractions containing polypeptides were collected to maximize the purity of the individual samples.

Relatively abundant polypeptide fractions were rechromatographed on a Vydac C4 column (Separations Group) 300 Angstrom pore size, 5 micron particle size (4.6×250 mm). The polypeptides were eluted from the column with a linear gradient from 20–60% (v/v) of acetonitrile in 0.05% (v/v) TFA at a flow-rate of 1.0 ml/min. The column eluent was monitored at 220 nm. Fractions containing the eluted polypeptides were collected to maximise the purity of the individual samples. Approximately 20 polypeptide samples were obtained and they were analysed for purity on a polyacrylamide gel according to the procedure of Laemmli (Laemmli, U. K., *Nature* 277:680–685, 1970).

The polypeptide fractions which were shown to contain significant contamination were further purified using a Mono Q column (Pharmacia Biotech) 10 micron particle size (5×50 mm) or a Vydac Diphenyl column (Separations Group) 300 Angstrom pore size, 5 micron particle size (4.6×250 mm). From a Mono Q column, polypeptides were eluted with a linear gradient from 0–0.5 M NaCl in 10 mM Tris HCl pH 8.0. From a Vydac Diphenyl column, polypeptides were eluted with a linear gradient of acetonitrile (20–60% v/v) in 0.1% TFA. The flow-rate was 1.0 ml/min and the column eluent was monitored at 220 nm for both columns. The polypeptide peak fractions were collected and analysed for purity on a 15% polyacrylamide gel as described above.

For sequencing, the polypeptides were individually dried onto Biobrene™ (Perlin Elmer/Applied BioSystems Division, Foster City, Calif.)—treated glass fiber filters. The filters with polypeptide were loaded onto a Perkin Elmer/Applied BioSystems Procise 492 protein sequencer and the polypeptides were sequenced from the amino terminal end using traditional Edman chemistry. The amino acid sequence was determined for each polypeptide by comparing the retention time of the PTH amino acid derivative to the appropriate PTH derivative standards.

Internal sequences were also determined on some antigens by digesting the antigen with the endoprotease Lys-C, or by chemically cleaving the antigen with cyanogen bromide. Peptides resulting from either of these procedures were separated by reversed-phase HPLC on a Vydac C 18 column using a mobile phase of 0.05% (v/v) trifluoroacetic acid with a gradient of acetonitrile containing 0.05% (v/v) TFA (1%/min). The eluent was monitored at 214 nm. Major internal peptides were identified by their UV absorbance, and their N-terminal sequences were determined as described above.

Using the procedures described above, six soluble *M. vaccae* antigens, designated GVc-1, GVc-2, GVc-7, GVc- 13, GVc-20 and GVc-22, were isolated. Determined N-terminal and internal sequences for GVc-1 are shown in SEQ ID NOS: 1, 2 and 3, respectively; the N-terminal sequence for GVc-2 is shown in SEQ ID NO: 4; internal sequences for GVc-7 are shown in SEQ ID NOS: 5–8; internal sequences for GVc-13 are shown in SEQ ID NOS: 9–11; internal sequence for GVc-20 is shown in SEQ ID NO: 12; and N-terminal and internal sequences for GVc-22 are shown in SEQ ID NO: 56–59, respectively. Each of the internal peptide sequences provided herein begins with an amino acid residue which is assumed to exist in this position in the polypeptide, based on the known cleavage specificity of cyanogen bromide (Met) or Lys-C (Lys).

Three additional polypeptides, designated GVc-16, GVc-18 and GVc-21, were isolated employing a preparative sodium dodecyl sulfate-polyacrylamide gel electrophoresis (SDS-PAGE) purification step in addition to the preparative isoelectric focusing procedure described above. Specifically, fractions comprising mixtures of polypeptides from the preparative isoelectric focusing purification step previously described were purified by preparative SDS-PAGE on a 15% polyacrylamide gel. The samples were dissolved in reducing sample buffer and applied to the gel. The separated proteins were transferred to a polyvinylidene difluoride (PVDF) membrane by electroblotting in 10 mM 3-(cyclohexylamino)-1-propanesulfonic acid (CAPS) buffer pH 11 containing 10% (v/v) methanol. The transferred protein bands were identified by staining the PVDF membrane with Coomassie blue. Regions of the PVDF membrane containing the most abundant polypeptide species were cut out and directly introduced into the sample cartridge of the Perkin Elmer/Applied BioSystems Procise 492 protein sequencer. Protein sequences were determined as described above. The N-terminal sequences for GVc-16, GVc-18 and GVc-21 are provided in SEQ ID NOS: 13, 14 and 15, respectively.

Additional antigens, designated GVc-12, GVc-14, GVc-15, GVc-17 and GVc-19, were isolated employing a preparative SDS-PAGE purification step in addition to the chromatographic procedures described above. Specifically, fractions comprising a mixture of antigens from the Vydac C4 HPLC purification step previously described were fractionated by preparative SDS-PAGE on a polyacrylamide gel. The samples were dissolved in non-reducing sample buffer and applied to the gel. The separated proteins were transferred to a PVDF membrane by electroblotting in 10 mM CAPS buffer, pH 11 containing 10% (v/v) methanol. The transferred protein bands were identified by staining the PVDF membrane with Coomassie blue. Regions of the PVDF membrane containing the most abundant polypeptide species were cut out and directly introduced into the sample cartridge of the Perkin Elmer/Applied BioSystems Procise 492 protein sequencer. Protein sequences were determined as described above. The determined N-terminal sequences for GVc-12, GVc-14, GVc-15, GVc-17 and GVc-19 are provided in SEQ ID NOS: 16–20, respectively.

All of the above amino acid sequences were compared to known amino acid sequences in the SwissProt data base (version R32) using the GeneAssist system. No significant homologies to the amino acid sequences GVc-2 to GVc-22 were obtained. The amino acid sequence for GVc-1 was found to bear some similarity to sequences previously identified from *M. bovis* and *M. tuberculosis*. In particular, GVc-1 was found to have some homology with *M. tuberculosis* MPT83, a cell surface protein, as well as MPT70. These proteins form part of a protein family (Harboe et al., *Scand. J. Immunol.* 42:46–51, 1995).

Subsequent studies led to the isolation of DNA sequences for GV-13c, GVc-14 and GVc-22 (SEQ ID NO: 142, 107 and 108, respectively). The corresponding predicted amino acid sequences for GV-13c, GVc-14 and GVc-22 are provided in SEQ ID NO: 143, 109 and 110, respectively. Further studies with GVc-22 suggested that only a part of the gene encoding GVc-22 was cloned. When sub-cloned into the expression vector pET16, no protein expression was obtained. Subsequent screening of the *M. vaccae* BamHI genomic DNA library with the incomplete gene fragment led to the isolation of the complete gene encoding GVc-22. To distinguish between the full-length clone and the partial GVc-22, the antigen expressed by the full-length gene was called GV-22B. The determined nucleotide sequence of the gene encoding GV-22B and the predicted amino acid sequence are provided in SEQ ID NOS: 144 and 145 respectively.

Amplifications primers AD86 and AD112 (SEQ ID NO: 60 and 61, respectively) were designed from the amino acid sequence of GVc-1 (SEQ ID NO: 1) and the *M. tuberculosis* MPT70 gene sequence. Using these primers, a 310 bp fragment was amplified from *M. vaccae* genomic DNA and cloned into EcoRV-digested vector pBluescript II $SK^+$ (Stratagene). The sequence of the cloned insert is provided in SEQ ID NO: 62. The insert of this clone was used to screen a *M. vaccae* genomic DNA library constructed in lambda ZAP-Express (Stratagene, La Jolla, Calif.). The clone isolated contained an open reading frame with homology to the *M. tuberculosis* antigen MPT83 and was re-named GV-1/83. This gene also had homology to the *M. bovis* antigen MPB83. The determined nucleotide sequence and predicted amino acid sequences are provided in SEQ ID NOS: 146 and 147 respectively.

From the amino acid sequences provided in SEQ ID NOS: 1 and 2, degenerate oligonucleotides EV59 and EV61 (SEQ ID NOS: 148 and 149 respectively) were designed. Using PCR, a 100 bp fragment was amplified, cloned into plasmid pBluescript II $SK^+$ and sequenced (SEQ ID NO: 150) following standard procedures (Maniatis) The cloned insert was used to screen a *M. vaccae* genomic DNA library constructed in lambda ZAP-Express. The clone isolated had homology to *M. tuberculosis* antigen MPT70 and *M. bovis* antigen MPB70, and was named GV-1/70. The determined nucleotide sequence and predicted amino acid sequence for GV-1/70 are provided in SEQ ID NOS: 151 and 152 respectively.

For expression and purification, the genes encoding GV1/83, GV1/70, GVc-13, GVc-14 and GV-22B were sub-cloned into the expression vector pET16 (Novagen, Madison, Wis.). Expression and purification were done according to the manufacturer's protocol.

The purified polypeptides were screened for the ability to induce T-cell proliferation and IFN-γ in peripheral blood cells from immune human donors. These donors were known to be PPD (purified protein derivative from *M. tuberculosis*) skin test positive and their T cells were shown to proliferate in response to PPD. Donor PBMCs and crude soluble proteins from *M. vaccae* culture filtrate were cultured in medium comprising RPMI 1640 supplemented with 10% (v/v) autologous serum, penicillin (60 μg/ml), streptomycin (100 μg/ml), and glutamine (2 mM).

After 3 days, 50 μl of medium was removed from each well for the determination of IFN-γ levels, as described below. The plates were cultured for a further 4 days and then pulsed with 1 μCi/well of tritiated thymidine for a further 18 hours, harvested and tritium uptake determined using a scintillation counter. Fractions that stimulated proliferation in both replicates two-fold greater than the proliferation observed in cells cultured in medium alone were considered positive.

IFN-γ was measured using an enzyme-linked immunosorbent assay (ELISA). ELISA plates were coated with a mouse monoclonal antibody directed to human IFN-γ (Endogen, Wobural, Mass. 1 μg/ml phosphate-buffered saline (PBS) for 4 hours at 4° C. Wells were blocked with PBS containing 0.2% Tween 20 for 1 hour at room temperature. The plates were then washed four times in PBS/0.2% Tween 20, and samples diluted 1:2 in culture medium in the ELISA plates were incubated overnight at room temperature. The plates were again washed, and a biotinylated polyclonal rabbit anti-human IFN-γ serum (Endogen), diluted to 1 μg/ml in PBS, was added to each well. The plates were then incubated for 1 hour at room temperature, washed, and horseradish peroxidase-coupled avidin A (Vector Laboratories, Burlingame, Calif.) was added at a 1:4,000 dilution in PBS. After a further 1 hour incubation at room temperature, the plates were washed and orthophenylenediamine (OPD) substrate added. The reaction was stopped after 10 min with 10% (v/v) HCl. The optical density (OD) was determined at 490 nm. Fractions that resulted in both replicates giving an OD two-fold greater than the mean OD from cells cultured in medium alone were considered positive.

Examples of polypeptides containing sequences that stimulate peripheral blood mononuclear cells (PBMC) T cells to proliferate and produce IFN-γ are shown in Table 1, wherein (-) indicates a lack of activity, (+/-) indicates polypeptides having a result less than twice higher than background activity of control media, (+) indicates polypeptides having activity two to four times above background, and (++) indicates polypeptides having activity greater than four times above background.

TABLE 1

| Antigen | Proliferation | IFN-γ |
|---------|---------------|-------|
| GVc-1   | ++            | +/-   |
| GVc-2   | +             | ++    |
| GVc-7   | +/-           | -     |
| GVc-13  | +             | ++    |
| GVc-14  | ++            | +     |
| GVc-15  | +             | +     |
| GVc-20  | +             | +     |

EXAMPLE 3

Purification and Characterisation of Polypeptides from *M. vaccae* Culture Filtrate by 2-Dimensional Polyacrylamide Gel Electrophoresis

*M. vaccae* soluble proteins were isolated from culture filtrate using 2-dimensional polyacrylamide gel electrophoresis as described below. Unless otherwise noted, all percentages in the following example are weight per volume.

*M. vaccae* (ATCC Number 15483) was cultured in sterile Medium 90 at 37° C. *M. tuberculosis* strain H37Rv (ATCC number 27294) was cultured in sterile Middlebrook 7H9 medium with Tween 80 and oleic acid/albumin/dextrose/catalase additive (Difco Laboratories, Detroit, Mich.). The cells were harvested by centrifugation, and transferred into sterile Middlebrook 7H9 medium with glucose at 37° C. for one day. The medium was then centrifuged (leaving the bulk of the cells) and filtered through a 0.45 μm filter into sterile bottles. The culture filtrate was concentrated by lyophilisation, and redissolved in MilliQ water. A small amount of insoluble material was removed by filtration through a 0.45 μm membrane filter.

The culture filtrate was desalted by membrane filtration in a 400 ml Amicon stirred cell which contained a 3 kDa MWCO membrane. The pressure was maintained at 60 psi using nitrogen gas. The culture filtrate was repeatedly concentrated by membrane filtration and diluted with water until the conductivity of the sample was less than 1.0 mS. This procedure reduced the 20 l volume to approximately 50 ml. Protein concentrations were determined by the Bradford protein assay (Bio-Rad, Hercules, Calif., USA).

The desalted culture filtrate was fractionated by ion exchange chromatography on a column of Q-Sepharose (Pharmacia Biotech) (16×100 mm) equilibrated with 10 mM TrisHCl buffer pH 8.0. Polypeptides were eluted with a linear gradient of NaCl from 0 to 1.0 M in the above buffer system. The column eluent was monitored at a wavelength of 280 nm.

Figure 2A:
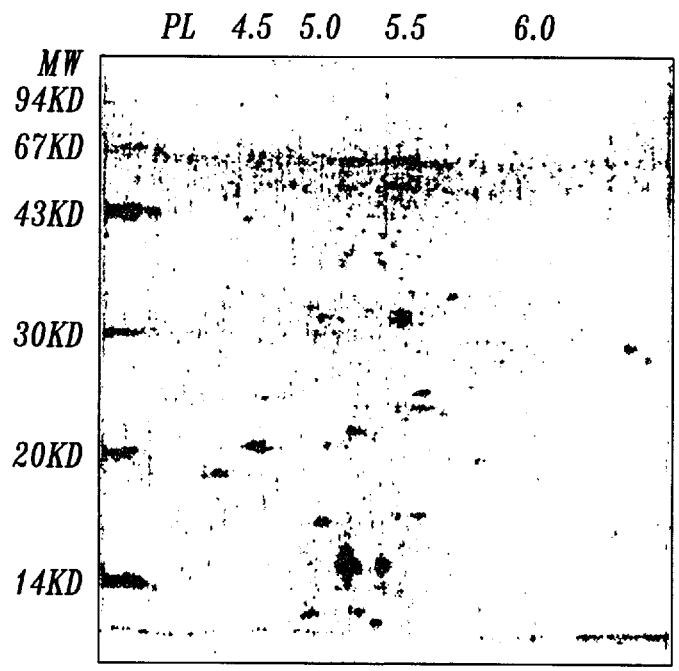
FIGS. 2A and B show components of *M. vaccae* and *M. tuberculosis* culture filtrates, respectively, as analysed by 2-dimensional polyacrylamide gel electrophoresis.
Figure 2B:
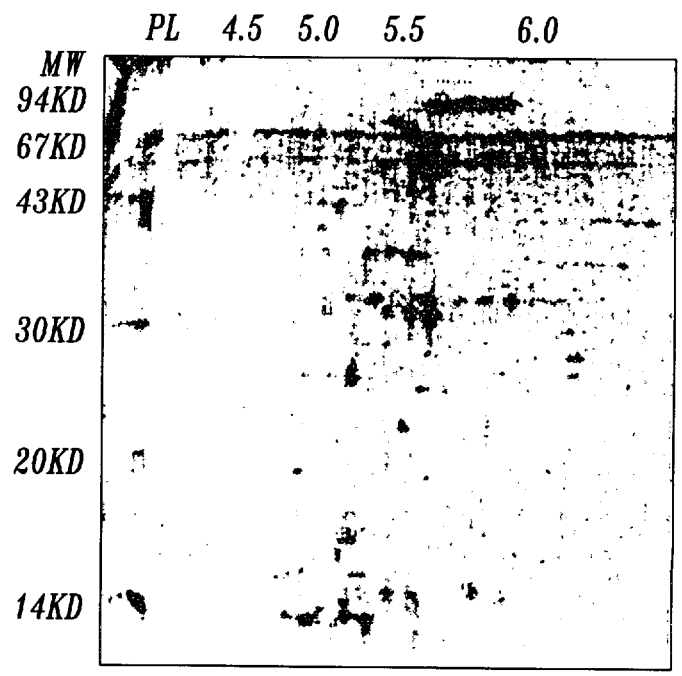

The pool of polypeptides eluting from the ion exchange column were fractionated by preparative 2D gel electrophoresis. Samples containing 200–500 μg of polypeptide were made 8 M in urea and applied to polyacrylamide isoelectric focusing rod gels (diameter 2 mm, length 150 mm, pH 5–7). After the isoelectric focusing step, the first dimension gels were equilibrated with reducing buffer and applied to second dimension gels (16% polyacrylamide). FIGS. 2A and 2B are the 2-D gel patterns observed with *M. vaccae* culture filtrate and *M. tuberculosis* H37Rv culture filtrate, respectively. Polypeptides from the second dimension separation were transferred to PVDF membranes by electroblotting in 10 mM CAPS buffer pH 11 containing 10% (v/v) methanol. The PVDF membranes were stained for protein with Coomassie blue. Regions of PVDF containing polypeptides of interest were cut out and directly introduced into the sample cartridge of the Perkin Elmer/Applied Bio-Systems Procise 492 protein sequencer. The polypeptides were sequenced from the amino terminal end using traditional Edman chemistry. The amino acid sequence was determined for each polypeptide by comparing the retention time of the PTH amino acid derivative to the appropriate PTH derivative standards. Using these procedures, eleven polypeptides, designated GVs-1, GVs-3, GVs-4, GVs-5, GVs-6, GVs-8, GVs-9, GVs-10, GVs-11, GV-34 and GV-35 were isolated. The determined N-terminal sequences for these polypeptides are shown in SEQ ID NOS: 21–29, 63 and 64, respectively. Using the purification procedure described above, more protein was purified to extend the amino acid sequence previously obtained for GVs-9. The extended amino acid sequence for GVs-9 is provided in SEQ ID NO: 65. Further studies resulted in the isolation of DNA sequences for GVs-9 (SEQ ID NO: 111) and GV-35 (SEQ ID NO: 155. The corresponding predicted amino acid sequences are provided in SEQ ID NO: 112 and 156, respectively. An extended DNA sequence for GVs-9 is provided in SEQ ID NO: 153, with the corresponding predicted amino acid sequence being provided in SEQ ID NO: 154.

All of these amino acid sequences were compared to known amino acid sequences in the SwissProt data base (version R32) using the GeneAssist system. No significant homologies were obtained, with the exceptions of GVs-3, GVs-4, GVs-5 and GVs-9. GVs-9 was found to bear some homology to two previously identified *M. tuberculosis* proteins, namely *M. tuberculosis* cutinase precursor and an *M. tuberculosis* hypothetical 22.6 kDa protein. GVs-3, GVs-4 and GVs-5 were found to bear some similarity to the antigen 85A and 85B proteins from *M. leprae* (SEQ ID NOS: 30 and 31, respectively), *M. tuberculosis* (SEQ ID NOS: 32 and 33, respectively) and *M. bovis* (SEQ ID NOS: 34 and 35, respectively), and the antigen 85C proteins from *M. leprae* (SEQ ID NO: 36) and *M. tuberculosis* (SEQ ID NO: 37). A comparison of the inventive antigen 85A protein from *M. vaccae* with those from *M. tuberculosis, M. bovis* and *M. leprae,* is presented in FIG. 3.

EXAMPLE 4

DNA Cloning Strategy for the *M. vaccae* Antigen 85 Series

Probes for antigens 85A, 85B, and 85C were prepared by the polymerase chain reaction (PCR) using degenerate oligonucleotides (SEQ ID NOS: 38 and 39) designed to regions of antigen 85 genomic sequence that are conserved between family members in a given mycobacterial species, and between mycobacterial species. These oligonucleotides were used under reduced stringency conditions to amplify target sequences from *M. vaccae* genomic DNA. An appropriately-sized 485 bp band was identified, purified, and cloned into T-tailed p Bluescript II SK (Stratagene, La Jolla, Calif.). Twenty-four individual colonies were screened at random for the presence of the antigen 85 PCR product, then sequenced using the Perkin Elmer/Applied Biosystems Model 377 automated sequencer and the M13-based primers, T3 and T7. Homology searches of the GenBank databases showed that twenty-three clones contained insert with significant homology to published antigen 85 genes from *M. tuberculosis* and *M. bovis.* Approximately half were most homologous to antigen 85C gene sequences, with the remainder being more similar to antigen 85B sequences. In addition, these two putative *M. vaccae* antigen 85 genomic sequences were 80% homologous to one another. Because of this high similarity, the antigen 85C PCR fragment was chosen to screen *M. vaccae* genomic libraries at low stringency for all three antigen 85 genes.

An *M. vaccae* genomic library was created in lambda Zap-Express (Stratagene, La Jolla, Calif.) by cloning BamHI partially-digested *M. vaccae* genomic DNA into similarly-digested X vector, with $3.4 \times 10^5$ independent plaque-forming units resulting. For screening purposes, twenty-seven thousand plaques from this non-amplified library were plated at low density onto eight 100 $cm^2$ plates. For each plate, duplicate plaque lifts were taken onto Hybond-N$^+$ nylon membrane (Amersham International, United Kingdom), and hybridised under reduced-stringency conditions (55° C.) to the radiolabelled antigen 85C PCR product. Autoradiography demonstrated that seventy-nine plaques consistently hybridised to the antigen 85C probe under these conditions. Thirteen positively-hybridising plaques were selected at random for further analysis and removed from the library plates, with each positive clone being used to generate secondary screening plates containing about two hundred plaques. Duplicate lifts of each plate were taken using Hybond-N$^+$ nylon membrane, and hybridised under the conditions used in primary screening. Multiple positively-hybridising plaques were identified on each of the thirteen plates screened. Two well-isolated positive phage from each secondary plate were picked for further analysis. Using in vitro excision, twenty-six plaques were converted into phagemid, and restriction-mapped. It was possible to group clones into four classes on the basis of this mapping. Sequence data from the 5' and 3' ends of inserts from several representatives of each group was obtained using the Perkin Elmer/Applied Biosystems Model 377 automated sequencer and the T3 and T7 primers. Sequence homologies were determined using FASTA analysis of the GenBank databases with the GeneAssist software package. Two of these sets of clones were found to be homologous to *M. bovis* and *M. tuberculosis* antigen 85A genes, each containing either the 5' or 3' ends of the *M. vaccae* gene (this gene was cleaved during library construction as it contains an internal BamHI site). The remaining clones were found to contain sequences homologous to antigens 85B and 85C from a number of mycobacterial species. To determine the remaining nucleotide sequence for each gene, appropriate subclones were constructed and sequenced. Overlapping sequences were aligned using the DNA Strider software. The determined DNA sequences for *M. vaccae* antigens 85A, 85B and 85C are shown in SEQ ID NOS: 40–42, respectively, with the predicted amino acid sequences being shown in SEQ ID NOS: 43–45, respectively.

The *M. vaccae* antigens GVs-3 and GVs-5 were expressed and purified as follows. Amplification primers were designed from the insert sequences of GVs-3 and GVs-5 (SEQ ID NO: 40 and 42, respectively) using sequence data downstream from the putative leader sequence and the 3' end of the clone. The sequences of the primers for GVs-3 are provided in SEQ ID NO: 66 and 67, and the sequences of the primers for GVs-5 are provided in SEQ ID NO: 68 and 69. A XhoI restriction site was added to the primers for GVs-3, and EcoRI and BamHI restriction sites were added to the primers for GVs-5 for cloning convenience. Following amplification from genomic *M. vaccae* DNA, fragments were cloned into the appropriate site of pProEX HT prokaryotic expression vector (Gibco BRL, Life Technologies, Gaithersburg, Md.) and submitted for sequencing to confirm the correct reading frame and orientation. Expression and purification of the recombinant protein was performed according to the manufacturer's protocol.

Expression of a fragment of the *M. vaccae* antigen GVs-4 (antigen 85B homolog) was performed as follows. The primers AD58 and AD59, described above, were used to amplify a 485 bp fragment from *M. vaccae* genomic DNA. This fragment was gel-purified using standard techniques and cloned into EcoRV-digested pBluescript containing added dTTP residues. The base sequences of inserts from five clones were determined and found to be identical to each other. These inserts had highest homology to Ag85B from *M. tuberculosis.* The insert from one of the clones was subcloned into the EcoRI/XhoI sites of pProEX HT prokaryotic expression vector (Gibco BRL), expressed and purified according to the manufacturer's protocol. This clone was renamed GV-4P because only a part of the gene was expressed. The amino acid and DNA sequences for the partial clone GV-4P are provided in SEQ ID NO: 70 and 106, respectively.

Similar to the cloning of GV-4P, the amplification primers AD58 and AD59 were used to amplify a 485 bp fragment from a clone containing GVs-5 (SEQ ID NO: 42). This fragment was cloned into the expression vector pET16 and was called GV-5P. The determined nucleotide sequence and predicted amino acid sequence of GV-5P are provided in SEQ ID NOS: 157 and 158, respectively.

In subsequent studies, using procedures similar to those described above, GVs-3, GV-4P and GVs-5 were re-cloned into the alternative vector pET16 (Novagen, Madison, Wis.).

The ability of purified recombinant GVs-3, GV-4P and GVs-5 to stimulate proliferation of T cells and interferon-γ production in human PBL from PPD-positive, healthy donors, was assayed as described above in Example 2. The results of this assay are shown in Table 2, wherein (−) indicates a lack of activity, (+/−) indicates polypeptides having a result less than twice higher than background activity of control media, (+) indicates polypeptides having activity two to four times above background, (++) indicates polypeptides having activity greater than four times above background, and ND indicates not determined.

vaccae genomic DNA library using standard protocols. A genomic clone containing genes encoding four different antigens was isolated. The determined DNA sequences for GVs-8A (re-named GV-30), GVs-8B (re-named GV-3 1), GVs-8C (re-named GV-32) and GVs-8D, re-named GV-33, are shown in SEQ ID NOS: 48–51, respectively, with the corresponding amino acid sequences being shown in SEQ ID NOS: 52–55, respectively. GV-30 contains regions showing some similarity to known prokaryotic valyl-tRNA syn-

TABLE 2

| | Donor G97005 | | Donor G97006 | | Donor G97007 | | Donor G97008 | | Donor G97009 | | Donor G97010 | |
|---|---|---|---|---|---|---|---|---|---|---|---|---|
| | Prolif | IFN-γ | Prolif | IFN-γ | Prolif | IFN-γ | Prolif | IFN-γ | Prolif | IFN-γ | Prolif | IFN-γ |
| GVs-3 | ++ | + | ND | ND | ++ | ++ | ++ | ++ | ++ | +/± | + | ++ |
| GV-4P | + | +/− | ND | ND | + | ++ | ++ | ++ | +/− | +/− | +/− | ++ |
| GVs-5 | ++ | ++ | ++ | ++ | ++ | ++ | + | ++ | ++ | + | + | ++ |

EXAMPLE 5

DNA Cloning Strategy for M. vaccae Antigens

An 84 bp probe for the M. vaccae antigen GVc-7 was amplified using degenerate oligonucleotides designed to the determined amino acid sequence of GVc-7 (SEQ ID NOS: 5–8). This probe was used to screen a M. vaccae genomic DNA library as described in Example 4. The determined nucleotide sequence for GVc-7 is shown in SEQ ID NO: 46 and predicted amino acid sequence in SEQ ID NO: 47. Comparison of these sequences with those in the databank revealed homology to a hypothetical 15.8 kDa membrane protein of M. tuberculosis.

The sequence of SEQ ID NO: 46 was used to design amplification primers (provided in SEQ ID NO: 71 and 72) for expression cloning of the GVc-7 gene using sequence data downstream from the putative leader sequence. A XhoI restriction site was added to the primers for cloning convenience. Following amplification from genomic M. vaccae DNA, fragments were cloned into the XhoI-site of pProEX HT prokaryotic expression vector (Gibco BRL) and submitted for sequencing to confirm the correct reading frame and orientation. Expression and purification of the fusion protein was performed according to the manufacturer's protocol. In subsequent studies, GVc-7 was re-cloned into the vector pET16 (Novagen).

The ability of purified recombinant GVc-7 to stimulate proliferation of T-cells and stimulation of interferon-γ production in human PBL, from PPD-positive, healthy donors, was assayed as described previously in Example 2. The results are shown in Table 3, wherein (−) indicates a lack of activity, (+/−) indicates polypeptides having a result less than twice higher than background activity of control media, (+) indicates polypeptides having activity two to four times above background, and (++) indicates polypeptides having activity greater than four times above background.

TABLE 3

| Donor | Proliferation | Interferon-γ |
|---|---|---|
| G97005 | ++ | +/− |
| G97008 | ++ | + |
| G97009 | + | +/− |
| G97010 | +/− | ++ |

A redundant oligonucleotide probe (SEQ ID NO 73, referred to as MPG15) was designed to the GVs-8 peptide sequence shown in SEQ ID NO: 26 and used to screen a M.

thetases; GV-31 shows some similarity to M. smegmatis aspartate semialdehyde dehydrogenase; and GV-32 shows some similarity to the H. influenza folylpolyglutamate synthase gene. GV-33 contains an open reading frame which shows some similarity to sequences previously identified in M. tuberculosis and M. leprae, but whose function has not been identified.

The determined partial DNA sequence for GV-33 is provided in SEQ ID NO:74 with the corresponding predicted amino acid sequence being provided in SEQ ID NO: 75. Sequence data from the 3' end of the clone showed homology to a previously identified 40.6 kDaa outer membrane protein of M. tuberculosis. Subsequent studies led to the isolation of a full-length DNA sequence for GV-33 (SEQ ID NO: 193). The corresponding predicted amino acid sequence is provided in SEQ ID NO: 194.

The gene encoding GV-33 was amplified from M. vaccae genomic DNA with primers based on the determined nucleotide sequence. This DNA fragment was cloned into EcoRv-digested pBluescript II SK+ (Stratagene), and then transferred to pET16 expression vector. Recombinant protein was purified following the manufacturer's protocol.

The ability of purified recombinant GV-33 to stimulate proliferation of T-cells and stimulation of interferon-γ production in human PBL was assayed as described previously in Example 2. The results are shown in Table 4, wherein (−) indicates a lack of activity, (+/−) indicates polypeptides having a result less than twice higher than background activity of control media, (+) indicates polypeptides having activity two to four times above background, and (++) indicates polypeptides having activity greater than four times above background.

TABLE 4

Stimulatory Activity of Polypeptides

| Donor | Proliferation | Interferon-γ |
|---|---|---|
| G97005 | ++ | + |
| G97006 | ++ | ++ |
| G97007 | − | +/− |
| G97008 | +/− | − |
| G97009 | +/− | − |
| G97010 | +/− | ++ |

EXAMPLE 6

Detection of Nonspecific Immune Amplifier from Whole M. vaccae and the Culture Filtrate of M. vaccae This example illustrates the preparation of whole *M. vaccae* and *M. vaccae* culture filtrate and its non-specific immune amplifying or 'adjuvant' property.

*M. vaccae* bacteria was cultured, pelleted and autoclaved as described in Example 1. Culture filtrates of live *M. vaccae* refer to the supernatant from 24 hour cultures of *M. vaccae* in 7H9 medium with glucose. A delipidated form of *M. vaccae* was prepared by sonicating autoclaved *M. vaccae* for four bursts of 30 seconds on ice using the Virsonic sonicator (Virtis, Disa, USA). The material was then centrifuged (9000 rpm, 20 minutes, JA10 rotor, brake=5). The resulting pellet was suspended in 100 ml of chloroform/methanol (2:1), incubated at room temperature for 1 hour; re-centrifuged, and the chloroform/methanol extraction repeated. The pellet was obtained by centrifugation, dried in vacuo, weighed and resuspended in PBS at 50 mg (dry weight) per ml as delipidated *M. vaccae*.

Glycolipids were removed from the delipidated *M. vaccae* preparation by refluxing in 50% v/v ethanol for 2 hours. The insoluble material was collected by centrifugation (10,000 rpm, JA20 rotor, 15 mins, brake=5). The extraction with 50% v/v ethanol under reflux was repeated twice more. The insoluble material was collected by centrifugation and washed in PBS. Proteins were extracted by resuspending the pellet in 2% SDS in PBS at 56° C. for 2 hours. The insoluble material was collected by centrifugation and the extraction with 2% SDS/PBS at 56° C. was repeated twice more. The pooled SDS extracts were cooled to 4° C., and precipitated SDS was removed by centrifugation (10,000 rpm, JA20 rotor, 15 mins, brake=5). Proteins were precipitated from the supernatant by adding an equal volume of acetone and incubating at −20° C. for 2 hours. The precipitated proteins were collected by centrifugation, washed in 50% v/v acetone, dried in vacuo, and redissolved in PBS.

*M. vaccae* culture supernatant (S/N), killed *M. vaccae* and delipidated *M. vaccae* were tested for adjuvant activity in the generation of cytotoxic T cell immune response to ovalbumin, a structurally unrelated protein, in the mouse. This anti-ovalbumin-specific cytotoxic response was detected as follows. C57BL/6 mice (2 per group) were immunized by the intraperitoneal injection of 100 µg of ovalbumin with the following test adjuvants: autoclaved *M. vaccae*; delipidated *M vaccae*; delipidated *M. vaccae* with glycolipids also extracted and proteins extracted with SDS; the SDS protein extract treated with Pronase (an enzyme which degrades protein); whole *M. vaccae* culture filtrate; and heat-killed *M. tuberculosis* or heat-killed *M. bovis* BCG, *M. phlei* or *M. smegmatis* or *M. vaccae* culture filtrate. After 10 days, spleen cells were stimulated in vitro for a further 6 days with E.G7 cells which are EL4 cells (a C57BL/6-derived T cell lymphoma) transfected with the ovalbumin gene and thus express ovalbumin. The spleen cells were then assayed for their ability to kill non-specifically EL4 target cells or to kill specifically the E.G7 ovalbumin expressing cells. Killing activity was detected by the release of 51 Chromium with which the EL4 and E.G7 cells have been labelled (100 µCi per 2×10$^6$), prior to the killing assay. Killing or cytolytic activity is expressed as % specific lysis using the formula:

$$\frac{\text{cpm in test cultures} - \text{cpm in control cultures}}{\text{total cpm} - \text{cpm in control cultures}} \times 100\%$$

It is generally known that ovalbumin-specific cytotoxic cells are generated only in mice immunized with ovalbumin with an adjuvant but not in mice immunized with ovalbumin alone.

The diagrams that make up FIG. 4 show the effect of various *M. vaccae* derived adjuvant preparations on the generation of cytotoxic T cells to ovalbumin in C57BL/6 mice. As shown in FIG. 4A, cytotoxic cells were generated in mice immunized with (i) 10 µg, (ii) 100 µg or (iii) 1 mg of autoclaved *M. vaccae* or (iv) 75 µg of *M. vaccae* culture filtrate. FIG. 4B shows that cytotoxic cells were generated in mice immunized with (i) 1 mg whole autoclaved *M. vaccae* or (ii) 1 mg delipidated and deglycolipidated (DD-) *M. vaccae*. As shown in FIG. 4C(i), cytotoxic cells were generated in mice immunized with 1 mg whole autoclaved *M. vaccae*; FIG. 4C(ii) shows the active material in *M. vaccae* soluble proteins extracted with SDS from DD-*M. vaccae*. FIG. 4C(iii) shows that active material in the adjuvant preparation of FIG. 4C(ii) was destroyed by treatment with the proteolytic enzyme Pronase. By way of comparison, 100 µg of the SDS-extracted proteins had significantly stronger immune-enhancing ability (FIG. 4C(ii)) than did 1 mg whole autoclaved *M. vaccae* (FIG. 4C(i)).

Figure 4A:
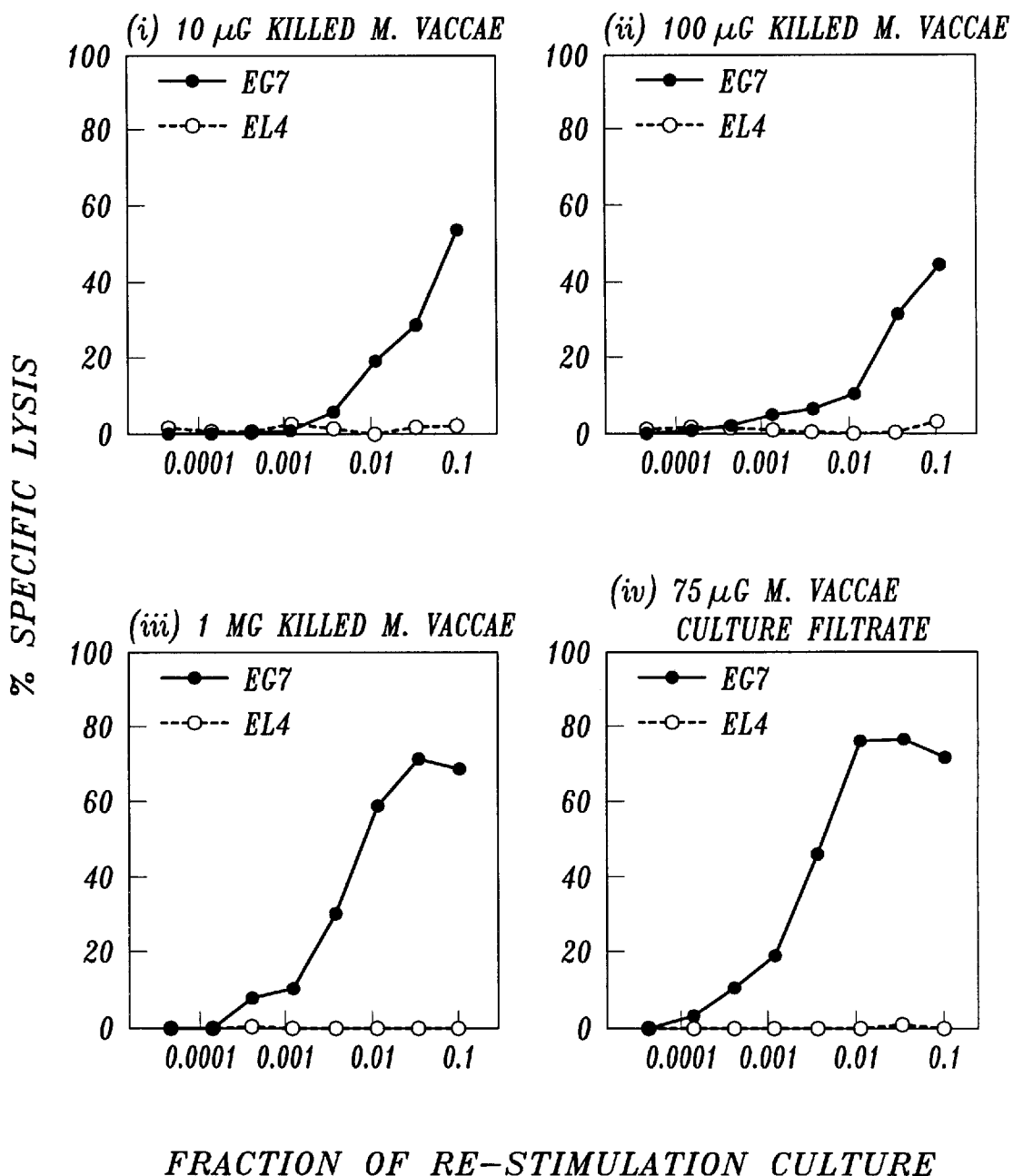
FIG. 4A(i)–(iv) illustrate the non-specific immune amplifying effects of 10 μg, 100 μg and 1 mg autoclaved *M. vaccae* and 75 μg unfractionated culture filtrates of *M. vaccae*, respectively.
Figure 4B:
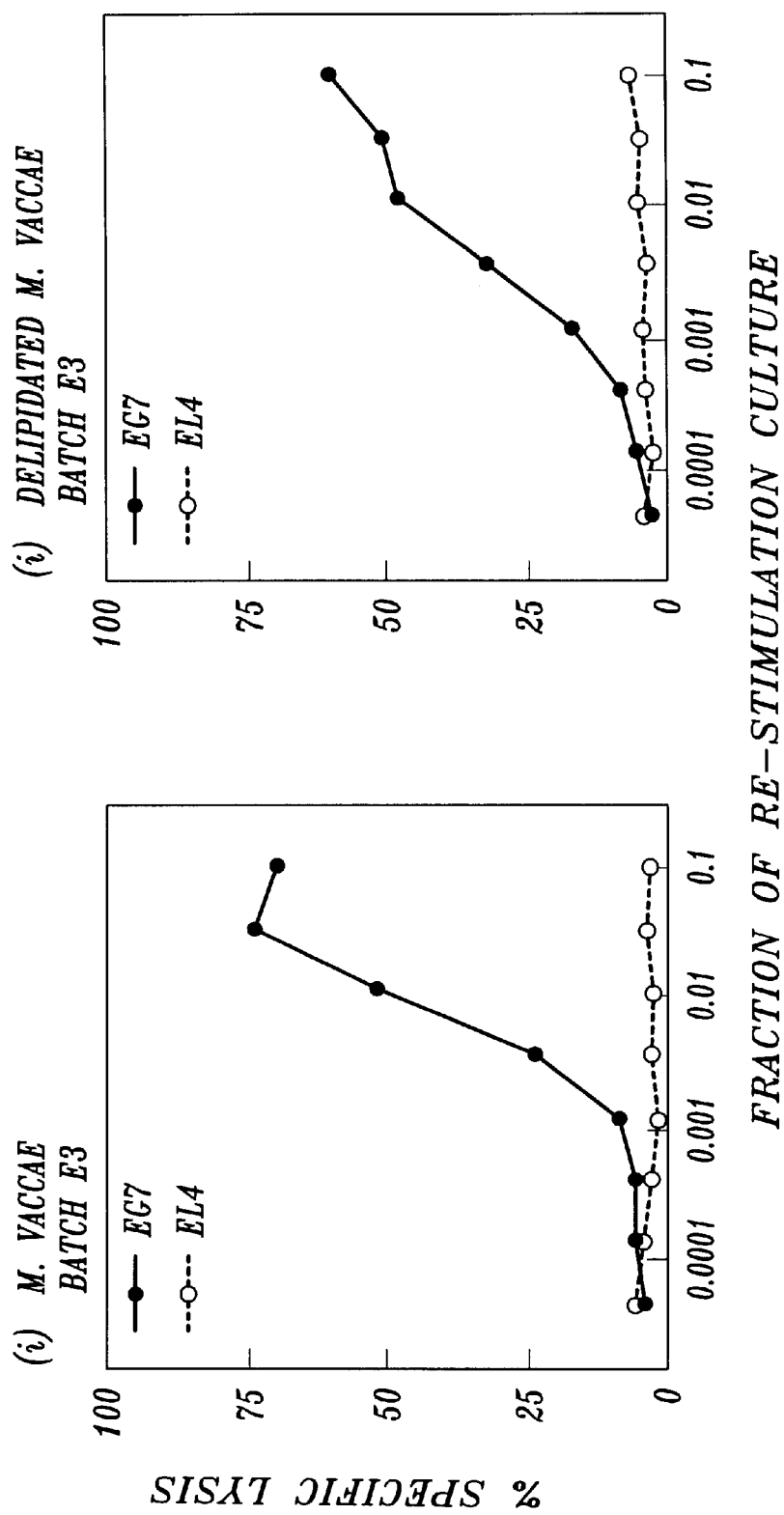
FIG. 4B(i) and (ii) illustrate the non-specific immune amplifying effects of autoclaved *M. vaccae*, and delipidated and deglycolipidated *M. vaccae*, respectively.
Figure 4C:
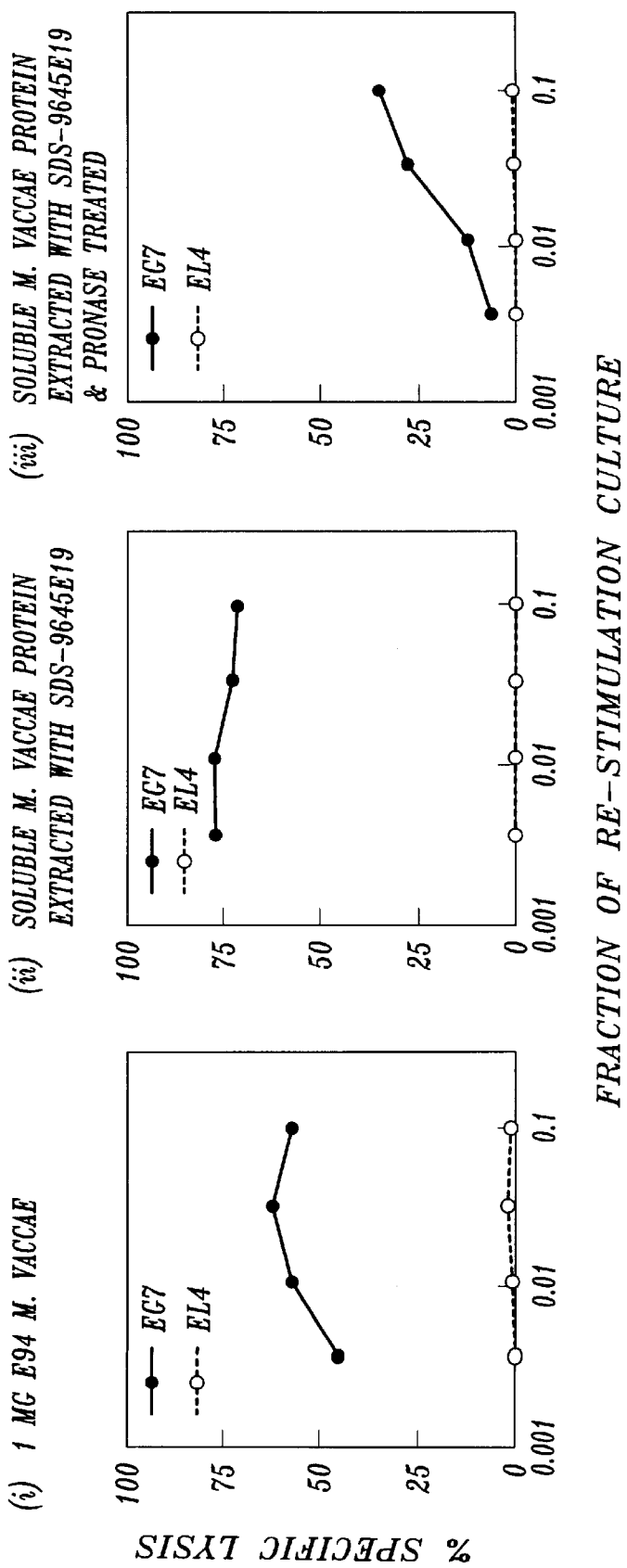
FIG. 4C(i) illustrates the non-specific immune amplifying effects of whole autoclaved *M. vaccae*.
Figure 4D:
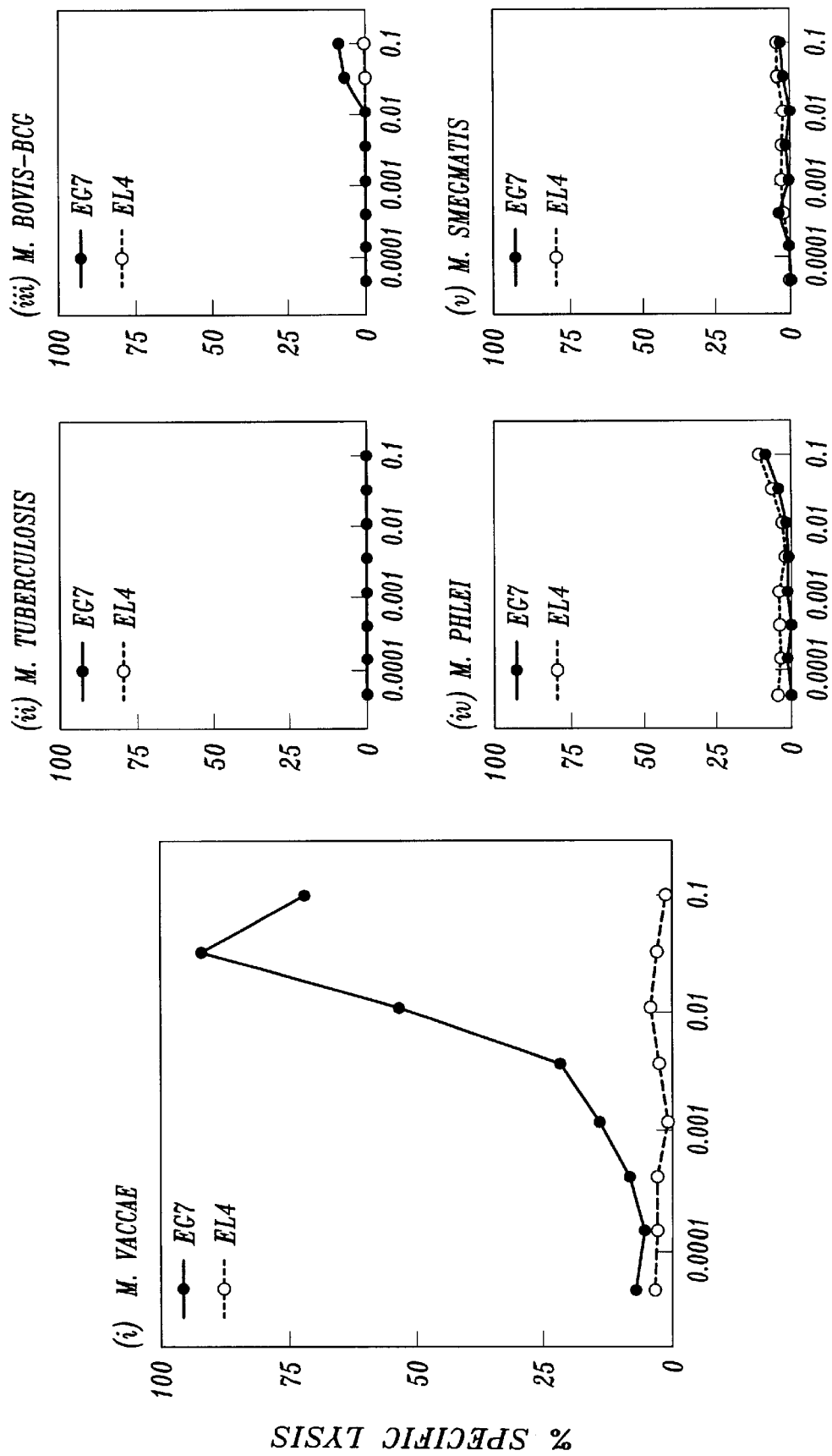
FIG. 4D illustrates the non-specific immune amplifying effects of heat-killed *M. vaccae* (FIG. 4D(i)),whereas a non-specific immune amplifying effect was not seen with heat-killed preparations of *M. tuberculosis* (FIG. 4D(ii)), *M. bovis* BCG (FIG. 4D(iii)), *M. phlei* (FIG. 4D(iv)) and *M. smegmatis* (FIG. 4D(v)).

Mice immunized with 1 mg heat-killed *M. vaccae* (FIG. 4D(i)) generated cytotoxic cells to ovalbumin, but mice immunized separately with 1 mg heat-killed *M. tuberculosis* (FIG. 4D(ii)), 1 mg *M. bovis* BCG (FIG. 4D(iii)), 1 mg *M. phlei* (FIG. 4D(iv)), or 1 mg *M. smegmatis* (FIG. 4D(v)) failed to generate cytotoxic cells.

These findings demonstrate that heat-killed *M. vaccae* and DD-*M. vaccae* have adjuvant properties not seen in other mycobacteria. Furthermore, delipidation and deglycolipidation of *M. vaccae* removes an NK cell-stimulating activity but does not result in a loss of T-cell stimulating activity.

Figure 5:
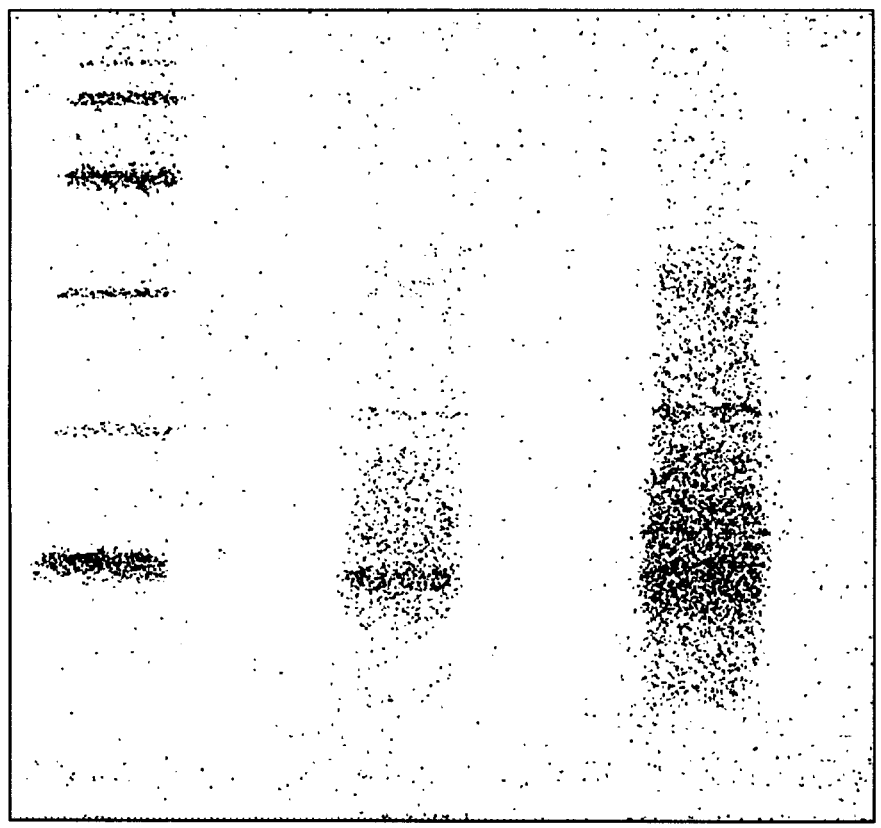
FIG. 5 shows the results of polyacrylamide gel electrophoresis analysis of SDS-extracted proteins derived from delipidated and deglycolipidated *M. vaccae*.

The SDS-extracted proteins derived from delipidated and deglycolipidated *M. vaccae* were analysed by polyacrylamide gel electrophoresis. As shown in FIG. 5, three major bands were observed after staining with silver.

Figure 6:
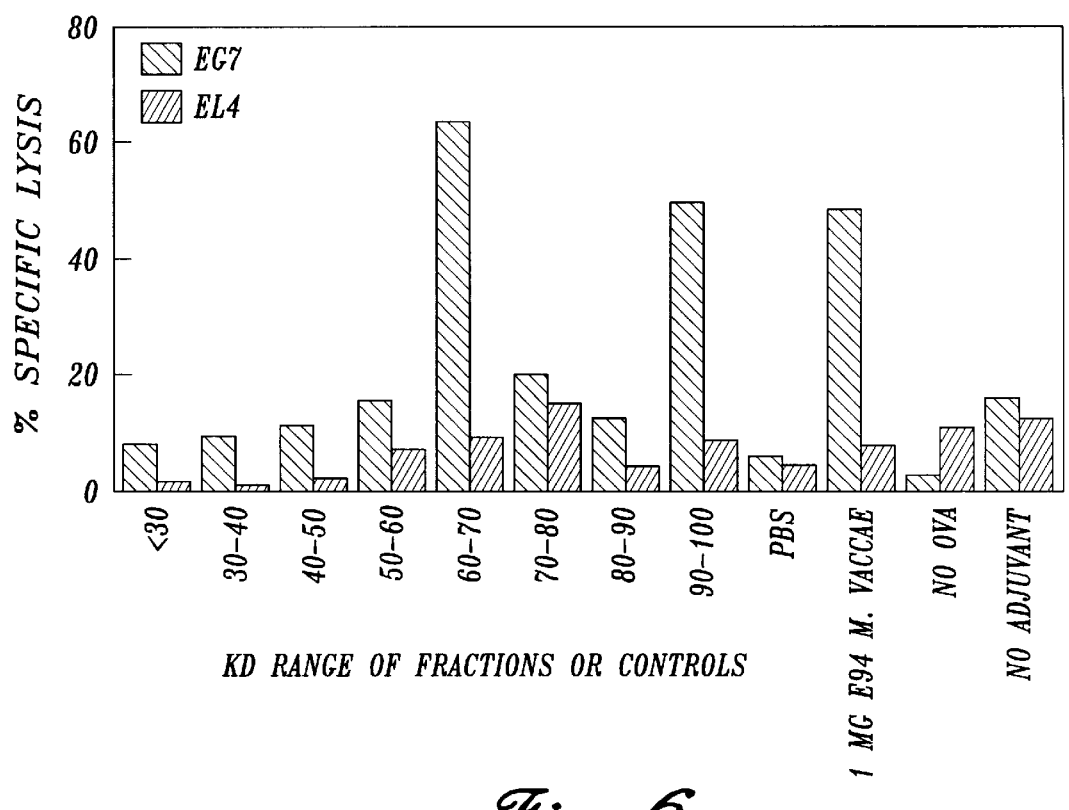
FIG. 6 illustrates the non-specific immune amplifying effects of different molecular weight fractions of SDS-extracted *M. vaccae* proteins.

In subsequent studies, more of the SDS-extracted proteins described above were prepared by preparative SDS-PAGE on a BioRad Prep Cell (Hercules, Calif.). Fractions corresponding to molecular weight ranges were precipitated by trichloroacetic acid to remove SDS before assaying for adjuvant activity in the anti-ovalbumin-specific cytotoxic response assay in C57BL/6 mice as described above. As seen in FIG. 6, the adjuvant activity was highest in the 60–70 kDa a fraction. The most abundant protein in this size range was purified by SDS-PAGE blotted on to a polyvinylidene difluoride (PVDF) membrane and then sequenced. The sequence of the first ten amino acid residues is provided in SEQ ID NO:76. Comparison of this sequence with those in the gene bank as described above, revealed homology to the heat shock protein 65 (GroEL) gene from *M. tuberculosis*, indicating that this protein is an *M. vaccae* member of the GroEL family.

An expression library of *M. vaccae* genomic DNA in BamH1-lambda ZAP- Express (Stratagene) was screened using sera from cynomolgus monkeys immunised with *M. vaccae* secreted proteins prepared as described above. Positive plaques were identified using a colorimetric system.

These plaques were re-screened until plaques were pure following standard procedures. pBK-CMV phagemid 2-1 containing an insert was excised from the lambda ZAP Express (Stratagene) vector in the presence of ExAssist helper phage following the manufacturer's protocol. The base sequence of the 5' end of the insert of this clone, hereinafter referred to as GV-27, was determined using Sanger sequencing with fluorescent primers on Perkin Elmer/Applied Biosystems Dvision automatic sequencer. The determined nucleotide sequence of the partial M. vaccae GroEL-homologue clone GV-27 is provided in SEQ ID NO: 77 and the predicted amino acid sequence in SEQ ID NO: 78. This clone was found to have homology to M. tuberculosis GroEL. A partial sequence of the 65 kDa heat shock protein of M. vaccae has been published by Kapur et al. (Arch Pathol. Lab. Med. 119 :131–138, 1995). The nucleotide sequence of the Kapur et al. fragment is shown in SEQ ID NO: 79 and the predicted amino acid sequence in SEQ ID NO: 80.

In subsequent studies, an extended (full-length except for the predicted 51 terminal nucleotides) DNA sequence for GV-27 was obtained (SEQ ID NO: 113). The corresponding predicted amino acid sequence is provided in SEQ ID NO: 114. Further studies led to the isolation of a full-length DNA sequence for GV-27 (SEQ ID NO: 159). The corresponding predicted amino acid sequence is provided in SEQ ID NO: 160. GV-27 was found to be 93.7% identical to the M. tuberculosis GroEL at the amino acid level.

Two peptide fragments, comprising the N-terminal sequence (hereinafter referred to as GV-27A) and the carboxy terminal sequence of GV-27 (hereinafter referred to as GV-27B) were prepared using techniques well known in the art. The nucleotide sequences for GV-27A and GV-27B are provided in SEQ ID NO: 115 and 116, respectively, with the corresponding amino acid sequences being provided in SEQ ID NO: 117 and 118. Subsequent studies led to the isolation of an extended DNA sequence for GV-27B. This sequence is provided in SEQ ID NO: 161, with the corresponding amino acid sequence being provided in SEQ ID NO: 162. The sequence of GV-27A is 95.8% identical to the M. tuberculosis GroEL sequence and contains the shorter M. vaccae sequence of Kapur et al. discussed above. The sequence for GV-27B shows about 92.2% identity to the corresponding region of M tuberculosis HSP65.

Following the same protocol as for the isolation of GV-27, pBK-CMV phagemid 3-1 was isolated. The antigen encoded by this DNA was named GV-29. The determined nucleotide sequences of the 5' and 3' ends of the gene are provided in SEQ ID NOS: 163 and 164, respectively, with the predicted corresponding amino acid sequences being provided in SEQ ID NOS: 165 and 166 respectively. GV-29 showed homology to yeast urea amidolyase. The DNA encoding GV-29 was sub-cloned into the vector pET16 (Novagen, Madison, Wis.) for expression and purification according to standard protocols.

Figure 7:
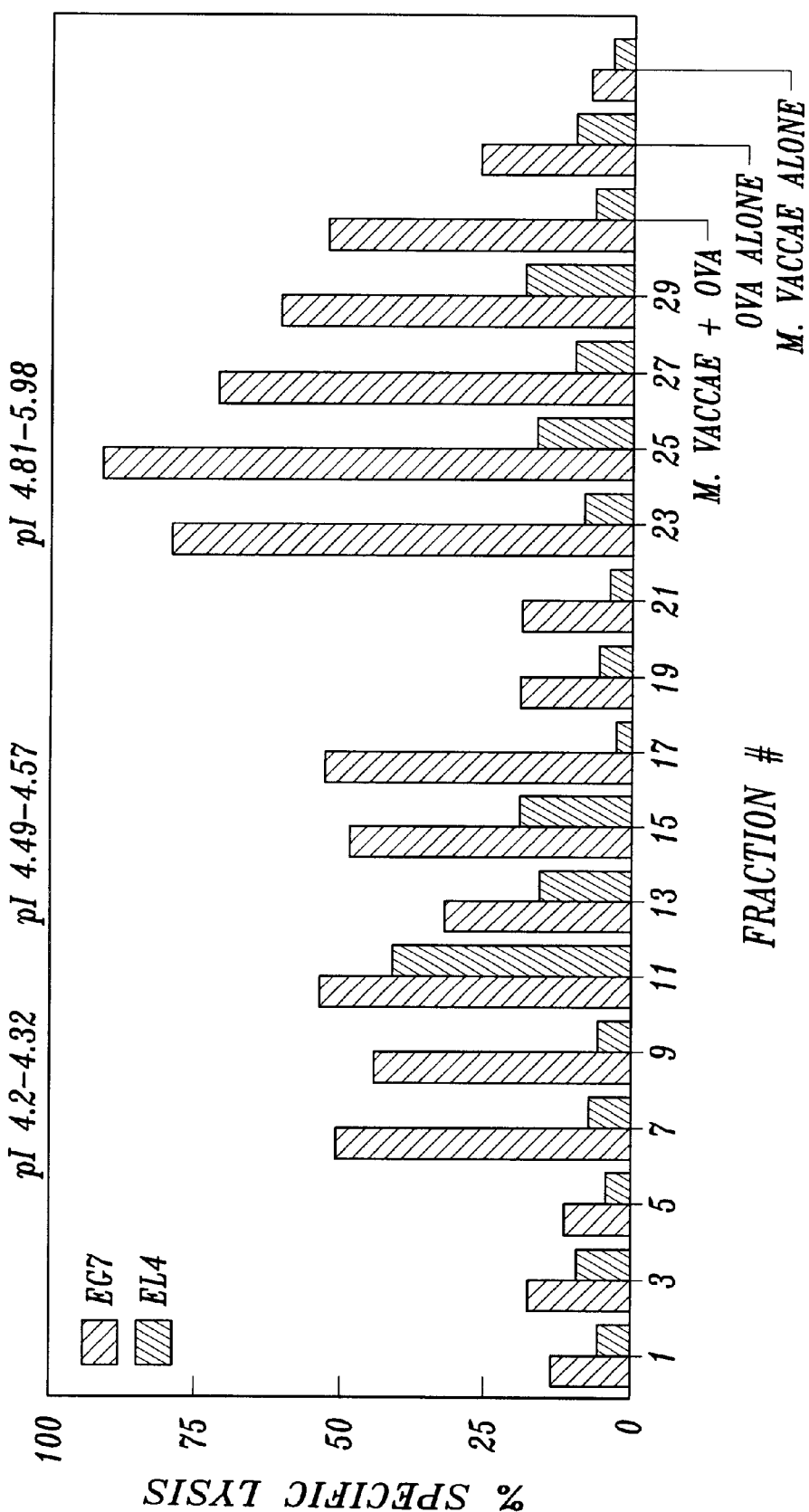
FIG. 7 illustrates the non-specific immune amplifying effects of different pI fractions of SDS-extracted *M. vaccae* proteins.

The M. vaccae culture filtrate described above was also fractionated by iso-electric focusing and the fractions assayed for adjuvant activity in the anti-ovalbumin-specific cytotoxic response assay in C57BL/6 mice as described above. As shown in FIG. 7, peak adjuvant activities were demonstrated in fractions corresponding to pI of 4.2–4.32 (fraction nos. 7–9), 4.49–4.57 (fraction nos. 13–17) and 4.81–5.98 (fraction nos. 23–27).

EXAMPLE 7

Autoclaved M. vaccae Generates Cytotoxid CD8 T Cells Against M. Tuberculosis Infected Macrophages This example illustrates the ability of killed M. vaccae to stimulate cytotoxic CD8 T cells which preferentially kill macrophages that have been infected with M. tuberculosis.

Mice were immunized by the intraperitoneal injection of 500 μg of killed M. vaccae which was prepared as described in Example 1. Two weeks after immunization, the spleen cells of immunized mice were passed through a CD8 T cell enrichment column (R&D Systems, St. Paul, Minn., USA). The spleen cells recovered from the column have been shown to be enriched up to 90% CD8 T cells. These T cells, as well as CD8 T cells from spleens of non-immunized mice, were tested for their ability to kill uninfected macrophages or macrophages which have been infected with M. tuberculosis.

Macrophages were obtained from the peritoneal cavity of mice five days after they have been given 1 ml of 3% thioglycolate intraperitoneally. The macrophages were infected overnight with M. tuberculosis at the ratio of 2 mycobacteria per macrophage. All macrophage preparations were labelled with $^{51}$Chromium at 2 μci per $10^4$ macrophages. The macrophages were then cultured with CD8 T cells overnight (16 hours) at killer to target ratios of 30:1. Specific killing was detected by the release of $^{51}$Chromium and expressed as % specific lysis, calculated as in Example 5.

The production of IFN-γ and its release into medium after 3 days of co-culture of CD8 T cells with macrophages was measured using an enzyme-linked immunosorbent assay (ELISA). ELISA plates were coated with a rat monoclonal antibody directed to mouse IFN-γ (Pharmigen, San Diego, Calif., USA) in PBS for 4 hours at 4° C. Wells were blocked with PBS containing 0.2% Tween 20 for 1 hour at room temperature. The plates were then washed four times in PBS containing 0.2% Tween 20, and samples diluted 1:2 in culture medium in the ELISA plates were incubated overnight at room temperature. The plates were again washed, and a biotinylated monoclonal rat anti-mouse IFN-γ antibody (Pharmigen), diluted to 1 μg/ml in PBS, was added to each well. The plates were then incubated for 1 hour at room temperature, washed, and horseradish peroxidase-coupled avidin D (Sigma A-3151) was added at a 1:4,000 dilution in PBS. After a further 1 hour incubation at room temperature, the plates were washed and OPD substrate added. The reaction was stopped after 10 min with 10% (v/v) HCl. The optical density was determined at 490 nm. Fractions that resulted in both replicates giving an OD two-fold greater than the mean OD from cells cultured in medium alone were considered positive.

As shown in Table 5, CD8 T cells from spleens of mice immunized with M. vaccae were cytotoxic for macrophages infected with M tuberculosis and did not lyse uninfected macrophages. The CD8 T cells from non-immunized mice did not lyse macrophages. CD8 T cells from naive or non-immunized mice do produce IFN-γ when cocultured with infected macrophages. The amount of IFN-γ produced in coculture was greater with CD8 T cells derived from M. vaccae immunized mice.

TABLE 5

EFFECT WITH M. TUBERCULOSIS INFECTED AND UNINFECTED MACROPHAGES

| CD8 T cells | % Specific Lysis of Macrophages | | IFN-γ (ng/ml) | |
| --- | --- | --- | --- | --- |
| | uninfected | infected | uninfected | infected |
| Control | 0 | 0 | 0.7 | 24.6 |
| M. vaccae Immunized | 0 | 95 | 2.2 | 43.8 |

EXAMPLE 8

DNA Cloning Strategy for the M. vaccae Antigens GV-23, GV-24, GV-25, GV-26, GV-38A and GV-38B M. vaccae (ATCC Number 15483) was grown in sterile Medium 90 at 37° C. for 4 days and harvested by centrifugation. Cells were resuspended in 1 ml Trizol (Gibco BRL, Life Technologies, Gaithersburg, Md.) and RNA extracted according to the standard manufacturer's protocol. M tuberculosis strain H37Rv (ATCC Number 27294) was grown in sterile Middlebrooke 7H9 medium with Tween 80™ and oleic acid/albumin/dextrose/catalase additive (Difco Laboratories, Detroit, Mich.) at 37° C. and harvested under appropriate laboratory safety conditions. Cells were resuspended in 1 ml Trizol (Gibco BRL) and RNA extracted according to the manufacturer's standard protocol.

Total *M. tuberculosis* and *M. vaccae* RNA was depleted of 16S and 23S ribosomal RNA (rRNA) by hybridisation of the total RNA fraction to oligonucleotides AD10 and AD 11 (SEQ ID NO: 81 and 82) complementary to *M. tuberculosis* rRNA. These oligonucleotides were designed from mycobacterial 16S rRNA sequences published by Bottger (*FEMS Microbiol Lett.* 65:171–176, 1989) and from sequences deposited in the databanks. Depletion was done by hybridisation of total RNA to oligonucleotides AD10 and AD11 immobilised on nylon membranes (Hybond N, Amersham International, United Kingdom). Hybridisation was repeated until rRNA bands were not visible on ethidium bromide-stained agarose gels. An oligonucleotide, AD12 (SEQ ID NO: 83), consisting of 20 dATP-residues, was ligated to the 3' ends of the enriched mRNA fraction using RNA ligase. First strand cDNA synthesis was performed following standard protocols, using oligonucleotide AD7 (SEQ ID NO: 84) containing a poly(dT) sequence.

The *M. tuberculosis* and *M. vaccae* cDNA was used as template for single-sided-specific PCR (3S-PCR). For this protocol, a degenerate oligonucleotide ADI (SEQ ID NO: 85) was designed based on conserved leader sequences and membrane protein sequences. After 30 cycles of amplification using primer AD1 as 5'-primer and AD7 as 3'-primer, products were separated on a urealpolyacrylamide gel. DNA bands unique to *M. vaccae* were excised and re-amplified using primers AD1 and AD7. After gel purification, bands were cloned into pGEM-T (Promega) and the base sequence determined.

Searches with the determined nucleotide and predicted amino acid sequences of band 12B21 (SEQ ID NOS: 86 and 87, respectively) showed homology to the *pota* gene of *E. coli* encoding the ATP-binding protein of the spermidine/putrescine ABC transporter complex published by Furuchi et al. (*Jnl. Biol. Chem.* 266: 20928–20933, 1991). The spermidine/putrescine transporter complex of *E. coli* consists of four genes and is a member of the ABC transporter family. The ABC (ATP-binding Cassette) transporters typically consist of four genes: an ATP-binding gene, a periplasmic, or substrate binding, gene and two transmembrane genes. The transmembrane genes encode proteins each characteristically having six membrane-spanning regions. Homologues (by similarity) of this ABC transporter have been identified in the genomes of *Haemophilus influenza* (Fleischmann et al. *Science* 269 :496–512, 1995) and *Mycoplasma genitalium* (Fraser, et al. *Science,* 270:397–403, 1995).

An *M. vaccae* genomic DNA library constructed in BamH1-digested lambda ZAP Express (Stratagene) was probed with the radiolabelled 238 bp band 12B21 following standard protocols. A plaque was purified to purity by repetitive screening and a phagemid containing a 4.5 kb insert was identified by Southern blotting and hybridisation. The nucleotide sequence of the full-length *M. vaccae* homologue of pota (ATP-binding protein) was identified by subcloning of the 4.5 kb fragment and base sequencing. The gene consisted of 1449 bp including an untranslated 5' region of 320 bp containing putative –10 and –35 promoter elements. The nucleotide and predicted amino acid sequences of the *M. vaccae pota* homologue are provided in SEQ ID NOS: 88 and 89, respectively.

The nucleotide sequence of the *M. vaccae pota* gene was used to design primers EV24 and EV25 (SEQ ID NO: 90 and 91) for expression cloning. The amplified DNA fragment was cloned into pProEX HT prokaryotic expression system (Gibco BRL) and expression in an appropriate *E. coli* host was induced by addition of 0.6 mM isopropylthio-β-galactoside (IPTG). The recombinant protein was named GV-23 and purified from inclusion bodies according to the manufacturer's protocol. In subsequent studies, GV-23 (SEQ ID NO: 88) was re-cloned into the alternative vector pET16 (Novagen).

A 322 bp Sal1-BamH1 subclone at the 3'-end of the 4.5 kb insert described above showed homology to the *potd* gene, (periplasmic protein), of the spermidine/putrescine ABC transporter complex of *E. coli*. The nucleotide sequence of this subclone is shown in SEQ ID NO: 92. To identify the gene, the radiolabelled insert of this subclone was used to probe a *M. vaccae* genomic DNA library constructed in the Sal1-site of lambda Zap Express (Stratagene) following standard protocols. A clone was identified of which 1342 bp showed homology with the potd gene of *E. coli*. The potd homologue of *M. vaccae* was identified by subcloning and base sequencing. The determined nucleotide and predicted amino acid sequences are shown in SEQ ID NO: 93 and 94.

For expression cloning, primers EV-26 and EV-27 (SEQ ID NOS: 95–96) were designed from the determined *M. vaccae potd* homologue. The amplified fragment was cloned into pProEX HT Prokaryotic expression system (Gibco BRL). Expression in an appropriate *E. coli* host was induced by addition of 0.6 mM IPTG and the recombinant protein named GV-24. The recombinant antigen was purified from inclusion bodies according to the protocol of the supplier. In subsequent studies, GV-24 (SEQ ID NO: 93) was re-cloned into the alternative vector pET16 (Novagen).

To improve the solubility of the purified recombinant antigen, the gene encoding GV-24, but excluding the signal peptide, was re-cloned into the expression vector, employing amplification primers EV101 and EV102 (SEQ ID NOS: 167 and 168). The construct was designated GV-24B. The nucleotide sequence of GV-24B is provided in SEQ ID NO: 169 and the predicted amino acid sequence in SEQ ID NO: 170. This fragment was cloned into pET16 for expression and purification of GV-24B according to the manufacturer's protocols.

The ability of purified recombinant protein GV-23 and GV-24 to stimulate proliferation of T cells and interferon-production in human PBL was determined as described in Example 2. The results of these assays are provided in Table 6, wherein (–) indicates a lack of activity, (+/–) indicates polypeptides having a result less than twice higher than background activity of control media, (+) indicates polypeptides having activity two to four times above background, (++) indicates polypeptides having activity greater than four times above background, and (ND) indicates not determined.

TABLE 6

| | Donor G97005 | | Donor G97006 | | Donor G97007 | | Donor G97008 | | Donor G97009 | | Donor G97010 | |
|---|---|---|---|---|---|---|---|---|---|---|---|---|
| | Prolif | IFN-γ | Prolif | IFN-γ | Prolif | IFN-γ | Prolif | IFN-γ | Prolif | IFN-γ | Prolif | IFN-γ |
| GV-23 | ++ | ++ | ++ | ++ | + | + | ++ | ++ | + | − | + | ++ |
| GV-24 | ++ | + | ++ | + | ND | ND | + | +/− | + | +/− | +/− | ++ |

Base sequence adjacent to the *M. vaccae potd* gene-homologue was found to show homology to the *potb* gene of the spermidine/putrescine ABC transporter complex of *E. coli,* which is one of two transmembrane proteins in the ABC transporter complex. The *M. vaccae* potb homologue (referred to as GV-25) was identified through further subcloning and base sequencing. The determined nucleotide and predicted amino acid sequences for GV-25 are shown in SEQ ID NOS: 97 and 98, respectively.

Further subcloning and base sequence analysis of the adjacent 509 bp failed to reveal significant homology to PotC, the second transmembrane protein of *E. coli,* and suggests that a second transmembrane protein is absent in the *M. vaccae* homologue of the ABC transporter. An open reading frame with homology to *M. tuberculosis* acetyl-CoA acetyl transferase, however, was identified starting 530 bp downstream of the transmembrane protein and the translated protein was named GV-26. The determined partial nucleotide sequence and predicted amino acid sequence for GV-26 are shown in SEQ ID NO:99 and 100.

Using a protocol similar to that described above for the isolation of GV-23, the 3S-PCR band 12B28 (SEQ ID NO: 119) was used to screen the *M. vaccae* genomic library constructed in the BamHI-site of lambda ZAP Express (Stratagene). The clone isolated from the library contained a novel open reading frame and the antigen encoded by this gene was named GV-38A. The determined nucleotide sequence and predicted amino acid sequence of GV-38A are shown in SEQ ID NO: 120 and 121, respectively. Subsequent studies led to the isolation of an extended DNA sequence for GV-38A, provided in SEQ ID NO: 171. The corresponding amino acid sequence is provided in SEQ ID NO: 172. Comparison of these sequences with those in the gene bank, revealed some homology to an unknown *M. tuberculosis* protein previously identified in cosmid MTCY428.12. (SPTREMBL:P71915).

Upstream of the GV-38A gene, a second novel open reading frame was identified and the antigen encoded by this gene was named GV-38B. The determined 5' and 3' nucleotide sequences for GV-38B are provided in SEQ ID NO: 122 and 123, respectively, with the corresponding predicted amino acid sequences being provided in SEQ ID NO: 124 and 125, respectively. Further studies led to the isolation of the full-length DNA sequence for GV-38B, provided in SEQ ID NO: 173. The corresponding amino acid sequence is provided in SEQ ID NO: 174. This protein was found to show homology to an unknown *M. tuberculosis* protein identified in cosmid MTCY428.11 (SPTREMBL: P71914).

Both the GV-38A and GV-38B antigens were amplified for expression cloning into pET16 (Novagen). GV-38A was amplified with primers KR11 and KR12 (SEQ ID NO: 126 and 127) and GV-38B with primers KR13 and KR14 (SEQ ID NO: 128 and 129). Protein expression in the host cells BL21(DE3) was induced with 1 mM IPTG, however no protein expression was obtained from these constructs. Hydrophobic regions were identified in the N-termini of antigens GV-38A and GV-38B which may inhibit expression of these constructs. The hydrophobic region present in GV-38A was identified as a possible transmembrane motif with six membrane spanning regions. To express the antigens without the hydrophobic regions, primers KR20 for GV-38A, (SEQ ID NO: 130) and KR21 for GV-38B (SEQ ID NO: 131) were designed. The truncated GV-38A gene was amplified with primers KR20 and KR12, and the truncated GV-38B gene with KR21 and KR14. The determined nucleotide sequences of truncated GV38A and GV-38B are shown in SEQ ID NO: 132 and 133, respectively, with the corresponding predicted amino acid sequences being shown in SEQ ID NO: 134 and 135, respectively. Extended DNA sequences for truncated GV-38A and GV-38B are provided in SEQ ID NO: 175 and 176, respectively, with the corresponding amino acid sequences being provided in SEQ ID NO: 177 and 178, respectively.

EXAMPLE 9

Purification and Characterisation of Polypeptides from *M. vaccae* Culture Filtrate by Preparative Isoelectric Focusing and Preparative Polyacrylamide Gel Electrophoresis

*M. vaccae* soluble proteins were isolated from culture filtrate using preparative isoelectric focusing and preparative polyacrylamide gel electrophoresis as described below. Unless otherwise noted, all percentages in the following example are weight per volume.

*M. vaccae* (ATCC Number 15483) was cultured in 250 l sterile Medium 90 which had been fractionated by ultrafiltration to remove all proteins of greater than 10 kDa molecular weight. The medium was centrifuged to remove the bacteria, and sterilised by filtration through a 0.45 μm filter. The sterile filtrate was concentrated by ultrafiltration over a 10 kDa molecular weight cut-off membrane.

Proteins were isolated from the concentrated culture filtrate by precipitation with 10% trichloroacetic acid. The precipitated proteins were re-dissolved in 100 mM Tris.HCl pH 8.0. and re-precipitated by the addition of an equal volume of acetone. The acetone precipitate was dissolved in water, and proteins were re-precipitated by the addition of an equal volume of chloroform:methanol 2:1 (v/v). The chloroform:methanol precipitate was dissolved in water, and the solution was freeze-dried.

The freeze-dried protein was dissolved in iso-electric focusing buffer, containing 8 M deionised urea, 2% Triton X-100, 10 mM dithiothreitol and 2% ampholytes (pH 2.5–5.0). The sample was fractionated by preparative isoelectric focusing on a horizontal bed of Ultrodex gel at 8 watts constant power for 16 hours. Proteins were eluted from the gel bed fractions with water and concentrated by precipitation with 10% trichloroacetic acid.

Pools of fractions containing proteins of interest were identified by analytical polyacrylamide gel electrophoresis and fractionated by preparative polyacrylamide gel electrophoresis. Samples were fractionated on 12.5% SDS-PAGE gels, and electroblotted onto nitrocellulose membranes. Proteins were located on the membranes by staining with Ponceau Red, destained with water and eluted from the membranes with 40% acetonitrile/0.1 M ammonium bicarbonate pH 8.9 and then concentrated by lyophilisation.

Eluted proteins were assayed for their ability to induce proliferation and interferon-γ secretion from the peripheral blood lymphocytes of immune donors as detailed in Example 2. Proteins inducing a strong response in these assays were selected for further study.

Selected proteins were further purified by reversed-phase chromatography on a Vydac Protein C4 column, using a trifluoroacetic acid-acetonitrile system. Purified proteins were prepared for protein sequence determination by SDS-polyacrylamide gel electrophoresis, and electroblotted onto PVDF membranes. Protein sequences were determined as in Example 3. The proteins were named GV-40, GV-41, GV-42, GV-43 and GV-44. The determined N-terminal sequences for these polypeptides are shown in SEQ ID NOS: 101–105, respectively. Subsequent studies led to the isolation of a 5', middle fragment and 3' DNA sequence for GV-42 (SEQ ID NO: 136, 137 and 138, respectively). The corresponding predicted amino acid sequences are provided in SEQ ID NO: 139, 140 and 141, respectively.

Following standard DNA amplification and cloning procedures as described in Example 5, the genes encoding GV-41 and GV-42 were cloned. The determined nucleotide sequences are provided in SEQ ID NOS: 179 and 180, respectively, and the predicted amino acid sequences in SEQ ID NOS: 181 and 182. GV-41 had homology to the ribosome recycling factor of *M. tuberculosis* and *M. leprae*, and GV-42 had homogy to a *M. avium* fibronectin attachment protein FAP-A. Within the full-length sequence of GV-42, the amino acid sequence determined for GV-43 (SEQ ID NO:104 ) was identified, indicating that the amino acid sequences for GV-42 and GV-43 were obtained from the same protein.

Murine polyclonal antisera were prepared against GV-40 and GV-44 following standard procedures. These antisera were used to screen a *M. vaccae* genomic DNA library consisting of randomly sheared DNA fragments. Clones encoding GV-40 and GV-44 were identified and sequenced. The determined nucleotide sequence of the partial gene encoding GV-40 is provided in SEQ ID NO: 183 and the predicted amino acid sequence in SEQ ID NO: 184. The determined nucleotide sequence of the gene encoding GV-44 is provided in SEQ ID NO: 185, and the predicted amino acid sequence in SEQ ID NO: 186. Homology of GV-40 to *M. leprae* Elongation factor G was found and GV-44 had homology to *M. leprae* glyceraldehyde-3-phosphate dehydrogenase.

EXAMPLE 10

Immune Modulating Properties of Delipidated and Deglycolipidated *M. vaccae* and Recombinant Proteins From *M. vaccae*

This example illustrates the processing of different constituents of *M. vaccae* and their immune modulating properties.

Heat-killed *M. vaccae* and *M. vaccae* culture filtrate

*M. vaccae* (ATCC Number 15483) was cultured in sterile Medium 90 (yeast extract, 2.5 g/l; tryptone, 5 g/l; glucose 1 g/l) at 37° C. The cells were harvested by centrifugation, and transferred into sterile Middlebrook 7H9 medium (Difco Laboratories, Detroit, Mich., USA) with glucose at 37° C. for one day. The medium was then centrifuged to pellet the bacteria, and the culture filtrate removed. The bacterial pellet was resuspended in phosphate buffered saline at a concentration of 10 mg/ml, equivalent to $10^{10}$ *M. vaccae* organisms per ml. The cell suspension was then autoclaved for 15 min at 120° C. The culture filtrate was passaged through a 0.45 µm filter into sterile bottles.

Preparation of Delipidated and Deglycolipidated (DD-) *M. vaccae* and Compositional Analysis To prepare delipidated *M. vaccae*, the autoclaved *M. vaccae* was pelleted by centrifugation, the pellet washed with water and collected again by centrifugation and then freeze-dried. An aliquot of this freeze-dried *M. vaccae* was set aside and referred to as lyophilised *M. vaccae*. When used in experiments it was resuspended in PBS to the desired concentration. Freeze-dried *M. vaccae* was treated with chloroform/methanol (2:1) for 60 mins at room temperature to extract lipids, and the extraction was repeated once. The delipidated residue from chloroform/methanol extraction was further treated with 50% ethanol to remove glycolipids by refluxing for two hours. The 50% ethanol extraction was repeated two times. The pooled 50% ethanol extracts were used as a source of *M. vaccae* glycolipids (see below). The residue from the 50% ethanol extraction was freeze-dried and weighed. The amount of delipidated and deglycolipidated *M. vaccae* prepared was equivalent to 11.1% of the starting wet weight of *M. vaccae* used. For bioassay, the delipidated and deglycolipidated *M. vaccae* (DD-*M. vaccae*; referred to as delipidated *M. vaccae* in FIG. 9), was resuspended in phosphate-buffered saline by sonication, and sterilised by autoclaving.

The compositional analyses of heat-killed *M. vaccae* and DD-*M. vaccae* are presented in Table 7. Major changes are seen in the fatty acid composition and amino acid composition of DD-*M. vaccae* as compared to the insoluble fraction of heat-killed *M. vaccae*. The data presented in Table 1 show that the insoluble fraction of heat-killed *M. vaccae* contains 10% w/w of lipid, and the total amino acid content is 2750 nmoles/mg, or approximately 33% w/w. DD-*M. vaccae* contains 1.3% w/w of lipid and 4250 nmoles/mg amino acids, which is approximately 51% w/w.

TABLE 7

Compositional analyses of heat-killed *M. vaccae* and DD-*M. vaccae*
MONOSACCHARIDE COMPOSITION

| sugar alditol | *M. vaccae* | DD-*M. vaccae* |
|---|---|---|
| Inositol | 3.2% | 1.7% |
| Ribitol* | 1.7% | 0.4% |
| Arabinitol | 22.7% | 27.0% |
| Mannitol | 8.3% | 3.3% |
| Galactitol | 11.5% | 12.6% |
| Glucitol | 52.7% | 55.2% |

| FATTY ACID COMPOSITION | | |
|---|---|---|
| Fatty acid | *M. vaccae* | DD-*M. vaccae* |
| C14:0 | 3.9% | 10.0% |
| C16:0 | 21.1% | 7.3% |
| C16:1 | 14.0% | 3.3% |
| C18:0 | 4.0% | 1.5% |
| C18:1* | 1.2% | 2.7% |
| C18:1w9 | 20.6% | 3.1% |

FATTY ACID COMPOSITION

| Fatty acid | M. vaccae | DD-M. vaccae |
|---|---|---|
| C18:1w7 | 12.5% | 5.9% |
| C22:0 | 12.1% | 43.0% |
| C24:1* | 6.5% | 22.9% |

The insoluble fraction of heat-killed M. vaccae contains 10% w/w of lipid, and DD-M. vaccae contains 1.3% W/W of lipid.

AMINO ACID COMPOSITION

| Nmoles/mg | M. vaccae | DD-M. vaccae |
|---|---|---|
| ASP | 231 | 361 |
| THR | 170 | 266 |
| SER | 131 | 199 |
| GLU | 319 | 505 |
| PRO | 216 | 262 |
| GLY | 263 | 404 |
| ALA | 416 | 621 |
| CYS* | 24 | 26 |
| VAL | 172 | 272 |
| MET* | 72 | 94 |
| ILE | 104 | 171 |
| LEU | 209 | 340 |
| TYR | 39 | 75 |
| PHE | 76 | 132 |
| GlcNH2 | 5 | 6 |
| HIS | 44 | 77 |
| LYS | 108 | 167 |
| ARG | 147 | 272 |

The total amino acid content of the insoluble fraction of heat-killed M. vaccae is 2750 nmoles/mg, or approximately 33% w/w. The total amino acid content of DD-M. vaccae is 4250 nmoles/mg, or approximately 51% w/w.

M. vaccae glycolipids

The pooled 50% ethanol extracts described above were dried by rotary evaporation, redissolved in water, and freeze-dried. The amount of glycolipid recovered was 1.2% of the starting wet weight of M. vaccae used. For bioassay, the glycolipids were dissolved in phosphate-buffered saline.

Production of Interleukin-12 from macrophages

Whole heat-killed M. vaccae and DD-M. vaccae were shown to have different cytokine stimulation properties. The stimulation of a Th1 immune response is enhanced by the production of interleukin-12 (IL-12) from macrophages. The ability of different M. vaccae preparations to stimulate IL-12 production was demonstrated as follows.

Figure 8:
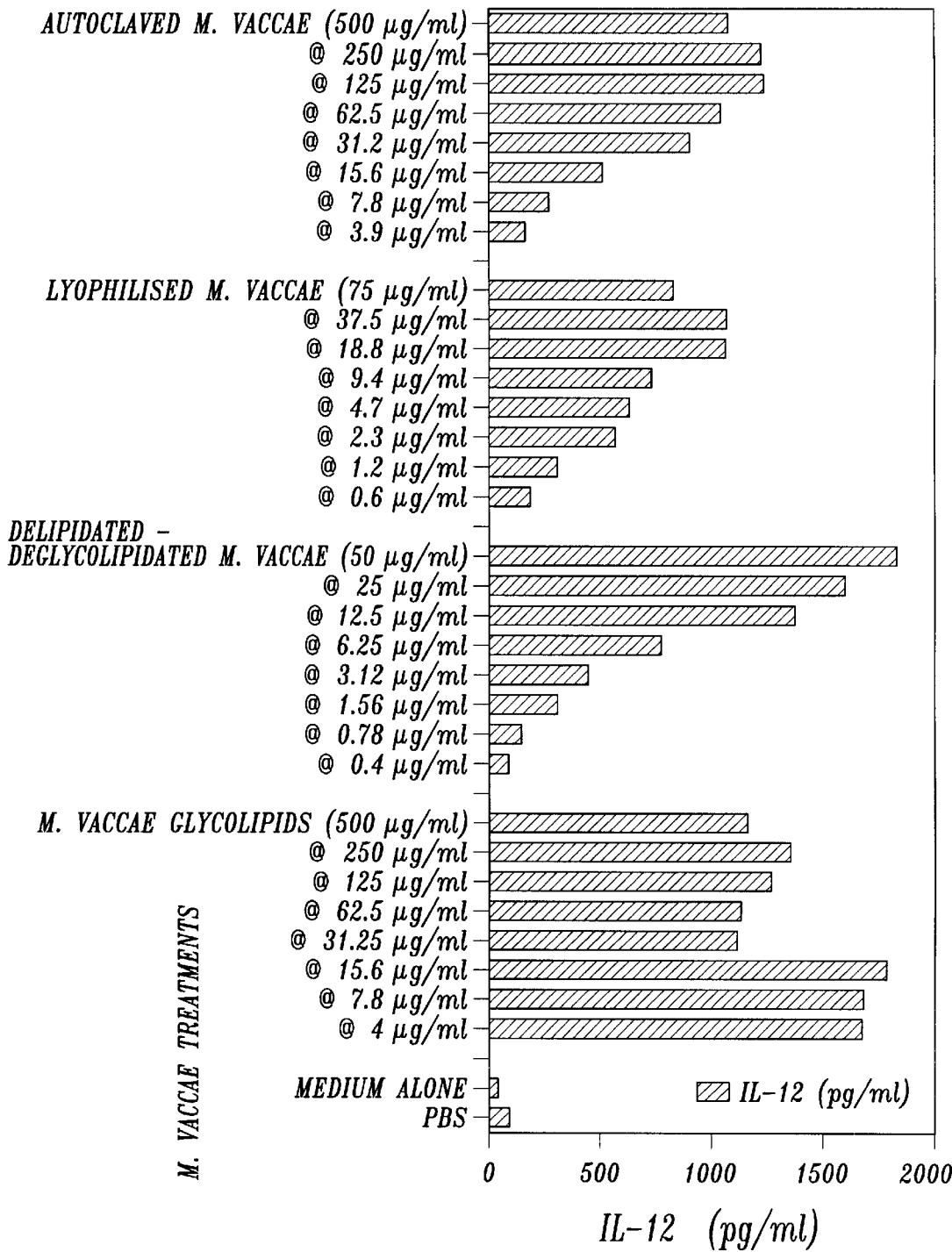
FIG. 8 illustrates the induction of IL-12 by autoclaved *M. vaccae*, lyophilized *M. vaccae*, delipidated and deglycolipidated *M. vaccae* and *M. vaccae* glycolipids.

A group of C57BL/6J mice were injected intraperitoneally with DIFCO thioglycolate and after three days, peritoneal macrophages were collected and placed in cell culture with interferon-gamma for three hours. The culture medium was replaced and various concentrations of whole heat-killed (autoclaved) M. vaccae, lyophilized M. vaccae, DD-M. vaccae (referred to as delipidated-deglycolipidated M. vaccae in FIG. 8) and M. vaccae glycolipids were added. After a further three days at 37° C., the culture supernatants were assayed for the presence of IL-12 produced by macrophages. As shown in FIG. 8, the M. vaccae preparations stimulated the production of IL-12 from macrophages.

Figure 10:
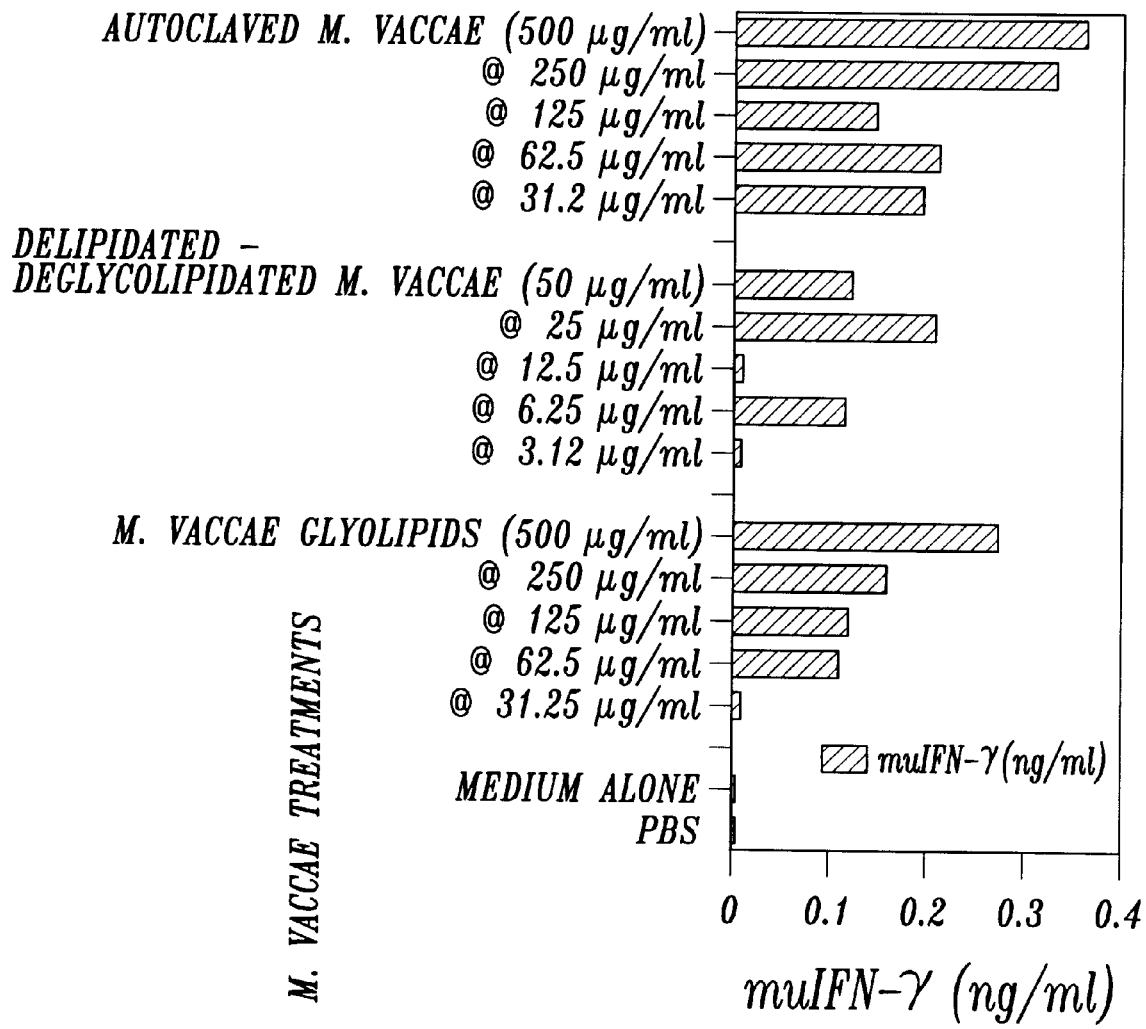
FIG. 10 compares the in vitro stimulation of interferon-gamma production in spleen cells from Severe Combined ImmunoDeficient (SCID) mice by different concentrations of heat-killed (autoclaved) *M. vaccae*, delipidated and deglycolipidated *M. vaccae*, and *M. vaccae* glycolipids.

By contrast, these same M. vaccae preparations were examined for the ability to stimulate interferon-gamma production from Natural Killer (NK) cells. Spleen cells were prepared from Severe Combined Immunodeficient (SCID) mice. These populations contain 75–80% NK cells. The spleen cells were incubated at 37° C. in culture with different concentrations of heat-killed M. vaccae, DD-M. vaccae, or M. vaccae glycolipids. The data shown in FIG. 10 demonstrates that, while heat-killed M. vaccae and M. vaccae glycolipids stimulate production of interferon-gamma, DD-M. vaccae stimulated relatively less interferon-gamma. The combined data from FIGS. 8 and 10 indicate that, compared with whole heat-killed M. vaccae, DD-M. vaccae is a better stimulator of IL-12 than interferon gamma.

Figure 9A:
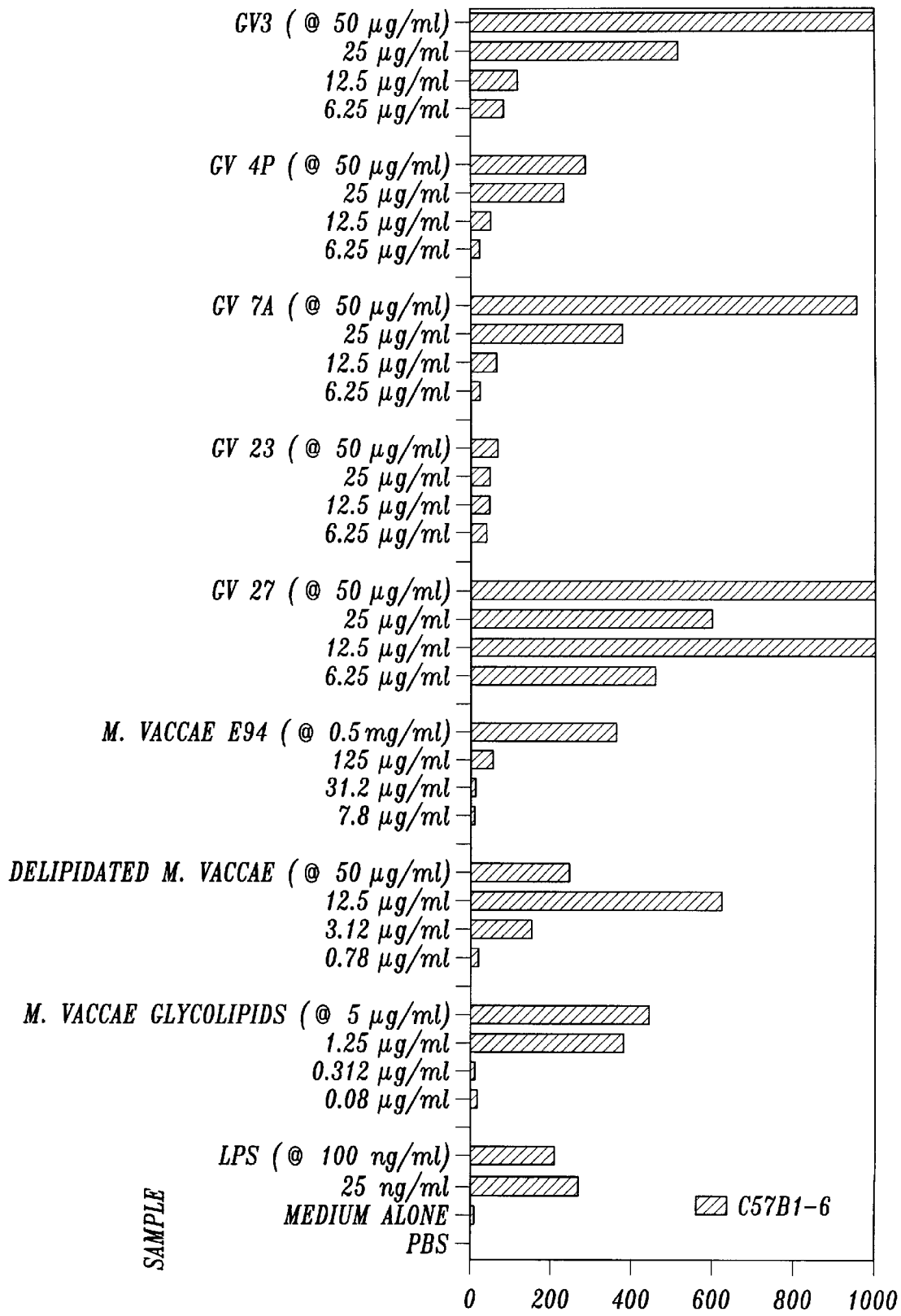
FIGS. 9A, B and C illustrate the stimulation of interferon-gamma production by different concentrations of *M. vaccae* recombinant proteins, heat-killed *M. vaccae*, delipidated and deglycolipidated *M. vaccae* (referred to in the figure as "delipidated *M. vaccae*"), *M. vaccae* glycolipids and lipopolysaccharide, in peritoneal macrophages from C57BL/6 mice (FIG. 9A), BALB/C mice (FIG. 9B) or C3H/HeJ mice (FIG. 9C).
Figure 9B:
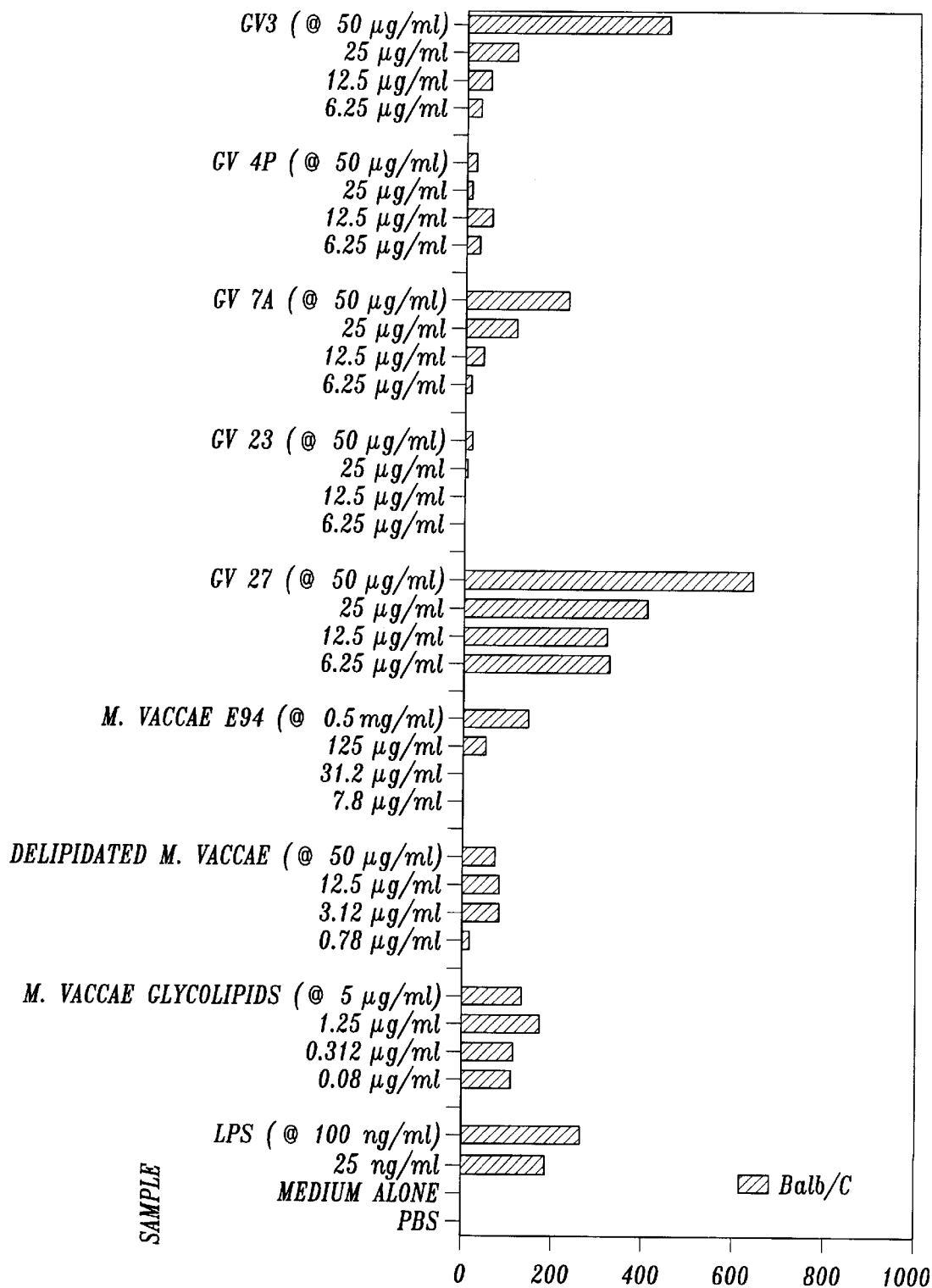
Figure 9C:
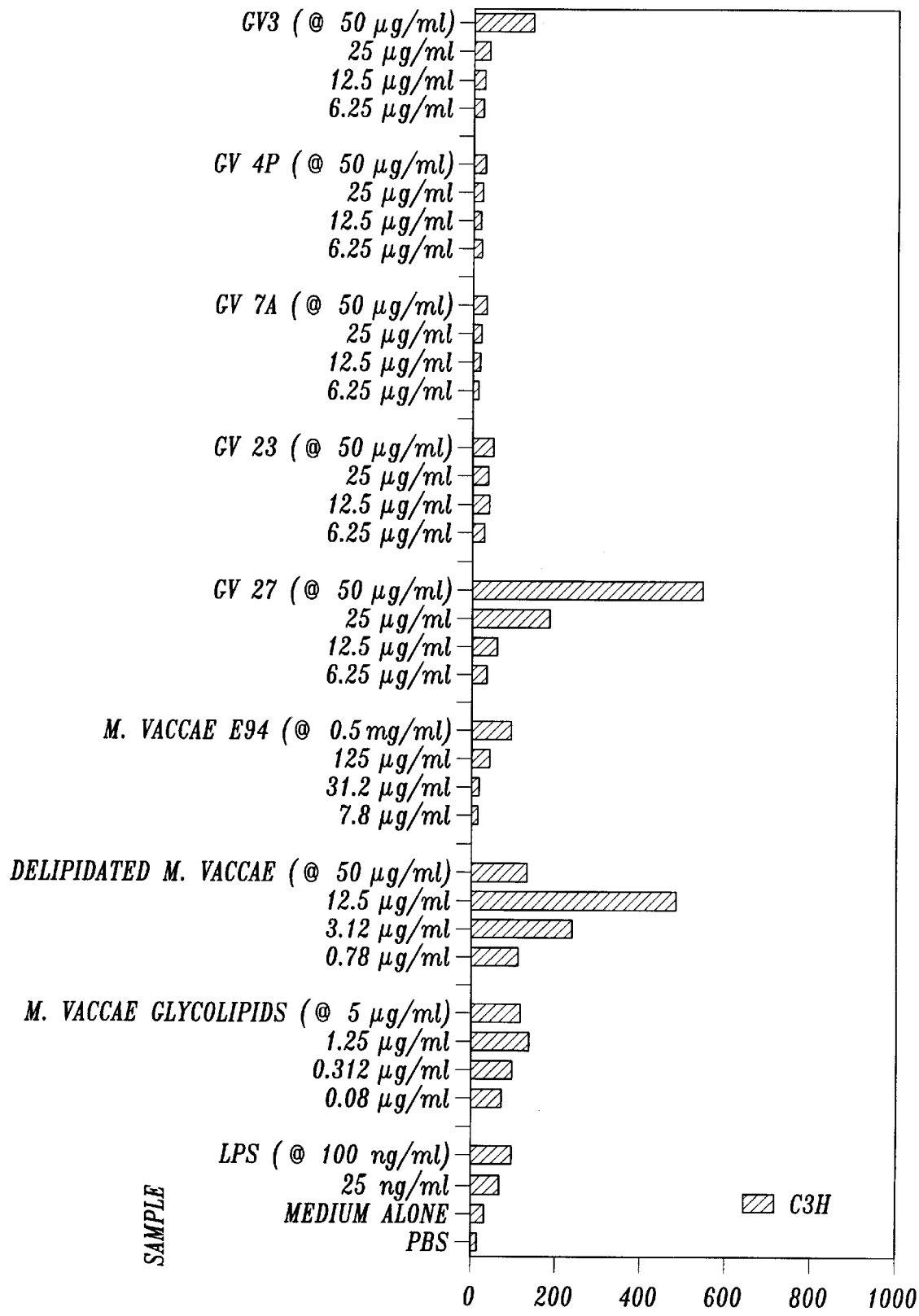

FIGS. 9A, B, and C show data from separate experiments in which groups of C57BL/6 mice (FIG. 9A), BALB/C mice (FIG. 9B) or C3H/HeJ mice (FIG. 9C) were given DIFCO thioglycolate intraperitoneally and, after three days, peritoneal macrophages were collected and placed in culture with interferon-gamma for three hours. The culture medium was replaced and various concentrations of M. vaccae recombinant proteins GVs-3 (GV-3), GV-4P (GV-4P), GVc-7 (GV-7), GV-23, GV-27, heat killed M. vaccae, DD-M. vaccae (referred to as delipidated M. vaccae in FIGS. 9A, B and C), M. vaccae glycolipids or lipopolysaccharide were added. After three days at 37° C., the culture supernatants were assayed for the presence of IL-12 produced by macrophages. As shown in FIGS. 9A, B and C, the recombinant proteins and M. vaccae preparations stimulated the production of IL-12 from macrophages.

EXAMPLE 11

Effect of Intradermal Route of Immunisation with M. vaccae on Tuberculosis in Cynomolgous Monkeys This example illustrates the effect of immunisation with M. vaccae or M. vaccae culture filtrate intradermally in cynomolgous monkeys prior to challenge with live M. tuberculosis.

M. vaccae (ATCC Number 15483) was cultured in sterile Medium 90 (yeast extract, 2.5 g/l; tryptone, 5 g/l; glucose, 1 g/l) at 37° C. The cells were harvested by centrifugation, and transferred into sterile Middlebrook 7H9 medium (Difco Laboratories, Detroit, Mich., USA) with glucose at 37° C. for one day. The medium was then centrifuged to pellet the bacteria, and the culture filtrate removed. The bacterial pellet was resuspended in phosphate buffered saline at a concentration of 10mg/ml, equivalent to $10^{10}$ M. vaccae organisms per ml. The cell suspension was then autoclaved for 15 min at 120° C. The culture filtrate was passaged through a 0.45 µM filter into sterile bottles.

Three groups of cynomolgous monkeys were included in this study, with each group containing 2 monkeys. One group of monkeys were immunised with whole heat-killed M. vaccae; one group were immunised with M. vaccae culture filtrate and a control group received no immunisations. The composition employed for immunisation, amount of immunogen and route of administration for each group of monkeys are provided in Table 7.

TABLE 7

COMPARISON OF INTRADERMAL ROUTE OF IMMUNISATION

| Group Number | Identification Number of Monkey | Amount of Antigen | Route of Immunisation |
|---|---|---|---|
| 1 (Controls) | S3101-E | 0 | — |
|  | 3144-B | 0 | — |

TABLE 7-continued

COMPARISON OF INTRADERMAL
ROUTE OF IMMUNISATION

| Group Number | Identification Number of Monkey | Amount of Antigen | Route of Immunisation |
|---|---|---|---|
| 2 (Immunised with heat-killed M. vaccae) | 4080-B | 500 μg | intradermal |
|  | 3586-B | 500 μg | intradermal |
| 3 (Immunised with culture filtrate) | 3564-B | 100 μg | intradermal |
|  | 3815-B | 100 μg | intradermal |

Prior to immunisation, all monkeys were weighed (Wt kgs), body temperature measured (temp), and a blood sample taken for determination of erythrocyte sedimentation rate (ESR mm/hr) and lymphocyte proliferation (LPA) to an in vitro challenge with purified protein (PPD) prepared from *Mycobacterium bovis*. At day 33 post-immunisation these measurements were repeated. At day 34, all monkeys received a second immunisation using the same amount of *M. vaccae*. On day 62, body weight, temperature, ESR and LPA to PPD were measured, then all monkeys were infected with 103 colony forming units of the Erdman strain of *M. tuberculosis*. Twenty eight days following infection, body weight, temperature, ESR and LPA to PPD were measured in all monkeys, and the lungs were X-rayed to determine whether infection with live *M. tuberculosis* had resulted in the onset of pneumonia As shown in Tables 8A, B and C, the monkeys in the control group showed radiologic evidence of pulmonary tuberculosis by 28 days after infection with *M. tuberculosis*. Clinical disease was not evident 84 days after infection in monkeys immunised intradermally with two doses of 500 μg of *M. vaccae*. The onset of clinical disease was delayed in both monkeys immunised intradermally with 100 μg of *M. vaccae* culture filtrate.

TABLE 8A

CONTROL MONKEYS

| ID# | Days | Wt. Kgs | Temp. | ESR Mm/hr | LPA PPD 10 μg | LPA PPD 1 μg | X-Ray |
|---|---|---|---|---|---|---|---|
| S3101E | 0 | 2.17 | 37.0 | 0 | 0.47 | 1.1 | Negative |
|  | 34 | 1.88 | 37.3 | ND | 0.85 | 1.4 | ND |
|  | 62 | 2.02 | 36.0 | ND | 1.3 | 1.5 | ND |
| → Time of Infection |  |  |  |  |  |  |  |
|  | 28 | 2.09 | 38.0 | 2 | 1.3 | 3.7 | Positive |
|  | 56 | 1.92 | 37.2 | 20 | 5.6 | 9.1 | Positive |
|  | 84 | 1.81 | 37.5 | 8 | 4.7 | 5.6 | Positive |
| 3144-B | 0 | 2.05 | 36.7 | 0 | 0.87 | 1.8 | Negative |
|  | 34 | 1.86 | 37.6 | ND | 2.2 | 1.4 | ND |
|  | 62 | 1.87 | 36.5 | ND | 1.6 | 1.6 | ND |
| → Time of Infection |  |  |  |  |  |  |  |
|  | 28 | 2.10 | 38.0 | 0 | 12 | 8.7 | Positive |
|  | 56 | 1.96 | 37.6 | 0 | 29.6 | 21.1 | Positive |
|  | 84 | 1.82 | 37.3 | 4 | 45.3 | 23.4 | Positive |

ND = Not Done

TABLE 8B

MONKEYS IMMUNISED WITH WHOLE HEAT-KILLED *M. VACCAE* (500 μg) INTRADERMALLY

| ID# | Days | Wt. Kgs | Temp. | ESR Mm/hr | LPA PPD 10 μg | LPA PPD 1 μg | X-Ray |
|---|---|---|---|---|---|---|---|
| 4080-B | 0 | 2.05 | 37.1 | 1 | 1.1 | 0.77 | Negative |
|  | 34 | 1.97 | 38.0 | ND | 1.7 | 1.4 | ND |
|  | 62 | 2.09 | 36.7 | ND | 1.5 | 1.5 | ND |
| → Time of Infection |  |  |  |  |  |  |  |
|  | 28 | 2.15 | 37.6 | 0 | 2.6 | 2.1 | Negative |
|  | 56 | 2.17 | 37.6 | 0 | 8.2 | 7.6 | Negative |
|  | 84 | 2.25 | 37.3 | 0 | 3.8 | 2.8 | Negative |
| 3586-B | 0 | 2.29 | 37.0 | 0 | 1.1 | 1.4 | Negative |
|  | 34 | 2.22 | 38.0 | ND | 1.9 | 1.6 | ND |
|  | 62 | 2.39 | 36.0 | ND | 1.3 | 1.6 | ND |
| → Time of Infection |  |  |  |  |  |  |  |
|  | 28 | 2.31 | 38.2 | 0 | 3.2 | 2.6 | Negative |
|  | 56 | 2.32 | 37.2 | 0 | 7.8 | 4.2 | Negative |
|  | 84 | 2.81 | 37.4 | 0 | 3.4 | 1.8 | Negative |

ND = Not Done

TABLE 8C

MONKEYS IMMUNISED WITH CULTURE FILTRATE (100 μg) INTRADERMALLY

| ID# | Days | Wt. Kgs | Temp. | ESR Mm/hr | LPA PPD 10 μg | LPA PPD 1 μg | X-Ray |
|---|---|---|---|---|---|---|---|
| 3564-B | 0 | 2.40 | 37.2 | 0 | 1.4 | 1.4 | Negative |
|  | 34 | 2.42 | 38.1 | ND | 3.3 | 2.7 | ND |
|  | 62 | 2.31 | 37.1 | ND | 3.1 | 3.4 | ND |
| → Time of Infection |  |  |  |  |  |  |  |
|  | 28 | 2.41 | 38.6 | 13 | 24 | 13.6 | Negative |
|  | 56 | 2.38 | 38.6 | 0 | 12.7 | 12.0 | Negative |
|  | 84 | 2.41 | 38.6 | 2 | 21.1 | 11.8 | Positive |
| 3815-B | 0 | 2.31 | 36.3 | 0 | 1.0 | 1.4 | Negative |
|  | 34 | 2.36 | 38.2 | ND | 1.9 | 2.0 | ND |
|  | 62 | 2.36 | 36.4 | ND | 3.7 | 2.8 | ND |
| → Time of Infection |  |  |  |  |  |  |  |
|  | 28 | 2.45 | 37.8 | 0 | 2.1 | 3.3 | Negative |
|  | 56 | 2.28 | 37.3 | 4 | 8.0 | 5.6 | Negative |
|  | 84 | 2.32 | 37.4 | 0 | 1.9 | 2.2 | Positive |

ND = Not Done

EXAMPLE 12

DNA Cloning Strategy for the DD-*M. vaccae* Antigen GV-45

Proteins were extracted from DD-*M. vaccae* (500 mg; prepared as described in Example 10) by suspension in 10 ml 2% SDS/PBS and heating to 50° C. for 2 h. The insoluble residue was removed by centrifugation, and proteins precipitated from the supernatant by adding an equal volume of acetone and incubating at −20° C. for 1 hr. The precipitated proteins were collected by centrifugation, dissolved in reducing sample buffer, and fractionated by preparative SDS-polyacrylamide gel electrophoresis. The separated proteins were electroblotted onto PVDF membrane in 10 mM CAPS/0.0 1% SDS pH 11.0, and N-terminal sequences were determined in a gas-phase sequenator.

The amino acid sequence obtained from these experiments was designated GV-45. The determined N-terminal sequence for GV-45 is provided in SEQ ID NO: 187.

From the amino acid sequence of GV-45, degenerate oligonucleotides KR32 and KR33 (SEQ ID NOS: 188 and 189, respectively) were designed. A 100 bp fragment was amplified, cloned into plasmid pBluescript II SK⁺ (Stratagene, La Jolla, Calif.) and sequenced (SEQ ID NO: 190) following standard procedures (Maniatis). The cloned insert was used to screen a *M. vaccae* genomic DNA library constructed in the BamHI-site of lambda ZAP-Express (Stratagene). The isolated clone showed homology to a 35 kDa *M. tuberculosis* and a 22 kDa *M. leprae* protein containing bacterial histone-like motifs at the N-terminus and a unique C-terminus consisting of a five amino acid basic repeat. The determined nucleotide sequence for GV-45 is provided in SEQ ID NO: 191, with the corresponding predicted amino acid sequence being provided in SEQ ID NO: 192.

Although the present invention has been described in some detail by way of illustration and example for purposes of clarity of understanding, changes and modifications can be carried out without departing from the scope of the invention which is intended to be limited only by the scope of the appended claims.

I claim:

1. A method for enhancing a non-specific immune response to an antigen comprising administering delipidated and deglycolipidated *M. vaccae* cells.

2. A composition comprising delipidated and deglycolipidated *M. vaccae* cells.

3. A method for inducing an immune response in a patient comprising administering a composition according to claim 2.

4. The composition of claim 2, wherein the delipidated and deglycolipidated *M. vaccae* cells comprise less than 10% by weight of lipids.

5. The composition of claim 2, wherein the delipidated and deglycolipidated *M. vaccae* cells comprise more than 33% by weight of amino acids.

* * * * *

UNITED STATES PATENT AND TRADEMARK OFFICE
CERTIFICATE OF CORRECTION

PATENT NO.  : 5,985,287
DATED       : November 16, 1999
INVENTOR(S) : Paul Tan, Margot Skinner and Ross Prestidge It is certified that error appears in the above-identified patent and that said Letters Patent is hereby corrected as shown below:

Column 10,
Line 4, replace "thereof," with -- thereof), --

Column 15,
Line 45, replace "portions thereof For" with -- portions thereof. For --

Column 18,
Line 46, replace "(Perlin Elmer" with -- (Perkin Elmer --

Column 23,
Line 43, replace "digested X vector" with -- digested $\lambda$ vector --

Column 25,
Table 2, replace "

TABLE 2

|       | Donor G97005 | | Donor G97006 | | Donor G97007 | | Donor G97008 | | Donor G97009 | | Donor G97010 | |
|-------|--------|-------|--------|-------|--------|-------|--------|-------|--------|-------|--------|-------|
|       | Prolif | IFN-γ | Prolif | IFN-γ | Prolif | IFN-γ | Prolif | IFN-γ | Prolif | IFN-γ | Prolif | IFN-γ |
| GVs-3 | ++     | +     | ND     | ND    | ++     | ++    | ++     | ++    | ++     | +/±   | +      | ++    |
| GV-4P | +      | +/-   | ND     | ND    | +      | ++    | ++     | ++    | +/-    | +/-   | +/-    | ++    |
| GVs-5 | ++     | ++    | ++     | ++    | --     | ++    | +      | ++    | ++     | +     | +      | ++    |

"

With ----

Table 2

|       | Donor G97005 | | Donor G97006 | | Donor G97007 | | Donor G97008 | | Donor G97009 | | Donor G97010 | |
|-------|--------|-------|--------|-------|--------|-------|--------|-------|--------|-------|--------|-------|
|       | Prolif | IFN-γ | Prolif | IFN-γ | Prolif | IFN-γ | Prolif | IFN-γ | Prolif | IFN-γ | Prolif | IFN-γ |
| GVs-3 | ++     | +     | ND     | ND    | ++     | ++    | ++     | ++    | ++     | +/-   | +      | ++    |
| GV-4P | +      | +/-   | ND     | ND    | +      | ++    | ++     | ++    | +/-    | +/-   | +/-    | ++    |
| GVs-5 | ++     | ++    | ++     | ++    | --     | ++    | +      | ++    | ++     | +     | +      | ++    |

---

(Note under "Donor G97009," column IFNγ, Row GVs-3, the +/-)

UNITED STATES PATENT AND TRADEMARK OFFICE
CERTIFICATE OF CORRECTION

PATENT NO. : 5,985,287
DATED : November 16, 1999
INVENTOR(S) : Paul Tan, Margot Skinner and Ross Prestidge It is certified that error appears in the above-identified patent and that said Letters Patent is hereby corrected as shown below:

Column 26,
Line 4, replace "(re-named GV3 1)" with -- (re-named GV-31) --

Column 31,
Line 35, replace "urealpolyacrylamide" with -- urea/polyacrylamide --

Column 39,
Line 29, replace "with 103" with -- $10^3$ --

Signed and Sealed this

Thirteenth Day of November, 2001

Attest:

NICHOLAS P. GODICI
Attesting Officer   Acting Director of the United States Patent and Trademark Office